US011098105B2

(12) United States Patent
Escobar-Cabrera

(10) Patent No.: US 11,098,105 B2
(45) Date of Patent: Aug. 24, 2021

(54) HETEROMULTIMERS WITH REDUCED OR SILENCED EFFECTOR FUNCTION

(71) Applicant: Zymeworks Inc., Vancouver (CA)

(72) Inventor: Eric Escobar-Cabrera, Burnaby (CA)

(73) Assignee: ZYMEWORKS INC., Vancouver (CA)

( * ) Notice: Subject to any disclaimer, the term of this patent is extended or adjusted under 35 U.S.C. 154(b) by 418 days.

(21) Appl. No.: 14/893,503

(22) PCT Filed: May 30, 2014

(86) PCT No.: PCT/CA2014/050507
§ 371 (c)(1),
(2) Date: Nov. 23, 2015

(87) PCT Pub. No.: WO2014/190441
PCT Pub. Date: Dec. 4, 2014

(65) Prior Publication Data

US 2016/0102135 A1 Apr. 14, 2016

Related U.S. Application Data

(60) Provisional application No. 61/829,973, filed on May 31, 2013.

(51) Int. Cl.

| | |
|---|---|
| ***C07K 1/00*** | (2006.01) |
| ***C07K 16/00*** | (2006.01) |
| ***C12P 21/08*** | (2006.01) |
| ***A61K 39/395*** | (2006.01) |
| ***C07K 16/28*** | (2006.01) |
| ***C07K 16/32*** | (2006.01) |

(52) U.S. Cl.
CPC .......... *C07K 16/00* (2013.01); *C07K 16/2887* (2013.01); *C07K 16/32* (2013.01); *C07K 2317/41* (2013.01); *C07K 2317/526* (2013.01); *C07K 2317/53* (2013.01); *C07K 2317/71* (2013.01); *C07K 2317/92* (2013.01); *C07K 2317/94* (2013.01)

(58) Field of Classification Search
None
See application file for complete search history.

(56) References Cited

U.S. PATENT DOCUMENTS 5,500,362 A 3/1996 Robinson et al.
5,624,821 A 4/1997 Winter et al.
5,677,171 A 10/1997 Hudziak et al.
5,736,137 A 4/1998 Anderson et al.
5,885,573 A 3/1999 Bluestone et al.
6,194,551 B1 2/2001 Idusogie et al.
6,737,056 B1 5/2004 Presta
7,317,091 B2 1/2008 Lazar et al.
7,632,497 B2 12/2009 Stavenhagen
7,951,917 B1* 5/2011 Arathoon .............. C07K 16/46 530/387.3
8,937,158 B2 1/2015 Lazar et al.
9,079,965 B2 7/2015 Zhou et al.
9,296,815 B2 3/2016 D'Angelo et al.
2003/0157108 A1 8/2003 Presta et al.
2004/0002587 A1 1/2004 Watkins et al.
2004/0110226 A1 6/2004 Lazar et al.
2004/0132101 A1 7/2004 Lazar et al.
2006/0235208 A1 10/2006 Lazar et al.
2008/0154025 A1 6/2008 Lazar
2012/0244578 A1* 9/2012 Kannan ................. C07K 16/00 435/69.6
2012/0251531 A1 10/2012 Baehner et al.
2013/0039913 A1 2/2013 Labrijn et al.
2013/0115208 A1 5/2013 Ho et al.
2014/0105889 A1* 4/2014 Igawa ................. C07K 16/303 424/133.1

(Continued)

FOREIGN PATENT DOCUMENTS

CA 2839539 A1 1/2013
CN 1705491 12/2005

(Continued)

OTHER PUBLICATIONS

U.S. Appl. No. 13/638,362 , "Restriction Requirement", dated Jan. 29, 2015, 9 pages.
U.S. Appl. No. 13/638,362 , "Non-Final Office Action", dated May 26, 2015, 12 pages.
U.S. Appl. No. 13/638,362 , "Notice of Allowance", dated Dec. 18, 2015, 9 pages.
U.S. Appl. No. 13/941,449 , "Non-Final Office Action", dated Apr. 13, 2016, 41 pages.
U.S. Appl. No. 13/941,449 , "Restriction Requirement", dated Dec. 3, 2015, 10 pages.
U.S. Appl. No. 14/399,789 , "Non-Final Office Action", dated Dec. 17, 2015, 31 pages.

(Continued)

*Primary Examiner* — Chun W Dahle
(74) *Attorney, Agent, or Firm* — Kilpatrick Townsend & Stockton LLP

(57) ABSTRACT

Provided herein are heteromultimer constructs with reduced or silenced effector function. In an embodiment is provided a heteromultimer construct comprising an IgG Fc construct having a first and a second Fc polypeptide, each Fc polypeptide comprising a modified lower hinge region wherein: the modified lower hinge region of said first Fc polypeptide comprises at least one amino acid modification, the modified lower hinge region of said second Fc polypeptide comprises at least one amino acid modification which is different from at least one amino acid modification of said first Fc polypeptide, and the IgG Fc construct displays reduced binding to all Fcγ receptors and to C1q protein as compared to a corresponding parent IgG Fc construct. Also provided are methods of producing such heteromultimer constructs, and methods of reducing ADCC for an antibody construct by reducing effector function.

16 Claims, 35 Drawing Sheets

Specification includes a Sequence Listing.

(56) References Cited

U.S. PATENT DOCUMENTS

| | | | | |
|---|---|---|---|---|
| 2014/0199294 | A1* | 7/2014 | Mimoto | C07K 16/00 424/133.1 |
| 2016/0093480 | A1 | 3/2016 | Gordon et al. | |
| 2016/0355588 | A1 | 12/2016 | Ng et al. | |

FOREIGN PATENT DOCUMENTS

| | | | |
|---|---|---|---|
| EP | 2698431 | A1 | 2/2014 |
| EP | 3208281 | A1 | 8/2017 |
| JP | 2006524039 | | 10/2006 |
| JP | 2012524522 | | 10/2012 |
| WO | 9958572 | | 11/1999 |
| WO | 0042072 | | 7/2000 |
| WO | 2004/029207 | A2 | 4/2004 |
| WO | 2004029207 | | 4/2004 |
| WO | 2004/063351 | A2 | 7/2004 |
| WO | 2007022520 | | 2/2007 |
| WO | 2008150494 | | 12/2008 |
| WO | 2010106180 | | 9/2010 |
| WO | 2011120134 | | 10/2011 |
| WO | 2012058768 | A1 | 5/2012 |
| WO | 2012125850 | A1 | 9/2012 |
| WO | 2012133782 | A1 | 10/2012 |
| WO | 2013063702 | A1 | 11/2012 |
| WO | 2013012733 | | 1/2013 |

OTHER PUBLICATIONS

U.S. Appl. No. 14/399,789 , "Restriction Requirement", dated Sep. 14, 2015, 11 pages.

U.S. Appl. No. 14/903,184, "U.S. Patent Application", filed Jan. 6, 2016, Titled: Bispecific CD3 and CD19 Antigen Binding Constructs.

U.S. Appl. No. 15/046,379, "U.S. Patent Application", filed Feb. 17, 2016, Titled: Antibodies With Enhanced or Suppressed Effector Function.

Alegre et al., "A non-activating "humanized" anti-CD3 monoclonal antibody retains immunosuppressive properties in vivo", Transplantation, vol. 57(11), Jun. 15, 1994, pp. 1537-1543.

Armour et al., "Differential binding to human FeyR11a and FcyRIIb receptors by human IgG wildtype and mutant antibodies", Mol. Immunol., vol. 40(9), Dec. 2003, pp. 585-593.

Armour et al., "Recombinant human IgG molecules lacking Fcgamma receptor I binding and monocyte triggering activities", Eur. J. Immunol., vol. 29(8), Aug. 1999, pp. 2613-2624.

Capel et al., "Heterogeneity of human IgG Fe receptors", Imunomethods, vol. 4(1), Feb. 1994, pp. 25-34.

Clynes et al., "Inhibitory Fe receptors modulate in vivo cytotoxicity against tumour targets", Nat. Med., vol. 6(4), Apr. 2000, pp. 443-446.

Daeron , "Fc receptor biology", Annu. Rev. Immunol., vol. 15, 1997, pp. 203-234 (Abstract Only).

De Haas , "Fc gamma receptors ofphagocytes", J. Lab. Clin. Med., vol. 126(4), Oct. 1995, pp. 330-341.

Duncan et al., "Localization of the binding site for the human high-affinity Fc receptor on IgG", Nature, vol. 332, No. 7, 1988, pp. 563-564.

Hinton et al., "Engineered human IgG antibodies with longer serum half-lives in primates", J. Biol. Chem., vol. 279(8), Feb. 20, 2004, pp. 6213-6216.

Hunter et al., "Inhibition of Fey receptor mediated phagocytosis by nonphagocytic Fcy receptor", Blood, vol. 91(5), Mar. 1, 1998, pp. 1762-1768.

Hutchins et al., "Improved biodistribution, tumor targeting, and reduced immunogenicity in mice with a gamma 4 variant of Campath-1H.", Proc. Natl. Acad. Sci., vol. 92, No. 26, Dec. 1995, pp. 11980-11984.

Idusogie et al., "Engineered antibodies with increased activity to recruit complement", J. Immunol., vol. 166, No. 4, Feb. 15, 2001, pp. 2571-2575.

Idusogie et al., "Mapping of the C1q binding site on rituxan, a chimeric antibody with a human IgG1 Fc", J. Immunol., vol. 164, No. 8, Apr. 15, 2000, pp. 4178-4184.

Jefferis et al., "Interaction sites on human IgG-Fc for FcgammaR: current models", Immunol. Lett., vol. 82, No. 1-2, 2002, pp. 57-65.

Jefferis et al., "Modulation of Fc(gamma)R and human complement activation by IgG3-core oligosaccharide interactions", Immunol. Lett., vol. 54, No. 2-3, Dec. 1996, pp. 101-104.

Jefferis et al., "Recognition sites on human IgG for Fe gamma receptors: the role of glycosylation", Immunol. Lett., vol. 44, No. 2-3, 1995, pp. 111-117.

Lazar et al., "Engineered antibody Fc variants with enhanced effector function", Proceedings of the National Academy of Sciences, vol. 103, No. 11, Mar. 14, 2006, pp. 4005-4010.

Lund et al., "Human Fe gamma RI and Fe gamma RII interact with distinct but overlapping sites on human IgG", J. Immunol., vol. 147, No. 8, Oct. 15, 1991, pp. 2657-2662.

Lund et al., "Multiple binding sites on the CH2 domain oflgG for mouse Fe gamma R11", Mol. Immunol., vol. 29, No. 1, 1992, pp. 53-59.

Lund et al., "Multiple interactions oflgG with its core oligosaccharide can modulate recognition by complement and human Fe gamma receptor I and influence the synthesis of its oligosaccharide chains", J. Immunol., vol. 157, No. 11, 1996, pp. 4963-4969.

Lund et al., "Oligosaccharide-protein interactions in IgG can modulate recognition by Fe gamma receptors", FASEB J., vol. 9, No. 1, Jan. 1995, pp. 115-119.

Moore et al., "Engineered Fc variant antibodies with enhanced ability to recruit complement and mediate effector functions", MABS, Landes Biosciences , vol. 2, No. 2, Mar. 2010, pp. 181-189.

Oganesyan et al., "Structural characterization of a human Fc fragment engineered for lack of effector functions", Acta Cryst., vol. D64, 2008, pp. 700-704.

Oganesyan et al., "Structural characterization of a mutated, ADCC-enhanced human Fc fragment", Mol. Immunol., vol. 45(7), Apr. 2008, 1872-82.

PCT/CA2011/000321 , "International Preliminary Report on Patentability", dated Oct. 2, 2012.

PCT/CA2011/000321 , "International Search Report and Written Opinion", dated Jul. 15, 2011, 15 pages.

PCT/CA2014/050507 , "International Preliminary Report on Patentability", dated Dec. 10, 2015, 9 pages.

Presta , "Antibody Engineering", Curr. Op. Struct. Biol., vol. 2, 1992, pp. 593-596.

Presta et al., "Engineering therapeutic antibodies for improved function", Biochem. Soc. Trans., vol. 30, No. 4, Aug. 2002, pp. 487-490.

Ravetch et al., "Fc receptors", Annu. Rev. Immunol., vol. 9, 1991, pp. 457-492.

Reddy et al., "Elimination of Fc receptor-dependent effector functions of a modified IgG4 monoclonal antibody to human CD4", J. Immunol., vol. 164, No. 4, Feb. 15, 2000, pp. 1925-1933.

Richards et al., "Optimization of antibody binding to FcaRIIa enhances macrophage phagocytosis of tumor cells", Molecular Cancer Therapeutics, vol. 7, No. 8, Aug. 2008, pp. 2517-2527.

Shields et al., "High resolution mapping of the binding site on human IgG1 for Fc gamma RI, Fc gamma RII, Fc gamma RIII, and FcRn and design of IgG1 variants with improved binding to the Fc gamma R", Journal of Biological Chemistry, vol. 276, No. 9, Mar. 2, 2001, pp. 6591-6604.

Shields et al., "Lack of fucose on human IgG1 N-linked oligosaccharide improves binding to human Fcgamma RiII and antibody-dependent cellular toxicity", J. Biol. Chem., vol. 77(30), Jul. 26, 2002, pp. 26733-26740.

Shinkawa et al., "The absence of fucose but not the presence of galactose or bisecting N-acetylglucosamine ofhuman IgG1 complex-type oligosaccharides shows the critical role of enhancing antibody-dependent cellular cytotoxicity", J. Biol. Chem., vol. 278(5), Jan. 31, 2003, pp. 3466-3473.

Stavenhagen et al., "Enhancing the potency of therapeutic monoclonal antibodies via Fc optimization", Adv. Enzyme Regul., vol. 48, 2008, pp. 152-164.

(56) References Cited

OTHER PUBLICATIONS

Stavenhagen et al., "Fc optimization of therapeutic antibodies enhances their ability to kill tumor cells in vitro and controls tumor expansion in vivo via low-affinity activating Fcgamma receptors.", Cancer Res., vol. 67(18), Sep. 15, 2007, pp. 8882-8890.
Van Sorge et al., "FcyR polymorphisms: Implications for function, disease susceptibility and immunotherapy", Tissue Antigens, vol. 61, 2003, pp. 189-202.
Veri et al., "Monoclonal antibodies capable of discriminating the human inhibitory Fcgamma-receptor IiB (CD32B) from the activating Fcgamma-receptor IIA (CD32A): biochemical, biological and functional characterization", Immunology, vol. 121(3), 2007, pp. 392-404.
Ward et al., "The effector functions of immunoglobulins: implications for therapy", Ther. Immunol., vol. 2(2), Apr. 1995, pp. 77-94.
Xu et al., "In vitro characterization of five humanized OKT3 effector function variant antibodies", Cell. Immunol., vol. 200, No. 1, Feb. 25, 2000, pp. 16-26.
U.S. Appl. No. 13/941,449, "Final Office Action", dated Oct. 31, 2016, 58 pages.
U.S. Appl. No. 14/399,789, "Final Office Action", dated Jul. 20, 2016, 30 pages.
An et al., "Igg2m4, an engineered antibody isotype with reduced fc function", MAbs, vol. 1, 2009, pp. 572-579.
EP14803370.7 , "Extended European Search Report", dated Dec. 6, 2016, 8 pages.
Gilles et al., "Improved circulating half-life and efficacy of an antibody-interleukin immunocytokine a based on reduced intracellular proteolysis", Clinical Cancer Research, the American Association for Cancer Research, US, vol. 8, No. 1, Jan. 2002, pp. 210-216.
Gillies et al., "Improving the efficacy of antibody-interleukin 2 fusion proteins by reducing their interaction with fc receptors", Cancer Research, vol. 59, 1999, pp. 2159-2166.
Hezareh et al., "Effector function activities of a panel of mutants of a broadly neutralizing antibody against human immunodeficiency virus type 1", Journal of Virology, the American Society for Microbiology, vol. 75, No. 24, Dec. 1, 2001, pp. 12161-12168.
Jubala et al., "CD20 Expression in Normal Canine B Cells and in Canine non-Hodgkin Lymphoma", Vet Pathol, vol. 42, 2005, pp. 468-476.
Labrijn et al., "When binding is enough: nonactivating antibody formats", Current Opinion in Immunology, vol. 20, 2008, pp. 479-485.
Mimoto et al., "Novel asymmetrically engineered antibody Fc variant with superior Fc[gamma]R binding affinity and specificity compared with afucosylated Fc variant", vol. 5. No. 2 XP55108766, Mar. 1, 2013, pp. 229-236.
Newman et al., "Modification of the fc Region of a Primatized IgG Antibody to Human CD4 Retains its Ability to Modulate CD4 Receptors but Does Not Deplete CD4+ T Cells in Chimpanzees", Clinical Immunology, vol. 98, 2001, pp. 164-174.
Radaev et al., "The structure of Human Type III Fey receptor in complex with fc", The Journal of Biological Chemistry, vol. 276, issue 19, 2001, pp. 16469-16477.
Robinson et al., "Targeting ErbB2 and ErbB3 with a bispecific single-chain Fv enhances 1-5 targeting selectivity and induces a therapeutic effect in vitro", Br. J. Cancer, vol. 99, Oct. 7, 2008, pp. 1415-1425.
Sondermann et al., "The 3.2-A crystal structure of the human IgG1 Fe fragment-Fey RiII complex", Nature, vol. 406, Jul. 20, 2000, pp. 267-273.
Strohl et al., "Antibody Fc engineering for optimal antibody performance", Therapeutic Antibody Engineering, Woodhead Publishing Limited, Cambridge 2012, pp. 225-249.
Strohl , "Optimization of fc-mediated effector function of monoclonal antibodies", Current Opinion in Biotechnology, vol. 20, 2009, pp. 685-691.
Tamm et al., "IgG Binding Sites on Human FCy Receptors", Internatopma; Reviews of Immunology, vol. 16, 1997, pp. 57-85.
Yu et al., "Interaction between Bevacizumab and Murine VEGF-A: A Reassessment", Investigative Ophthalmology & Visual Science, vol. 49(2), Feb. 2008, pp. 522-527.
U.S. Appl. No. 15/741,984, entitled "Drug-Conjugated Bs-Specific Antigen-Binding Constructs", submitted Jan. 4, 2018.
Bruhns, P., et al., Specificity and Affinity of Human Fc Receptors and their Polymorphic Variants for Human IgG sublasses., Blood, Apr. 16, 2009, 113 (16), pp. 3716-3725.
Office Action received in U.S. Appl. No. 15/046,379, dated Jun. 15, 2018.
Robert L. et al., "High Resolution Mapping of the Binding Site on Human IgG1 for FcyRI, FcyRII, FcyRIII and FcRn and Design of IgG1 Variants with Improved Binding to the FcyR", Journal of Biological Chem, 276(9): 6591-6604, 2000.

* cited by examiner

SEQ ID NO:1:

EPKSCDKTHTCPPCPAPELLGGPSVFLFPPKPKDTLMISRTPEVTCVVVDVSHEDPEVKF
NWYVDGVEVHNAKTKPREEQYNSTYRVVSVLTVLHQDWLNGKEYKCKVSNKALPAPIE
KTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK

SEQ ID NO:2:

>Trastuzumab_Heavy chain

EVQLVESGGGLVQPGGSLRLSCAASGFNIKDTYIHWVRQAPGKGLEWVARIYPTNGYT
RYADSVKGRFTISADTSKNTAYLQMNSLRAEDTAVYYCSRWGGDGFYAMDYWGQGTL
VTVSSASTKGPSVFPLAPSSKSTSGGTAALGCLVKDYFPEPVTVSWNSGALTSGVHTFP
AVLQSSGLYSLSSVVTVPSSSLGTQTYICNVNHKPSNTKVDKKVEPKSCDKTHTCPPCP
APELLGGPSVFLFPPKPKDTLMISRTPEVTCVVVDVSHEDPEVKFNWYVDGVEVHNAKT
KPREEQYNSTYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVLDSDGSFFLY
SKLTVDKSRWQQGNVFSCSVMHEALHNHYTQKSLSLSPGK

SEQ ID NO:3:

>Trastuzumab_Light chain

DIQMTQSPSSLSASVGDRVTITCRASQDVNTAVAWYQQKPGKAPKLLIYSASFLYSGVP
SRFSGSRSGTDFTLTISSLQPEDFATYYCQQHYTTPPTFGQGTKVEIKRTVAAPSVFIFPP
SDEQLKSGTASVVCLLNNFYPREAKVQWKVDNALQSGNSQESVTEQDSKDSTYSLSST
LTLSKADYEKHKVYACEVTHQGLSSPVTKSFNRGEC

SEQ ID NO:4:

>Rituximab+Heavy chain

QVQLQQPGAELVKPGASVKMSCKASGYTFTSYNMHWVKQTPGRGLEWIGAIYPGNGD
TSYNQKFKGKATLTADKSSSTAYMQLSSLTSEDSAVYYCARSTYYGGDWYFNVWGAGT
TVTVSAASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPPC
PAPELLGGPSVFLFPPKPKDTLMISRTPEVTCVVVDVSHEDPEVKFNWYVDGVEVHNAK
TKPREEQYNSTYRVVSVLTVLHQDWLNGKEYKCKVSNKALPAPIEKTISKAKGQPREPQ
VYTLPPSRDELTKNQVSLTCLVKGFYPSDIAVEWESNGQPENNYKTTPPVLDSDGSFFL
YSKLTVDKSRWQQGNVFSCSVMHEALHNHYTQKSLSLSPGK

SEQ ID NO:5:

>Rituximab+Light chain

QIVLSQSPAILSASPGEKVTMTCRASSSVSYIHWFQQKPGSSPKPWIYATSNLASGVPVR
FSGSGSGTSYSLTISRVEAEDAATYYCQQWTSNPPTFGGGTKLEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGEC

FIG. 5

| SEQ ID NO: | Type | |
|---|---|---|
| 6 | polypeptide | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYVYPPSRDELTKNQVSLTCLVKGFYPSDIAVEWESNGQPENNYKTTPPVLDEDGSFALVSKLTVDKSRWQQGNVFSCSVMHEALHNHYTQKSLSLSPGK |
| 8 | polypeptide | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYVLPPSRDELTKNQVSLLCLVKGFYPSDIAVEWESNGQPENRYMTWPPVLDSDGSFFLYSKLTVDKSRWQQGNVFSCSVMHEALHNHYTQKSLSLSPGK |
| 10 | polypeptide | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEDEGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYVYPPSRDELTKNQVSLTCLVKGFYPSDIAVEWESNGQPENNYKTTPPVLDEDGSFALVSKLTVDKSRWQQGNVFSCSVMHEALHNHYTQKSLSLSPGK |
| 12 | polypeptide | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPADEGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYVYPPSRDELTKNQVSLTCLVKGFYPSDIAVEWESNGQPENNYKTTPPVLDEDGSFALVSKLTVDKSRWQQGNVFSCSVMHEALHNHYTQKSLSLSPGK |

FIG. 8A

| 14 | polypeptide | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSRW GGDGFYAMDYWGQGTLVTVSSASTKGPSVFPLAPSSKSTSGGTAALGCL VKDYFPEPVTVSWNSGALTSGVHTFPAVLQSSGLYSLSSVVTVPSSSLGTQ TYICNVNHKPSNTKVDKKVEPKSCDKTHTCPPCPAPAKAGGPSVFLFPPK PKDTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQPRE PQVYVYPPSRDELTKNQVSLTCLVKGFYPSDIAVEWESNGQPENNYKTTP PVLDEDGSFALVSKLTVDKSRWQQGNVFSCSVMHEALHNHYTQKSLSLS PGK |
|---|---|---|
| 16 | polypeptide | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSRW GGDGFYAMDYWGQGTLVTVSSASTKGPSVFPLAPSSKSTSGGTAALGCL VKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKP KDTLMISRTPEVTCVVVDVSHQNPEVKFNWYVDGVEVHNAKTKPREEQ YNSTYRVVSVLTVLHQDWLNGKEYKCKVSNKALPAPIEKTISKAKGQPRE PQVYVYPPSRDELTKNQVSLTCLVKGFYPSDIAVEWESNGQPENNYKTTP PVLDEDGSFALVSKLTVDKSRWQQGNVFSCSVMHEALHNHYTQKSLSLS PGK |
| 18 | polypeptide | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSRW GGDGFYAMDYWGQGTLVTVSSASTKGPSVFPLAPSSKSTSGGTAALGCL VKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP QVYVYPPSRDELTKNQVSLTCLVKGFYPSDIAVEWESNGQPENNYKTTPP VLDEDGSFALVSKLTVDKSRWQQGNVFSCSVMHEALHNHYTQKSLSLSP GK |
| 20 | polypeptide | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSRW GGDGFYAMDYWGQGTLVTVSSASTKGPSVFPLAPSSKSTSGGTAALGCL VKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKP KDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP QVYVLPPSRDELTKNQVSLLCLVKGFYPSDIAVEWESNGQPENRYMTWP PVLDSDGSFFLYSKLTVDKSRWQQGNVFSCSVMHEALHNHYTQKSLSLS PGK |
| 22 | polypeptide | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSRW GGDGFYAMDYWGQGTLVTVSSASTKGPSVFPLAPSSKSTSGGTAALGCL VKDYFPEPVTVSWNSGALTSGVHTFPAVLQSSGLYSLSSVVTVPSSSLGTQ TYICNVNHKPSNTKVDKKVEPKSCDKTHTCPPCPAPEKKGGPSVFLFPPKP KDTLMISRTPEVTCVVVDVSHEDPEVKFNWYVDGVEVHNAKTKPREEQY NSTYRVVSVLTVLHQDWLNGKEYKCKVSNKALPAPIEKTISKAKGQPREP |

FIG. 8B

| | | |
|---|---|---|
| | | QVYVLPPSRDELTKNQVSLLCLVKGFYPSDIAVEWESNGQPENRYMTWP PVLDSDGSFFLYSKLTVDKSRWQQGNVFSCSVMHEALHNHYTQKSLSLS PGK |
| 24 | polypeptide | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSRW GGDGFYAMDYWGQGTLVTVSSASTKGPSVFPLAPSSKSTSGGTAALGCL VKDYFPEPVTVSWNSGALTSGVHTFPAVLQSSGLYSLSSVVTVPSSSLGTQ TYICNVNHKPSNTKVDKKVEPKSCDKTHTCPPCPAPARRGGPSVFLFPPK PKDTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQPRE PQVYVLPPSRDELTKNQVSLLCLVKGFYPSDIAVEWESNGQPENRYMTW PPVLDSDGSFFLYSKLTVDKSRWQQGNVFSCSVMHEALHNHYTQKSLSL SPGK |
| 26 | polypeptide | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSRW GGDGFYAMDYWGQGTLVTVSSASTKGPSVFPLAPSSKSTSGGTAALGCL VKDYFPEPVTVSWNSGALTSGVHTFPAVLQSSGLYSLSSVVTVPSSSLGTQ TYICNVNHKPSNTKVDKKVEPKSCDKTHTCPPCPAPKRRGGPSVFLFPPK PKDTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQPRE PQVYVLPPSRDELTKNQVSLLCLVKGFYPSDIAVEWESNGQPENRYMTW PPVLDSDGSFFLYSKLTVDKSRWQQGNVFSCSVMHEALHNHYTQKSLSL SPGK |
| 28 | polypeptide | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSRW GGDGFYAMDYWGQGTLVTVSSASTKGPSVFPLAPSSKSTSGGTAALGCL VKDYFPEPVTVSWNSGALTSGVHTFPAVLQSSGLYSLSSVVTVPSSSLGTQ TYICNVNHKPSNTKVDKKVEPKSCDKTHTCPPCPAPKAKGGPSVFLFPPK PKDTLMISRTPEVTCVVVDVSHEDPEVKFNWYVDGVEVHNAKTKPREEQ YNSTYRVVSVLTVLHQDWLNGKEYKCKVSNKALPAPIEKTISKAKGQPRE PQVYVLPPSRDELTKNQVSLLCLVKGFYPSDIAVEWESNGQPENRYMTW PPVLDSDGSFFLYSKLTVDKSRWQQGNVFSCSVMHEALHNHYTQKSLSL SPGK |
| 30 | polypeptide | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSRW GGDGFYAMDYWGQGTLVTVSSASTKGPSVFPLAPSSKSTSGGTAALGCL VKDYFPEPVTVSWNSGALTSGVHTFPAVLQSSGLYSLSSVVTVPSSSLGTQ TYICNVNHKPSNTKVDKKVEPKSCDKTHTCPPCPAPELLGGPSVFLFPPKP KDTLMISRTPEVTCVVVDVSHKRPEVKFNWYVDGVEVHNAKTKPREEQY NSTYRVVSVLTVLHQDWLNGKEYKCKVSNKALPAPIEKTISKAKGQPREP QVYVLPPSRDELTKNQVSLLCLVKGFYPSDIAVEWESNGQPENRYMTWP PVLDSDGSFFLYSKLTVDKSRWQQGNVFSCSVMHEALHNHYTQKSLSLS PGK |
| 32 | polypeptide | EVQLVESGGGLVQPGGSLRLSCAASGFNIKDTYIHWVRQAPGKGLEWVA RIYPTNGYTRYADSVKGRFTISADTSKNTAYLQMNSLRAEDTAVYYCSRW GGDGFYAMDYWGQGTLVTVSSASTKGPSVFPLAPSSKSTSGGTAALGCL VKDYFPEPVTVSWNSGALTSGVHTFPAVLQSSGLYSLSSVVTVPSSSLGTQ |

FIG. 8C

| | | |
|---|---|---|
| | | TYICNVNHKPSNTKVDKKVEPKSCDKTHTCPPCPAPELKGGPSVFLFPPKPKDTLMISRTPEVTCVVVDVSHEDPEVKFNWYVDGVEVHNAKTKPREEQYNSTYRVVSVLTVLHQDWLNGKEYKCKVSNKKLPAPIEKTISKAKGQPREPQVYVLPPSRDELTKNQVSLLCLVKGFYPSDIAVEWESNGQPENRYMTWPPVLDSDGSFFLYSKLTVDKSRWQQGNVFSCSVMHEALHNHYTQKSLSLSPGK |
| 35 | polypeptide | QVQLQQPGAELVKPGASVKMSCKASGYTFTSYNMHWVKQTPGRGLEWIGAIYPGNGDTSYNQKFKGKATLTADKSSSTAYMQLSSLTSEDSAVYYCARSTYYGGDWYFNVWGAGTTVTVSAASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYVYPPSRDELTKNQVSLTCLVKGFYPSDIAVEWESNGQPENNYKTTPPVLDSDGSFALVSKLTVDKSRWQQGNVFSCSVMHEALHNHYTQKSLSLSPGK |
| 37 | polypeptide | QVQLQQPGAELVKPGASVKMSCKASGYTFTSYNMHWVKQTPGRGLEWIGAIYPGNGDTSYNQKFKGKATLTADKSSSTAYMQLSSLTSEDSAVYYCARSTYYGGDWYFNVWGAGTTVTVSAASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYVLPPSRDELTKNQVSLLCLVKGFYPSDIAVEWESNGQPENNYLTWPPVLDSDGSFFLYSKLTVDKSRWQQGNVFSCSVMHEALHNHYTQKSLSLSPGK |
| 39 | polypeptide | QVQLQQPGAELVKPGASVKMSCKASGYTFTSYNMHWVKQTPGRGLEWIGAIYPGNGDTSYNQKFKGKATLTADKSSSTAYMQLSSLTSEDSAVYYCARSTYYGGDWYFNVWGAGTTVTVSAASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPEDEGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYVYPPSRDELTKNQVSLTCLVKGFYPSDIAVEWESNGQPENNYKTTPPVLDSDGSFALVSKLTVDKSRWQQGNVFSCSVMHEALHNHYTQKSLSLSPGK |
| 41 | polypeptide | QVQLQQPGAELVKPGASVKMSCKASGYTFTSYNMHWVKQTPGRGLEWIGAIYPGNGDTSYNQKFKGKATLTADKSSSTAYMQLSSLTSEDSAVYYCARSTYYGGDWYFNVWGAGTTVTVSAASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCDKTHTCPPCPAPKRRGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYVLPPSRDELTKNQVSLLCLVKGFYPSDIAVEWESNGQPENNYLTWPPVLDSDGSFFLYSKLTVDKSRWQQGNVFSCSVMHEALHNHYTQKSLSLSPGK |

FIG. 8D

| | | |
|---|---|---|
| 43 | polypeptide | QVQLQQPGAELVKPGASVKMSCKASGYTFTSYNMHWVKQTPGRGLE WIGAIYPGNGDTSYNQKFKGKATLTADKSSSTAYMQLSSLTSEDSAVYYC ARSTYYGGDWYFNVWGAGTTVTVSAASTKGPSVFPLAPSSKSTSGGTAA LGCLVKDYFPEPVTVSWNSGALTSGVHTFPAVLQSSGLYSLSSVVTVPSSS LGTQTYICNVNHKPSNTKVDKKVEPKSCDKTHTCPPCPAPEDEGGPSVFL FPPKPKDTLMISRTPEVTCVVVSVSHEDPEVKFNWYVDGVEVHNAKTKP REEQYNSTYRVVSVLTVLHQDWLNGKEYKCKVSNKALPAPIEKTISKAKG QPREPQVYVYPPSRDELTKNQVSLTCLVKGFYPSDIAVEWESNGQPENN YKTTPPVLDSDGSFALVSKLTVDKSRWQQGNVFSCSVMHEALHNHYTQ KSLSLSPGK |
| 45 | polypeptide | QVQLQQPGAELVKPGASVKMSCKASGYTFTSYNMHWVKQTPGRGLE WIGAIYPGNGDTSYNQKFKGKATLTADKSSSTAYMQLSSLTSEDSAVYYC ARSTYYGGDWYFNVWGAGTTVTVSAASTKGPSVFPLAPSSKSTSGGTAA LGCLVKDYFPEPVTVSWNSGALTSGVHTFPAVLQSSGLYSLSSVVTVPSSS LGTQTYICNVNHKPSNTKVDKKVEPKSCDKTHTCPPCPAPKRRGGPSVFL FPPKPKDTLMISRTPEVTCVVVSVSHEDPEVKFNWYVDGVEVHNAKTKP REEQYNSTYRVVSVLTVLHQDWLNGKEYKCKVSNKALPAPIEKTISKAKG QPREPQVYVLPPSRDELTKNQVSLLCLVKGFYPSDIAVEWESNGQPENNY LTWPPVLDSDGSFFLYSKLTVDKSRWQQGNVFSCSVMHEALHNHYTQK SLSLSPGK |
| 47 | polypeptide | QVQLQQPGAELVKPGASVKMSCKASGYTFTSYNMHWVKQTPGRGLE WIGAIYPGNGDTSYNQKFKGKATLTADKSSSTAYMQLSSLTSEDSAVYYC ARSTYYGGDWYFNVWGAGTTVTVSAASTKGPSVFPLAPSSKSTSGGTAA LGCLVKDYFPEPVTVSWNSGALTSGVHTFPAVLQSSGLYSLSSVVTVPSSS LGTQTYICNVNHKPSNTKVDKKVEPKSCDKTHTCPPCPAPEDEGGPSVFL FPPKPKDTLMISRTPEVTCVVVDVSHKDPEVKFNWYVDGVEVHNAKTKP REEQYNSTYRVVSVLTVLHQDWLNGKEYKCKVSNKALPAPIEKTISKAKG QPREPQVYVYPPSRDELTKNQVSLTCLVKGFYPSDIAVEWESNGQPENN YKTTPPVLDSDGSFALVSKLTVDKSRWQQGNVFSCSVMHEALHNHYTQ KSLSLSPGK |
| 49 | polypeptide | QVQLQQPGAELVKPGASVKMSCKASGYTFTSYNMHWVKQTPGRGLE WIGAIYPGNGDTSYNQKFKGKATLTADKSSSTAYMQLSSLTSEDSAVYYC ARSTYYGGDWYFNVWGAGTTVTVSAASTKGPSVFPLAPSSKSTSGGTAA LGCLVKDYFPEPVTVSWNSGALTSGVHTFPAVLQSSGLYSLSSVVTVPSSS LGTQTYICNVNHKPSNTKVDKKVEPKSCDKTHTCPPCPAPKRRGGPSVFL FPPKPKDTLMISRTPEVTCVVVDVSHKDPEVKFNWYVDGVEVHNAKTKP REEQYNSTYRVVSVLTVLHQDWLNGKEYKCKVSNKALPAPIEKTISKAKG QPREPQVYVLPPSRDELTKNQVSLLCLVKGFYPSDIAVEWESNGQPENNY LTWPPVLDSDGSFFLYSKLTVDKSRWQQGNVFSCSVMHEALHNHYTQK SLSLSPGK |
| 51 | polypeptide | QVQLQQPGAELVKPGASVKMSCKASGYTFTSYNMHWVKQTPGRGLE WIGAIYPGNGDTSYNQKFKGKATLTADKSSSTAYMQLSSLTSEDSAVYYC ARSTYYGGDWYFNVWGAGTTVTVSAASTKGPSVFPLAPSSKSTSGGTAA LGCLVKDYFPEPVTVSWNSGALTSGVHTFPAVLQSSGLYSLSSVVTVPSSS LGTQTYICNVNHKPSNTKVDKKVEPKSCDKTHTCPPCPAPEDEGGPSVFL FPPKPKDTLMISRTPEVTCVVVDVSHEDPEVKFNWYVDGVEVHNAKTKP REEQYNSTYRVVSVLTVLHQDWLNGKEYKCAVSNKALPAPIEKTISKAKG |

FIG. 8E

| | | |
|---|---|---|
| | | QPREPQVYVYPPSRDELTKNQVSLTCLVKGFYPSDIAVEWESNGQPENN YKTTPPVLDSDGSFALVSKLTVDKSRWQQGNVFSCSVMHEALHNHYTQ KSLSLSPGK |
| 53 | polypeptide | QVQLQQPGAELVKPGASVKMSCKASGYTFTSYNMHWVKQTPGRGLE WIGAIYPGNGDTSYNQKFKGKATLTADKSSSTAYMQLSSLTSEDSAVYYC ARSTYYGGDWYFNVWGAGTTVTVSAASTKGPSVFPLAPSSKSTSGGTAA LGCLVKDYFPEPVTVSWNSGALTSGVHTFPAVLQSSGLYSLSSVVTVPSSS LGTQTYICNVNHKPSNTKVDKKVEPKSCDKTHTCPPCPAPKRRGGPSVFL FPPKPKDTLMISRTPEVTCVVVDVSHEDPEVKFNWYVDGVEVHNAKTKP REEQYNSTYRVVSVLTVLHQDWLNGKEYKCAVSNKALPAPIEKTISKAKG QPREPQVYVLPPSRDELTKNQVSLLCLVKGFYPSDIAVEWESNGQPENNY LTWPPVLDSDGSFFLYSKLTVDKSRWQQGNVFSCSVMHEALHNHYTQK SLSLSPGK |
| 55 | polypeptide | QVQLQQPGAELVKPGASVKMSCKASGYTFTSYNMHWVKQTPGRGLE WIGAIYPGNGDTSYNQKFKGKATLTADKSSSTAYMQLSSLTSEDSAVYYC ARSTYYGGDWYFNVWGAGTTVTVSAASTKGPSVFPLAPSSKSTSGGTAA LGCLVKDYFPEPVTVSWNSGALTSGVHTFPAVLQSSGLYSLSSVVTVPSSS LGTQTYICNVNHKPSNTKVDKKVEPKSCDKTHTCPPCPAPEDEGGPSVFL FPPKPKDTLMISRTPEVTCVVVDVSHEDPEVKFNWYVDGVEVHNAKTKP REEQYNSTYRVVSVLTVLHQDWLNGKEYKCKVSNKALWAPIEKTISKAKG QPREPQVYVYPPSRDELTKNQVSLTCLVKGFYPSDIAVEWESNGQPENN YKTTPPVLDSDGSFALVSKLTVDKSRWQQGNVFSCSVMHEALHNHYTQ KSLSLSPGK |
| 57 | polypeptide | QVQLQQPGAELVKPGASVKMSCKASGYTFTSYNMHWVKQTPGRGLE WIGAIYPGNGDTSYNQKFKGKATLTADKSSSTAYMQLSSLTSEDSAVYYC ARSTYYGGDWYFNVWGAGTTVTVSAASTKGPSVFPLAPSSKSTSGGTAA LGCLVKDYFPEPVTVSWNSGALTSGVHTFPAVLQSSGLYSLSSVVTVPSSS LGTQTYICNVNHKPSNTKVDKKVEPKSCDKTHTCPPCPAPKRRGGPSVFL FPPKPKDTLMISRTPEVTCVVVDVSHEDPEVKFNWYVDGVEVHNAKTKP REEQYNSTYRVVSVLTVLHQDWLNGKEYKCKVSNKALWAPIEKTISKAKG QPREPQVYVLPPSRDELTKNQVSLLCLVKGFYPSDIAVEWESNGQPENNY LTWPPVLDSDGSFFLYSKLTVDKSRWQQGNVFSCSVMHEALHNHYTQK SLSLSPGK |
| 59 | polypeptide | QVQLQQPGAELVKPGASVKMSCKASGYTFTSYNMHWVKQTPGRGLE WIGAIYPGNGDTSYNQKFKGKATLTADKSSSTAYMQLSSLTSEDSAVYYC ARSTYYGGDWYFNVWGAGTTVTVSAASTKGPSVFPLAPSSKSTSGGTAA LGCLVKDYFPEPVTVSWNSGALTSGVHTFPAVLQSSGLYSLSSVVTVPSSS LGTQTYICNVNHKPSNTKVDKKVEPKSCDKTHTCPPCPAPEDEGGPSVFL FPPKPKDTLMISRTPEVTCVVVSVSHKDPEVKFNWYVDGVEVHNAKTKP REEQYNSTYRVVSVLTVLHQDWLNGKEYKCAVSNKALPAPIEKTISKAKG QPREPQVYVYPPSRDELTKNQVSLTCLVKGFYPSDIAVEWESNGQPENN YKTTPPVLDSDGSFALVSKLTVDKSRWQQGNVFSCSVMHEALHNHYTQ KSLSLSPGK |
| 61 | polypeptide | QVQLQQPGAELVKPGASVKMSCKASGYTFTSYNMHWVKQTPGRGLE WIGAIYPGNGDTSYNQKFKGKATLTADKSSSTAYMQLSSLTSEDSAVYYC ARSTYYGGDWYFNVWGAGTTVTVSAASTKGPSVFPLAPSSKSTSGGTAA LGCLVKDYFPEPVTVSWNSGALTSGVHTFPAVLQSSGLYSLSSVVTVPSSS |

FIG. 8F

| | | |
|---|---|---|
| | | LGTQTYICNVNHKPSNTKVDKKVEPKSCDKTHTCPPCPAPKRRGGPSVFL FPPKPKDTLMISRTPEVTCVVVSVSHKDPEVKFNWYVDGVEVHNAKTKP REEQYNSTYRVVSVLTVLHQDWLNGKEYKCAVSNKALPAPIEKTISKAKG QPREPQVYVLPPSRDELTKNQVSLLCLVKGFYPSDIAVEWESNGQPENNY LTWPPVLDSDGSFFLYSKLTVDKSRWQQGNVFSCSVMHEALHNHYTQK SLSLSPGK |
| 63 | polypeptide | QVQLQQPGAELVKPGASVKMSCKASGYTFTSYNMHWVKQTPGRGLE WIGAIYPGNGDTSYNQKFKGKATLTADKSSSTAYMQLSSLTSEDSAVYYC ARSTYYGGDWYFNVWGAGTTVTVSAASTKGPSVFPLAPSSKSTSGGTAA LGCLVKDYFPEPVTVSWNSGALTSGVHTFPAVLQSSGLYSLSSVVTVPSSS LGTQTYICNVNHKPSNTKVDKKVEPKSCDKTHTCPPCPAPEDEGGPSVFL FPPKPKDTLMISRTPEVTCVVVSVSHKDPEVKFNWYVDGVEVHNAKTKP REEQYNSTYRVVSVLTVLHQDWLNGKEYKCEVSNKALPAPIKKTISKAKG QPREPQVYVYPPSRDELTKNQVSLTCLVKGFYPSDIAVEWESNGQPENN YKTTPPVLDSDGSFALVSKLTVDKSRWQQGNVFSCSVMHEALHNHYTQ KSLSLSPGK |
| 65 | polypeptide | QVQLQQPGAELVKPGASVKMSCKASGYTFTSYNMHWVKQTPGRGLE WIGAIYPGNGDTSYNQKFKGKATLTADKSSSTAYMQLSSLTSEDSAVYYC ARSTYYGGDWYFNVWGAGTTVTVSAASTKGPSVFPLAPSSKSTSGGTAA LGCLVKDYFPEPVTVSWNSGALTSGVHTFPAVLQSSGLYSLSSVVTVPSSS LGTQTYICNVNHKPSNTKVDKKVEPKSCDKTHTCPPCPAPKRRGGPSVFL FPPKPKDTLMISRTPEVTCVVVSVSHKDPEVKFNWYVDGVEVHNAKTKP REEQYNSTYRVVSVLTVLHQDWLNGKEYKCEVSNKALPAPIKKTISKAKG QPREPQVYVLPPSRDELTKNQVSLLCLVKGFYPSDIAVEWESNGQPENNY LTWPPVLDSDGSFFLYSKLTVDKSRWQQGNVFSCSVMHEALHNHYTQK SLSLSPGK |
| 67 | polypeptide | DIQMTQSPSSLSASVGDRVTITCRASQDVNTAVAWYQQKPGKAPKLLIYS ASFLYSGVPSRFSGSRSGTDFTLTISSLQPEDFATYYCQQHYTTPPTFGQGT KVEIKRTVAAPSVFIFPPSDEQLKSGTASVVCLLNNFYPREAKVQWKVDN ALQSGNSQESVTEQDSKDSTYSLSSTLTLSKADYEKHKVYACEVTHQGLSS PVTKSFNRGEC |
| 68 | polypeptide | QIVLSQSPAILSASPGEKVTMTCRASSSVSYIHWFQQKPGSSPKPWIYATS NLASGVPVRFSGSGSGTSYSLTISRVEAEDAATYYCQQWTSNPPTFGGGT KLEIKRTVAAPSVFIFPPSDEQLKSGTASVVCLLNNFYPREAKVQWKVDNA LQSGNSQESVTEQDSKDSTYSLSSTLTLSKADYEKHKVYACEVTHQGLSSP VTKSFNRGEC |
| | | |
| 7 | DNA | GAGGTGCAGCTGGTGGAAAGCGGAGGAGGACTGGTGCAGCCAGGA GGATCTCTGCGACTGAGTTGCGCCGCTTCAGGATTCAACATCAAGGAC ACCTACATTCACTGGGTGCGACAGGCTCCAGGAAAAGGACTGGAGTG GGTGGCTCGAATCTATCCCACTAATGGATACACCCGGTATGCCGACTC CGTGAAGGGGAGGTTTACTATTAGCGCCGATACATCCAAAAACACTG CTTACCTGCAGATGAACAGCCTGCGAGCCGAAGATACCGCTGTGTACT ATTGCAGTCGATGGGGAGGAGACGGATTCTACGCTATGGATTATTGG GGACAGGGGACCCTGGTGACAGTGAGCTCCGCCTCTACCAAGGGCCC CAGTGTGTTTCCCCTGGCTCCTTCTAGTAAATCCACCTCTGGAGGGAC AGCCGCTCTGGGATGTCTGGTGAAGGACTATTTCCCCGAGCCTGTGAC |

FIG. 8G

| | | |
|---|---|---|
| | | CGTGAGTTGGAACTCAGGCGCCCTGACAAGCGGAGTGCACACTTTTC<br>CTGCTGTGCTGCAGTCAAGCGGGCTGTACTCCCTGTCCTCTGTGGTGA<br>CAGTGCCAAGTTCAAGCCTGGGCACACAGACTTATATCTGCAACGTGA<br>ATCATAAGCCCTCAAATACAAAAGTGGACAAGAAAGTGGAGCCCAAG<br>AGCTGTGATAAGACCCACACCTGCCCTCCCTGTCCAGCTCCAGAAGCC<br>GCCGGAGGACCTAGCGTGTTCCTGTTTCCCCCTAAGCCAAAAGACACT<br>CTGATGATTTCCAGGACTCCCGAGGTGACCTGCGTGGTGGTGGACGT<br>GTCTCACGAGGACCCCGAAGTGAAGTTCAACTGGTACGTGGATGGCG<br>TGGAAGTGCATAATGCTAAGACAAAACCAAGAGAGGAACAGTACAAC<br>TCCACTTATCGCGTCGTGAGCGTGCTGACCGTGCTGCACCAGGACTGG<br>CTGAACGGGAAGGAGTATAAGTGCAAAGTCAGTAATAAGGCCCTGCC<br>TGCTCCAATCGAAAAAACCATCTCTAAGGCCAAAGGCCAGCCAAGGG<br>AGCCCCAGGTGTACGTGTACCCACCCAGCAGAGACGAACTGACCAAG<br>AACCAGGTGTCCCTGACATGTCTGGTGAAAGGCTTCTATCCTAGTGAT<br>ATTGCTGTGGAGTGGGAATCAAATGGACAGCCAGAGAACAATTACAA<br>GACCACACCTCCAGTGCTGGACGAGGATGGCAGCTTCGCCCTGGTGT<br>CCAAGCTGACAGTGGATAAATCTCGATGGCAGCAGGGGAACGTGTTT<br>AGTTGTTCAGTGATGCATGAAGCCCTGCACAATCATTACACTCAGAAG<br>AGCCTGTCCCTGTCTCCCGGCAAA |
| 9 | DNA | GAGGTGCAGCTGGTGGAAAGCGGAGGAGGACTGGTGCAGCCAGGA<br>GGATCTCTGCGACTGAGTTGCGCCGCTTCAGGATTCAACATCAAGGAC<br>ACCTACATTCACTGGGTGCGACAGGCTCCAGGAAAAGGACTGGAGTG<br>GGTGGCTCGAATCTATCCCACTAATGGATACACCCGGTATGCCGACTC<br>CGTGAAGGGGAGGTTTACTATTAGCGCCGATACATCCAAAAACACTG<br>CTTACCTGCAGATGAACAGCCTGCGAGCCGAAGATACCGCTGTGTACT<br>ATTGCAGTCGATGGGGAGGAGACGGATTCTACGCTATGGATTATTGG<br>GGACAGGGGACCCTGGTGACAGTGAGCTCCGCCTCTACCAAGGGCCC<br>CAGTGTGTTTCCCCTGGCTCCTTCTAGTAAATCCACCTCTGGAGGGAC<br>AGCCGCTCTGGGATGTCTGGTGAAGGACTATTTCCCCGAGCCTGTGAC<br>CGTGAGTTGGAACTCAGGCGCCCTGACAAGCGGAGTGCACACTTTTC<br>CTGCTGTGCTGCAGTCAAGCGGGCTGTACTCCCTGTCCTCTGTGGTGA<br>CAGTGCCAAGTTCAAGCCTGGGCACACAGACTTATATCTGCAACGTGA<br>ATCATAAGCCCTCAAATACAAAAGTGGACAAGAAAGTGGAGCCCAAG<br>AGCTGTGATAAGACCCACACCTGCCCTCCCTGTCCAGCTCCAGAAGCC<br>GCCGGAGGACCTAGCGTGTTCCTGTTTCCCCCTAAGCCAAAAGACACT<br>CTGATGATTTCCAGGACTCCCGAGGTGACCTGCGTGGTGGTGGACGT<br>GTCTCACGAGGACCCCGAAGTGAAGTTCAACTGGTACGTGGATGGCG<br>TGGAAGTGCATAATGCTAAGACAAAACCAAGAGAGGAACAGTACAAC<br>TCCACTTATCGCGTCGTGAGCGTGCTGACCGTGCTGCACCAGGACTGG<br>CTGAACGGGAAGGAGTATAAGTGCAAAGTCAGTAATAAGGCCCTGCC<br>TGCTCCAATCGAAAAAACCATCTCTAAGGCCAAAGGCCAGCCAAGGG<br>AGCCCCAGGTGTACGTGCTGCCACCCAGCAGAGACGAACTGACCAAG<br>AACCAGGTGTCCCTGCTGTGTCTGGTGAAAGGCTTCTATCCTAGTGAT<br>ATTGCTGTGGAGTGGGAATCAAATGGACAGCCAGAGAACAGATACAT<br>GACCTGGCCTCCAGTGCTGGACAGCGATGGCAGCTTCTTCCTGTATTC<br>CAAGCTGACAGTGGATAAATCTCGATGGCAGCAGGGGAACGTGTTTA<br>GTTGTTCAGTGATGCATGAAGCCCTGCACAATCATTACACTCAGAAGA |

FIG. 8H

| | | |
|---|---|---|
| | | GCCTGTCCCTGTCTCCCGGCAAA |
| 11 | DNA | GAGGTGCAGCTGGTGGAAAGCGGAGGAGGACTGGTGCAGCCAGGA GGATCTCTGCGACTGAGTTGCGCCGCTTCAGGATTCAACATCAAGGAC ACCTACATTCACTGGGTGCGACAGGCTCCAGGAAAAGGACTGGAGTG GGTGGCTCGAATCTATCCCACTAATGGATACACCCGGTATGCCGACTC CGTGAAGGGGAGGTTTACTATTAGCGCCGATACATCCAAAAACACTG CTTACCTGCAGATGAACAGCCTGCGAGCCGAAGATACCGCTGTGTACT ATTGCAGTCGATGGGGAGGAGACGGATTCTACGCTATGGATTATTGG GGACAGGGGACCCTGGTGACAGTGAGCTCCGCCTCTACCAAGGGCCC CAGTGTGTTTCCCCTGGCTCCTTCTAGTAAATCCACCTCTGGAGGGAC AGCCGCTCTGGGATGTCTGGTGAAGGACTATTTCCCCGAGCCTGTGAC CGTGAGTTGGAACTCAGGCGCCCTGACAAGCGGAGTGCACACTTTTC CTGCTGTGCTGCAGTCAAGCGGGCTGTACTCCCTGTCCTCTGTGGTGA CAGTGCCAAGTTCAAGCCTGGGCACACAGACTTATATCTGCAACGTGA ATCATAAGCCCTCAAATACAAAAGTGGACAAGAAAGTGGAGCCCAAG AGCTGTGATAAGACCCACACCTGCCCTCCCTGTCCAGCTCCAGAAGAC GAGGGAGGACCTAGCGTGTTCCTGTTTCCCCCTAAGCCAAAAGACACT CTGATGATTTCCAGGACTCCCGAGGTGACCTGCGTGGTGGTGGACGT GTCTCACGAGGACCCCGAAGTGAAGTTCAACTGGTACGTGGATGGCG TGGAAGTGCATAATGCTAAGACAAAACCAAGAGAGGAACAGTACAAC TCCACTTATCGCGTCGTGAGCGTGCTGACCGTGCTGCACCAGGACTGG CTGAACGGGAAGGAGTATAAGTGCAAAGTCAGTAATAAGGCCCTGCC TGCTCCAATCGAAAAAACCATCTCTAAGGCCAAAGGCCAGCCAAGGG AGCCCCAGGTGTACGTGTACCCACCCAGCAGAGACGAACTGACCAAG AACCAGGTGTCCCTGACATGTCTGGTGAAAGGCTTCTATCCTAGTGAT ATTGCTGTGGAGTGGGAATCAAATGGACAGCCAGAGAACAATTACAA GACCACACCTCCAGTGCTGGACGAGGATGGCAGCTTCGCCCTGGTGT CCAAGCTGACAGTGGATAAATCTCGATGGCAGCAGGGGAACGTGTTT AGTTGTTCAGTGATGCATGAAGCCCTGCACAATCATTACACTCAGAAG AGCCTGTCCCTGTCTCCCGGCAAA |
| 13 | DNA | GAGGTGCAGCTGGTGGAAAGCGGAGGAGGACTGGTGCAGCCAGGA GGATCTCTGCGACTGAGTTGCGCCGCTTCAGGATTCAACATCAAGGAC ACCTACATTCACTGGGTGCGACAGGCTCCAGGAAAAGGACTGGAGTG GGTGGCTCGAATCTATCCCACTAATGGATACACCCGGTATGCCGACTC CGTGAAGGGGAGGTTTACTATTAGCGCCGATACATCCAAAAACACTG CTTACCTGCAGATGAACAGCCTGCGAGCCGAAGATACCGCTGTGTACT ATTGCAGTCGATGGGGAGGAGACGGATTCTACGCTATGGATTATTGG GGACAGGGGACCCTGGTGACAGTGAGCTCCGCCTCTACCAAGGGCCC CAGTGTGTTTCCCCTGGCTCCTTCTAGTAAATCCACCTCTGGAGGGAC AGCCGCTCTGGGATGTCTGGTGAAGGACTATTTCCCCGAGCCTGTGAC CGTGAGTTGGAACTCAGGCGCCCTGACAAGCGGAGTGCACACTTTTC |

FIG. 8I

| | | |
|---|---|---|
| | | CTGCTGTGCTGCAGTCAAGCGGGCTGTACTCCCTGTCCTCTGTGGTGA CAGTGCCAAGTTCAAGCCTGGGCACACAGACTTATATCTGCAACGTGA ATCATAAGCCCTCAAATACAAAAGTGGACAAGAAAGTGGAGCCCAAG AGCTGTGATAAGACCCACACCTGCCCTCCCTGTCCAGCTCCAGCCGAC GAGGGAGGACCTAGCGTGTTCCTGTTTCCCCCTAAGCCAAAAGACACT CTGATGATTTCCAGGACTCCCGAGGTGACCTGCGTGGTGGTGGACGT GTCTCACGAGGACCCCGAAGTGAAGTTCAACTGGTACGTGGATGGCG TGGAAGTGCATAATGCTAAGACAAAACCAAGAGAGGAACAGTACAAC TCCACTTATCGCGTCGTGAGCGTGCTGACCGTGCTGCACCAGGACTGG CTGAACGGGAAGGAGTATAAGTGCAAAGTCAGTAATAAGGCCCTGCC TGCTCCAATCGAAAAAACCATCTCTAAGGCCAAAGGCCAGCCAAGGG AGCCCCAGGTGTACGTGTACCCACCCAGCAGAGACGAACTGACCAAG AACCAGGTGTCCCTGACATGTCTGGTGAAAGGCTTCTATCCTAGTGAT ATTGCTGTGGAGTGGGAATCAAATGGACAGCCAGAGAACAATTACAA GACCACACCTCCAGTGCTGGACGAGGATGGCAGCTTCGCCCTGGTGT CCAAGCTGACAGTGGATAAATCTCGATGGCAGCAGGGGAACGTGTTT AGTTGTTCAGTGATGCATGAAGCCCTGCACAATCATTACACTCAGAAG AGCCTGTCCCTGTCTCCCGGCAAA |
| 15 | DNA | GAGGTGCAGCTGGTGGAAAGCGGAGGAGGACTGGTGCAGCCAGGA GGATCTCTGCGACTGAGTTGCGCCGCTTCAGGATTCAACATCAAGGAC ACCTACATTCACTGGGTGCGACAGGCTCCAGGAAAAGGACTGGAGTG GGTGGCTCGAATCTATCCCACTAATGGATACACCCGGTATGCCGACTC CGTGAAGGGGAGGTTTACTATTAGCGCCGATACATCCAAAAACACTG CTTACCTGCAGATGAACAGCCTGCGAGCCGAAGATACCGCTGTGTACT ATTGCAGTCGATGGGGAGGAGACGGATTCTACGCTATGGATTATTGG GGACAGGGGACCCTGGTGACAGTGAGCTCCGCCTCTACCAAGGGCCC CAGTGTGTTTCCCCTGGCTCCTTCTAGTAAATCCACCTCTGGAGGGAC AGCCGCTCTGGGATGTCTGGTGAAGGACTATTTCCCCGAGCCTGTGAC CGTGAGTTGGAACTCAGGCGCCCTGACAAGCGGAGTGCACACTTTTC CTGCTGTGCTGCAGTCAAGCGGGCTGTACTCCCTGTCCTCTGTGGTGA CAGTGCCAAGTTCAAGCCTGGGCACACAGACTTATATCTGCAACGTGA ATCATAAGCCCTCAAATACAAAAGTGGACAAGAAAGTGGAGCCCAAG AGCTGTGATAAGACCCACACCTGCCCTCCCTGTCCAGCTCCAGCCAAG GCCGGAGGACCTAGCGTGTTCCTGTTTCCCCCTAAGCCAAAAGACACT CTGATGATTTCCAGGACTCCCGAGGTGACCTGCGTGGTGGTGGACGT GTCTCACGAGGACCCCGAAGTGAAGTTCAACTGGTACGTGGATGGCG TGGAAGTGCATAATGCTAAGACAAAACCAAGAGAGGAACAGTACAAC TCCACTTATCGCGTCGTGAGCGTGCTGACCGTGCTGCACCAGGACTGG CTGAACGGGAAGGAGTATAAGTGCAAAGTCAGTAATAAGGCCCTGCC TGCTCCAATCGAAAAAACCATCTCTAAGGCCAAAGGCCAGCCAAGGG AGCCCCAGGTGTACGTGTACCCACCCAGCAGAGACGAACTGACCAAG AACCAGGTGTCCCTGACATGTCTGGTGAAAGGCTTCTATCCTAGTGAT ATTGCTGTGGAGTGGGAATCAAATGGACAGCCAGAGAACAATTACAA GACCACACCTCCAGTGCTGGACGAGGATGGCAGCTTCGCCCTGGTGT CCAAGCTGACAGTGGATAAATCTCGATGGCAGCAGGGGAACGTGTTT AGTTGTTCAGTGATGCATGAAGCCCTGCACAATCATTACACTCAGAAG AGCCTGTCCCTGTCTCCCGGCAAA |

FIG. 8J

| | | |
|---|---|---|
| 17 | DNA | GAGGTGCAGCTGGTGGAAAGCGGAGGAGGACTGGTGCAGCCAGGA GGATCTCTGCGACTGAGTTGCGCCGCTTCAGGATTCAACATCAAGGAC ACCTACATTCACTGGGTGCGACAGGCTCCAGGAAAAGGACTGGAGTG GGTGGCTCGAATCTATCCCACTAATGGATACACCCGGTATGCCGACTC CGTGAAGGGGAGGTTTACTATTAGCGCCGATACATCCAAAAACACTG CTTACCTGCAGATGAACAGCCTGCGAGCCGAAGATACCGCTGTGTACT ATTGCAGTCGATGGGGAGGAGACGGATTCTACGCTATGGATTATTGG GGACAGGGGACCCTGGTGACAGTGAGCTCCGCCTCTACCAAGGGCCC CAGTGTGTTTCCCCTGGCTCCTTCTAGTAAATCCACCTCTGGAGGGAC AGCCGCTCTGGGATGTCTGGTGAAGGACTATTTCCCCGAGCCTGTGAC CGTGAGTTGGAACTCAGGCGCCCTGACAAGCGGAGTGCACACTTTTC CTGCTGTGCTGCAGTCAAGCGGGCTGTACTCCCTGTCCTCTGTGGTGA CAGTGCCAAGTTCAAGCCTGGGCACACAGACTTATATCTGCAACGTGA ATCATAAGCCCTCAAATACAAAAGTGGACAAGAAAGTGGAGCCCAAG AGCTGTGATAAGACCCACACCTGCCCTCCCTGTCCAGCTCCAGAACTG CTGGGAGGACCTAGCGTGTTCCTGTTTCCCCCTAAGCCAAAAGACACT CTGATGATTTCCAGGACTCCCGAGGTGACCTGCGTGGTGGTGGACGT GTCTCACCAGAACCCCGAAGTGAAGTTCAACTGGTACGTGGATGGCG TGGAAGTGCATAATGCTAAGACAAAACCAAGAGAGGAACAGTACAAC TCCACTTATCGCGTCGTGAGCGTGCTGACCGTGCTGCACCAGGACTGG CTGAACGGGAAGGAGTATAAGTGCAAAGTCAGTAATAAGGCCCTGCC TGCTCCAATCGAAAAAACCATCTCTAAGGCCAAAGGCCAGCCAAGGG AGCCCCAGGTGTACGTGTACCCACCCAGCAGAGACGAACTGACCAAG AACCAGGTGTCCCTGACATGTCTGGTGAAAGGCTTCTATCCTAGTGAT ATTGCTGTGGAGTGGGAATCAAATGGACAGCCAGAGAACAATTACAA GACCACACCTCCAGTGCTGGACGAGGATGGCAGCTTCGCCCTGGTGT CCAAGCTGACAGTGGATAAATCTCGATGGCAGCAGGGGAACGTGTTT AGTTGTTCAGTGATGCATGAAGCCCTGCACAATCATTACACTCAGAAG AGCCTGTCCCTGTCTCCCGGCAAA |
| 19 | DNA | GAGGTGCAGCTGGTGGAAAGCGGAGGAGGACTGGTGCAGCCAGGA GGATCTCTGCGACTGAGTTGCGCCGCTTCAGGATTCAACATCAAGGAC ACCTACATTCACTGGGTGCGACAGGCTCCAGGAAAAGGACTGGAGTG GGTGGCTCGAATCTATCCCACTAATGGATACACCCGGTATGCCGACTC CGTGAAGGGGAGGTTTACTATTAGCGCCGATACATCCAAAAACACTG CTTACCTGCAGATGAACAGCCTGCGAGCCGAAGATACCGCTGTGTACT ATTGCAGTCGATGGGGAGGAGACGGATTCTACGCTATGGATTATTGG GGACAGGGGACCCTGGTGACAGTGAGCTCCGCCTCTACCAAGGGCCC CAGTGTGTTTCCCCTGGCTCCTTCTAGTAAATCCACCTCTGGAGGGAC AGCCGCTCTGGGATGTCTGGTGAAGGACTATTTCCCCGAGCCTGTGAC CGTGAGTTGGAACTCAGGCGCCCTGACAAGCGGAGTGCACACTTTTC CTGCTGTGCTGCAGTCAAGCGGGCTGTACTCCCTGTCCTCTGTGGTGA CAGTGCCAAGTTCAAGCCTGGGCACACAGACTTATATCTGCAACGTGA ATCATAAGCCCTCAAATACAAAAGTGGACAAGAAAGTGGAGCCCAAG AGCTGTGATAAGACCCACACCTGCCCTCCCTGTCCAGCTCCAGAACTG CTGGGAGGACCTAGCGTGTTCCTGTTTCCCCCTAAGCCAAAAGACACT CTGATGATTTCCAGGACTCCCGAGGTGACCTGCGTGGTGGTGGACGT GTCTCACGAGGACCCCGAAGTGAAGTTCAACTGGTACGTGGATGGCG |

FIG. 8K

| | | |
|---|---|---|
| | | TGGAAGTGCATAATGCTAAGACAAAACCAAGAGAGGAACAGTACAAC TCCACTTATCGCGTCGTGAGCGTGCTGACCGTGCTGCACCAGGACTGG CTGAACGGGAAGGAGTATAAGTGCAAAGTCAGTAATAAGGCCCTGCC TGCTCCAATCGAAAAAACCATCTCTAAGGCCAAAGGCCAGCCAAGGG AGCCCCAGGTGTACGTGTACCCACCCAGCAGAGACGAACTGACCAAG AACCAGGTGTCCCTGACATGTCTGGTGAAAGGCTTCTATCCTAGTGAT ATTGCTGTGGAGTGGGAATCAAATGGACAGCCAGAGAACAATTACAA GACCACACCTCCAGTGCTGGACGAGGATGGCAGCTTCGCCCTGGTGT CCAAGCTGACAGTGGATAAATCTCGATGGCAGCAGGGGAACGTGTTT AGTTGTTCAGTGATGCATGAAGCCCTGCACAATCATTACACTCAGAAG AGCCTGTCCCTGTCTCCCGGCAAA |
| 21 | DNA | GAGGTGCAGCTGGTGGAAAGCGGAGGAGGACTGGTGCAGCCAGGA GGATCTCTGCGACTGAGTTGCGCCGCTTCAGGATTCAACATCAAGGAC ACCTACATTCACTGGGTGCGACAGGCTCCAGGAAAAGGACTGGAGTG GGTGGCTCGAATCTATCCCACTAATGGATACACCCGGTATGCCGACTC CGTGAAGGGGAGGTTTACTATTAGCGCCGATACATCCAAAAACACTG CTTACCTGCAGATGAACAGCCTGCGAGCCGAAGATACCGCTGTGTACT ATTGCAGTCGATGGGGAGGAGACGGATTCTACGCTATGGATTATTGG GGACAGGGGACCCTGGTGACAGTGAGCTCCGCCTCTACCAAGGGCCC CAGTGTGTTTCCCCTGGCTCCTTCTAGTAAATCCACCTCTGGAGGGAC AGCCGCTCTGGGATGTCTGGTGAAGGACTATTTCCCCGAGCCTGTGAC CGTGAGTTGGAACTCAGGCGCCCTGACAAGCGGAGTGCACACTTTTC CTGCTGTGCTGCAGTCAAGCGGGCTGTACTCCCTGTCCTCTGTGGTGA CAGTGCCAAGTTCAAGCCTGGGCACACAGACTTATATCTGCAACGTGA ATCATAAGCCCTCAAATACAAAAGTGGACAAGAAAGTGGAGCCCAAG AGCTGTGATAAGACCCACACCTGCCCTCCCTGTCCAGCTCCAGAACTG CTGGGAGGACCTAGCGTGTTCCTGTTTCCCCCTAAGCCAAAAGACACT CTGATGATTTCCAGGACTCCCGAGGTGACCTGCGTGGTGGTGGACGT GTCTCACGAGGACCCCGAAGTGAAGTTCAACTGGTACGTGGATGGCG TGGAAGTGCATAATGCTAAGACAAAACCAAGAGAGGAACAGTACAAC TCCACTTATCGCGTCGTGAGCGTGCTGACCGTGCTGCACCAGGACTGG CTGAACGGGAAGGAGTATAAGTGCAAAGTCAGTAATAAGGCCCTGCC TGCTCCAATCGAAAAAACCATCTCTAAGGCCAAAGGCCAGCCAAGGG AGCCCCAGGTGTACGTGCTGCCACCCAGCAGAGACGAACTGACCAAG AACCAGGTGTCCCTGCTGTGTCTGGTGAAAGGCTTCTATCCTAGTGAT ATTGCTGTGGAGTGGGAATCAAATGGACAGCCAGAGAACAGATACAT GACCTGGCCTCCAGTGCTGGACAGCGATGGCAGCTTCTTCCTGTATTC CAAGCTGACAGTGGATAAATCTCGATGGCAGCAGGGGAACGTGTTTA GTTGTTCAGTGATGCATGAAGCCCTGCACAATCATTACACTCAGAAGA GCCTGTCCCTGTCTCCCGGCAAA |
| 23 | DNA | GAGGTGCAGCTGGTGGAAAGCGGAGGAGGACTGGTGCAGCCAGGA GGATCTCTGCGACTGAGTTGCGCCGCTTCAGGATTCAACATCAAGGAC ACCTACATTCACTGGGTGCGACAGGCTCCAGGAAAAGGACTGGAGTG GGTGGCTCGAATCTATCCCACTAATGGATACACCCGGTATGCCGACTC CGTGAAGGGGAGGTTTACTATTAGCGCCGATACATCCAAAAACACTG CTTACCTGCAGATGAACAGCCTGCGAGCCGAAGATACCGCTGTGTACT ATTGCAGTCGATGGGGAGGAGACGGATTCTACGCTATGGATTATTGG |

FIG. 8L

| | | |
|---|---|---|
| | | GGACAGGGGACCCTGGTGACAGTGAGCTCCGCCTCTACCAAGGGCCC CAGTGTGTTTCCCCTGGCTCCTTCTAGTAAATCCACCTCTGGAGGGAC AGCCGCTCTGGGATGTCTGGTGAAGGACTATTTCCCCGAGCCTGTGAC CGTGAGTTGGAACTCAGGCGCCCTGACAAGCGGAGTGCACACTTTTC CTGCTGTGCTGCAGTCAAGCGGGCTGTACTCCCTGTCCTCTGTGGTGA CAGTGCCAAGTTCAAGCCTGGGCACACAGACTTATATCTGCAACGTGA ATCATAAGCCCTCAAATACAAAAGTGGACAAGAAAGTGGAGCCCAAG AGCTGTGATAAGACCCACACCTGCCCTCCCTGTCCAGCTCCAGAAAAG AAGGGAGGACCTAGCGTGTTCCTGTTTCCCCCTAAGCCAAAAGACACT CTGATGATTTCCAGGACTCCCGAGGTGACCTGCGTGGTGGTGGACGT GTCTCACGAGGACCCCGAAGTGAAGTTCAACTGGTACGTGGATGGCG TGGAAGTGCATAATGCTAAGACAAAACCAAGAGAGGAACAGTACAAC TCCACTTATCGCGTCGTGAGCGTGCTGACCGTGCTGCACCAGGACTGG CTGAACGGGAAGGAGTATAAGTGCAAAGTCAGTAATAAGGCCCTGCC TGCTCCAATCGAAAAAACCATCTCTAAGGCCAAAGGCCAGCCAAGGG AGCCCCAGGTGTACGTGCTGCCACCCAGCAGAGACGAACTGACCAAG AACCAGGTGTCCCTGCTGTGTCTGGTGAAAGGCTTCTATCCTAGTGAT ATTGCTGTGGAGTGGGAATCAAATGGACAGCCAGAGAACAGATACAT GACCTGGCCTCCAGTGCTGGACAGCGATGGCAGCTTCTTCCTGTATTC CAAGCTGACAGTGGATAAATCTCGATGGCAGCAGGGGAACGTGTTTA GTTGTTCAGTGATGCATGAAGCCCTGCACAATCATTACACTCAGAAGA GCCTGTCCCTGTCTCCCGGCAAA |
| 25 | DNA | GAGGTGCAGCTGGTGGAAAGCGGAGGAGGACTGGTGCAGCCAGGA GGATCTCTGCGACTGAGTTGCGCCGCTTCAGGATTCAACATCAAGGAC ACCTACATTCACTGGGTGCGACAGGCTCCAGGAAAAGGACTGGAGTG GGTGGCTCGAATCTATCCCACTAATGGATACACCCGGTATGCCGACTC CGTGAAGGGGAGGTTTACTATTAGCGCCGATACATCCAAAAACACTG CTTACCTGCAGATGAACAGCCTGCGAGCCGAAGATACCGCTGTGTACT ATTGCAGTCGATGGGGAGGAGACGGATTCTACGCTATGGATTATTGG GGACAGGGGACCCTGGTGACAGTGAGCTCCGCCTCTACCAAGGGCCC CAGTGTGTTTCCCCTGGCTCCTTCTAGTAAATCCACCTCTGGAGGGAC AGCCGCTCTGGGATGTCTGGTGAAGGACTATTTCCCCGAGCCTGTGAC CGTGAGTTGGAACTCAGGCGCCCTGACAAGCGGAGTGCACACTTTTC CTGCTGTGCTGCAGTCAAGCGGGCTGTACTCCCTGTCCTCTGTGGTGA CAGTGCCAAGTTCAAGCCTGGGCACACAGACTTATATCTGCAACGTGA ATCATAAGCCCTCAAATACAAAAGTGGACAAGAAAGTGGAGCCCAAG AGCTGTGATAAGACCCACACCTGCCCTCCCTGTCCAGCTCCAGCCAGA AGAGGAGGACCTAGCGTGTTCCTGTTTCCCCCTAAGCCAAAAGACACT CTGATGATTTCCAGGACTCCCGAGGTGACCTGCGTGGTGGTGGACGT GTCTCACGAGGACCCCGAAGTGAAGTTCAACTGGTACGTGGATGGCG TGGAAGTGCATAATGCTAAGACAAAACCAAGAGAGGAACAGTACAAC TCCACTTATCGCGTCGTGAGCGTGCTGACCGTGCTGCACCAGGACTGG CTGAACGGGAAGGAGTATAAGTGCAAAGTCAGTAATAAGGCCCTGCC TGCTCCAATCGAAAAAACCATCTCTAAGGCCAAAGGCCAGCCAAGGG AGCCCCAGGTGTACGTGCTGCCACCCAGCAGAGACGAACTGACCAAG AACCAGGTGTCCCTGCTGTGTCTGGTGAAAGGCTTCTATCCTAGTGAT ATTGCTGTGGAGTGGGAATCAAATGGACAGCCAGAGAACAGATACAT |

FIG. 8M

| | | |
|---|---|---|
| | | GACCTGGCCTCCAGTGCTGGACAGCGATGGCAGCTTCTTCCTGTATTC CAAGCTGACAGTGGATAAATCTCGATGGCAGCAGGGGAACGTGTTTA GTTGTTCAGTGATGCATGAAGCCCTGCACAATCATTACACTCAGAAGA GCCTGTCCCTGTCTCCCGGCAAA |
| 27 | DNA | GAGGTGCAGCTGGTGGAAAGCGGAGGAGGACTGGTGCAGCCAGGA GGATCTCTGCGACTGAGTTGCGCCGCTTCAGGATTCAACATCAAGGAC ACCTACATTCACTGGGTGCGACAGGCTCCAGGAAAAGGACTGGAGTG GGTGGCTCGAATCTATCCCACTAATGGATACACCCGGTATGCCGACTC CGTGAAGGGGAGGTTTACTATTAGCGCCGATACATCCAAAAACACTG CTTACCTGCAGATGAACAGCCTGCGAGCCGAAGATACCGCTGTGTACT ATTGCAGTCGATGGGGAGGAGACGGATTCTACGCTATGGATTATTGG GGACAGGGGACCCTGGTGACAGTGAGCTCCGCCTCTACCAAGGGCCC CAGTGTGTTTCCCCTGGCTCCTTCTAGTAAATCCACCTCTGGAGGGAC AGCCGCTCTGGGATGTCTGGTGAAGGACTATTTCCCCGAGCCTGTGAC CGTGAGTTGGAACTCAGGCGCCCTGACAAGCGGAGTGCACACTTTTC CTGCTGTGCTGCAGTCAAGCGGGCTGTACTCCCTGTCCTCTGTGGTGA CAGTGCCAAGTTCAAGCCTGGGCACACAGACTTATATCTGCAACGTGA ATCATAAGCCCTCAAATACAAAAGTGGACAAGAAAGTGGAGCCCAAG AGCTGTGATAAGACCCACACCTGCCCTCCCTGTCCAGCTCCAAAGAGA AGAGGAGGACCTAGCGTGTTCCTGTTTCCCCCTAAGCCAAAAGACACT CTGATGATTTCCAGGACTCCCGAGGTGACCTGCGTGGTGGTGGACGT GTCTCACGAGGACCCCGAAGTGAAGTTCAACTGGTACGTGGATGGCG TGGAAGTGCATAATGCTAAGACAAAACCAAGAGAGGAACAGTACAAC TCCACTTATCGCGTCGTGAGCGTGCTGACCGTGCTGCACCAGGACTGG CTGAACGGGAAGGAGTATAAGTGCAAAGTCAGTAATAAGGCCCTGCC TGCTCCAATCGAAAAAACCATCTCTAAGGCCAAAGGCCAGCCAAGGG AGCCCCAGGTGTACGTGCTGCCACCCAGCAGAGACGAACTGACCAAG AACCAGGTGTCCCTGCTGTGTCTGGTGAAAGGCTTCTATCCTAGTGAT ATTGCTGTGGAGTGGGAATCAAATGGACAGCCAGAGAACAGATACAT GACCTGGCCTCCAGTGCTGGACAGCGATGGCAGCTTCTTCCTGTATTC CAAGCTGACAGTGGATAAATCTCGATGGCAGCAGGGGAACGTGTTTA GTTGTTCAGTGATGCATGAAGCCCTGCACAATCATTACACTCAGAAGA GCCTGTCCCTGTCTCCCGGCAAA |
| 29 | DNA | GAGGTGCAGCTGGTGGAAAGCGGAGGAGGACTGGTGCAGCCAGGA GGATCTCTGCGACTGAGTTGCGCCGCTTCAGGATTCAACATCAAGGAC ACCTACATTCACTGGGTGCGACAGGCTCCAGGAAAAGGACTGGAGTG GGTGGCTCGAATCTATCCCACTAATGGATACACCCGGTATGCCGACTC CGTGAAGGGGAGGTTTACTATTAGCGCCGATACATCCAAAAACACTG CTTACCTGCAGATGAACAGCCTGCGAGCCGAAGATACCGCTGTGTACT ATTGCAGTCGATGGGGAGGAGACGGATTCTACGCTATGGATTATTGG GGACAGGGGACCCTGGTGACAGTGAGCTCCGCCTCTACCAAGGGCCC CAGTGTGTTTCCCCTGGCTCCTTCTAGTAAATCCACCTCTGGAGGGAC AGCCGCTCTGGGATGTCTGGTGAAGGACTATTTCCCCGAGCCTGTGAC CGTGAGTTGGAACTCAGGCGCCCTGACAAGCGGAGTGCACACTTTTC |

FIG. 8N

| | | |
|---|---|---|
| | | CTGCTGTGCTGCAGTCAAGCGGGCTGTACTCCCTGTCCTCTGTGGTGA CAGTGCCAAGTTCAAGCCTGGGCACACAGACTTATATCTGCAACGTGA ATCATAAGCCCTCAAATACAAAAGTGGACAAGAAAGTGGAGCCCAAG AGCTGTGATAAGACCCACACCTGCCCTCCCTGTCCAGCTCCAAAGGCC AAGGGAGGACCTAGCGTGTTCCTGTTTCCCCCTAAGCCAAAAGACACT CTGATGATTTCCAGGACTCCCGAGGTGACCTGCGTGGTGGTGGACGT GTCTCACGAGGACCCCGAAGTGAAGTTCAACTGGTACGTGGATGGCG TGGAAGTGCATAATGCTAAGACAAAACCAAGAGAGGAACAGTACAAC TCCACTTATCGCGTCGTGAGCGTGCTGACCGTGCTGCACCAGGACTGG CTGAACGGGAAGGAGTATAAGTGCAAAGTCAGTAATAAGGCCCTGCC TGCTCCAATCGAAAAAACCATCTCTAAGGCCAAAGGCCAGCCAAGGG AGCCCCAGGTGTACGTGCTGCCACCCAGCAGAGACGAACTGACCAAG AACCAGGTGTCCCTGCTGTGTCTGGTGAAAGGCTTCTATCCTAGTGAT ATTGCTGTGGAGTGGGAATCAAATGGACAGCCAGAGAACAGATACAT GACCTGGCCTCCAGTGCTGGACAGCGATGGCAGCTTCTTCCTGTATTC CAAGCTGACAGTGGATAAATCTCGATGGCAGCAGGGGAACGTGTTTA GTTGTTCAGTGATGCATGAAGCCCTGCACAATCATTACACTCAGAAGA GCCTGTCCCTGTCTCCCGGCAAA |
| 31 | DNA | GAGGTGCAGCTGGTGGAAAGCGGAGGAGGACTGGTGCAGCCAGGA GGATCTCTGCGACTGAGTTGCGCCGCTTCAGGATTCAACATCAAGGAC ACCTACATTCACTGGGTGCGACAGGCTCCAGGAAAAGGACTGGAGTG GGTGGCTCGAATCTATCCCACTAATGGATACACCCGGTATGCCGACTC CGTGAAGGGGAGGTTTACTATTAGCGCCGATACATCCAAAAACACTG CTTACCTGCAGATGAACAGCCTGCGAGCCGAAGATACCGCTGTGTACT ATTGCAGTCGATGGGGAGGAGACGGATTCTACGCTATGGATTATTGG GGACAGGGGACCCTGGTGACAGTGAGCTCCGCCTCTACCAAGGGCCC CAGTGTGTTTCCCCTGGCTCCTTCTAGTAAATCCACCTCTGGAGGGAC AGCCGCTCTGGGATGTCTGGTGAAGGACTATTTCCCCGAGCCTGTGAC CGTGAGTTGGAACTCAGGCGCCCTGACAAGCGGAGTGCACACTTTTC CTGCTGTGCTGCAGTCAAGCGGGCTGTACTCCCTGTCCTCTGTGGTGA CAGTGCCAAGTTCAAGCCTGGGCACACAGACTTATATCTGCAACGTGA ATCATAAGCCCTCAAATACAAAAGTGGACAAGAAAGTGGAGCCCAAG AGCTGTGATAAGACCCACACCTGCCCTCCCTGTCCAGCTCCAGAACTG CTGGGAGGACCTAGCGTGTTCCTGTTTCCCCCTAAGCCAAAAGACACT CTGATGATTTCCAGGACTCCCGAGGTGACCTGCGTGGTGGTGGACGT GTCTCACAAGAGACCCGAAGTGAAGTTCAACTGGTACGTGGATGGCG TGGAAGTGCATAATGCTAAGACAAAACCAAGAGAGGAACAGTACAAC TCCACTTATCGCGTCGTGAGCGTGCTGACCGTGCTGCACCAGGACTGG CTGAACGGGAAGGAGTATAAGTGCAAAGTCAGTAATAAGGCCCTGCC TGCTCCAATCGAAAAAACCATCTCTAAGGCCAAAGGCCAGCCAAGGG AGCCCCAGGTGTACGTGCTGCCACCCAGCAGAGACGAACTGACCAAG AACCAGGTGTCCCTGCTGTGTCTGGTGAAAGGCTTCTATCCTAGTGAT ATTGCTGTGGAGTGGGAATCAAATGGACAGCCAGAGAACAGATACAT GACCTGGCCTCCAGTGCTGGACAGCGATGGCAGCTTCTTCCTGTATTC CAAGCTGACAGTGGATAAATCTCGATGGCAGCAGGGGAACGTGTTTA GTTGTTCAGTGATGCATGAAGCCCTGCACAATCATTACACTCAGAAGA GCCTGTCCCTGTCTCCCGGCAAA |

FIG. 8O

| | | |
|---|---|---|
| 33 | DNA | GAGGTGCAGCTGGTGGAAAGCGGAGGAGGACTGGTGCAGCCAGGA GGATCTCTGCGACTGAGTTGCGCCGCTTCAGGATTCAACATCAAGGAC ACCTACATTCACTGGGTGCGACAGGCTCCAGGAAAAGGACTGGAGTG GGTGGCTCGAATCTATCCCACTAATGGATACACCCGGTATGCCGACTC CGTGAAGGGGAGGTTTACTATTAGCGCCGATACATCCAAAAACACTG CTTACCTGCAGATGAACAGCCTGCGAGCCGAAGATACCGCTGTGTACT ATTGCAGTCGATGGGGAGGAGACGGATTCTACGCTATGGATTATTGG GGACAGGGGACCCTGGTGACAGTGAGCTCCGCCTCTACCAAGGGCCC CAGTGTGTTTCCCCTGGCTCCTTCTAGTAAATCCACCTCTGGAGGGAC AGCCGCTCTGGGATGTCTGGTGAAGGACTATTTCCCCGAGCCTGTGAC CGTGAGTTGGAACTCAGGCGCCCTGACAAGCGGAGTGCACACTTTTC CTGCTGTGCTGCAGTCAAGCGGGCTGTACTCCCTGTCCTCTGTGGTGA CAGTGCCAAGTTCAAGCCTGGGCACACAGACTTATATCTGCAACGTGA ATCATAAGCCCTCAAATACAAAAGTGGACAAGAAAGTGGAGCCCAAG AGCTGTGATAAGACCCACACCTGCCCTCCCTGTCCAGCTCCAGAACTG AAGGGAGGACCTAGCGTGTTCCTGTTTCCCCCTAAGCCAAAAGACACT CTGATGATTTCCAGGACTCCCGAGGTGACCTGCGTGGTGGTGGACGT GTCTCACGAGGACCCCGAAGTGAAGTTCAACTGGTACGTGGATGGCG TGGAAGTGCATAATGCTAAGACAAAACCAAGAGAGGAACAGTACAAC TCCACTTATCGCGTCGTGAGCGTGCTGACCGTGCTGCACCAGGACTGG CTGAACGGGAAGGAGTATAAGTGCAAAGTCAGTAATAAGAAGCTGCC TGCTCCAATCGAAAAAACCATCTCTAAGGCCAAAGGCCAGCCAAGGG AGCCCCAGGTGTACGTGCTGCCACCCAGCAGAGACGAACTGACCAAG AACCAGGTGTCCCTGCTGTGTCTGGTGAAAGGCTTCTATCCTAGTGAT ATTGCTGTGGAGTGGGAATCAAATGGACAGCCAGAGAACAGATACAT GACCTGGCCTCCAGTGCTGGACAGCGATGGCAGCTTCTTCCTGTATTC CAAGCTGACAGTGGATAAATCTCGATGGCAGCAGGGGAACGTGTTTA GTTGTTCAGTGATGCATGAAGCCCTGCACAATCATTACACTCAGAAGA GCCTGTCCCTGTCTCCCGGCAAA |
| 34 | DNA | GACATCCAGATGACCCAGTCTCCATCCTCCCTGTCTGCATCTGTAGGA GACAGAGTCACCATCACTTGCCGGGCAAGTCAGGACGTTAACACCGC TGTAGCTTGGTATCAGCAGAAACCAGGGAAAGCCCCTAAGCTCCTGAT CTATTCTGCATCCTTTTTGTACAGTGGGGTCCCATCAAGGTTCAGTGGC AGTCGATCTGGGACAGATTTCACTCTCACCATCAGCAGTCTGCAACCT GAAGATTTTGCAACTTACTACTGTCAACAGCATTACACTACCCCACCCA CTTTCGGCCAAGGGACCAAAGTGGAGATCAAACGAACTGTGGCTGCA CCATCTGTCTTCATCTTCCCGCCATCTGATGAGCAGTTGAAATCTGGAA CTGCCTCTGTTGTGTGCCTGCTGAATAACTTCTATCCCAGAGAGGCCA AAGTACAGTGGAAGGTGGATAACGCCCTCCAATCGGGTAACTCCCAA GAGAGTGTCACAGAGCAGGACAGCAAGGACAGCACCTACAGCCTCA GCAGCACCCTGACGCTGAGCAAAGCAGACTACGAGAAACACAAAGTC TACGCCTGCGAAGTCACCCATCAGGGCCTGAGCTCGCCCGTCACAAAG AGCTTCAACAGGGGAGAGTGT |
| 36 | DNA | CAGGTCCAGCTGCAGCAGCCCGGAGCTGAACTGGTCAAACCTGGCGC ATCCGTGAAAATGTCTTGCAAGGCTAGTGGCTACACATTCACTTCCTAT AACATGCACTGGGTGAAGCAGACACCAGGACGAGGACTGGAGTGGA TCGGAGCAATCTACCCTGGAAACGGCGACACTTCTTATAATCAGAAGT |

FIG. 8P

| | | |
|---|---|---|
| | | TTAAAGGCAAGGCCACCCTGACAGCTGATAAGAGCTCCTCTACCGCCT ACATGCAGCTGAGTTCACTGACAAGTGAAGACTCAGCAGTGTACTATT GCGCCAGAAGCACCTACTATGGCGGGGATTGGTACTTCAACGTGTGG GGGGCAGGAACCACAGTCACCGTGAGCGCCGCTTCCACAAAAGGACC AAGCGTGTTTCCACTGGCACCAAGCTCCAAGTCAACCAGCGGAGGAA CAGCAGCCCTGGGATGTCTGGTGAAGGACTACTTCCCAGAGCCCGTC ACCGTGTCTTGGAACAGTGGCGCCCTGACAAGCGGGGTCCATACTTTT CCCGCTGTGCTGCAGTCTAGTGGCCTGTACAGCCTGTCAAGCGTGGTC ACCGTCCCTTCCTCTAGTCTGGGGACTCAGACCTATATCTGCAACGTG AATCACAAACCTTCTAATACAAAGGTCGACAAGAAAGTGGAACCAAA AAGTTGTGATAAGACACATACTTGCCCACCTTGTCCTGCACCAGAGCT GCTGGGAGGACCATCCGTGTTCCTGTTTCCACCCAAACCCAAGGACAC TCTGATGATTAGCCGGACTCCTGAAGTCACCTGCGTGGTCGTGGACGT GAGCCACGAGGACCCCGAAGTCAAATTCAACTGGTACGTGGATGGCG TCGAGGTGCATAATGCCAAAACAAAGCCCCGGGAGGAACAGTACAAC TCAACATATAGAGTCGTGAGCGTCCTGACTGTGCTGCACCAGGACTG GCTGAACGGCAAGGAGTATAAATGCAAGGTGTCCAACAAGGCCCTGC CCGCACCTATCGAGAAGACTATTTCTAAAGCCAAGGGCCAGCCTAGG GAACCACAGGTGTACGTGTACCCTCCAAGCCGCGACGAGCTGACTAA AAACCAGGTCTCCCTGACCTGTCTGGTGAAGGGGTTCTATCCAAGTGA TATCGCTGTGGAGTGGGAATCAAATGGACAGCCCGAGAACAATTACA AGACTACCCCCCCTGTGCTGGACTCAGATGGGAGCTTCGCCCTGGTGT CCAAACTGACCGTGGATAAGTCTCGGTGGCAGCAGGGAAATGTCTTT TCCTGTTCTGTGATGCACGAAGCACTGCACAATCACTACACCCAGAAG TCCCTGAGCCTGTCACCCGGCAAA |
| 38 | DNA | CAGGTCCAGCTGCAGCAGCCCGGAGCTGAACTGGTCAAACCTGGCGC ATCCGTGAAAATGTCTTGCAAGGCTAGTGGCTACACATTCACTTCCTAT AACATGCACTGGGTGAAGCAGACACCAGGACGAGGACTGGAGTGGA TCGGAGCAATCTACCCTGGAAACGGCGACACTTCTTATAATCAGAAGT TTAAAGGCAAGGCCACCCTGACAGCTGATAAGAGCTCCTCTACCGCCT ACATGCAGCTGAGTTCACTGACAAGTGAAGACTCAGCAGTGTACTATT GCGCCAGAAGCACCTACTATGGCGGGGATTGGTACTTCAACGTGTGG GGGGCAGGAACCACAGTCACCGTGAGCGCCGCTTCCACAAAAGGACC AAGCGTGTTTCCACTGGCACCAAGCTCCAAGTCAACCAGCGGAGGAA CAGCAGCCCTGGGATGTCTGGTGAAGGACTACTTCCCAGAGCCCGTC ACCGTGTCTTGGAACAGTGGCGCCCTGACAAGCGGGGTCCATACTTTT CCCGCTGTGCTGCAGTCTAGTGGCCTGTACAGCCTGTCAAGCGTGGTC ACCGTCCCTTCCTCTAGTCTGGGGACTCAGACCTATATCTGCAACGTG AATCACAAACCTTCTAATACAAAGGTCGACAAGAAAGTGGAACCAAA AAGTTGTGATAAGACACATACTTGCCCACCTTGTCCTGCACCAGAGCT GCTGGGAGGACCATCCGTGTTCCTGTTTCCACCCAAACCCAAGGACAC TCTGATGATTAGCCGGACTCCTGAAGTCACCTGCGTGGTCGTGGACGT GAGCCACGAGGACCCCGAAGTCAAATTCAACTGGTACGTGGATGGCG TCGAGGTGCATAATGCCAAAACAAAGCCCCGGGAGGAACAGTACAAC TCAACATATAGAGTCGTGAGCGTCCTGACTGTGCTGCACCAGGACTG GCTGAACGGCAAGGAGTATAAATGCAAGGTGTCCAACAAGGCCCTGC CCGCACCTATCGAGAAGACTATTTCTAAAGCCAAGGGCCAGCCTAGG |

FIG. 8Q

| | | |
|---|---|---|
| | | GAACCACAGGTGTACGTGCTGCCTCCAAGCCGCGACGAGCTGACTAA AAACCAGGTCTCCCTGCTGTGTCTGGTGAAGGGGTTCTATCCAAGTGA TATCGCTGTGGAGTGGGAATCAAATGGACAGCCCGAGAACAATTACC TGACTTGGCCCCCTGTGCTGGACTCAGATGGGAGCTTCTTTCTGTATTC CAAACTGACCGTGGATAAGTCTCGGTGGCAGCAGGGAAATGTCTTTT CCTGTTCTGTGATGCACGAAGCACTGCACAATCACTACACCCAGAAGT CCCTGAGCCTGTCACCCGGCAAA |
| 40 | DNA | CAGGTCCAGCTGCAGCAGCCCGGAGCTGAACTGGTCAAACCTGGCGC ATCCGTGAAAATGTCTTGCAAGGCTAGTGGCTACACATTCACTTCCTAT AACATGCACTGGGTGAAGCAGACACCAGGACGAGGACTGGAGTGGA TCGGAGCAATCTACCCTGGAAACGGCGACACTTCTTATAATCAGAAGT TTAAAGGCAAGGCCACCCTGACAGCTGATAAGAGCTCCTCTACCGCCT ACATGCAGCTGAGTTCACTGACAAGTGAAGACTCAGCAGTGTACTATT GCGCCAGAAGCACCTACTATGGCGGGGATTGGTACTTCAACGTGTGG GGGGCAGGAACCACAGTCACCGTGAGCGCCGCTTCCACAAAAGGACC AAGCGTGTTTCCACTGGCACCAAGCTCCAAGTCAACCAGCGGAGGAA CAGCAGCCCTGGGATGTCTGGTGAAGGACTACTTCCCAGAGCCCGTC ACCGTGTCTTGGAACAGTGGCGCCCTGACAAGCGGGGTCCATACTTTT CCCGCTGTGCTGCAGTCTAGTGGCCTGTACAGCCTGTCAAGCGTGGTC ACCGTCCCTTCCTCTAGTCTGGGGACTCAGACCTATATCTGCAACGTG AATCACAAACCTTCTAATACAAAGGTCGACAAGAAAGTGGAACCAAA AAGTTGTGATAAGACACATACTTGCCCACCTTGTCCTGCACCAGAGGA CGAGGGAGGACCATCCGTGTTCCTGTTTCCACCCAAACCCAAGGACAC TCTGATGATTAGCCGGACTCCTGAAGTCACCTGCGTGGTCGTGGACGT GAGCCACGAGGACCCCGAAGTCAAATTCAACTGGTACGTGGATGGCG TCGAGGTGCATAATGCCAAAACAAAGCCCCGGGAGGAACAGTACAAC TCAACATATAGAGTCGTGAGCGTCCTGACTGTGCTGCACCAGGACTG GCTGAACGGCAAGGAGTATAAATGCAAGGTGTCCAACAAGGCCCTGC CCGCACCTATCGAGAAGACTATTTCTAAAGCCAAGGGCCAGCCTAGG GAACCACAGGTGTACGTGTACCCTCCAAGCCGCGACGAGCTGACTAA AAACCAGGTCTCCCTGACCTGTCTGGTGAAGGGGTTCTATCCAAGTGA TATCGCTGTGGAGTGGGAATCAAATGGACAGCCCGAGAACAATTACA AGACTACCCCCCCTGTGCTGGACTCAGATGGGAGCTTCGCCCTGGTGT CCAAACTGACCGTGGATAAGTCTCGGTGGCAGCAGGGAAATGTCTTT TCCTGTTCTGTGATGCACGAAGCACTGCACAATCACTACACCCAGAAG TCCCTGAGCCTGTCACCCGGCAAA |
| 42 | DNA | CAGGTCCAGCTGCAGCAGCCCGGAGCTGAACTGGTCAAACCTGGCGC ATCCGTGAAAATGTCTTGCAAGGCTAGTGGCTACACATTCACTTCCTAT AACATGCACTGGGTGAAGCAGACACCAGGACGAGGACTGGAGTGGA TCGGAGCAATCTACCCTGGAAACGGCGACACTTCTTATAATCAGAAGT TTAAAGGCAAGGCCACCCTGACAGCTGATAAGAGCTCCTCTACCGCCT ACATGCAGCTGAGTTCACTGACAAGTGAAGACTCAGCAGTGTACTATT GCGCCAGAAGCACCTACTATGGCGGGGATTGGTACTTCAACGTGTGG GGGGCAGGAACCACAGTCACCGTGAGCGCCGCTTCCACAAAAGGACC AAGCGTGTTTCCACTGGCACCAAGCTCCAAGTCAACCAGCGGAGGAA CAGCAGCCCTGGGATGTCTGGTGAAGGACTACTTCCCAGAGCCCGTC ACCGTGTCTTGGAACAGTGGCGCCCTGACAAGCGGGGTCCATACTTTT |

FIG. 8R

| | | |
|---|---|---|
| | | CCCGCTGTGCTGCAGTCTAGTGGCCTGTACAGCCTGTCAAGCGTGGTC ACCGTCCCTTCCTCTAGTCTGGGGACTCAGACCTATATCTGCAACGTG AATCACAAACCTTCTAATACAAAGGTCGACAAGAAAGTGGAACCAAA AAGTTGTGATAAGACACATACTTGCCCACCTTGTCCTGCACCAAAGAG AAGAGGAGGACCATCCGTGTTCCTGTTTCCACCCAAACCCAAGGACAC TCTGATGATTAGCCGGACTCCTGAAGTCACCTGCGTGGTCGTGGACGT GAGCCACGAGGACCCCGAAGTCAAATTCAACTGGTACGTGGATGGCG TCGAGGTGCATAATGCCAAAACAAAGCCCCGGGAGGAACAGTACAAC TCAACATATAGAGTCGTGAGCGTCCTGACTGTGCTGCACCAGGACTG GCTGAACGGCAAGGAGTATAAATGCAAGGTGTCCAACAAGGCCCTGC CCGCACCTATCGAGAAGACTATTTCTAAAGCCAAGGGCCAGCCTAGG GAACCACAGGTGTACGTGCTGCCTCCAAGCCGCGACGAGCTGACTAA AAACCAGGTCTCCCTGCTGTGTCTGGTGAAGGGGTTCTATCCAAGTGA TATCGCTGTGGAGTGGGAATCAAATGGACAGCCCGAGAACAATTACC TGACTTGGCCCCCTGTGCTGGACTCAGATGGGAGCTTCTTTCTGTATTC CAAACTGACCGTGGATAAGTCTCGGTGGCAGCAGGGAAATGTCTTTT CCTGTTCTGTGATGCACGAAGCACTGCACAATCACTACACCCAGAAGT CCCTGAGCCTGTCACCCGGCAAA |
| 44 | DNA | CAGGTCCAGCTGCAGCAGCCCGGAGCTGAACTGGTCAAACCTGGCGC ATCCGTGAAAATGTCTTGCAAGGCTAGTGGCTACACATTCACTTCCTAT AACATGCACTGGGTGAAGCAGACACCAGGACGAGGACTGGAGTGGA TCGGAGCAATCTACCCTGGAAACGGCGACACTTCTTATAATCAGAAGT TTAAAGGCAAGGCCACCCTGACAGCTGATAAGAGCTCCTCTACCGCCT ACATGCAGCTGAGTTCACTGACAAGTGAAGACTCAGCAGTGTACTATT GCGCCAGAAGCACCTACTATGGCGGGGATTGGTACTTCAACGTGTGG GGGGCAGGAACCACAGTCACCGTGAGCGCCGCTTCCACAAAAGGACC AAGCGTGTTTCCACTGGCACCAAGCTCCAAGTCAACCAGCGGAGGAA CAGCAGCCCTGGGATGTCTGGTGAAGGACTACTTCCCAGAGCCCGTC ACCGTGTCTTGGAACAGTGGCGCCCTGACAAGCGGGGTCCATACTTTT CCCGCTGTGCTGCAGTCTAGTGGCCTGTACAGCCTGTCAAGCGTGGTC ACCGTCCCTTCCTCTAGTCTGGGGACTCAGACCTATATCTGCAACGTG AATCACAAACCTTCTAATACAAAGGTCGACAAGAAAGTGGAACCAAA AAGTTGTGATAAGACACATACTTGCCCACCTTGTCCTGCACCAGAGGA CGAGGGAGGACCATCCGTGTTCCTGTTTCCACCCAAACCCAAGGACAC TCTGATGATTAGCCGGACTCCTGAAGTCACCTGCGTGGTCGTGAGCGT GAGCCACGAGGACCCCGAAGTCAAATTCAACTGGTACGTGGATGGCG TCGAGGTGCATAATGCCAAAACAAAGCCCCGGGAGGAACAGTACAAC TCAACATATAGAGTCGTGAGCGTCCTGACTGTGCTGCACCAGGACTG GCTGAACGGCAAGGAGTATAAATGCAAGGTGTCCAACAAGGCCCTGC CCGCACCTATCGAGAAGACTATTTCTAAAGCCAAGGGCCAGCCTAGG GAACCACAGGTGTACGTGTACCCTCCAAGCCGCGACGAGCTGACTAA AAACCAGGTCTCCCTGACCTGTCTGGTGAAGGGGTTCTATCCAAGTGA TATCGCTGTGGAGTGGGAATCAAATGGACAGCCCGAGAACAATTACA AGACTACCCCCCCTGTGCTGGACTCAGATGGGAGCTTCGCCCTGGTGT CCAAACTGACCGTGGATAAGTCTCGGTGGCAGCAGGGAAATGTCTTT TCCTGTTCTGTGATGCACGAAGCACTGCACAATCACTACACCCAGAAG TCCCTGAGCCTGTCACCCGGCAAA |

FIG. 8S

| | | |
|---|---|---|
| 46 | DNA | CAGGTCCAGCTGCAGCAGCCCGGAGCTGAACTGGTCAAACCTGGCGC<br>ATCCGTGAAAATGTCTTGCAAGGCTAGTGGCTACACATTCACTTCCTAT<br>AACATGCACTGGGTGAAGCAGACACCAGGACGAGGACTGGAGTGGA<br>TCGGAGCAATCTACCCTGGAAACGGCGACACTTCTTATAATCAGAAGT<br>TTAAAGGCAAGGCCACCCTGACAGCTGATAAGAGCTCCTCTACCGCCT<br>ACATGCAGCTGAGTTCACTGACAAGTGAAGACTCAGCAGTGTACTATT<br>GCGCCAGAAGCACCTACTATGGCGGGGATTGGTACTTCAACGTGTGG<br>GGGGCAGGAACCACAGTCACCGTGAGCGCCGCTTCCACAAAAGGACC<br>AAGCGTGTTTCCACTGGCACCAAGCTCCAAGTCAACCAGCGGAGGAA<br>CAGCAGCCCTGGGATGTCTGGTGAAGGACTACTTCCCAGAGCCCGTC<br>ACCGTGTCTTGGAACAGTGGCGCCCTGACAAGCGGGGTCCATACTTTT<br>CCCGCTGTGCTGCAGTCTAGTGGCCTGTACAGCCTGTCAAGCGTGGTC<br>ACCGTCCCTTCCTCTAGTCTGGGGACTCAGACCTATATCTGCAACGTG<br>AATCACAAACCTTCTAATACAAAGGTCGACAAGAAAGTGGAACCAAA<br>AAGTTGTGATAAGACACATACTTGCCCACCTTGTCCTGCACCAAAGAG<br>AAGAGGAGGACCATCCGTGTTCCTGTTTCCACCCAAACCCAAGGACAC<br>TCTGATGATTAGCCGGACTCCTGAAGTCACCTGCGTGGTCGTGAGCGT<br>GAGCCACGAGGACCCCGAAGTCAAATTCAACTGGTACGTGGATGGCG<br>TCGAGGTGCATAATGCCAAAACAAAGCCCCGGGAGGAACAGTACAAC<br>TCAACATATAGAGTCGTGAGCGTCCTGACTGTGCTGCACCAGGACTG<br>GCTGAACGGCAAGGAGTATAAATGCAAGGTGTCCAACAAGGCCCTGC<br>CCGCACCTATCGAGAAGACTATTTCTAAAGCCAAGGGCCAGCCTAGG<br>GAACCACAGGTGTACGTGCTGCCTCCAAGCCGCGACGAGCTGACTAA<br>AAACCAGGTCTCCCTGCTGTGTCTGGTGAAGGGGTTCTATCCAAGTGA<br>TATCGCTGTGGAGTGGGAATCAAATGGACAGCCCGAGAACAATTACC<br>TGACTTGGCCCCCTGTGCTGGACTCAGATGGGAGCTTCTTTCTGTATTC<br>CAAACTGACCGTGGATAAGTCTCGGTGGCAGCAGGGAAATGTCTTTT<br>CCTGTTCTGTGATGCACGAAGCACTGCACAATCACTACACCCAGAAGT<br>CCCTGAGCCTGTCACCCGGCAAA |
| 48 | DNA | CAGGTCCAGCTGCAGCAGCCCGGAGCTGAACTGGTCAAACCTGGCGC<br>ATCCGTGAAAATGTCTTGCAAGGCTAGTGGCTACACATTCACTTCCTAT<br>AACATGCACTGGGTGAAGCAGACACCAGGACGAGGACTGGAGTGGA<br>TCGGAGCAATCTACCCTGGAAACGGCGACACTTCTTATAATCAGAAGT<br>TTAAAGGCAAGGCCACCCTGACAGCTGATAAGAGCTCCTCTACCGCCT<br>ACATGCAGCTGAGTTCACTGACAAGTGAAGACTCAGCAGTGTACTATT<br>GCGCCAGAAGCACCTACTATGGCGGGGATTGGTACTTCAACGTGTGG<br>GGGGCAGGAACCACAGTCACCGTGAGCGCCGCTTCCACAAAAGGACC<br>AAGCGTGTTTCCACTGGCACCAAGCTCCAAGTCAACCAGCGGAGGAA<br>CAGCAGCCCTGGGATGTCTGGTGAAGGACTACTTCCCAGAGCCCGTC<br>ACCGTGTCTTGGAACAGTGGCGCCCTGACAAGCGGGGTCCATACTTTT<br>CCCGCTGTGCTGCAGTCTAGTGGCCTGTACAGCCTGTCAAGCGTGGTC<br>ACCGTCCCTTCCTCTAGTCTGGGGACTCAGACCTATATCTGCAACGTG<br>AATCACAAACCTTCTAATACAAAGGTCGACAAGAAAGTGGAACCAAA<br>AAGTTGTGATAAGACACATACTTGCCCACCTTGTCCTGCACCAGAGGA<br>CGAGGGAGGACCATCCGTGTTCCTGTTTCCACCCAAACCCAAGGACAC<br>TCTGATGATTAGCCGGACTCCTGAAGTCACCTGCGTGGTCGTGGACGT<br>GAGCCACAAGGACCCCGAAGTCAAATTCAACTGGTACGTGGATGGCG |

FIG. 8T

| | | |
|---|---|---|
| | | TCGAGGTGCATAATGCCAAAACAAAGCCCCGGGAGGAACAGTACAAC TCAACATATAGAGTCGTGAGCGTCCTGACTGTGCTGCACCAGGACTG GCTGAACGGCAAGGAGTATAAATGCAAGGTGTCCAACAAGGCCCTGC CCGCACCTATCGAGAAGACTATTTCTAAAGCCAAGGGCCAGCCTAGG GAACCACAGGTGTACGTGTACCCTCCAAGCCGCGACGAGCTGACTAA AAACCAGGTCTCCCTGACCTGTCTGGTGAAGGGGTTCTATCCAAGTGA TATCGCTGTGGAGTGGGAATCAAATGGACAGCCCGAGAACAATTACA AGACTACCCCCCCTGTGCTGGACTCAGATGGGAGCTTCGCCCTGGTGT CCAAACTGACCGTGGATAAGTCTCGGTGGCAGCAGGGAAATGTCTTT TCCTGTTCTGTGATGCACGAAGCACTGCACAATCACTACACCCAGAAG TCCCTGAGCCTGTCACCCGGCAAA |
| 50 | DNA | CAGGTCCAGCTGCAGCAGCCCGGAGCTGAACTGGTCAAACCTGGCGC ATCCGTGAAAATGTCTTGCAAGGCTAGTGGCTACACATTCACTTCCTAT AACATGCACTGGGTGAAGCAGACACCAGGACGAGGACTGGAGTGGA TCGGAGCAATCTACCCTGGAAACGGCGACACTTCTTATAATCAGAAGT TTAAAGGCAAGGCCACCCTGACAGCTGATAAGAGCTCCTCTACCGCCT ACATGCAGCTGAGTTCACTGACAAGTGAAGACTCAGCAGTGTACTATT GCGCCAGAAGCACCTACTATGGCGGGGATTGGTACTTCAACGTGTGG GGGGCAGGAACCACAGTCACCGTGAGCGCCGCTTCCACAAAAGGACC AAGCGTGTTTCCACTGGCACCAAGCTCCAAGTCAACCAGCGGAGGAA CAGCAGCCCTGGGATGTCTGGTGAAGGACTACTTCCCAGAGCCCGTC ACCGTGTCTTGGAACAGTGGCGCCCTGACAAGCGGGGTCCATACTTTT CCCGCTGTGCTGCAGTCTAGTGGCCTGTACAGCCTGTCAAGCGTGGTC ACCGTCCCTTCCTCTAGTCTGGGGACTCAGACCTATATCTGCAACGTG AATCACAAACCTTCTAATACAAAGGTCGACAAGAAAGTGGAACCAAA AAGTTGTGATAAGACACATACTTGCCCACCTTGTCCTGCACCAAAGAG AAGAGGAGGACCATCCGTGTTCCTGTTTCCACCCAAACCCAAGGACAC TCTGATGATTAGCCGGACTCCTGAAGTCACCTGCGTGGTCGTGGACGT GAGCCACAAGGACCCCGAAGTCAAATTCAACTGGTACGTGGATGGCG TCGAGGTGCATAATGCCAAAACAAAGCCCCGGGAGGAACAGTACAAC TCAACATATAGAGTCGTGAGCGTCCTGACTGTGCTGCACCAGGACTG GCTGAACGGCAAGGAGTATAAATGCAAGGTGTCCAACAAGGCCCTGC CCGCACCTATCGAGAAGACTATTTCTAAAGCCAAGGGCCAGCCTAGG GAACCACAGGTGTACGTGCTGCCTCCAAGCCGCGACGAGCTGACTAA AAACCAGGTCTCCCTGCTGTGTCTGGTGAAGGGGTTCTATCCAAGTGA TATCGCTGTGGAGTGGGAATCAAATGGACAGCCCGAGAACAATTACC TGACTTGGCCCCCTGTGCTGGACTCAGATGGGAGCTTCTTTCTGTATTC CAAACTGACCGTGGATAAGTCTCGGTGGCAGCAGGGAAATGTCTTTT CCTGTTCTGTGATGCACGAAGCACTGCACAATCACTACACCCAGAAGT CCCTGAGCCTGTCACCCGGCAAA |
| 52 | DNA | CAGGTCCAGCTGCAGCAGCCCGGAGCTGAACTGGTCAAACCTGGCGC ATCCGTGAAAATGTCTTGCAAGGCTAGTGGCTACACATTCACTTCCTAT AACATGCACTGGGTGAAGCAGACACCAGGACGAGGACTGGAGTGGA TCGGAGCAATCTACCCTGGAAACGGCGACACTTCTTATAATCAGAAGT TTAAAGGCAAGGCCACCCTGACAGCTGATAAGAGCTCCTCTACCGCCT ACATGCAGCTGAGTTCACTGACAAGTGAAGACTCAGCAGTGTACTATT GCGCCAGAAGCACCTACTATGGCGGGGATTGGTACTTCAACGTGTGG |

FIG. 8U

| | | |
|---|---|---|
| | | GGGGCAGGAACCACAGTCACCGTGAGCGCCGCTTCCACAAAAGGACC AAGCGTGTTTCCACTGGCACCAAGCTCCAAGTCAACCAGCGGAGGAA CAGCAGCCCTGGGATGTCTGGTGAAGGACTACTTCCCAGAGCCCGTC ACCGTGTCTTGGAACAGTGGCGCCCTGACAAGCGGGGTCCATACTTTT CCCGCTGTGCTGCAGTCTAGTGGCCTGTACAGCCTGTCAAGCGTGGTC ACCGTCCCTTCCTCTAGTCTGGGGACTCAGACCTATATCTGCAACGTG AATCACAAACCTTCTAATACAAAGGTCGACAAGAAAGTGGAACCAAA AAGTTGTGATAAGACACATACTTGCCCACCTTGTCCTGCACCAGAGGA CGAGGGAGGACCATCCGTGTTCCTGTTTCCACCCAAACCCAAGGACAC TCTGATGATTAGCCGGACTCCTGAAGTCACCTGCGTGGTCGTGGACGT GAGCCACGAGGACCCCGAAGTCAAATTCAACTGGTACGTGGATGGCG TCGAGGTGCATAATGCCAAAACAAAGCCCCGGGAGGAACAGTACAAC TCAACATATAGAGTCGTGAGCGTCCTGACTGTGCTGCACCAGGACTG GCTGAACGGCAAGGAGTATAAATGCGCCGTGTCCAACAAGGCCCTGC CCGCACCTATCGAGAAGACTATTTCTAAAGCCAAGGGCCAGCCTAGG GAACCACAGGTGTACGTGTACCCTCCAAGCCGCGACGAGCTGACTAA AAACCAGGTCTCCCTGACCTGTCTGGTGAAGGGGTTCTATCCAAGTGA TATCGCTGTGGAGTGGGAATCAAATGGACAGCCCGAGAACAATTACA AGACTACCCCCCCTGTGCTGGACTCAGATGGGAGCTTCGCCCTGGTGT CCAAACTGACCGTGGATAAGTCTCGGTGGCAGCAGGGAAATGTCTTT TCCTGTTCTGTGATGCACGAAGCACTGCACAATCACTACACCCAGAAG TCCCTGAGCCTGTCACCCGGCAAA |
| 54 | DNA | CAGGTCCAGCTGCAGCAGCCCGGAGCTGAACTGGTCAAACCTGGCGC ATCCGTGAAAATGTCTTGCAAGGCTAGTGGCTACACATTCACTTCCTAT AACATGCACTGGGTGAAGCAGACACCAGGACGAGGACTGGAGTGGA TCGGAGCAATCTACCCTGGAAACGGCGACACTTCTTATAATCAGAAGT TTAAAGGCAAGGCCACCCTGACAGCTGATAAGAGCTCCTCTACCGCCT ACATGCAGCTGAGTTCACTGACAAGTGAAGACTCAGCAGTGTACTATT GCGCCAGAAGCACCTACTATGGCGGGGATTGGTACTTCAACGTGTGG GGGGCAGGAACCACAGTCACCGTGAGCGCCGCTTCCACAAAAGGACC AAGCGTGTTTCCACTGGCACCAAGCTCCAAGTCAACCAGCGGAGGAA CAGCAGCCCTGGGATGTCTGGTGAAGGACTACTTCCCAGAGCCCGTC ACCGTGTCTTGGAACAGTGGCGCCCTGACAAGCGGGGTCCATACTTTT CCCGCTGTGCTGCAGTCTAGTGGCCTGTACAGCCTGTCAAGCGTGGTC ACCGTCCCTTCCTCTAGTCTGGGGACTCAGACCTATATCTGCAACGTG AATCACAAACCTTCTAATACAAAGGTCGACAAGAAAGTGGAACCAAA AAGTTGTGATAAGACACATACTTGCCCACCTTGTCCTGCACCAAAGAG AAGAGGAGGACCATCCGTGTTCCTGTTTCCACCCAAACCCAAGGACAC TCTGATGATTAGCCGGACTCCTGAAGTCACCTGCGTGGTCGTGGACGT GAGCCACGAGGACCCCGAAGTCAAATTCAACTGGTACGTGGATGGCG TCGAGGTGCATAATGCCAAAACAAAGCCCCGGGAGGAACAGTACAAC TCAACATATAGAGTCGTGAGCGTCCTGACTGTGCTGCACCAGGACTG GCTGAACGGCAAGGAGTATAAATGCGCCGTGTCCAACAAGGCCCTGC CCGCACCTATCGAGAAGACTATTTCTAAAGCCAAGGGCCAGCCTAGG GAACCACAGGTGTACGTGCTGCCTCCAAGCCGCGACGAGCTGACTAA AAACCAGGTCTCCCTGCTGTGTCTGGTGAAGGGGTTCTATCCAAGTGA TATCGCTGTGGAGTGGGAATCAAATGGACAGCCCGAGAACAATTACC |

FIG. 8V

| | | |
|---|---|---|
| | | TGACTTGGCCCCCTGTGCTGGACTCAGATGGGAGCTTCTTTCTGTATTC CAAACTGACCGTGGATAAGTCTCGGTGGCAGCAGGGAAATGTCTTTT CCTGTTCTGTGATGCACGAAGCACTGCACAATCACTACACCCAGAAGT CCCTGAGCCTGTCACCCGGCAAA |
| 56 | DNA | CAGGTCCAGCTGCAGCAGCCCGGAGCTGAACTGGTCAAACCTGGCGC ATCCGTGAAAATGTCTTGCAAGGCTAGTGGCTACACATTCACTTCCTAT AACATGCACTGGGTGAAGCAGACACCAGGACGAGGACTGGAGTGGA TCGGAGCAATCTACCCTGGAAACGGCGACACTTCTTATAATCAGAAGT TTAAAGGCAAGGCCACCCTGACAGCTGATAAGAGCTCCTCTACCGCCT ACATGCAGCTGAGTTCACTGACAAGTGAAGACTCAGCAGTGTACTATT GCGCCAGAAGCACCTACTATGGCGGGGATTGGTACTTCAACGTGTGG GGGGCAGGAACCACAGTCACCGTGAGCGCCGCTTCCACAAAAGGACC AAGCGTGTTTCCACTGGCACCAAGCTCCAAGTCAACCAGCGGAGGAA CAGCAGCCCTGGGATGTCTGGTGAAGGACTACTTCCCAGAGCCCGTC ACCGTGTCTTGGAACAGTGGCGCCCTGACAAGCGGGGTCCATACTTTT CCCGCTGTGCTGCAGTCTAGTGGCCTGTACAGCCTGTCAAGCGTGGTC ACCGTCCCTTCCTCTAGTCTGGGGACTCAGACCTATATCTGCAACGTG AATCACAAACCTTCTAATACAAAGGTCGACAAGAAAGTGGAACCAAA AAGTTGTGATAAGACACATACTTGCCCACCTTGTCCTGCACCAGAGGA CGAGGGAGGACCATCCGTGTTCCTGTTTCCACCCAAACCCAAGGACAC TCTGATGATTAGCCGGACTCCTGAAGTCACCTGCGTGGTCGTGGACGT GAGCCACGAGGACCCCGAAGTCAAATTCAACTGGTACGTGGATGGCG TCGAGGTGCATAATGCCAAAACAAAGCCCCGGGAGGAACAGTACAAC TCAACATATAGAGTCGTGAGCGTCCTGACTGTGCTGCACCAGGACTG GCTGAACGGCAAGGAGTATAAATGCAAGGTGTCCAACAAGGCCCTGT GGGCACCTATCGAGAAGACTATTTCTAAAGCCAAGGGCCAGCCTAGG GAACCACAGGTGTACGTGTACCCTCCAAGCCGCGACGAGCTGACTAA AAACCAGGTCTCCCTGACCTGTCTGGTGAAGGGGTTCTATCCAAGTGA TATCGCTGTGGAGTGGGAATCAAATGGACAGCCCGAGAACAATTACA AGACTACCCCCCCTGTGCTGGACTCAGATGGGAGCTTCGCCCTGGTGT CCAAACTGACCGTGGATAAGTCTCGGTGGCAGCAGGGAAATGTCTTT TCCTGTTCTGTGATGCACGAAGCACTGCACAATCACTACACCCAGAAG TCCCTGAGCCTGTCACCCGGCAAA |
| 58 | DNA | CAGGTCCAGCTGCAGCAGCCCGGAGCTGAACTGGTCAAACCTGGCGC ATCCGTGAAAATGTCTTGCAAGGCTAGTGGCTACACATTCACTTCCTAT AACATGCACTGGGTGAAGCAGACACCAGGACGAGGACTGGAGTGGA TCGGAGCAATCTACCCTGGAAACGGCGACACTTCTTATAATCAGAAGT TTAAAGGCAAGGCCACCCTGACAGCTGATAAGAGCTCCTCTACCGCCT ACATGCAGCTGAGTTCACTGACAAGTGAAGACTCAGCAGTGTACTATT GCGCCAGAAGCACCTACTATGGCGGGGATTGGTACTTCAACGTGTGG GGGGCAGGAACCACAGTCACCGTGAGCGCCGCTTCCACAAAAGGACC AAGCGTGTTTCCACTGGCACCAAGCTCCAAGTCAACCAGCGGAGGAA CAGCAGCCCTGGGATGTCTGGTGAAGGACTACTTCCCAGAGCCCGTC ACCGTGTCTTGGAACAGTGGCGCCCTGACAAGCGGGGTCCATACTTTT |

FIG. 8W

| | | |
|---|---|---|
| | | CCCGCTGTGCTGCAGTCTAGTGGCCTGTACAGCCTGTCAAGCGTGGTC<br>ACCGTCCCTTCCTCTAGTCTGGGGACTCAGACCTATATCTGCAACGTG<br>AATCACAAACCTTCTAATACAAAGGTCGACAAGAAAGTGGAACCAAA<br>AAGTTGTGATAAGACACATACTTGCCCACCTTGTCCTGCACCAAAGAG<br>AAGAGGAGGACCATCCGTGTTCCTGTTTCCACCCAAACCCAAGGACAC<br>TCTGATGATTAGCCGGACTCCTGAAGTCACCTGCGTGGTCGTGGACGT<br>GAGCCACGAGGACCCCGAAGTCAAATTCAACTGGTACGTGGATGGCG<br>TCGAGGTGCATAATGCCAAAACAAAGCCCCGGGAGGAACAGTACAAC<br>TCAACATATAGAGTCGTGAGCGTCCTGACTGTGCTGCACCAGGACTG<br>GCTGAACGGCAAGGAGTATAAATGCAAGGTGTCCAACAAGGCCCTGT<br>GGGCACCTATCGAGAAGACTATTTCTAAAGCCAAGGGCCAGCCTAGG<br>GAACCACAGGTGTACGTGCTGCCTCCAAGCCGCGACGAGCTGACTAA<br>AAACCAGGTCTCCCTGCTGTGTCTGGTGAAGGGGTTCTATCCAAGTGA<br>TATCGCTGTGGAGTGGGAATCAAATGGACAGCCCGAGAACAATTACC<br>TGACTTGGCCCCCTGTGCTGGACTCAGATGGGAGCTTCTTTCTGTATTC<br>CAAACTGACCGTGGATAAGTCTCGGTGGCAGCAGGGAAATGTCTTTT<br>CCTGTTCTGTGATGCACGAAGCACTGCACAATCACTACACCCAGAAGT<br>CCCTGAGCCTGTCACCCGGCAAA |
| 60 | DNA | CAGGTCCAGCTGCAGCAGCCCGGAGCTGAACTGGTCAAACCTGGCGC<br>ATCCGTGAAAATGTCTTGCAAGGCTAGTGGCTACACATTCACTTCCTAT<br>AACATGCACTGGGTGAAGCAGACACCAGGACGAGGACTGGAGTGGA<br>TCGGAGCAATCTACCCTGGAAACGGCGACACTTCTTATAATCAGAAGT<br>TTAAAGGCAAGGCCACCCTGACAGCTGATAAGAGCTCCTCTACCGCCT<br>ACATGCAGCTGAGTTCACTGACAAGTGAAGACTCAGCAGTGTACTATT<br>GCGCCAGAAGCACCTACTATGGCGGGGATTGGTACTTCAACGTGTGG<br>GGGGCAGGAACCACAGTCACCGTGAGCGCCGCTTCCACAAAAGGACC<br>AAGCGTGTTTCCACTGGCACCAAGCTCCAAGTCAACCAGCGGAGGAA<br>CAGCAGCCCTGGGATGTCTGGTGAAGGACTACTTCCCAGAGCCCGTC<br>ACCGTGTCTTGGAACAGTGGCGCCCTGACAAGCGGGGTCCATACTTTT<br>CCCGCTGTGCTGCAGTCTAGTGGCCTGTACAGCCTGTCAAGCGTGGTC<br>ACCGTCCCTTCCTCTAGTCTGGGGACTCAGACCTATATCTGCAACGTG<br>AATCACAAACCTTCTAATACAAAGGTCGACAAGAAAGTGGAACCAAA<br>AAGTTGTGATAAGACACATACTTGCCCACCTTGTCCTGCACCAGAGGA<br>CGAGGGAGGACCATCCGTGTTCCTGTTTCCACCCAAACCCAAGGACAC<br>TCTGATGATTAGCCGGACTCCTGAAGTCACCTGCGTGGTCGTGAGCGT<br>GAGCCACAAGGACCCCGAAGTCAAATTCAACTGGTACGTGGATGGCG<br>TCGAGGTGCATAATGCCAAAACAAAGCCCCGGGAGGAACAGTACAAC<br>TCAACATATAGAGTCGTGAGCGTCCTGACTGTGCTGCACCAGGACTG<br>GCTGAACGGCAAGGAGTATAAATGCGCCGTGTCCAACAAGGCCCTGC<br>CCGCACCTATCGAGAAGACTATTTCTAAAGCCAAGGGCCAGCCTAGG<br>GAACCACAGGTGTACGTGTACCCTCCAAGCCGCGACGAGCTGACTAA<br>AAACCAGGTCTCCCTGACCTGTCTGGTGAAGGGGTTCTATCCAAGTGA<br>TATCGCTGTGGAGTGGGAATCAAATGGACAGCCCGAGAACAATTACA<br>AGACTACCCCCCCTGTGCTGGACTCAGATGGGAGCTTCGCCCTGGTGT<br>CCAAACTGACCGTGGATAAGTCTCGGTGGCAGCAGGGAAATGTCTTT<br>TCCTGTTCTGTGATGCACGAAGCACTGCACAATCACTACACCCAGAAG<br>TCCCTGAGCCTGTCACCCGGCAAA |

FIG. 8X

| 62 | DNA | CAGGTCCAGCTGCAGCAGCCCGGAGCTGAACTGGTCAAACCTGGCGC<br>ATCCGTGAAAATGTCTTGCAAGGCTAGTGGCTACACATTCACTTCCTAT<br>AACATGCACTGGGTGAAGCAGACACCAGGACGAGGACTGGAGTGGA<br>TCGGAGCAATCTACCCTGGAAACGGCGACACTTCTTATAATCAGAAGT<br>TTAAAGGCAAGGCCACCCTGACAGCTGATAAGAGCTCCTCTACCGCCT<br>ACATGCAGCTGAGTTCACTGACAAGTGAAGACTCAGCAGTGTACTATT<br>GCGCCAGAAGCACCTACTATGGCGGGGATTGGTACTTCAACGTGTGG<br>GGGGCAGGAACCACAGTCACCGTGAGCGCCGCTTCCACAAAAGGACC<br>AAGCGTGTTTCCACTGGCACCAAGCTCCAAGTCAACCAGCGGAGGAA<br>CAGCAGCCCTGGGATGTCTGGTGAAGGACTACTTCCCAGAGCCCGTC<br>ACCGTGTCTTGGAACAGTGGCGCCCTGACAAGCGGGGTCCATACTTTT<br>CCCGCTGTGCTGCAGTCTAGTGGCCTGTACAGCCTGTCAAGCGTGGTC<br>ACCGTCCCTTCCTCTAGTCTGGGGACTCAGACCTATATCTGCAACGTG<br>AATCACAAACCTTCTAATACAAAGGTCGACAAGAAAGTGGAACCAAA<br>AAGTTGTGATAAGACACATACTTGCCCACCTTGTCCTGCACCAAAGAG<br>AAGAGGAGGACCATCCGTGTTCCTGTTTCCACCCAAACCCAAGGACAC<br>TCTGATGATTAGCCGGACTCCTGAAGTCACCTGCGTGGTCGTGAGCGT<br>GAGCCACAAGGACCCCGAAGTCAAATTCAACTGGTACGTGGATGGCG<br>TCGAGGTGCATAATGCCAAAACAAAGCCCCGGGAGGAACAGTACAAC<br>TCAACATATAGAGTCGTGAGCGTCCTGACTGTGCTGCACCAGGACTG<br>GCTGAACGGCAAGGAGTATAAATGCGCCGTGTCCAACAAGGCCCTGC<br>CCGCACCTATCGAGAAGACTATTTCTAAAGCCAAGGGCCAGCCTAGG<br>GAACCACAGGTGTACGTGCTGCCTCCAAGCCGCGACGAGCTGACTAA<br>AAACCAGGTCTCCCTGCTGTGTCTGGTGAAGGGGTTCTATCCAAGTGA<br>TATCGCTGTGGAGTGGGAATCAAATGGACAGCCCGAGAACAATTACC<br>TGACTTGGCCCCCTGTGCTGGACTCAGATGGGAGCTTCTTTCTGTATTC<br>CAAACTGACCGTGGATAAGTCTCGGTGGCAGCAGGGAAATGTCTTTT<br>CCTGTTCTGTGATGCACGAAGCACTGCACAATCACTACACCCAGAAGT<br>CCCTGAGCCTGTCACCCGGCAAA |
|---|---|---|
| 64 | DNA | CAGGTCCAGCTGCAGCAGCCCGGAGCTGAACTGGTCAAACCTGGCGC<br>ATCCGTGAAAATGTCTTGCAAGGCTAGTGGCTACACATTCACTTCCTAT<br>AACATGCACTGGGTGAAGCAGACACCAGGACGAGGACTGGAGTGGA<br>TCGGAGCAATCTACCCTGGAAACGGCGACACTTCTTATAATCAGAAGT<br>TTAAAGGCAAGGCCACCCTGACAGCTGATAAGAGCTCCTCTACCGCCT<br>ACATGCAGCTGAGTTCACTGACAAGTGAAGACTCAGCAGTGTACTATT<br>GCGCCAGAAGCACCTACTATGGCGGGGATTGGTACTTCAACGTGTGG<br>GGGGCAGGAACCACAGTCACCGTGAGCGCCGCTTCCACAAAAGGACC<br>AAGCGTGTTTCCACTGGCACCAAGCTCCAAGTCAACCAGCGGAGGAA<br>CAGCAGCCCTGGGATGTCTGGTGAAGGACTACTTCCCAGAGCCCGTC<br>ACCGTGTCTTGGAACAGTGGCGCCCTGACAAGCGGGGTCCATACTTTT<br>CCCGCTGTGCTGCAGTCTAGTGGCCTGTACAGCCTGTCAAGCGTGGTC<br>ACCGTCCCTTCCTCTAGTCTGGGGACTCAGACCTATATCTGCAACGTG<br>AATCACAAACCTTCTAATACAAAGGTCGACAAGAAAGTGGAACCAAA<br>AAGTTGTGATAAGACACATACTTGCCCACCTTGTCCTGCACCAGAGGA<br>CGAGGGAGGACCATCCGTGTTCCTGTTTCCACCCAAACCCAAGGACAC<br>TCTGATGATTAGCCGGACTCCTGAAGTCACCTGCGTGGTCGTGAGCGT<br>GAGCCACAAGGACCCCGAAGTCAAATTCAACTGGTACGTGGATGGCG |

FIG. 8Y

| | | |
|---|---|---|
| | | TCGAGGTGCATAATGCCAAAACAAAGCCCCGGGAGGAACAGTACAAC<br>TCAACATATAGAGTCGTGAGCGTCCTGACTGTGCTGCACCAGGACTG<br>GCTGAACGGCAAGGAGTATAAATGCGAGGTGTCCAACAAGGCCCTGC<br>CCGCACCTATCAAGAAGACTATTTCTAAAGCCAAGGGCCAGCCTAGG<br>GAACCACAGGTGTACGTGTACCCTCCAAGCCGCGACGAGCTGACTAA<br>AAACCAGGTCTCCCTGACCTGTCTGGTGAAGGGGTTCTATCCAAGTGA<br>TATCGCTGTGGAGTGGGAATCAAATGGACAGCCCGAGAACAATTACA<br>AGACTACCCCCCCTGTGCTGGACTCAGATGGGAGCTTCGCCCTGGTGT<br>CCAAACTGACCGTGGATAAGTCTCGGTGGCAGCAGGGAAATGTCTTT<br>TCCTGTTCTGTGATGCACGAAGCACTGCACAATCACTACACCCAGAAG<br>TCCCTGAGCCTGTCACCCGGCAAA |
| 66 | DNA | CAGGTCCAGCTGCAGCAGCCCGGAGCTGAACTGGTCAAACCTGGCGC<br>ATCCGTGAAAATGTCTTGCAAGGCTAGTGGCTACACATTCACTTCCTAT<br>AACATGCACTGGGTGAAGCAGACACCAGGACGAGGACTGGAGTGGA<br>TCGGAGCAATCTACCCTGGAAACGGCGACACTTCTTATAATCAGAAGT<br>TTAAAGGCAAGGCCACCCTGACAGCTGATAAGAGCTCCTCTACCGCCT<br>ACATGCAGCTGAGTTCACTGACAAGTGAAGACTCAGCAGTGTACTATT<br>GCGCCAGAAGCACCTACTATGGCGGGGATTGGTACTTCAACGTGTGG<br>GGGGCAGGAACCACAGTCACCGTGAGCGCCGCTTCCACAAAAGGACC<br>AAGCGTGTTTCCACTGGCACCAAGCTCCAAGTCAACCAGCGGAGGAA<br>CAGCAGCCCTGGGATGTCTGGTGAAGGACTACTTCCCAGAGCCCGTC<br>ACCGTGTCTTGGAACAGTGGCGCCCTGACAAGCGGGGTCCATACTTTT<br>CCCGCTGTGCTGCAGTCTAGTGGCCTGTACAGCCTGTCAAGCGTGGTC<br>ACCGTCCCTTCCTCTAGTCTGGGGACTCAGACCTATATCTGCAACGTG<br>AATCACAAACCTTCTAATACAAAGGTCGACAAGAAAGTGGAACCAAA<br>AAGTTGTGATAAGACACATACTTGCCCACCTTGTCCTGCACCAAAGAG<br>AAGAGGAGGACCATCCGTGTTCCTGTTTCCACCCAAACCCAAGGACAC<br>TCTGATGATTAGCCGGACTCCTGAAGTCACCTGCGTGGTCGTGAGCGT<br>GAGCCACAAGGACCCCGAAGTCAAATTCAACTGGTACGTGGATGGCG<br>TCGAGGTGCATAATGCCAAAACAAAGCCCCGGGAGGAACAGTACAAC<br>TCAACATATAGAGTCGTGAGCGTCCTGACTGTGCTGCACCAGGACTG<br>GCTGAACGGCAAGGAGTATAAATGCGAGGTGTCCAACAAGGCCCTGC<br>CCGCACCTATCAAGAAGACTATTTCTAAAGCCAAGGGCCAGCCTAGG<br>GAACCACAGGTGTACGTGCTGCCTCCAAGCCGCGACGAGCTGACTAA<br>AAACCAGGTCTCCCTGCTGTGTCTGGTGAAGGGGTTCTATCCAAGTGA<br>TATCGCTGTGGAGTGGGAATCAAATGGACAGCCCGAGAACAATTACC<br>TGACTTGGCCCCCTGTGCTGGACTCAGATGGGAGCTTCTTTCTGTATTC<br>CAAACTGACCGTGGATAAGTCTCGGTGGCAGCAGGGAAATGTCTTTT<br>CCTGTTCTGTGATGCACGAAGCACTGCACAATCACTACACCCAGAAGT<br>CCCTGAGCCTGTCACCCGGCAAA |
| 69 | DNA | CAGATTGTCCTGTCTCAGAGTCCCGCTATCCTGTCAGCAAGCCCTGGG<br>GAGAAGGTGACCATGACATGCCGAGCCAGCTCCTCTGTCAGCTACATC<br>CACTGGTTCCAGCAGAAGCCAGGCAGTTCACCTAAACCATGGATCTAC<br>GCCACATCTAACCTGGCTAGTGGAGTGCCCGTCCGGTTTTCCGGCTCT<br>GGGAGTGGAACATCATACAGCCTGACTATTTCCAGAGTGGAGGCCGA<br>AGACGCCGCTACCTACTATTGCCAGCAGTGGACCTCTAATCCCCCTAC<br>ATTCGGCGGGGGAACTAAGCTGGAGATCAAAAGGACTGTGGCAGCC |

FIG. 8Z

| | | |
|---|---|---|
| | | CCTTCTGTCTTCATTTTTCCACCCAGTGACGAACAGCTGAAATCAGGAACCGCTTCCGTGGTCTGTCTGCTGAACAACTTCTACCCCCGCGAGGCAAAGGTGCAGTGGAAAGTCGATAACGCCCTGCAGTCCGGCAATTCTCAGGAGAGTGTGACCGAACAGGACTCAAAGGATAGCACATATTCCCTGAGCTCCACTCTGACCCTGTCCAAAGCTGATTACGAAAAGCATAAAGTGTATGCATGTGAGGTCACCCACCAGGGGCTGAGTAGTCCCGTCACAAAGAGTTTCAATAGAGGAGAGTGT |

FIG. 8AA

SEQUENCE LISTING

```
<160> NUMBER OF SEQ ID NOS: 81

<210> SEQ ID NO 1
<211> LENGTH: 232
<212> TYPE: PRT
<213> ORGANISM: Homo sapiens

<400> SEQUENCE: 1

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

```
Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 2
<211> LENGTH: 450
<212> TYPE: PRT
<213> ORGANISM: Artificial Sequence
<220> FEATURE:
<223> OTHER INFORMATION: synthetic monoclonal antibody sequence -
      trastuzumab heavy chain

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
```

```
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 3
<211> LENGTH: 214
<212> TYPE: PRT
<213> ORGANISM: Artificial Sequence
<220> FEATURE:
<223> OTHER INFORMATION: synthetic monoclonal antibody sequence -
      trastuzumab light chain

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 4
<211> LENGTH: 451
<212> TYPE: PRT
<213> ORGANISM: Artificial Sequence
<220> FEATURE:
<223> OTHER INFORMATION: synthetic monoclonal antibody sequence -
      Rituximab+Heavy chain

<400> SEQUENCE: 4

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365
```

```
Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 5
<211> LENGTH: 213
<212> TYPE: PRT
<213> ORGANISM: Artificial Sequence
<220> FEATURE:
<223> OTHER INFORMATION: synthetic monoclonal antibody sequence -
      Rituximab+Light chain

<400> SEQUENCE: 5

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210


<210> SEQ ID NO 6
<211> LENGTH: 450
<212> TYPE: PRT
<213> ORGANISM: Artificial Sequence
<220> FEATURE:
<223> OTHER INFORMATION: synthetic monoclonal antibody polypeptide
```

sequence - variant

<400> SEQUENCE: 6

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Tyr Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Glu Asp Gly Ser Phe Ala Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 7
<211> LENGTH: 1350
<212> TYPE: DNA
<213> ORGANISM: Artificial Sequence
<220> FEATURE:
<223> OTHER INFORMATION: synthetic monoclonal antibody nucleotide
      sequence - variant

<400> SEQUENCE: 7

gaggtgcagc tggtggaaag cggaggagga ctggtgcagc caggaggatc tctgcgactg      60

agttgcgccg cttcaggatt caacatcaag gacacctaca ttcactgggt gcgacaggct     120

ccaggaaaag gactggagtg ggtggctcga atctatccca ctaatggata cacccggtat     180

gccgactccg tgaaggggag gtttactatt agcgccgata catccaaaaa cactgcttac     240

ctgcagatga acagcctgcg agccgaagat accgctgtgt actattgcag tcgatgggga     300

ggagacggat tctacgctat ggattattgg ggacagggga ccctggtgac agtgagctcc     360

gcctctacca agggccccag tgtgtttccc ctggctcctt ctagtaaatc cacctctgga     420

gggacagccg ctctgggatg tctggtgaag gactatttcc ccgagcctgt gaccgtgagt     480

tggaactcag gcgccctgac aagcggagtg cacacttttc ctgctgtgct gcagtcaagc     540

gggctgtact ccctgtcctc tgtggtgaca gtgccaagtt caagcctggg cacacagact     600

tatatctgca acgtgaatca taagccctca aatacaaaag tggacaagaa agtggagccc     660

aagagctgtg ataagaccca cacctgccct ccctgtccag ctccagaagc cgccggagga     720

cctagcgtgt tcctgtttcc ccctaagcca aaagacactc tgatgatttc caggactccc     780

gaggtgacct gcgtggtggt ggacgtgtct cacgaggacc ccgaagtgaa gttcaactgg     840

tacgtggatg gcgtggaagt gcataatgct aagacaaaac caagagagga acagtacaac     900

tccacttatc gcgtcgtgag cgtgctgacc gtgctgcacc aggactggct gaacgggaag     960

gagtataagt gcaaagtcag taataaggcc ctgcctgctc caatcgaaaa aaccatctct    1020

aaggccaaag gccagccaag ggagccccag gtgtacgtgt acccacccag cagagacgaa    1080

ctgaccaaga accaggtgtc cctgacatgt ctggtgaaag gcttctatcc tagtgatatt    1140

gctgtggagt gggaatcaaa tggacagcca gagaacaatt acaagaccac acctccagtg    1200

ctggacgagg atggcagctt cgccctggtg tccaagctga cagtggataa atctcgatgg    1260

cagcagggga acgtgtttag ttgttcagtg atgcatgaag ccctgcacaa tcattacact    1320

cagaagagcc tgtccctgtc tcccggcaaa                                     1350


<210> SEQ ID NO 8
<211> LENGTH: 450
<212> TYPE: PRT
<213> ORGANISM: Artificial Sequence
<220> FEATURE:
<223> OTHER INFORMATION: synthetic monoclonal antibody polypeptide
      sequence - variant

<400> SEQUENCE: 8
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Leu Pro Pro Ser Arg Asp Glu Leu Thr Lys Asn Gln Val Ser Leu
        355                 360                 365

Leu Cys Leu Val Lys Gly Phe Tyr Pro Ser Asp Ile Ala Val Glu Trp
    370                 375                 380

Glu Ser Asn Gly Gln Pro Glu Asn Arg Tyr Met Thr Trp Pro Pro Val
385                 390                 395                 400

Leu Asp Ser Asp Gly Ser Phe Phe Leu Tyr Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 9
<211> LENGTH: 1350
<212> TYPE: DNA
<213> ORGANISM: Artificial Sequence
<220> FEATURE:
<223> OTHER INFORMATION: synthetic monoclonal antibody nucleotide
      sequence - variant

<400> SEQUENCE: 9

gaggtgcagc tggtggaaag cggaggagga ctggtgcagc caggaggatc tctgcgactg     60

agttgcgccg cttcaggatt caacatcaag gacacctaca ttcactgggt gcgacaggct    120

ccaggaaaag gactggagtg ggtggctcga atctatccca ctaatggata cacccggtat    180

gccgactccg tgaaggggag gtttactatt agcgccgata catccaaaaa cactgcttac    240

ctgcagatga acagcctgcg agccgaagat accgctgtgt actattgcag tcgatgggga    300

ggagacggat tctacgctat ggattattgg ggacagggga ccctggtgac agtgagctcc    360

gcctctacca agggccccag tgtgtttccc ctggctcctt ctagtaaatc cacctctgga    420

gggacagccg ctctgggatg tctggtgaag gactatttcc ccgagcctgt gaccgtgagt    480

tggaactcag gcgccctgac aagcggagtg cacacttttc ctgctgtgct gcagtcaagc    540

gggctgtact ccctgtcctc tgtggtgaca gtgccaagtt caagcctggg cacacagact    600

tatatctgca acgtgaatca taagccctca aatacaaaag tggacaagaa agtggagccc    660

aagagctgtg ataagaccca cacctgccct ccctgtccag ctccagaagc cgccggagga    720

cctagcgtgt tcctgtttcc ccctaagcca aaagacactc tgatgatttc caggactccc    780

gaggtgacct gcgtggtggt ggacgtgtct cacgaggacc ccgaagtgaa gttcaactgg    840

tacgtggatg gcgtggaagt gcataatgct aagacaaaac caagagagga acagtacaac    900

tccacttatc gcgtcgtgag cgtgctgacc gtgctgcacc aggactggct gaacgggaag    960

gagtataagt gcaaagtcag taataaggcc ctgcctgctc caatcgaaaa aaccatctct   1020

aaggccaaag gccagccaag ggagccccag gtgtacgtgc tgccacccag cagagacgaa   1080

ctgaccaaga accaggtgtc cctgctgtgt ctggtgaaag gcttctatcc tagtgatatt   1140

gctgtggagt gggaatcaaa tggacagcca gagaacagat acatgacctg gcctccagtg   1200

ctggacagcg atggcagctt cttcctgtat tccaagctga cagtggataa atctcgatgg   1260

cagcagggga acgtgtttag ttgttcagtg atgcatgaag ccctgcacaa tcattacact   1320

cagaagagcc tgtccctgtc tcccggcaaa                                     1350


<210> SEQ ID NO 10
<211> LENGTH: 450
<212> TYPE: PRT
<213> ORGANISM: Artificial Sequence
<220> FEATURE:
<223> OTHER INFORMATION: synthetic monoclonal antibody polypeptide
      sequence - variant

<400> SEQUENCE: 10

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Asp Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Tyr Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Glu Asp Gly Ser Phe Ala Leu Val Ser Lys Leu Thr Val Asp
                405                 410                 415

Lys Ser Arg Trp Gln Gln Gly Asn Val Phe Ser Cys Ser Val Met His
            420                 425                 430
```

```
Glu Ala Leu His Asn His Tyr Thr Gln Lys Ser Leu Ser Leu Ser Pro
        435                 440                 445

Gly Lys
    450


<210> SEQ ID NO 11
<211> LENGTH: 1350
<212> TYPE: DNA
<213> ORGANISM: Artificial Sequence
<220> FEATURE:
<223> OTHER INFORMATION: synthetic monoclonal antibody nucleotide
      sequence - variant

<400> SEQUENCE: 11

gaggtgcagc tggtggaaag cggaggagga ctggtgcagc caggaggatc tctgcgactg     60

agttgcgccg cttcaggatt caacatcaag gacacctaca ttcactgggt gcgacaggct    120

ccaggaaaag gactggagtg ggtggctcga atctatccca ctaatggata cacccggtat    180

gccgactccg tgaaggggag gtttactatt agcgccgata catccaaaaa cactgcttac    240

ctgcagatga acagcctgcg agccgaagat accgctgtgt actattgcag tcgatgggga    300

ggagacggat tctacgctat ggattattgg ggacagggga ccctggtgac agtgagctcc    360

gcctctacca agggccccag tgtgtttccc ctggctcctt ctagtaaatc cacctctgga    420

gggacagccg ctctgggatg tctggtgaag gactatttcc ccgagcctgt gaccgtgagt    480

tggaactcag gcgccctgac aagcggagtg cacacttttc ctgctgtgct gcagtcaagc    540

gggctgtact ccctgtcctc tgtggtgaca gtgccaagtt caagcctggg cacacagact    600

tatatctgca acgtgaatca taagccctca aatacaaaag tggacaagaa agtggagccc    660

aagagctgtg ataagaccca cacctgccct ccctgtccag ctccagaaga cgagggagga    720

cctagcgtgt tcctgtttcc ccctaagcca aaagacactc tgatgatttc caggactccc    780

gaggtgacct gcgtggtggt ggacgtgtct cacgaggacc ccgaagtgaa gttcaactgg    840

tacgtggatg gcgtggaagt gcataatgct aagacaaaac caagagagga acagtacaac    900

tccacttatc gcgtcgtgag cgtgctgacc gtgctgcacc aggactggct gaacgggaag    960

gagtataagt gcaaagtcag taataaggcc ctgcctgctc caatcgaaaa aaccatctct   1020

aaggccaaag gccagccaag ggagccccag gtgtacgtgt acccacccag cagagacgaa   1080

ctgaccaaga accaggtgtc cctgacatgt ctggtgaaag gcttctatcc tagtgatatt   1140

gctgtggagt gggaatcaaa tggacagcca gagaacaatt acaagaccac acctccagtg   1200

ctggacgagg atggcagctt cgccctggtg tccaagctga cagtggataa atctcgatgg   1260

cagcagggga acgtgtttag ttgttcagtg atgcatgaag ccctgcacaa tcattacact   1320

cagaagagcc tgtccctgtc tcccggcaaa                                     1350


<210> SEQ ID NO 12
<211> LENGTH: 450
<212> TYPE: PRT
<213> ORGANISM: Artificial Sequence
<220> FEATURE:
<223> OTHER INFORMATION: synthetic monoclonal antibody polypeptide
      sequence - variant

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30
```

```
Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Ala Asp Glu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Tyr Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Glu Asp Gly Ser Phe Ala Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445
```

```
Gly Lys
    450


<210> SEQ ID NO 13
<211> LENGTH: 1350
<212> TYPE: DNA
<213> ORGANISM: Artificial Sequence
<220> FEATURE:
<223> OTHER INFORMATION: synthetic monoclonal antibody nucleotide
      sequence - variant

<400> SEQUENCE: 13

gaggtgcagc tggtggaaag cggaggagga ctggtgcagc caggaggatc tctgcgactg      60

agttgcgccg cttcaggatt caacatcaag gacacctaca ttcactgggt gcgacaggct     120

ccaggaaaag gactggagtg ggtggctcga atctatccca ctaatggata cacccggtat     180

gccgactccg tgaaggggag gtttactatt agcgccgata catccaaaaa cactgcttac     240

ctgcagatga acagcctgcg agccgaagat accgctgtgt actattgcag tcgatgggga     300

ggagacggat tctacgctat ggattattgg ggacagggga ccctggtgac agtgagctcc     360

gcctctacca agggccccag tgtgtttccc ctggctcctt ctagtaaatc cacctctgga     420

gggacagccg ctctgggatg tctggtgaag gactatttcc ccgagcctgt gaccgtgagt     480

tggaactcag gcgccctgac aagcggagtg cacacttttc ctgctgtgct gcagtcaagc     540

gggctgtact ccctgtcctc tgtggtgaca gtgccaagtt caagcctggg cacacagact     600

tatatctgca acgtgaatca taagccctca aatacaaaag tggacaagaa agtggagccc     660

aagagctgtg ataagaccca cacctgccct ccctgtccag ctccagccga cgagggagga     720

cctagcgtgt tcctgtttcc ccctaagcca aaagacactc tgatgatttc caggactccc     780

gaggtgacct gcgtggtggt ggacgtgtct cacgaggacc ccgaagtgaa gttcaactgg     840

tacgtggatg gcgtggaagt gcataatgct aagacaaaac caagagagga acagtacaac     900

tccacttatc gcgtcgtgag cgtgctgacc gtgctgcacc aggactggct gaacgggaag     960

gagtataagt gcaaagtcag taataaggcc ctgcctgctc caatcgaaaa aaccatctct    1020

aaggccaaag gccagccaag ggagccccag gtgtacgtgt acccacccag cagagacgaa    1080

ctgaccaaga accaggtgtc cctgacatgt ctggtgaaag gcttctatcc tagtgatatt    1140

gctgtggagt gggaatcaaa tggacagcca gagaacaatt acaagaccac acctccagtg    1200

ctggacgagg atggcagctt cgccctggtg tccaagctga cagtggataa atctcgatgg    1260

cagcagggga acgtgtttag ttgttcagtg atgcatgaag ccctgcacaa tcattacact    1320

cagaagagcc tgtccctgtc tcccggcaaa                                     1350


<210> SEQ ID NO 14
<211> LENGTH: 450
<212> TYPE: PRT
<213> ORGANISM: Artificial Sequence
<220> FEATURE:
<223> OTHER INFORMATION: synthetic monoclonal antibody polypeptide
      sequence - variant

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45
```

```
Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Ala Lys Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Tyr Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Glu Asp Gly Ser Phe Ala Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 15
<211> LENGTH: 1350
<212> TYPE: DNA
<213> ORGANISM: Artificial Sequence
<220> FEATURE:
<223> OTHER INFORMATION: synthetic monoclonal antibody nucleotide sequence - variant

<400> SEQUENCE: 15

```
gaggtgcagc tggtggaaag cggaggagga ctggtgcagc caggaggatc tctgcgactg     60

agttgcgccg cttcaggatt caacatcaag gacacctaca ttcactgggt gcgacaggct    120

ccaggaaaag gactggagtg ggtggctcga atctatccca ctaatggata cacccggtat    180

gccgactccg tgaaggggag gtttactatt agcgccgata catccaaaaa cactgcttac    240

ctgcagatga acagcctgcg agccgaagat accgctgtgt actattgcag tcgatgggga    300

ggagacggat tctacgctat ggattattgg ggacagggga ccctggtgac agtgagctcc    360

gcctctacca agggccccag tgtgtttccc ctggctcctt ctagtaaatc cacctctgga    420

gggacagccg ctctgggatg tctggtgaag gactatttcc ccgagcctgt gaccgtgagt    480

tggaactcag gcgccctgac aagcggagtg cacacttttc ctgctgtgct gcagtcaagc    540

gggctgtact ccctgtcctc tgtggtgaca gtgccaagtt caagcctggg cacacagact    600

tatatctgca acgtgaatca taagccctca aatacaaaag tggacaagaa agtggagccc    660

aagagctgtg ataagaccca cacctgccct ccctgtccag ctccagccaa ggccggagga    720

cctagcgtgt tcctgtttcc ccctaagcca aaagacactc tgatgatttc caggactccc    780

gaggtgacct gcgtggtggt ggacgtgtct cacgaggacc ccgaagtgaa gttcaactgg    840

tacgtggatg gcgtggaagt gcataatgct aagacaaaac caagagagga acagtacaac    900

tccacttatc gcgtcgtgag cgtgctgacc gtgctgcacc aggactggct gaacgggaag    960

gagtataagt gcaaagtcag taataaggcc ctgcctgctc caatcgaaaa aaccatctct   1020

aaggccaaag gccagccaag ggagccccag gtgtacgtgt acccacccag cagagacgaa   1080

ctgaccaaga accaggtgtc cctgacatgt ctggtgaaag gcttctatcc tagtgatatt   1140

gctgtggagt gggaatcaaa tggacagcca gagaacaatt acaagaccac acctccagtg   1200

ctggacgagg atggcagctt cgccctggtg tccaagctga cagtggataa atctcgatgg   1260

cagcagggga acgtgtttag ttgttcagtg atgcatgaag ccctgcacaa tcattacact   1320

cagaagagcc tgtccctgtc tcccggcaaa                                    1350
```

<210> SEQ ID NO 16
<211> LENGTH: 450
<212> TYPE: PRT
<213> ORGANISM: Artificial Sequence
<220> FEATURE:
<223> OTHER INFORMATION: synthetic monoclonal antibody polypeptide sequence - variant

<400> SEQUENCE: 16

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60
```

```
Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Gln
            260                 265                 270

Asn Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Tyr Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Glu Asp Gly Ser Phe Ala Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 17
<211> LENGTH: 1350

```
<212> TYPE: DNA
<213> ORGANISM: Artificial Sequence
<220> FEATURE:
<223> OTHER INFORMATION: synthetic monoclonal antibody nucleotide
      sequence - variant

<400> SEQUENCE: 17

gaggtgcagc tggtggaaag cggaggagga ctggtgcagc caggaggatc tctgcgactg     60

agttgcgccg cttcaggatt caacatcaag gacacctaca ttcactgggt gcgacaggct    120

ccaggaaaag gactggagtg ggtggctcga atctatccca ctaatggata cacccggtat    180

gccgactccg tgaaggggag gtttactatt agcgccgata catccaaaaa cactgcttac    240

ctgcagatga acagcctgcg agccgaagat accgctgtgt actattgcag tcgatgggga    300

ggagacggat tctacgctat ggattattgg ggacagggga ccctggtgac agtgagctcc    360

gcctctacca agggccccag tgtgtttccc ctggctcctt ctagtaaatc cacctctgga    420

gggacagccg ctctgggatg tctggtgaag gactatttcc ccgagcctgt gaccgtgagt    480

tggaactcag gcgccctgac aagcggagtg cacacttttc ctgctgtgct gcagtcaagc    540

gggctgtact ccctgtcctc tgtggtgaca gtgccaagtt caagcctggg cacacagact    600

tatatctgca acgtgaatca taagccctca aatacaaaag tggacaagaa agtggagccc    660

aagagctgtg ataagaccca cacctgccct ccctgtccag ctccagaact gctgggagga    720

cctagcgtgt tcctgtttcc ccctaagcca aaagacactc tgatgatttc caggactccc    780

gaggtgacct gcgtggtggt ggacgtgtct caccagaacc ccgaagtgaa gttcaactgg    840

tacgtggatg gcgtggaagt gcataatgct aagacaaaac caagagagga acagtacaac    900

tccacttatc gcgtcgtgag cgtgctgacc gtgctgcacc aggactggct gaacgggaag    960

gagtataagt gcaaagtcag taataaggcc ctgcctgctc caatcgaaaa aaccatctct   1020

aaggccaaag gccagccaag ggagccccag gtgtacgtgt acccacccag cagagacgaa   1080

ctgaccaaga accaggtgtc cctgacatgt ctggtgaaag gcttctatcc tagtgatatt   1140

gctgtggagt gggaatcaaa tggacagcca gagaacaatt acaagaccac acctccagtg   1200

ctggacgagg atggcagctt cgccctggtg tccaagctga cagtggataa atctcgatgg   1260

cagcagggga acgtgtttag ttgttcagtg atgcatgaag ccctgcacaa tcattacact   1320

cagaagagcc tgtccctgtc tcccggcaaa                                    1350


<210> SEQ ID NO 18
<211> LENGTH: 450
<212> TYPE: PRT
<213> ORGANISM: Artificial Sequence
<220> FEATURE:
<223> OTHER INFORMATION: synthetic monoclonal antibody polypeptide
      sequence - variant

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80
```

```
Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Tyr Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Glu Asp Gly Ser Phe Ala Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 19
<211> LENGTH: 1350
<212> TYPE: DNA
<213> ORGANISM: Artificial Sequence
<220> FEATURE:

```
<223> OTHER INFORMATION: synthetic monoclonal antibody nucleotide
      sequence - variant

<400> SEQUENCE: 19

gaggtgcagc tggtggaaag cggaggagga ctggtgcagc caggaggatc tctgcgactg      60

agttgcgccg cttcaggatt caacatcaag gacacctaca ttcactgggt gcgacaggct     120

ccaggaaaag gactggagtg ggtggctcga atctatccca ctaatggata cacccggtat     180

gccgactccg tgaaggggag gtttactatt agcgccgata catccaaaaa cactgcttac     240

ctgcagatga acagcctgcg agccgaagat accgctgtgt actattgcag tcgatgggga     300

ggagacggat tctacgctat ggattattgg ggacagggga ccctggtgac agtgagctcc     360

gcctctacca agggccccag tgtgtttccc ctggctcctt ctagtaaatc cacctctgga     420

gggacagccg ctctgggatg tctggtgaag gactatttcc ccgagcctgt gaccgtgagt     480

tggaactcag gcgccctgac aagcggagtg cacacttttc ctgctgtgct gcagtcaagc     540

gggctgtact ccctgtcctc tgtggtgaca gtgccaagtt caagcctggg cacacagact     600

tatatctgca acgtgaatca taagccctca aatacaaaag tggacaagaa agtggagccc     660

aagagctgtg ataagaccca cacctgccct ccctgtccag ctccagaact gctgggagga     720

cctagcgtgt tcctgtttcc ccctaagcca aaagacactc tgatgatttc caggactccc     780

gaggtgacct gcgtggtggt ggacgtgtct cacgaggacc ccgaagtgaa gttcaactgg     840

tacgtggatg gcgtggaagt gcataatgct aagacaaaac caagagagga acagtacaac     900

tccacttatc gcgtcgtgag cgtgctgacc gtgctgcacc aggactggct gaacgggaag     960

gagtataagt gcaaagtcag taataaggcc ctgcctgctc caatcgaaaa aaccatctct    1020

aaggccaaag gccagccaag ggagccccag gtgtacgtgt acccacccag cagagacgaa    1080

ctgaccaaga accaggtgtc cctgacatgt ctggtgaaag gcttctatcc tagtgatatt    1140

gctgtggagt gggaatcaaa tggacagcca gagaacaatt acaagaccac acctccagtg    1200

ctggacgagg atggcagctt cgccctggtg tccaagctga cagtggataa atctcgatgg    1260

cagcagggga acgtgtttag ttgttcagtg atgcatgaag ccctgcacaa tcattacact    1320

cagaagagcc tgtccctgtc tcccggcaaa                                      1350


<210> SEQ ID NO 20
<211> LENGTH: 450
<212> TYPE: PRT
<213> ORGANISM: Artificial Sequence
<220> FEATURE:
<223> OTHER INFORMATION: synthetic monoclonal antibody polypeptide
      sequence - variant

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

```
Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Leu Pro Pro Ser Arg Asp Glu Leu Thr Lys Asn Gln Val Ser Leu
        355                 360                 365

Leu Cys Leu Val Lys Gly Phe Tyr Pro Ser Asp Ile Ala Val Glu Trp
    370                 375                 380

Glu Ser Asn Gly Gln Pro Glu Asn Arg Tyr Met Thr Trp Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 21
<211> LENGTH: 1350
<212> TYPE: DNA
<213> ORGANISM: Artificial Sequence
<220> FEATURE:
<223> OTHER INFORMATION: synthetic monoclonal antibody nucleotide
sequence - variant

<400> SEQUENCE: 21

```
gaggtgcagc tggtggaaag cggaggagga ctggtgcagc caggaggatc tctgcgactg     60
agttgcgccg cttcaggatt caacatcaag gacacctaca ttcactgggt gcgacaggct    120
ccaggaaaag gactggagtg ggtggctcga atctatccca ctaatggata cacccggtat    180
gccgactccg tgaaggggag gtttactatt agcgccgata catccaaaaa cactgcttac    240
ctgcagatga acagcctgcg agccgaagat accgctgtgt actattgcag tcgatgggga    300
ggagacggat tctacgctat ggattattgg ggacagggga ccctggtgac agtgagctcc    360
gcctctacca agggccccag tgtgtttccc ctggctcctt ctagtaaatc cacctctgga    420
gggacagccg ctctgggatg tctggtgaag gactatttcc ccgagcctgt gaccgtgagt    480
tggaactcag gcgccctgac aagcggagtg cacacttttc ctgctgtgct gcagtcaagc    540
gggctgtact ccctgtcctc tgtggtgaca gtgccaagtt caagcctggg cacacagact    600
tatatctgca acgtgaatca taagccctca aatacaaaag tggacaagaa agtggagccc    660
aagagctgtg ataagaccca cacctgccct ccctgtccag ctccagaact gctgggagga    720
cctagcgtgt tcctgtttcc ccctaagcca aaagacactc tgatgatttc caggactccc    780
gaggtgacct gcgtggtggt ggacgtgtct cacgaggacc ccgaagtgaa gttcaactgg    840
tacgtggatg gcgtggaagt gcataatgct aagacaaaac caagagagga acagtacaac    900
tccacttatc gcgtcgtgag cgtgctgacc gtgctgcacc aggactggct gaacgggaag    960
gagtataagt gcaaagtcag taataaggcc ctgcctgctc caatcgaaaa aaccatctct   1020
aaggccaaag gccagccaag ggagccccag gtgtacgtgc tgccacccag cagagacgaa   1080
ctgaccaaga accaggtgtc cctgctgtgt ctggtgaaag gcttctatcc tagtgatatt   1140
gctgtggagt gggaatcaaa tggacagcca gagaacagat acatgacctg gcctccagtg   1200
ctggacagcg atggcagctt cttcctgtat tccaagctga cagtggataa atctcgatgg   1260
cagcagggga acgtgtttag ttgttcagtg atgcatgaag ccctgcacaa tcattacact   1320
cagaagagcc tgtccctgtc tcccggcaaa                                    1350
```

<210> SEQ ID NO 22
<211> LENGTH: 450
<212> TYPE: PRT
<213> ORGANISM: Artificial Sequence
<220> FEATURE:
<223> OTHER INFORMATION: synthetic monoclonal antibody polypeptide sequence - variant

<400> SEQUENCE: 22

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110
```

```
Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Lys Lys Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Leu Pro Pro Ser Arg Asp Glu Leu Thr Lys Asn Gln Val Ser Leu
        355                 360                 365

Leu Cys Leu Val Lys Gly Phe Tyr Pro Ser Asp Ile Ala Val Glu Trp
    370                 375                 380

Glu Ser Asn Gly Gln Pro Glu Asn Arg Tyr Met Thr Trp Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 23
<211> LENGTH: 1350
<212> TYPE: DNA
<213> ORGANISM: Artificial Sequence
<220> FEATURE:
<223> OTHER INFORMATION: synthetic monoclonal antibody nucleotide
      sequence - variant

<400> SEQUENCE: 23

gaggtgcagc tggtggaaag cggaggagga ctggtgcagc caggaggatc tctgcgactg      60
```

```
agttgcgccg cttcaggatt caacatcaag gacacctaca ttcactgggt gcgacaggct    120

ccaggaaaag gactggagtg ggtggctcga atctatccca ctaatggata cacccggtat    180

gccgactccg tgaaggggag gtttactatt agcgccgata catccaaaaa cactgcttac    240

ctgcagatga acagcctgcg agccgaagat accgctgtgt actattgcag tcgatgggga    300

ggagacggat tctacgctat ggattattgg ggacagggga ccctggtgac agtgagctcc    360

gcctctacca agggccccag tgtgtttccc ctggctcctt ctagtaaatc cacctctgga    420

gggacagccg ctctgggatg tctggtgaag gactatttcc ccgagcctgt gaccgtgagt    480

tggaactcag gcgccctgac aagcggagtg cacacttttc ctgctgtgct gcagtcaagc    540

gggctgtact ccctgtcctc tgtggtgaca gtgccaagtt caagcctggg cacacagact    600

tatatctgca acgtgaatca taagccctca aatacaaaag tggacaagaa agtggagccc    660

aagagctgtg ataagaccca cacctgccct ccctgtccag ctccagaaaa gaagggagga    720

cctagcgtgt tcctgtttcc ccctaagcca aaagacactc tgatgatttc caggactccc    780

gaggtgacct gcgtggtggt ggacgtgtct cacgaggacc ccgaagtgaa gttcaactgg    840

tacgtggatg gcgtggaagt gcataatgct aagacaaaac caagagagga acagtacaac    900

tccacttatc gcgtcgtgag cgtgctgacc gtgctgcacc aggactggct gaacgggaag    960

gagtataagt gcaaagtcag taataaggcc ctgcctgctc caatcgaaaa aaccatctct   1020

aaggccaaag gccagccaag ggagccccag gtgtacgtgc tgccacccag cagagacgaa   1080

ctgaccaaga accaggtgtc cctgctgtgt ctggtgaaag gcttctatcc tagtgatatt   1140

gctgtggagt gggaatcaaa tggacagcca gagaacagat acatgacctg gcctccagtg   1200

ctggacagcg atggcagctt cttcctgtat tccaagctga cagtggataa atctcgatgg   1260

cagcagggga acgtgtttag ttgttcagtg atgcatgaag ccctgcacaa tcattacact   1320

cagaagagcc tgtccctgtc tcccggcaaa                                    1350
```

<210> SEQ ID NO 24
<211> LENGTH: 450
<212> TYPE: PRT
<213> ORGANISM: Artificial Sequence
<220> FEATURE:
<223> OTHER INFORMATION: synthetic monoclonal antibody polypeptide sequence - variant

<400> SEQUENCE: 24

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Ala Arg Arg Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Leu Pro Pro Ser Arg Asp Glu Leu Thr Lys Asn Gln Val Ser Leu
        355                 360                 365

Leu Cys Leu Val Lys Gly Phe Tyr Pro Ser Asp Ile Ala Val Glu Trp
    370                 375                 380

Glu Ser Asn Gly Gln Pro Glu Asn Arg Tyr Met Thr Trp Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 25
<211> LENGTH: 1350
<212> TYPE: DNA
<213> ORGANISM: Artificial Sequence
<220> FEATURE:
<223> OTHER INFORMATION: synthetic monoclonal antibody nucleotide sequence - variant

<400> SEQUENCE: 25

```
gaggtgcagc tggtggaaag cggaggagga ctggtgcagc caggaggatc tctgcgactg      60

agttgcgccg cttcaggatt caacatcaag gacacctaca ttcactgggt gcgacaggct     120
```

```
ccaggaaaag gactggagtg ggtggctcga atctatccca ctaatggata cacccggtat    180

gccgactccg tgaaggggag gtttactatt agcgccgata catccaaaaa cactgcttac    240

ctgcagatga acagcctgcg agccgaagat accgctgtgt actattgcag tcgatgggga    300

ggagacggat tctacgctat ggattattgg ggacagggga ccctggtgac agtgagctcc    360

gcctctacca agggccccag tgtgtttccc ctggctcctt ctagtaaatc cacctctgga    420

gggacagccg ctctgggatg tctggtgaag gactatttcc ccgagcctgt gaccgtgagt    480

tggaactcag gcgccctgac aagcggagtg cacacttttc ctgctgtgct gcagtcaagc    540

gggctgtact ccctgtcctc tgtggtgaca gtgccaagtt caagcctggg cacacagact    600

tatatctgca acgtgaatca taagccctca aatacaaaag tggacaagaa agtggagccc    660

aagagctgtg ataagaccca cacctgccct ccctgtccag ctccagccag aagaggagga    720

cctagcgtgt tcctgtttcc ccctaagcca aaagacactc tgatgatttc caggactccc    780

gaggtgacct gcgtggtggt ggacgtgtct cacgaggacc ccgaagtgaa gttcaactgg    840

tacgtggatg gcgtggaagt gcataatgct aagacaaaac caagagagga acagtacaac    900

tccacttatc gcgtcgtgag cgtgctgacc gtgctgcacc aggactggct gaacgggaag    960

gagtataagt gcaaagtcag taataaggcc ctgcctgctc caatcgaaaa aaccatctct   1020

aaggccaaag gccagccaag ggagccccag gtgtacgtgc tgccacccag cagagacgaa   1080

ctgaccaaga accaggtgtc cctgctgtgt ctggtgaaag gcttctatcc tagtgatatt   1140

gctgtggagt gggaatcaaa tggacagcca gagaacagat acatgacctg gcctccagtg   1200

ctggacagcg atggcagctt cttcctgtat tccaagctga cagtggataa atctcgatgg   1260

cagcagggga acgtgtttag ttgttcagtg atgcatgaag ccctgcacaa tcattacact   1320

cagaagagcc tgtccctgtc tcccggcaaa                                     1350
```

<210> SEQ ID NO 26
<211> LENGTH: 450
<212> TYPE: PRT
<213> ORGANISM: Artificial Sequence
<220> FEATURE:
<223> OTHER INFORMATION: synthetic monoclonal antibody polypeptide sequence - variant

<400> SEQUENCE: 26

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140
```

```
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Lys Arg Arg Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Leu Pro Pro Ser Arg Asp Glu Leu Thr Lys Asn Gln Val Ser Leu
        355                 360                 365

Leu Cys Leu Val Lys Gly Phe Tyr Pro Ser Asp Ile Ala Val Glu Trp
    370                 375                 380

Glu Ser Asn Gly Gln Pro Glu Asn Arg Tyr Met Thr Trp Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 27
<211> LENGTH: 1350
<212> TYPE: DNA
<213> ORGANISM: Artificial Sequence
<220> FEATURE:
<223> OTHER INFORMATION: synthetic monoclonal antibody nucleotide
      sequence - variant

<400> SEQUENCE: 27

gaggtgcagc tggtggaaag cggaggagga ctggtgcagc caggaggatc tctgcgactg      60

agttgcgccg cttcaggatt caacatcaag gacacctaca ttcactgggt gcgacaggct     120

ccaggaaaag gactggagtg ggtggctcga atctatccca ctaatggata cacccggtat     180

gccgactccg tgaaggggag gtttactatt agcgccgata catccaaaaa cactgcttac     240
```

```
ctgcagatga acagcctgcg agccgaagat accgctgtgt actattgcag tcgatgggga    300

ggagacggat tctacgctat ggattattgg ggacagggga ccctggtgac agtgagctcc    360

gcctctacca agggccccag tgtgtttccc ctggctcctt ctagtaaatc cacctctgga    420

gggacagccg ctctgggatg tctggtgaag gactatttcc ccgagcctgt gaccgtgagt    480

tggaactcag gcgccctgac aagcggagtg cacacttttc ctgctgtgct gcagtcaagc    540

gggctgtact ccctgtcctc tgtggtgaca gtgccaagtt caagcctggg cacacagact    600

tatatctgca acgtgaatca taagccctca aatacaaaag tggacaagaa agtggagccc    660

aagagctgtg ataagaccca cacctgccct ccctgtccag ctccaaagag aagaggagga    720

cctagcgtgt tcctgtttcc ccctaagcca aaagacactc tgatgatttc caggactccc    780

gaggtgacct gcgtggtggt ggacgtgtct cacgaggacc ccgaagtgaa gttcaactgg    840

tacgtggatg gcgtggaagt gcataatgct aagacaaaac caagagagga acagtacaac    900

tccacttatc gcgtcgtgag cgtgctgacc gtgctgcacc aggactggct gaacgggaag    960

gagtataagt gcaaagtcag taataaggcc ctgcctgctc caatcgaaaa aaccatctct   1020

aaggccaaag gccagccaag ggagccccag gtgtacgtgc tgccacccag cagagacgaa   1080

ctgaccaaga accaggtgtc cctgctgtgt ctggtgaaag gcttctatcc tagtgatatt   1140

gctgtggagt gggaatcaaa tggacagcca gagaacagat acatgacctg gcctccagtg   1200

ctggacagcg atggcagctt cttcctgtat tccaagctga cagtggataa atctcgatgg   1260

cagcagggga acgtgtttag ttgttcagtg atgcatgaag ccctgcacaa tcattacact   1320

cagaagagcc tgtccctgtc tcccggcaaa                                     1350
```

<210> SEQ ID NO 28
<211> LENGTH: 450
<212> TYPE: PRT
<213> ORGANISM: Artificial Sequence
<220> FEATURE:
<223> OTHER INFORMATION: synthetic monoclonal antibody polypeptide sequence - variant

<400> SEQUENCE: 28

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160
```

```
Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Lys Ala Lys Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Leu Pro Pro Ser Arg Asp Glu Leu Thr Lys Asn Gln Val Ser Leu
        355                 360                 365

Leu Cys Leu Val Lys Gly Phe Tyr Pro Ser Asp Ile Ala Val Glu Trp
    370                 375                 380

Glu Ser Asn Gly Gln Pro Glu Asn Arg Tyr Met Thr Trp Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 29
<211> LENGTH: 1350
<212> TYPE: DNA
<213> ORGANISM: Artificial Sequence
<220> FEATURE:
<223> OTHER INFORMATION: synthetic monoclonal antibody nucleotide
      sequence - variant

<400> SEQUENCE: 29

gaggtgcagc tggtggaaag cggaggagga ctggtgcagc caggaggatc tctgcgactg      60

agttgcgccg cttcaggatt caacatcaag gacacctaca ttcactgggt gcgacaggct     120

ccaggaaaag gactggagtg ggtggctcga atctatccca ctaatggata cacccggtat     180

gccgactccg tgaaggggag gtttactatt agcgccgata catccaaaaa cactgcttac     240

ctgcagatga acagcctgcg agccgaagat accgctgtgt actattgcag tcgatgggga     300
```

```
ggagacggat tctacgctat ggattattgg ggacagggga ccctggtgac agtgagctcc    360

gcctctacca agggccccag tgtgtttccc ctggctcctt ctagtaaatc cacctctgga    420

gggacagccg ctctgggatg tctggtgaag gactatttcc ccgagcctgt gaccgtgagt    480

tggaactcag gcgccctgac aagcggagtg cacacttttc ctgctgtgct gcagtcaagc    540

gggctgtact ccctgtcctc tgtggtgaca gtgccaagtt caagcctggg cacacagact    600

tatatctgca acgtgaatca taagccctca aatacaaaag tggacaagaa agtggagccc    660

aagagctgtg ataagaccca cacctgccct ccctgtccag ctccaaaggc caagggagga    720

cctagcgtgt tcctgtttcc ccctaagcca aaagacactc tgatgatttc caggactccc    780

gaggtgacct gcgtggtggt ggacgtgtct cacgaggacc ccgaagtgaa gttcaactgg    840

tacgtggatg gcgtggaagt gcataatgct aagacaaaac caagagagga acagtacaac    900

tccacttatc gcgtcgtgag cgtgctgacc gtgctgcacc aggactggct gaacgggaag    960

gagtataagt gcaaagtcag taataaggcc ctgcctgctc caatcgaaaa aaccatctct   1020

aaggccaaag gccagccaag ggagccccag gtgtacgtgc tgccacccag cagagacgaa   1080

ctgaccaaga accaggtgtc cctgctgtgt ctggtgaaag gcttctatcc tagtgatatt   1140

gctgtggagt gggaatcaaa tggacagcca gagaacagat acatgacctg gcctccagtg   1200

ctggacagcg atggcagctt cttcctgtat tccaagctga cagtggataa atctcgatgg   1260

cagcagggga acgtgtttag ttgttcagtg atgcatgaag ccctgcacaa tcattacact   1320

cagaagagcc tgtccctgtc tcccggcaaa                                     1350
```

<210> SEQ ID NO 30
<211> LENGTH: 450
<212> TYPE: PRT
<213> ORGANISM: Artificial Sequence
<220> FEATURE:
<223> OTHER INFORMATION: synthetic monoclonal antibody polypeptide sequence - variant

<400> SEQUENCE: 30

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Lys
            260                 265                 270

Arg Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Leu Pro Pro Ser Arg Asp Glu Leu Thr Lys Asn Gln Val Ser Leu
        355                 360                 365

Leu Cys Leu Val Lys Gly Phe Tyr Pro Ser Asp Ile Ala Val Glu Trp
    370                 375                 380

Glu Ser Asn Gly Gln Pro Glu Asn Arg Tyr Met Thr Trp Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 31
<211> LENGTH: 1350
<212> TYPE: DNA
<213> ORGANISM: Artificial Sequence
<220> FEATURE:
<223> OTHER INFORMATION: synthetic monoclonal antibody nucleotide sequence - variant

<400> SEQUENCE: 31

```
gaggtgcagc tggtggaaag cggaggagga ctggtgcagc caggaggatc tctgcgactg      60

agttgcgccg cttcaggatt caacatcaag gacacctaca ttcactgggt gcgacaggct     120

ccaggaaaag gactggagtg ggtggctcga atctatccca ctaatggata cacccggtat     180

gccgactccg tgaaggggag gtttactatt agcgccgata catccaaaaa cactgcttac     240

ctgcagatga acagcctgcg agccgaagat accgctgtgt actattgcag tcgatgggga     300

ggagacggat tctacgctat ggattattgg ggacagggga ccctggtgac agtgagctcc     360

gcctctacca agggccccag tgtgtttccc ctggctcctt ctagtaaatc cacctctgga     420
```

```
gggacagccg ctctgggatg tctggtgaag gactatttcc ccgagcctgt gaccgtgagt    480

tggaactcag gcgccctgac aagcggagtg cacacttttc ctgctgtgct gcagtcaagc    540

gggctgtact ccctgtcctc tgtggtgaca gtgccaagtt caagcctggg cacacagact    600

tatatctgca acgtgaatca taagccctca aatacaaaag tggacaagaa agtggagccc    660

aagagctgtg ataagaccca cacctgccct ccctgtccag ctccagaact gctgggagga    720

cctagcgtgt tcctgtttcc ccctaagcca aaagacactc tgatgatttc caggactccc    780

gaggtgacct gcgtggtggt ggacgtgtct cacaagagac ccgaagtgaa gttcaactgg    840

tacgtggatg gcgtggaagt gcataatgct aagacaaaac caagagagga acagtacaac    900

tccacttatc gcgtcgtgag cgtgctgacc gtgctgcacc aggactggct gaacgggaag    960

gagtataagt gcaaagtcag taataaggcc ctgcctgctc caatcgaaaa aaccatctct   1020

aaggccaaag gccagccaag ggagccccag gtgtacgtgc tgccacccag cagagacgaa   1080

ctgaccaaga accaggtgtc cctgctgtgt ctggtgaaag gcttctatcc tagtgatatt   1140

gctgtggagt gggaatcaaa tggacagcca gagaacagat acatgacctg gcctccagtg   1200

ctggacagcg atggcagctt cttcctgtat tccaagctga cagtggataa atctcgatgg   1260

cagcagggga acgtgtttag ttgttcagtg atgcatgaag ccctgcacaa tcattacact   1320

cagaagagcc tgtccctgtc tcccggcaaa                                    1350
```

<210> SEQ ID NO 32
<211> LENGTH: 450
<212> TYPE: PRT
<213> ORGANISM: Artificial Sequence
<220> FEATURE:
<223> OTHER INFORMATION: synthetic monoclonal antibody polypeptide sequence - variant

<400> SEQUENCE: 32

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190
```

```
Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Lys Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Lys Leu Pro Ala Pro Ile Glu
                325                 330                 335

Lys Thr Ile Ser Lys Ala Lys Gly Gln Pro Arg Glu Pro Gln Val Tyr
            340                 345                 350

Val Leu Pro Pro Ser Arg Asp Glu Leu Thr Lys Asn Gln Val Ser Leu
        355                 360                 365

Leu Cys Leu Val Lys Gly Phe Tyr Pro Ser Asp Ile Ala Val Glu Trp
    370                 375                 380

Glu Ser Asn Gly Gln Pro Glu Asn Arg Tyr Met Thr Trp Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 33
<211> LENGTH: 1350
<212> TYPE: DNA
<213> ORGANISM: Artificial Sequence
<220> FEATURE:
<223> OTHER INFORMATION: synthetic monoclonal antibody nucleotide sequence - variant

<400> SEQUENCE: 33

```
gaggtgcagc tggtggaaag cggaggagga ctggtgcagc caggaggatc tctgcgactg     60

agttgcgccg cttcaggatt caacatcaag gacacctaca ttcactgggt gcgacaggct    120

ccaggaaaag gactggagtg ggtggctcga atctatccca ctaatggata cacccggtat    180

gccgactccg tgaaggggag gtttactatt agcgccgata catccaaaaa cactgcttac    240

ctgcagatga acagcctgcg agccgaagat accgctgtgt actattgcag tcgatgggga    300

ggagacggat tctacgctat ggattattgg ggacagggga ccctggtgac agtgagctcc    360

gcctctacca agggccccag tgtgtttccc ctggctcctt ctagtaaatc cacctctgga    420

gggacagccg ctctgggatg tctggtgaag gactatttcc ccgagcctgt gaccgtgagt    480
```

```
tggaactcag gcgccctgac aagcggagtg cacacttttc ctgctgtgct gcagtcaagc    540

gggctgtact ccctgtcctc tgtggtgaca gtgccaagtt caagcctggg cacacagact    600

tatatctgca acgtgaatca taagccctca aatacaaaag tggacaagaa agtggagccc    660

aagagctgtg ataagaccca cacctgccct ccctgtccag ctccagaact gaagggagga    720

cctagcgtgt tcctgtttcc ccctaagcca aaagacactc tgatgatttc caggactccc    780

gaggtgacct gcgtggtggt ggacgtgtct cacgaggacc ccgaagtgaa gttcaactgg    840

tacgtggatg gcgtggaagt gcataatgct aagacaaaac caagagagga acagtacaac    900

tccacttatc gcgtcgtgag cgtgctgacc gtgctgcacc aggactggct gaacgggaag    960

gagtataagt gcaaagtcag taataagaag ctgcctgctc caatcgaaaa aaccatctct   1020

aaggccaaag gccagccaag ggagccccag gtgtacgtgc tgccacccag cagagacgaa   1080

ctgaccaaga accaggtgtc cctgctgtgt ctggtgaaag gcttctatcc tagtgatatt   1140

gctgtggagt gggaatcaaa tggacagcca gagaacagat acatgacctg gcctccagtg   1200

ctggacagcg atggcagctt cttcctgtat tccaagctga cagtggataa atctcgatgg   1260

cagcagggga acgtgtttag ttgttcagtg atgcatgaag ccctgcacaa tcattacact   1320

cagaagagcc tgtccctgtc tcccggcaaa                                     1350
```

<210> SEQ ID NO 34
<211> LENGTH: 642
<212> TYPE: DNA
<213> ORGANISM: Artificial Sequence
<220> FEATURE:
<223> OTHER INFORMATION: synthetic nucleotide sequence - variant trastuzumab light chain

<400> SEQUENCE: 34

```
gacatccaga tgacccagtc tccatcctcc ctgtctgcat ctgtaggaga cagagtcacc     60

atcacttgcc gggcaagtca ggacgttaac accgctgtag cttggtatca gcagaaacca    120

gggaaagccc ctaagctcct gatctattct gcatcctttt tgtacagtgg ggtcccatca    180

aggttcagtg gcagtcgatc tgggacagat ttcactctca ccatcagcag tctgcaacct    240

gaagattttg caacttacta ctgtcaacag cattacacta ccccacccac tttcggccaa    300

gggaccaaag tggagatcaa acgaactgtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccaa    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gt                       642
```

<210> SEQ ID NO 35
<211> LENGTH: 451
<212> TYPE: PRT
<213> ORGANISM: Artificial Sequence
<220> FEATURE:
<223> OTHER INFORMATION: synthetic monoclonal antibody polypeptide sequence - rituximab variant

<400> SEQUENCE: 35

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30
```

```
Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Val Tyr Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Ala Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445
```

```
Pro Gly Lys
    450


<210> SEQ ID NO 36
<211> LENGTH: 1353
<212> TYPE: DNA
<213> ORGANISM: Artificial Sequence
<220> FEATURE:
<223> OTHER INFORMATION: synthetic monoclonal antibody nucleotide
      sequence - rituximab variant

<400> SEQUENCE: 36

caggtccagc tgcagcagcc cggagctgaa ctggtcaaac ctggcgcatc cgtgaaaatg      60

tcttgcaagg ctagtggcta cacattcact tcctataaca tgcactgggt gaagcagaca     120

ccaggacgag gactggagtg gatcggagca atctaccctg gaaacggcga cacttcttat     180

aatcagaagt ttaaaggcaa ggccaccctg acagctgata agagctcctc taccgcctac     240

atgcagctga gttcactgac aagtgaagac tcagcagtgt actattgcgc cagaagcacc     300

tactatggcg gggattggta cttcaacgtg tggggggcag gaaccacagt caccgtgagc     360

gccgcttcca caaaaggacc aagcgtgttt ccactggcac caagctccaa gtcaaccagc     420

ggaggaacag cagccctggg atgtctggtg aaggactact tcccagagcc cgtcaccgtg     480

tcttggaaca gtggcgccct gacaagcggg gtccatactt ttcccgctgt gctgcagtct     540

agtggcctgt acagcctgtc aagcgtggtc accgtccctt cctctagtct ggggactcag     600

acctatatct gcaacgtgaa tcacaaacct tctaatacaa aggtcgacaa gaaagtggaa     660

ccaaaaagtt gtgataagac acatacttgc ccaccttgtc ctgcaccaga gctgctggga     720

ggaccatccg tgttcctgtt tccacccaaa cccaaggaca ctctgatgat tagccggact     780

cctgaagtca cctgcgtggt cgtggacgtg agccacgagg accccgaagt caaattcaac     840

tggtacgtgg atggcgtcga ggtgcataat gccaaaacaa agccccggga ggaacagtac     900

aactcaacat atagagtcgt gagcgtcctg actgtgctgc accaggactg gctgaacggc     960

aaggagtata aatgcaaggt gtccaacaag gccctgcccg cacctatcga gaagactatt    1020

tctaaagcca agggccagcc tagggaacca caggtgtacg tgtaccctcc aagccgcgac    1080

gagctgacta aaaaccaggt ctccctgacc tgtctggtga aggggttcta tccaagtgat    1140

atcgctgtgg agtgggaatc aaatggacag cccgagaaca attacaagac taccccccct    1200

gtgctggact cagatgggag cttcgccctg gtgtccaaac tgaccgtgga taagtctcgg    1260

tggcagcagg gaaatgtctt ttcctgttct gtgatgcacg aagcactgca caatcactac    1320

acccagaagt ccctgagcct gtcacccggc aaa                                 1353


<210> SEQ ID NO 37
<211> LENGTH: 451
<212> TYPE: PRT
<213> ORGANISM: Artificial Sequence
<220> FEATURE:
<223> OTHER INFORMATION: synthetic monoclonal antibody polypeptide
      sequence - rituximab variant

<400> SEQUENCE: 37

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45
```

```
Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Val Leu Pro Pro Ser Arg Asp Glu Leu Thr Lys Asn Gln Val Ser
        355                 360                 365

Leu Leu Cys Leu Val Lys Gly Phe Tyr Pro Ser Asp Ile Ala Val Glu
    370                 375                 380

Trp Glu Ser Asn Gly Gln Pro Glu Asn Asn Tyr Leu Thr Trp Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 38
<211> LENGTH: 1353
<212> TYPE: DNA
<213> ORGANISM: Artificial Sequence
<220> FEATURE:
<223> OTHER INFORMATION: synthetic monoclonal antibody nucleotide sequence - rituximab variant

<400> SEQUENCE: 38

```
caggtccagc tgcagcagcc cggagctgaa ctggtcaaac ctggcgcatc cgtgaaaatg     60

tcttgcaagg ctagtggcta cacattcact tcctataaca tgcactgggt gaagcagaca    120

ccaggacgag gactggagtg gatcggagca atctaccctg gaaacggcga cacttcttat    180

aatcagaagt ttaaaggcaa ggccaccctg acagctgata agagctcctc taccgcctac    240

atgcagctga gttcactgac aagtgaagac tcagcagtgt actattgcgc cagaagcacc    300

tactatggcg gggattggta cttcaacgtg tgggggggcag gaaccacagt caccgtgagc    360

gccgcttcca caaaaggacc aagcgtgttt ccactggcac caagctccaa gtcaaccagc    420

ggaggaacag cagccctggg atgtctggtg aaggactact tcccagagcc cgtcaccgtg    480

tcttggaaca gtggcgccct gacaagcggg gtccatactt ttcccgctgt gctgcagtct    540

agtggcctgt acagcctgtc aagcgtggtc accgtccctt cctctagtct ggggactcag    600

acctatatct gcaacgtgaa tcacaaacct tctaatacaa aggtcgacaa gaaagtggaa    660

ccaaaaagtt gtgataagac acatacttgc ccaccttgtc ctgcaccaga gctgctggga    720

ggaccatccg tgttcctgtt tccacccaaa cccaaggaca ctctgatgat tagccggact    780

cctgaagtca cctgcgtggt cgtggacgtg agccacgagg accccgaagt caaattcaac    840

tggtacgtgg atggcgtcga ggtgcataat gccaaaacaa agccccggga ggaacagtac    900

aactcaacat atagagtcgt gagcgtcctg actgtgctgc accaggactg gctgaacggc    960

aaggagtata aatgcaaggt gtccaacaag gccctgcccg cacctatcga gaagactatt   1020

tctaaagcca agggccagcc tagggaacca caggtgtacg tgctgcctcc aagccgcgac   1080

gagctgacta aaaaccaggt ctccctgctg tgtctggtga aggggttcta tccaagtgat   1140

atcgctgtgg agtgggaatc aaatggacag cccgagaaca attacctgac ttggcccccct   1200

gtgctggact cagatgggag cttctttctg tattccaaac tgaccgtgga taagtctcgg   1260

tggcagcagg gaaatgtctt ttcctgttct gtgatgcacg aagcactgca caatcactac   1320

acccagaagt ccctgagcct gtcacccggc aaa                                1353
```

<210> SEQ ID NO 39
<211> LENGTH: 451
<212> TYPE: PRT
<213> ORGANISM: Artificial Sequence
<220> FEATURE:
<223> OTHER INFORMATION: synthetic monoclonal antibody polypeptide sequence - rituximab variant

<400> SEQUENCE: 39

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60
```

```
Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Asp Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Val Tyr Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Ala Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 40
<211> LENGTH: 1353

```
<212> TYPE: DNA
<213> ORGANISM: Artificial Sequence
<220> FEATURE:
<223> OTHER INFORMATION: synthetic monoclonal antibody nucleotide
      sequence - rituximab variant

<400> SEQUENCE: 40

caggtccagc tgcagcagcc cggagctgaa ctggtcaaac ctggcgcatc cgtgaaaatg     60

tcttgcaagg ctagtggcta cacattcact tcctataaca tgcactgggt gaagcagaca    120

ccaggacgag gactggagtg gatcggagca atctaccctg gaaacggcga cacttcttat    180

aatcagaagt ttaaaggcaa ggccaccctg acagctgata agagctcctc taccgcctac    240

atgcagctga gttcactgac aagtgaagac tcagcagtgt actattgcgc cagaagcacc    300

tactatggcg gggattggta cttcaacgtg tgggggggcag gaaccacagt caccgtgagc    360

gccgcttcca caaaaggacc aagcgtgttt ccactggcac caagctccaa gtcaaccagc    420

ggaggaacag cagccctggg atgtctggtg aaggactact tcccagagcc cgtcaccgtg    480

tcttggaaca gtggcgccct gacaagcggg gtccatactt ttcccgctgt gctgcagtct    540

agtggcctgt acagcctgtc aagcgtggtc accgtccctt cctctagtct ggggactcag    600

acctatatct gcaacgtgaa tcacaaacct tctaatacaa aggtcgacaa gaaagtggaa    660

ccaaaaagtt gtgataagac acatacttgc ccaccttgtc ctgcaccaga ggacgaggga    720

ggaccatccg tgttcctgtt tccacccaaa cccaaggaca ctctgatgat tagccggact    780

cctgaagtca cctgcgtggt cgtggacgtg agccacgagg accccgaagt caaattcaac    840

tggtacgtgg atggcgtcga ggtgcataat gccaaaacaa agccccggga ggaacagtac    900

aactcaacat atagagtcgt gagcgtcctg actgtgctgc accaggactg gctgaacggc    960

aaggagtata aatgcaaggt gtccaacaag gccctgcccg cacctatcga gaagactatt   1020

tctaaagcca agggccagcc tagggaacca caggtgtacg tgtaccctcc aagccgcgac   1080

gagctgacta aaaaccaggt ctccctgacc tgtctggtga aggggttcta tccaagtgat   1140

atcgctgtgg agtgggaatc aaatggacag cccgagaaca attacaagac taccccccct   1200

gtgctggact cagatgggag cttcgccctg gtgtccaaac tgaccgtgga taagtctcgg   1260

tggcagcagg gaaatgtctt ttcctgttct gtgatgcacg aagcactgca caatcactac   1320

acccagaagt ccctgagcct gtcacccggc aaa                                1353


<210> SEQ ID NO 41
<211> LENGTH: 451
<212> TYPE: PRT
<213> ORGANISM: Artificial Sequence
<220> FEATURE:
<223> OTHER INFORMATION: synthetic monoclonal antibody polypeptide
      sequence - rituximab variant

<400> SEQUENCE: 41

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80
```

```
Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Lys Arg Arg Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Val Leu Pro Pro Ser Arg Asp Glu Leu Thr Lys Asn Gln Val Ser
        355                 360                 365

Leu Leu Cys Leu Val Lys Gly Phe Tyr Pro Ser Asp Ile Ala Val Glu
    370                 375                 380

Trp Glu Ser Asn Gly Gln Pro Glu Asn Asn Tyr Leu Thr Trp Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 42
<211> LENGTH: 1353
<212> TYPE: DNA
<213> ORGANISM: Artificial Sequence
<220> FEATURE:

<223> OTHER INFORMATION: synthetic monoclonal antibody nucleotide sequence - rituximab variant

<400> SEQUENCE: 42

```
caggtccagc tgcagcagcc cggagctgaa ctggtcaaac ctggcgcatc cgtgaaaatg     60

tcttgcaagg ctagtggcta cacattcact tcctataaca tgcactgggt gaagcagaca    120

ccaggacgag gactggagtg gatcggagca atctaccctg gaaacggcga cacttcttat    180

aatcagaagt ttaaaggcaa ggccaccctg acagctgata agagctcctc taccgcctac    240

atgcagctga gttcactgac aagtgaagac tcagcagtgt actattgcgc cagaagcacc    300

tactatggcg gggattggta cttcaacgtg tggggggcag gaaccacagt caccgtgagc    360

gccgcttcca caaaaggacc aagcgtgttt ccactggcac caagctccaa gtcaaccagc    420

ggaggaacag cagccctggg atgtctggtg aaggactact tcccagagcc cgtcaccgtg    480

tcttggaaca gtggcgccct gacaagcggg gtccatactt ttcccgctgt gctgcagtct    540

agtggcctgt acagcctgtc aagcgtggtc accgtccctt cctctagtct ggggactcag    600

acctatatct gcaacgtgaa tcacaaacct tctaatacaa aggtcgacaa gaaagtggaa    660

ccaaaaagtt gtgataagac acatacttgc ccaccttgtc ctgcaccaaa gagaagagga    720

ggaccatccg tgttcctgtt tccacccaaa cccaaggaca ctctgatgat tagccggact    780

cctgaagtca cctgcgtggt cgtggacgtg agccacgagg accccgaagt caaattcaac    840

tggtacgtgg atggcgtcga ggtgcataat gccaaaacaa agccccggga ggaacagtac    900

aactcaacat atagagtcgt gagcgtcctg actgtgctgc accaggactg gctgaacggc    960

aaggagtata aatgcaaggt gtccaacaag gccctgcccg cacctatcga gaagactatt   1020

tctaaagcca agggccagcc tagggaacca caggtgtacg tgctgcctcc aagccgcgac   1080

gagctgacta aaaaccaggt ctccctgctg tgtctggtga aggggttcta tccaagtgat   1140

atcgctgtgg agtgggaatc aaatggacag cccgagaaca attacctgac ttggcccccct   1200

gtgctggact cagatgggag cttctttctg tattccaaac tgaccgtgga taagtctcgg   1260

tggcagcagg gaaatgtctt ttcctgttct gtgatgcacg aagcactgca caatcactac   1320

acccagaagt ccctgagcct gtcacccggc aaa                                1353
```

<210> SEQ ID NO 43
<211> LENGTH: 451
<212> TYPE: PRT
<213> ORGANISM: Artificial Sequence
<220> FEATURE:
<223> OTHER INFORMATION: synthetic monoclonal antibody polypeptide sequence - rituximab variant

<400> SEQUENCE: 43

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95
```

```
Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Asp Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ser Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Val Tyr Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Ala Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 44
<211> LENGTH: 1353
<212> TYPE: DNA
<213> ORGANISM: Artificial Sequence
<220> FEATURE:
<223> OTHER INFORMATION: synthetic monoclonal antibody nucleotide sequence - rituximab variant

<400> SEQUENCE: 44

```
caggtccagc tgcagcagcc cggagctgaa ctggtcaaac ctggcgcatc cgtgaaaatg      60
tcttgcaagg ctagtggcta cacattcact tcctataaca tgcactgggt gaagcagaca     120
ccaggacgag gactggagtg gatcggagca atctaccctg gaaacggcga cacttcttat     180
aatcagaagt ttaaaggcaa ggccaccctg acagctgata agagctcctc taccgcctac     240
atgcagctga gttcactgac aagtgaagac tcagcagtgt actattgcgc cagaagcacc     300
tactatggcg gggattggta cttcaacgtg tggggggcag gaaccacagt caccgtgagc     360
gccgcttcca caaaaggacc aagcgtgttt ccactggcac caagctccaa gtcaaccagc     420
ggaggaacag cagccctggg atgtctggtg aaggactact tcccagagcc cgtcaccgtg     480
tcttggaaca gtggcgccct gacaagcggg gtccatactt ttcccgctgt gctgcagtct     540
agtggcctgt acagcctgtc aagcgtggtc accgtccctt cctctagtct ggggactcag     600
acctatatct gcaacgtgaa tcacaaacct tctaatacaa aggtcgacaa gaaagtggaa     660
ccaaaaagtt gtgataagac acatacttgc ccaccttgtc ctgcaccaga ggacgaggga     720
ggaccatccg tgttcctgtt tccacccaaa cccaaggaca ctctgatgat tagccggact     780
cctgaagtca cctgcgtggt cgtgagcgtg agccacgagg accccgaagt caaattcaac     840
tggtacgtgg atggcgtcga ggtgcataat gccaaaacaa agccccggga ggaacagtac     900
aactcaacat atagagtcgt gagcgtcctg actgtgctgc accaggactg gctgaacggc     960
aaggagtata aatgcaaggt gtccaacaag gccctgcccg cacctatcga gaagactatt    1020
tctaaagcca agggccagcc tagggaacca caggtgtacg tgtaccctcc aagccgcgac    1080
gagctgacta aaaaccaggt ctccctgacc tgtctggtga aggggttcta tccaagtgat    1140
atcgctgtgg agtgggaatc aaatggacag cccgagaaca attacaagac tacccccccct    1200
gtgctggact cagatgggag cttcgccctg gtgtccaaac tgaccgtgga taagtctcgg    1260
tggcagcagg gaaatgtctt ttcctgttct gtgatgcacg aagcactgca caatcactac    1320
acccagaagt ccctgagcct gtcacccggc aaa                                 1353
```

<210> SEQ ID NO 45
<211> LENGTH: 451
<212> TYPE: PRT
<213> ORGANISM: Artificial Sequence
<220> FEATURE:
<223> OTHER INFORMATION: synthetic monoclonal antibody polypeptide
      sequence - rituximab variant

<400> SEQUENCE: 45

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110
```

```
Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Lys Arg Arg Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ser Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Val Leu Pro Pro Ser Arg Asp Glu Leu Thr Lys Asn Gln Val Ser
        355                 360                 365

Leu Leu Cys Leu Val Lys Gly Phe Tyr Pro Ser Asp Ile Ala Val Glu
    370                 375                 380

Trp Glu Ser Asn Gly Gln Pro Glu Asn Asn Tyr Leu Thr Trp Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 46
<211> LENGTH: 1353
<212> TYPE: DNA
<213> ORGANISM: Artificial Sequence
<220> FEATURE:
<223> OTHER INFORMATION: synthetic monoclonal antibody nucleotide
      sequence - rituximab variant

<400> SEQUENCE: 46

caggtccagc tgcagcagcc cggagctgaa ctggtcaaac ctggcgcatc cgtgaaaatg      60
```

```
tcttgcaagg ctagtggcta cacattcact tcctataaca tgcactgggt gaagcagaca    120

ccaggacgag gactggagtg gatcggagca atctaccctg gaaacggcga cacttcttat    180

aatcagaagt ttaaaggcaa ggccaccctg acagctgata agagctcctc taccgcctac    240

atgcagctga gttcactgac aagtgaagac tcagcagtgt actattgcgc cagaagcacc    300

tactatggcg ggattggta cttcaacgtg tggggggcag gaaccacagt caccgtgagc     360

gccgcttcca caaaaggacc aagcgtgttt ccactggcac caagctccaa gtcaaccagc    420

ggaggaacag cagccctggg atgtctggtg aaggactact tcccagagcc cgtcaccgtg    480

tcttggaaca gtggcgccct gacaagcggg gtccatactt ttcccgctgt gctgcagtct    540

agtggcctgt acagcctgtc aagcgtggtc accgtccctt cctctagtct ggggactcag    600

acctatatct gcaacgtgaa tcacaaacct tctaatacaa aggtcgacaa gaaagtggaa    660

ccaaaaagtt gtgataagac acatacttgc ccaccttgtc ctgcaccaaa gagaagagga    720

ggaccatccg tgttcctgtt tccacccaaa cccaaggaca ctctgatgat tagccggact    780

cctgaagtca cctgcgtggt cgtgagcgtg agccacgagg accccgaagt caaattcaac    840

tggtacgtgg atggcgtcga ggtgcataat gccaaaacaa agccccggga ggaacagtac    900

aactcaacat atagagtcgt gagcgtcctg actgtgctgc accaggactg gctgaacggc    960

aaggagtata aatgcaaggt gtccaacaag gccctgcccg cacctatcga gaagactatt   1020

tctaaagcca agggccagcc tagggaacca caggtgtacg tgctgcctcc aagccgcgac   1080

gagctgacta aaaaccaggt ctccctgctg tgtctggtga aggggttcta tccaagtgat   1140

atcgctgtgg agtgggaatc aaatggacag cccgagaaca attacctgac ttggcccccct  1200

gtgctggact cagatgggag cttctttctg tattccaaac tgaccgtgga taagtctcgg   1260

tggcagcagg gaaatgtctt ttcctgttct gtgatgcacg aagcactgca caatcactac   1320

acccagaagt ccctgagcct gtcacccggc aaa                                1353
```

```
<210> SEQ ID NO 47
<211> LENGTH: 451
<212> TYPE: PRT
<213> ORGANISM: Artificial Sequence
<220> FEATURE:
<223> OTHER INFORMATION: synthetic monoclonal antibody polypeptide
      sequence - rituximab variant

<400> SEQUENCE: 47

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125
```

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Asp Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Lys Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Val Tyr Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Ala Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 48
<211> LENGTH: 1353
<212> TYPE: DNA
<213> ORGANISM: Artificial Sequence
<220> FEATURE:
<223> OTHER INFORMATION: synthetic monoclonal antibody nucleotide sequence - rituximab variant

<400> SEQUENCE: 48

```
caggtccagc tgcagcagcc cggagctgaa ctggtcaaac ctggcgcatc cgtgaaaatg     60

tcttgcaagg ctagtggcta cacattcact tcctataaca tgcactgggt gaagcagaca    120
```

```
ccaggacgag gactggagtg gatcggagca atctaccctg gaaacggcga cacttcttat    180
aatcagaagt ttaaaggcaa ggccaccctg acagctgata agagctcctc taccgcctac    240
atgcagctga gttcactgac aagtgaagac tcagcagtgt actattgcgc cagaagcacc    300
tactatggcg gggattggta cttcaacgtg tggggggcag gaaccacagt caccgtgagc    360
gccgcttcca caaaaggacc aagcgtgttt ccactggcac caagctccaa gtcaaccagc    420
ggaggaacag cagccctggg atgtctggtg aaggactact tcccagagcc cgtcaccgtg    480
tcttggaaca gtggcgccct gacaagcggg gtccatactt ttcccgctgt gctgcagtct    540
agtggcctgt acagcctgtc aagcgtggtc accgtccctt cctctagtct ggggactcag    600
acctatatct gcaacgtgaa tcacaaacct tctaatacaa aggtcgacaa gaaagtggaa    660
ccaaaaagtt gtgataagac acatacttgc ccaccttgtc ctgcaccaga ggacgaggga    720
ggaccatccg tgttcctgtt tccacccaaa cccaaggaca ctctgatgat tagccggact    780
cctgaagtca cctgcgtggt cgtggacgtg agccacaagg accccgaagt caaattcaac    840
tggtacgtgg atggcgtcga ggtgcataat gccaaaacaa agccccggga ggaacagtac    900
aactcaacat atagagtcgt gagcgtcctg actgtgctgc accaggactg gctgaacggc    960
aaggagtata aatgcaaggt gtccaacaag gccctgcccg cacctatcga gaagactatt   1020
tctaaagcca agggccagcc tagggaacca caggtgtacg tgtaccctcc aagccgcgac   1080
gagctgacta aaaaccaggt ctccctgacc tgtctggtga aggggttcta tccaagtgat   1140
atcgctgtgg agtgggaatc aaatggacag cccgagaaca attacaagac taccccccct   1200
gtgctggact cagatgggag cttcgccctg gtgtccaaac tgaccgtgga taagtctcgg   1260
tggcagcagg gaaatgtctt ttcctgttct gtgatgcacg aagcactgca caatcactac   1320
acccagaagt ccctgagcct gtcacccggc aaa                                1353
```

<210> SEQ ID NO 49
<211> LENGTH: 451
<212> TYPE: PRT
<213> ORGANISM: Artificial Sequence
<220> FEATURE:
<223> OTHER INFORMATION: synthetic monoclonal antibody polypeptide sequence - rituximab variant

<400> SEQUENCE: 49

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Lys Arg Arg Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Lys Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Val Leu Pro Pro Ser Arg Asp Glu Leu Thr Lys Asn Gln Val Ser
        355                 360                 365

Leu Leu Cys Leu Val Lys Gly Phe Tyr Pro Ser Asp Ile Ala Val Glu
    370                 375                 380

Trp Glu Ser Asn Gly Gln Pro Glu Asn Asn Tyr Leu Thr Trp Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 50
<211> LENGTH: 1353
<212> TYPE: DNA
<213> ORGANISM: Artificial Sequence
<220> FEATURE:
<223> OTHER INFORMATION: synthetic monoclonal antibody nucleotide sequence - rituximab variant

<400> SEQUENCE: 50

```
caggtccagc tgcagcagcc cggagctgaa ctggtcaaac ctggcgcatc cgtgaaaatg     60

tcttgcaagg ctagtggcta cacattcact tcctataaca tgcactgggt gaagcagaca    120

ccaggacgag gactggagtg gatcggagca atctaccctg gaaacggcga cacttcttat    180

aatcagaagt ttaaaggcaa ggccaccctg acagctgata agagctcctc taccgcctac    240
```

```
atgcagctga gttcactgac aagtgaagac tcagcagtgt actattgcgc cagaagcacc    300
tactatggcg gggattggta cttcaacgtg tggggggcag gaaccacagt caccgtgagc    360
gccgcttcca caaaaggacc aagcgtgttt ccactggcac caagctccaa gtcaaccagc    420
ggaggaacag cagccctggg atgtctggtg aaggactact tcccagagcc cgtcaccgtg    480
tcttggaaca gtggcgccct gacaagcggg gtccatactt ttcccgctgt gctgcagtct    540
agtggcctgt acagcctgtc aagcgtggtc accgtccctt cctctagtct ggggactcag    600
acctatatct gcaacgtgaa tcacaaacct tctaatacaa aggtcgacaa gaaagtggaa    660
ccaaaaagtt gtgataagac acatacttgc ccaccttgtc ctgcaccaaa gagaagagga    720
ggaccatccg tgttcctgtt tccacccaaa cccaaggaca ctctgatgat tagccggact    780
cctgaagtca cctgcgtggt cgtggacgtg agccacaagg accccgaagt caaattcaac    840
tggtacgtgg atggcgtcga ggtgcataat gccaaaacaa agccccggga ggaacagtac    900
aactcaacat atagagtcgt gagcgtcctg actgtgctgc accaggactg gctgaacggc    960
aaggagtata aatgcaaggt gtccaacaag gccctgcccg cacctatcga gaagactatt   1020
tctaaagcca agggccagcc tagggaacca caggtgtacg tgctgcctcc aagccgcgac   1080
gagctgacta aaaaccaggt ctccctgctg tgtctggtga aggggttcta tccaagtgat   1140
atcgctgtgg agtgggaatc aaatggacag cccgagaaca attacctgac ttggcccccct  1200
gtgctggact cagatgggag cttctttctg tattccaaac tgaccgtgga taagtctcgg   1260
tggcagcagg gaaatgtctt ttcctgttct gtgatgcacg aagcactgca caatcactac   1320
acccagaagt ccctgagcct gtcacccggc aaa                                1353
```

<210> SEQ ID NO 51
<211> LENGTH: 451
<212> TYPE: PRT
<213> ORGANISM: Artificial Sequence
<220> FEATURE:
<223> OTHER INFORMATION: synthetic monoclonal antibody polypeptide sequence - rituximab variant

<400> SEQUENCE: 51

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

```
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Asp Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Ala Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Val Tyr Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Ala Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 52
<211> LENGTH: 1353
<212> TYPE: DNA
<213> ORGANISM: Artificial Sequence
<220> FEATURE:
<223> OTHER INFORMATION: synthetic monoclonal antibody nucleotide sequence - rituximab variant

<400> SEQUENCE: 52

```
caggtccagc tgcagcagcc cggagctgaa ctggtcaaac ctggcgcatc cgtgaaaatg      60

tcttgcaagg ctagtggcta cacattcact tcctataaca tgcactgggt gaagcagaca     120

ccaggacgag gactggagtg gatcggagca atctaccctg gaaacggcga cacttcttat     180

aatcagaagt ttaaaggcaa ggccaccctg acagctgata agagctcctc taccgcctac     240

atgcagctga gttcactgac aagtgaagac tcagcagtgt actattgcgc cagaagcacc     300
```

```
tactatggcg gggattggta cttcaacgtg tggggggcag gaaccacagt caccgtgagc    360
gccgcttcca caaaaggacc aagcgtgttt ccactggcac caagctccaa gtcaaccagc    420
ggaggaacag cagccctggg atgtctggtg aaggactact tcccagagcc cgtcaccgtg    480
tcttggaaca gtggcgccct gacaagcggg gtccatactt ttcccgctgt gctgcagtct    540
agtggcctgt acagcctgtc aagcgtggtc accgtccctt cctctagtct ggggactcag    600
acctatatct gcaacgtgaa tcacaaacct tctaatacaa aggtcgacaa gaaagtggaa    660
ccaaaaagtt gtgataagac acatacttgc ccaccttgtc ctgcaccaga ggacgaggga    720
ggaccatccg tgttcctgtt tccacccaaa cccaaggaca ctctgatgat tagccggact    780
cctgaagtca cctgcgtggt cgtggacgtg agccacgagg accccgaagt caaattcaac    840
tggtacgtgg atggcgtcga ggtgcataat gccaaaacaa agccccggga ggaacagtac    900
aactcaacat atagagtcgt gagcgtcctg actgtgctgc accaggactg gctgaacggc    960
aaggagtata aatgcgccgt gtccaacaag gccctgcccg cacctatcga gaagactatt   1020
tctaaagcca agggccagcc tagggaacca caggtgtacg tgtaccctcc aagccgcgac   1080
gagctgacta aaaaccaggt ctccctgacc tgtctggtga aggggttcta tccaagtgat   1140
atcgctgtgg agtgggaatc aaatggacag cccgagaaca attacaagac tacccccccct   1200
gtgctggact cagatgggag cttcgccctg gtgtccaaac tgaccgtgga taagtctcgg   1260
tggcagcagg gaaatgtctt ttcctgttct gtgatgcacg aagcactgca caatcactac   1320
acccagaagt ccctgagcct gtcacccggc aaa                                1353
```

```
<210> SEQ ID NO 53
<211> LENGTH: 451
<212> TYPE: PRT
<213> ORGANISM: Artificial Sequence
<220> FEATURE:
<223> OTHER INFORMATION: synthetic monoclonal antibody polypeptide
      sequence - rituximab variant

<400> SEQUENCE: 53

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

```
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Lys Arg Arg Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Ala Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Val Leu Pro Pro Ser Arg Asp Glu Leu Thr Lys Asn Gln Val Ser
        355                 360                 365

Leu Leu Cys Leu Val Lys Gly Phe Tyr Pro Ser Asp Ile Ala Val Glu
    370                 375                 380

Trp Glu Ser Asn Gly Gln Pro Glu Asn Asn Tyr Leu Thr Trp Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 54
<211> LENGTH: 1353
<212> TYPE: DNA
<213> ORGANISM: Artificial Sequence
<220> FEATURE:
<223> OTHER INFORMATION: synthetic monoclonal antibody nucleotide sequence - rituximab variant

<400> SEQUENCE: 54

```
caggtccagc tgcagcagcc cggagctgaa ctggtcaaac ctggcgcatc cgtgaaaatg      60

tcttgcaagg ctagtggcta cacattcact tcctataaca tgcactgggt gaagcagaca     120

ccaggacgag gactggagtg gatcggagca atctaccctg gaaacggcga cacttcttat     180

aatcagaagt ttaaaggcaa ggccaccctg acagctgata agagctcctc taccgcctac     240

atgcagctga gttcactgac aagtgaagac tcagcagtgt actattgcgc cagaagcacc     300

tactatggcg gggattggta cttcaacgtg tgggggcag gaaccacagt caccgtgagc      360

gccgcttcca caaaaggacc aagcgtgttt ccactggcac caagctccaa gtcaaccagc     420
```

```
ggaggaacag cagccctggg atgtctggtg aaggactact tcccagagcc cgtcaccgtg    480

tcttggaaca gtggcgccct gacaagcggg gtccatactt ttcccgctgt gctgcagtct    540

agtggcctgt acagcctgtc aagcgtggtc accgtccctt cctctagtct ggggactcag    600

acctatatct gcaacgtgaa tcacaaacct tctaatacaa aggtcgacaa gaaagtggaa    660

ccaaaaagtt gtgataagac acatacttgc ccaccttgtc ctgcaccaaa gagaagagga    720

ggaccatccg tgttcctgtt tccacccaaa cccaaggaca ctctgatgat tagccggact    780

cctgaagtca cctgcgtggt cgtggacgtg agccacgagg accccgaagt caaattcaac    840

tggtacgtgg atggcgtcga ggtgcataat gccaaaacaa agccccggga ggaacagtac    900

aactcaacat atagagtcgt gagcgtcctg actgtgctgc accaggactg gctgaacggc    960

aaggagtata aatgcgccgt gtccaacaag gccctgcccg cacctatcga gaagactatt   1020

tctaaagcca agggccagcc tagggaacca caggtgtacg tgctgcctcc aagccgcgac   1080

gagctgacta aaaaccaggt ctccctgctg tgtctggtga aggggttcta tccaagtgat   1140

atcgctgtgg agtgggaatc aaatggacag cccgagaaca attacctgac ttggcccccct   1200

gtgctggact cagatgggag cttctttctg tattccaaac tgaccgtgga taagtctcgg   1260

tggcagcagg gaaatgtctt ttcctgttct gtgatgcacg aagcactgca caatcactac   1320

acccagaagt ccctgagcct gtcacccggc aaa                                1353
```

```
<210> SEQ ID NO 55
<211> LENGTH: 451
<212> TYPE: PRT
<213> ORGANISM: Artificial Sequence
<220> FEATURE:
<223> OTHER INFORMATION: synthetic monoclonal antibody polypeptide
      sequence - rituximab variant

<400> SEQUENCE: 55

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190
```

```
Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Asp Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Trp Ala Pro Ile
                325                 330                 335

Glu Lys Thr Ile Ser Lys Ala Lys Gly Gln Pro Arg Glu Pro Gln Val
            340                 345                 350

Tyr Val Tyr Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Ala Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 56
<211> LENGTH: 1353
<212> TYPE: DNA
<213> ORGANISM: Artificial Sequence
<220> FEATURE:
<223> OTHER INFORMATION: synthetic monoclonal antibody nucleotide
      sequence - rituximab variant

<400> SEQUENCE: 56

caggtccagc tgcagcagcc cggagctgaa ctggtcaaac ctggcgcatc cgtgaaaatg      60

tcttgcaagg ctagtggcta cacattcact tcctataaca tgcactgggt gaagcagaca     120

ccaggacgag gactggagtg gatcggagca atctaccctg gaaacggcga cacttcttat     180

aatcagaagt ttaaaggcaa ggccaccctg acagctgata agagctcctc taccgcctac     240

atgcagctga gttcactgac aagtgaagac tcagcagtgt actattgcgc cagaagcacc     300

tactatggcg gggattggta cttcaacgtg tggggggcag gaaccacagt caccgtgagc     360

gccgcttcca caaaaggacc aagcgtgttt ccactggcac caagctccaa gtcaaccagc     420

ggaggaacag cagccctggg atgtctggtg aaggactact tcccagagcc cgtcaccgtg     480
```

```
tcttggaaca gtggcgccct gacaagcggg gtccatactt ttcccgctgt gctgcagtct    540

agtggcctgt acagcctgtc aagcgtggtc accgtccctt cctctagtct ggggactcag    600

acctatatct gcaacgtgaa tcacaaacct tctaatacaa aggtcgacaa gaaagtggaa    660

ccaaaaagtt gtgataagac acatacttgc ccaccttgtc ctgcaccaga ggacgaggga    720

ggaccatccg tgttcctgtt tccacccaaa cccaaggaca ctctgatgat tagccggact    780

cctgaagtca cctgcgtggt cgtggacgtg agccacgagg accccgaagt caaattcaac    840

tggtacgtgg atggcgtcga ggtgcataat gccaaaacaa agccccggga ggaacagtac    900

aactcaacat atagagtcgt gagcgtcctg actgtgctgc accaggactg gctgaacggc    960

aaggagtata aatgcaaggt gtccaacaag gccctgtggg cacctatcga gaagactatt   1020

tctaaagcca agggccagcc tagggaacca caggtgtacg tgtaccctcc aagccgcgac   1080

gagctgacta aaaaccaggt ctccctgacc tgtctggtga aggggttcta tccaagtgat   1140

atcgctgtgg agtgggaatc aaatggacag cccgagaaca attacaagac tacccccccct  1200

gtgctggact cagatgggag cttcgccctg gtgtccaaac tgaccgtgga taagtctcgg   1260

tggcagcagg gaaatgtctt ttcctgttct gtgatgcacg aagcactgca caatcactac   1320

acccagaagt ccctgagcct gtcacccggc aaa                                 1353
```

```
<210> SEQ ID NO 57
<211> LENGTH: 451
<212> TYPE: PRT
<213> ORGANISM: Artificial Sequence
<220> FEATURE:
<223> OTHER INFORMATION: synthetic monoclonal antibody polypeptide
      sequence - rituximab variant

<400> SEQUENCE: 57

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205
```

```
Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Lys Arg Arg Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Trp Ala Pro Ile
                325                 330                 335

Glu Lys Thr Ile Ser Lys Ala Lys Gly Gln Pro Arg Glu Pro Gln Val
            340                 345                 350

Tyr Val Leu Pro Pro Ser Arg Asp Glu Leu Thr Lys Asn Gln Val Ser
        355                 360                 365

Leu Leu Cys Leu Val Lys Gly Phe Tyr Pro Ser Asp Ile Ala Val Glu
    370                 375                 380

Trp Glu Ser Asn Gly Gln Pro Glu Asn Asn Tyr Leu Thr Trp Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450


<210> SEQ ID NO 58
<211> LENGTH: 1353
<212> TYPE: DNA
<213> ORGANISM: Artificial Sequence
<220> FEATURE:
<223> OTHER INFORMATION: synthetic monoclonal antibody nucleotide
      sequence - rituximab variant

<400> SEQUENCE: 58

caggtccagc tgcagcagcc cggagctgaa ctggtcaaac ctggcgcatc cgtgaaaatg      60

tcttgcaagg ctagtggcta cacattcact tcctataaca tgcactgggt gaagcagaca     120

ccaggacgag gactggagtg gatcggagca atctaccctg gaaacggcga cacttcttat     180

aatcagaagt ttaaaggcaa ggccaccctg acagctgata agagctcctc taccgcctac     240

atgcagctga gttcactgac aagtgaagac tcagcagtgt actattgcgc cagaagcacc     300

tactatggcg gggattggta cttcaacgtg tggggggcag gaaccacagt caccgtgagc     360

gccgcttcca caaaaggacc aagcgtgttt ccactggcac caagctccaa gtcaaccagc     420

ggaggaacag cagccctggg atgtctggtg aaggactact tcccagagcc cgtcaccgtg     480

tcttggaaca gtggcgccct gacaagcggg gtccatactt ttcccgctgt gctgcagtct     540

agtggcctgt acagcctgtc aagcgtggtc accgtccctt cctctagtct ggggactcag     600
```

```
acctatatct gcaacgtgaa tcacaaacct tctaatacaa aggtcgacaa gaaagtggaa    660
ccaaaaagtt gtgataagac acatacttgc ccaccttgtc ctgcaccaaa gagaagagga    720
ggaccatccg tgttcctgtt tccacccaaa cccaaggaca ctctgatgat tagccggact    780
cctgaagtca cctgcgtggt cgtggacgtg agccacgagg accccgaagt caaattcaac    840
tggtacgtgg atggcgtcga ggtgcataat gccaaaacaa agccccggga ggaacagtac    900
aactcaacat atagagtcgt gagcgtcctg actgtgctgc accaggactg gctgaacggc    960
aaggagtata aatgcaaggt gtccaacaag gccctgtggg cacctatcga gaagactatt   1020
tctaaagcca agggccagcc tagggaacca caggtgtacg tgctgcctcc aagccgcgac   1080
gagctgacta aaaaccaggt ctccctgctg tgtctggtga aggggttcta tccaagtgat   1140
atcgctgtgg agtgggaatc aaatggacag cccgagaaca attacctgac ttggcccccct   1200
gtgctggact cagatgggag cttctttctg tattccaaac tgaccgtgga taagtctcgg   1260
tggcagcagg gaaatgtctt ttcctgttct gtgatgcacg aagcactgca caatcactac   1320
acccagaagt ccctgagcct gtcacccggc aaa                                 1353
```

<210> SEQ ID NO 59
<211> LENGTH: 451
<212> TYPE: PRT
<213> ORGANISM: Artificial Sequence
<220> FEATURE:
<223> OTHER INFORMATION: synthetic monoclonal antibody polypeptide sequence - rituximab variant

<400> SEQUENCE: 59

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220
```

```
Asp Lys Thr His Thr Cys Pro Pro Cys Pro Ala Pro Glu Asp Glu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ser Val Ser His
            260                 265                 270

Lys Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Ala Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Val Tyr Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Ala Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 60
<211> LENGTH: 1353
<212> TYPE: DNA
<213> ORGANISM: Artificial Sequence
<220> FEATURE:
<223> OTHER INFORMATION: synthetic monoclonal antibody nucleotide sequence - rituximab variant

<400> SEQUENCE: 60

```
caggtccagc tgcagcagcc cggagctgaa ctggtcaaac ctggcgcatc cgtgaaaatg     60

tcttgcaagg ctagtggcta cacattcact tcctataaca tgcactgggt gaagcagaca    120

ccaggacgag gactggagtg gatcggagca atctaccctg gaaacggcga cacttcttat    180

aatcagaagt ttaaaggcaa ggccaccctg acagctgata agagctcctc taccgcctac    240

atgcagctga gttcactgac aagtgaagac tcagcagtgt actattgcgc cagaagcacc    300

tactatggcg gggattggta cttcaacgtg tggggggcag gaaccacagt caccgtgagc    360

gccgcttcca caaaaggacc aagcgtgttt ccactggcac caagctccaa gtcaaccagc    420

ggaggaacag cagccctggg atgtctggtg aaggactact tcccagagcc cgtcaccgtg    480

tcttggaaca gtggcgccct gacaagcggg gtccatactt ttcccgctgt gctgcagtct    540

agtggcctgt acagcctgtc aagcgtggtc accgtccctt cctctagtct ggggactcag    600

acctatatct gcaacgtgaa tcacaaacct tctaatacaa aggtcgacaa gaaagtggaa    660
```

```
ccaaaaagtt gtgataagac acatacttgc ccaccttgtc ctgcaccaga ggacgaggga     720

ggaccatccg tgttcctgtt tccacccaaa cccaaggaca ctctgatgat tagccggact     780

cctgaagtca cctgcgtggt cgtgagcgtg agccacaagg accccgaagt caaattcaac     840

tggtacgtgg atggcgtcga ggtgcataat gccaaaacaa agccccggga ggaacagtac     900

aactcaacat atagagtcgt gagcgtcctg actgtgctgc accaggactg gctgaacggc     960

aaggagtata aatgcgccgt gtccaacaag gccctgcccg cacctatcga gaagactatt    1020

tctaaagcca agggccagcc tagggaacca caggtgtacg tgtaccctcc aagccgcgac    1080

gagctgacta aaaaccaggt ctccctgacc tgtctggtga aggggttcta tccaagtgat    1140

atcgctgtgg agtgggaatc aaatggacag cccgagaaca attacaagac tacccccccct   1200

gtgctggact cagatgggag cttcgccctg gtgtccaaac tgaccgtgga taagtctcgg    1260

tggcagcagg gaaatgtctt ttcctgttct gtgatgcacg aagcactgca caatcactac    1320

acccagaagt ccctgagcct gtcacccggc aaa                                 1353
```

```
<210> SEQ ID NO 61
<211> LENGTH: 451
<212> TYPE: PRT
<213> ORGANISM: Artificial Sequence
<220> FEATURE:
<223> OTHER INFORMATION: synthetic monoclonal antibody polypeptide
      sequence - rituximab variant

<400> SEQUENCE: 61

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Lys Arg Arg Gly
225                 230                 235                 240
```

```
Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ser Val Ser His
            260                 265                 270

Lys Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Ala Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Val Leu Pro Pro Ser Arg Asp Glu Leu Thr Lys Asn Gln Val Ser
        355                 360                 365

Leu Leu Cys Leu Val Lys Gly Phe Tyr Pro Ser Asp Ile Ala Val Glu
    370                 375                 380

Trp Glu Ser Asn Gly Gln Pro Glu Asn Asn Tyr Leu Thr Trp Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 62
<211> LENGTH: 1353
<212> TYPE: DNA
<213> ORGANISM: Artificial Sequence
<220> FEATURE:
<223> OTHER INFORMATION: synthetic monoclonal antibody nucleotide sequence - rituximab variant

<400> SEQUENCE: 62

```
caggtccagc tgcagcagcc cggagctgaa ctggtcaaac ctggcgcatc cgtgaaaatg      60

tcttgcaagg ctagtggcta cacattcact tcctataaca tgcactgggt gaagcagaca     120

ccaggacgag gactggagtg gatcggagca atctaccctg gaaacggcga cacttcttat     180

aatcagaagt ttaaaggcaa ggccaccctg acagctgata agagctcctc taccgcctac     240

atgcagctga gttcactgac aagtgaagac tcagcagtgt actattgcgc cagaagcacc     300

tactatggcg gggattggta cttcaacgtg tggggggcag gaaccacagt caccgtgagc     360

gccgcttcca caaaaggacc aagcgtgttt ccactggcac caagctccaa gtcaaccagc     420

ggaggaacag cagccctggg atgtctggtg aaggactact tcccagagcc cgtcaccgtg     480

tcttggaaca gtggcgccct gacaagcggg gtccatactt ttcccgctgt gctgcagtct     540

agtggcctgt acagcctgtc aagcgtggtc accgtccctt cctctagtct ggggactcag     600

acctatatct gcaacgtgaa tcacaaacct tctaatacaa aggtcgacaa gaaagtggaa     660

ccaaaaagtt gtgataagac acatacttgc ccaccttgtc ctgcaccaaa gagaagagga     720

ggaccatccg tgttcctgtt tccacccaaa cccaaggaca ctctgatgat tagccggact     780
```

```
cctgaagtca cctgcgtggt cgtgagcgtg agccacaagg accccgaagt caaattcaac    840

tggtacgtgg atggcgtcga ggtgcataat gccaaaacaa agccccggga ggaacagtac    900

aactcaacat atagagtcgt gagcgtcctg actgtgctgc accaggactg gctgaacggc    960

aaggagtata aatgcgccgt gtccaacaag gccctgcccg cacctatcga gaagactatt   1020

tctaaagcca agggccagcc tagggaacca caggtgtacg tgctgcctcc aagccgcgac   1080

gagctgacta aaaaccaggt ctccctgctg tgtctggtga aggggttcta tccaagtgat   1140

atcgctgtgg agtgggaatc aaatggacag cccgagaaca attacctgac ttggcccccct  1200

gtgctggact cagatgggag cttctttctg tattccaaac tgaccgtgga taagtctcgg   1260

tggcagcagg gaaatgtctt ttcctgttct gtgatgcacg aagcactgca caatcactac   1320

acccagaagt ccctgagcct gtcacccggc aaa                                1353
```

```
<210> SEQ ID NO 63
<211> LENGTH: 451
<212> TYPE: PRT
<213> ORGANISM: Artificial Sequence
<220> FEATURE:
<223> OTHER INFORMATION: synthetic monoclonal antibody polypeptide
      sequence - rituximab variant

<400> SEQUENCE: 63

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Asp Glu Gly
225                 230                 235                 240

Gly Pro Ser Val Phe Leu Phe Pro Pro Lys Pro Lys Asp Thr Leu Met
                245                 250                 255
```

```
Ile Ser Arg Thr Pro Glu Val Thr Cys Val Val Val Ser Val Ser His
            260                 265                 270

Lys Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Glu Val Ser Asn Lys Ala Leu Pro Ala Pro Ile
                325                 330                 335

Lys Lys Thr Ile Ser Lys Ala Lys Gly Gln Pro Arg Glu Pro Gln Val
            340                 345                 350

Tyr Val Tyr Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Ala Leu Val Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

```
<210> SEQ ID NO 64
<211> LENGTH: 1353
<212> TYPE: DNA
<213> ORGANISM: Artificial Sequence
<220> FEATURE:
<223> OTHER INFORMATION: synthetic monoclonal antibody nucleotide
      sequence - rituximab variant

<400> SEQUENCE: 64

caggtccagc tgcagcagcc cggagctgaa ctggtcaaac ctggcgcatc cgtgaaaatg      60

tcttgcaagg ctagtggcta cacattcact tcctataaca tgcactgggt gaagcagaca     120

ccaggacgag gactggagtg gatcggagca atctaccctg gaaacggcga cacttcttat     180

aatcagaagt ttaaaggcaa ggccaccctg acagctgata agagctcctc taccgcctac     240

atgcagctga gttcactgac aagtgaagac tcagcagtgt actattgcgc cagaagcacc     300

tactatggcg gggattggta cttcaacgtg tggggggcag gaaccacagt caccgtgagc     360

gccgcttcca caaaaggacc aagcgtgttt ccactggcac caagctccaa gtcaaccagc     420

ggaggaacag cagccctggg atgtctggtg aaggactact tcccagagcc cgtcaccgtg     480

tcttggaaca gtggcgccct gacaagcggg gtccatactt ttcccgctgt gctgcagtct     540

agtggcctgt acagcctgtc aagcgtggtc accgtccctt cctctagtct ggggactcag     600

acctatatct gcaacgtgaa tcacaaacct tctaatacaa aggtcgacaa gaaagtggaa     660

ccaaaaagtt gtgataagac acatacttgc ccaccttgtc ctgcaccaga ggacgaggga     720

ggaccatccg tgttcctgtt tccacccaaa cccaaggaca ctctgatgat tagccggact     780

cctgaagtca cctgcgtggt cgtgagcgtg agccacaagg accccgaagt caaattcaac     840
```

```
tggtacgtgg atggcgtcga ggtgcataat gccaaaacaa agccccggga ggaacagtac    900

aactcaacat atagagtcgt gagcgtcctg actgtgctgc accaggactg gctgaacggc    960

aaggagtata aatgcgaggt gtccaacaag gccctgcccg cacctatcaa gaagactatt   1020

tctaaagcca agggccagcc tagggaacca caggtgtacg tgtaccctcc aagccgcgac   1080

gagctgacta aaaaccaggt ctccctgacc tgtctggtga aggggttcta tccaagtgat   1140

atcgctgtgg agtgggaatc aaatggacag cccgagaaca attacaagac tacccccccct  1200

gtgctggact cagatgggag cttcgccctg gtgtccaaac tgaccgtgga taagtctcgg   1260

tggcagcagg gaaatgtctt ttcctgttct gtgatgcacg aagcactgca caatcactac   1320

acccagaagt ccctgagcct gtcacccggc aaa                                1353
```

```
<210> SEQ ID NO 65
<211> LENGTH: 451
<212> TYPE: PRT
<213> ORGANISM: Artificial Sequence
<220> FEATURE:
<223> OTHER INFORMATION: synthetic monoclonal antibody polypeptide
      sequence - rituximab variant

<400> SEQUENCE: 65

Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Lys Arg Arg Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Ser Val Ser His
            260                 265                 270
```

```
Lys Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Glu Val Ser Asn Lys Ala Leu Pro Ala Pro Ile
                325                 330                 335

Lys Lys Thr Ile Ser Lys Ala Lys Gly Gln Pro Arg Glu Pro Gln Val
            340                 345                 350

Tyr Val Leu Pro Pro Ser Arg Asp Glu Leu Thr Lys Asn Gln Val Ser
        355                 360                 365

Leu Leu Cys Leu Val Lys Gly Phe Tyr Pro Ser Asp Ile Ala Val Glu
    370                 375                 380

Trp Glu Ser Asn Gly Gln Pro Glu Asn Asn Tyr Leu Thr Trp Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450
```

<210> SEQ ID NO 66
<211> LENGTH: 1353
<212> TYPE: DNA
<213> ORGANISM: Artificial Sequence
<220> FEATURE:
<223> OTHER INFORMATION: synthetic monoclonal antibody nucleotide sequence - rituximab variant

<400> SEQUENCE: 66

```
caggtccagc tgcagcagcc cggagctgaa ctggtcaaac ctggcgcatc cgtgaaaatg     60

tcttgcaagg ctagtggcta cacattcact tcctataaca tgcactgggt gaagcagaca    120

ccaggacgag gactggagtg gatcggagca atctaccctg gaaacggcga cacttcttat    180

aatcagaagt ttaaaggcaa ggccaccctg acagctgata agagctcctc taccgcctac    240

atgcagctga gttcactgac aagtgaagac tcagcagtgt actattgcgc cagaagcacc    300

tactatggcg gggattggta cttcaacgtg tggggggcag gaaccacagt caccgtgagc    360

gccgcttcca caaaaggacc aagcgtgttt ccactggcac caagctccaa gtcaaccagc    420

ggaggaacag cagccctggg atgtctggtg aaggactact tcccagagcc cgtcaccgtg    480

tcttggaaca gtggcgccct gacaagcggg gtccatactt ttcccgctgt gctgcagtct    540

agtggcctgt acagcctgtc aagcgtggtc accgtccctt cctctagtct ggggactcag    600

acctatatct gcaacgtgaa tcacaaacct tctaatacaa aggtcgacaa gaaagtggaa    660

ccaaaaagtt gtgataagac acatacttgc ccaccttgtc ctgcaccaaa gagaagagga    720

ggaccatccg tgttcctgtt tccacccaaa cccaaggaca ctctgatgat tagccggact    780

cctgaagtca cctgcgtggt cgtgagcgtg agccacaagg accccgaagt caaattcaac    840

tggtacgtgg atggcgtcga ggtgcataat gccaaaacaa agccccggga ggaacagtac    900

aactcaacat atagagtcgt gagcgtcctg actgtgctgc accaggactg gctgaacggc    960
```

```
aaggagtata aatgcgaggt gtccaacaag gccctgcccg cacctatcaa gaagactatt   1020

tctaaagcca agggccagcc tagggaacca caggtgtacg tgctgcctcc aagccgcgac   1080

gagctgacta aaaaccaggt ctccctgctg tgtctggtga aggggttcta tccaagtgat   1140

atcgctgtgg agtgggaatc aaatggacag cccgagaaca attacctgac ttggccccct   1200

gtgctggact cagatgggag cttctttctg tattccaaac tgaccgtgga taagtctcgg   1260

tggcagcagg gaaatgtctt ttcctgttct gtgatgcacg aagcactgca caatcactac   1320

acccagaagt ccctgagcct gtcacccggc aaa                                1353


<210> SEQ ID NO 67
<211> LENGTH: 214
<212> TYPE: PRT
<213> ORGANISM: Artificial Sequence
<220> FEATURE:
<223> OTHER INFORMATION: synthetic polypeptide sequence - variant
      trastuzumab light chain

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 68
<211> LENGTH: 213
<212> TYPE: PRT
<213> ORGANISM: Artificial Sequence
<220> FEATURE:
<223> OTHER INFORMATION: synthetic polypeptide sequence - variant
      rituxiumab light chain

<400> SEQUENCE: 68
```

```
Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
            20                  25                  30

His Trp Phe Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 69
<211> LENGTH: 639
<212> TYPE: DNA
<213> ORGANISM: Artificial Sequence
<220> FEATURE:
<223> OTHER INFORMATION: synthetic nucleotide sequence - variant rituxiumab light chain

<400> SEQUENCE: 69

```
cagattgtcc tgtctcagag tcccgctatc ctgtcagcaa gccctgggga gaaggtgacc     60

atgacatgcc gagccagctc ctctgtcagc tacatccact ggttccagca gaagccaggc    120

agttcaccta aaccatggat ctacgccaca tctaacctgg ctagtggagt gcccgtccgg    180

ttttccggct ctgggagtgg aacatcatac agcctgacta tttccagagt ggaggccgaa    240

gacgccgcta cctactattg ccagcagtgg acctctaatc cccctacatt cggcgggggga    300

actaagctgg agatcaaaag gactgtggca gccccttctg tcttcatttt tccacccagt    360

gacgaacagc tgaaatcagg aaccgcttcc gtggtctgtc tgctgaacaa cttctacccc    420

cgcgaggcaa aggtgcagtg gaaagtcgat aacgccctgc agtccggcaa ttctcaggag    480

agtgtgaccg aacaggactc aaaggatagc acatattccc tgagctccac tctgaccctg    540

tccaaagctg attacgaaaa gcataaagtg tatgcatgtg aggtcaccca ccaggggctg    600

agtagtcccg tcacaaagag tttcaataga ggagagtgt                           639
```

<210> SEQ ID NO 70
<211> LENGTH: 217
<212> TYPE: PRT

<213> ORGANISM: Homo sapiens

<400> SEQUENCE: 70

```
Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215
```

<210> SEQ ID NO 71
<211> LENGTH: 5
<212> TYPE: PRT
<213> ORGANISM: Artificial Sequence
<220> FEATURE:
<223> OTHER INFORMATION: synthetic IgG polypeptide sequence CH1 for IgG1, IgG3 and IgG4

<400> SEQUENCE: 71

```
Val Asp Lys Arg Val
1               5
```

<210> SEQ ID NO 72
<211> LENGTH: 10
<212> TYPE: PRT
<213> ORGANISM: Artificial Sequence
<220> FEATURE:
<223> OTHER INFORMATION: synthetic ‘upper’ hinge IgG polypeptide sequence for IgG1

<400> SEQUENCE: 72

```
Glu Pro Lys Ser Cys Asp Lys Thr His Thr
1               5                   10
```

<210> SEQ ID NO 73
<211> LENGTH: 5
<212> TYPE: PRT
<213> ORGANISM: Artificial Sequence
<220> FEATURE:
<223> OTHER INFORMATION: synthetic 'core' hinge IgG polypeptide sequence
for IgG1 and IgG2

<400> SEQUENCE: 73

Cys Pro Pro Cys Pro
1 5

<210> SEQ ID NO 74
<211> LENGTH: 8
<212> TYPE: PRT
<213> ORGANISM: Artificial Sequence
<220> FEATURE:
<223> OTHER INFORMATION: synthetic 'lower' hinge (CH2) IgG polypeptide
sequence for IgG1, IgG3 and IgG4

<400> SEQUENCE: 74

Ala Pro Glu Leu Leu Gly Gly Pro
1 5

<210> SEQ ID NO 75
<211> LENGTH: 5
<212> TYPE: PRT
<213> ORGANISM: Artificial Sequence
<220> FEATURE:
<223> OTHER INFORMATION: synthetic IgG polypeptide sequence CH1 for IgG2

<400> SEQUENCE: 75

Val Asp Lys Thr Val
1 5

<210> SEQ ID NO 76
<211> LENGTH: 7
<212> TYPE: PRT
<213> ORGANISM: Artificial Sequence
<220> FEATURE:
<223> OTHER INFORMATION: synthetic 'upper' hinge IgG polypeptide
sequence for IgG2

<400> SEQUENCE: 76

Glu Leu Lys Cys Cys Val Glu
1 5

<210> SEQ ID NO 77
<211> LENGTH: 7
<212> TYPE: PRT
<213> ORGANISM: Artificial Sequence
<220> FEATURE:
<223> OTHER INFORMATION: synthetic 'lower' hinge (CH2) IgG polypeptide
sequence for IgG2

<400> SEQUENCE: 77

Ala Pro Pro Val Ala Gly Pro
1 5

<210> SEQ ID NO 78
<211> LENGTH: 12
<212> TYPE: PRT
<213> ORGANISM: Artificial Sequence
<220> FEATURE:
<223> OTHER INFORMATION: synthetic 'upper' hinge IgG polypeptide
sequence for IgG3

<400> SEQUENCE: 78

Glu Leu Lys Thr Pro Leu Gly Asp Thr Thr His Thr
1 5 10

-continued

```
<210> SEQ ID NO 79
<211> LENGTH: 45
<212> TYPE: PRT
<213> ORGANISM: Artificial Sequence
<220> FEATURE:
<223> OTHER INFORMATION: synthetic 'core' hinge IgG polypeptide sequence
      for IgG3

<400> SEQUENCE: 79

Glu Pro Lys Ser Cys Asp Thr Pro Pro Pro Cys Pro Arg Cys Pro Glu
1               5                   10                  15

Pro Lys Ser Cys Asp Thr Pro Pro Pro Cys Pro Arg Cys Pro Glu Pro
            20                  25                  30

Lys Ser Cys Asp Thr Pro Pro Pro Cys Pro Arg Cys Pro
        35                  40                  45


<210> SEQ ID NO 80
<211> LENGTH: 7
<212> TYPE: PRT
<213> ORGANISM: Artificial Sequence
<220> FEATURE:
<223> OTHER INFORMATION: synthetic 'upper' hinge IgG polypeptide
      sequence for IgG4

<400> SEQUENCE: 80

Glu Ser Lys Tyr Gly Pro Pro
1               5


<210> SEQ ID NO 81
<211> LENGTH: 5
<212> TYPE: PRT
<213> ORGANISM: Artificial Sequence
<220> FEATURE:
<223> OTHER INFORMATION: synthetic 'core' hinge IgG polypeptide sequence
      for IgG4

<400> SEQUENCE: 81

Cys Pro Ser Cys Pro
1               5
```

HETEROMULTIMERS WITH REDUCED OR SILENCED EFFECTOR FUNCTION

CROSS-REFERENCE

This application claims the benefit of U.S. Provisional Application No. 61/829,973, filed May 31, 2013, which application is incorporated herein by reference in its entirety for all purposes.

SEQUENCE LISTING

The instant application contains a Sequence Listing which has been submitted electronically in ASCII format and is hereby incorporated by reference in its entirety. Said ASCII copy, created on Jan. 25, 2016, is named 097993-0964931SL.txt and is 200 kilobytes in size.

INTRODUCTION

2.1. Field of the Invention

The present invention relates to the field of therapeutic antibody design and specifically to polypeptides: comprising a heterodimeric Fc region which has been modified in order to silence effector functions mediated by the Fc region.

2.2 Background of the Invention

Therapeutic antibodies have been developed for the treatment of many disease indications. In some of these cases the efficacy of the therapeutic antibody results, at least in part, from the ability of the Fc region of the antibody to mediate one or more effector functions. These effector functions result from the interaction of antibodies and antibody-antigen complexes with cells of the immune system to stimulate a variety of responses, including antibody-dependent cell-mediated cytotoxicity (ADCC) and complement dependent cytotoxicity (CDC) (reviewed in Daeron, Annu. Rev. Immunol. 15:203-234 (1997); Ward and Ghetie, Therapeutic Immunol. 2:77-94 (1995); and Ravetch and Kinet, Annu. Rev. Immunol. 9:457-492 (1991)). Several antibody effector functions are mediated by Fc receptors (FcRs), which bind the Fc region of an antibody. FcRs are defined by their specificity for immunoglobulin isotypes; Fc receptors for IgG antibodies are referred to as FcγR, for IgE antibodies as FcεR, for IgA antibodies as FcαR and so on. The Fc region of antibodies also mediates functions, such as binding to FcRn, that operate independently of antigen binding and that confer persistence in the circulation and the ability to be transferred across cellular barriers by transcytosis (Ward and Ghetie, Therapeutic Immunology 2:77-94 (1995)).

For certain disease indications, however, effector functions mediated by the Fc region of the antibody can cause undesirable adverse effects and thus efforts have been made to engineer antibodies with reduced or silenced effector functions.

Recent publications describe strategies that have been used to engineer antibodies with reduced or silenced effector activity (see Strohl, W R (2009), Curr Opin Biotech 20:685-91, and Strohl, W R and Strohl L M, "Antibody Fc engineering for optimal antibody performance" In Therapeutic Antibody Engineering, Cambridge: Woodhead Publishing (2012), pp 225-249). These strategies include reduction of effector function through modification of glycosylation, use of IgG2/IgG4 scaffolds, or the introduction of mutations in the hinge or CH2 regions of the Fc region of the antibody.

In addition, US Patent Publication No. 2011/0212087 (Strohl) describe antibodies and other Fc-containing molecules with variations in the Fc region that reduce binding to FcγRs (Fc gamma receptors) and resulting activity and can be used in the treatment of various diseases and disorders.

International Patent Publication No. WO 2006/105338 (Xencor) describes Fc variants with optimized properties, methods for their generation, Fc polypeptides comprising Fc variants with optimized properties, and methods for using Fc variants with optimized properties.

US Patent Publication No. 2012/0225058 (Xencor) describes an Fc variant of a parent IgG Fc construct, wherein said Fc variant exhibits altered binding to one or more FcγRs, wherein said Fc variant comprises at least one amino acid insertion in the Fc region of said parent IgG Fc construct.

US Patent Publication No. 2012/0251531 (Genentech) describes engineered polypeptides comprising Fc variants and their uses, and more specifically, Fc variants exhibiting reduced effector function. These variants are also described as causing a benefit for a patient suffering from a disease which could be treated with an antibody for which it is desirable to reduce the effector function elicited by antibodies.

Strop et al ((2012) J. Mol. Biol. 420: 204-219) describe the introduction of charged mutations in the core hinge region and CH3 region of human IgG1 and IgG2 to improve bi-specific antibody formation.

SUMMARY OF THE INVENTION

Provided herein are heteromultimers comprising an IgG Fc construct having a first and a second Fc polypeptide, each Fc polypeptide comprising a modified lower hinge region wherein: the modified lower hinge region of said first Fc polypeptide comprises at least one amino acid modification, the modified lower hinge region of said second Fc polypeptide comprises at least one amino acid modification which is different from at least one amino acid modification of said first Fc polypeptide, and the IgG Fc construct displays reduced binding to all Fcγ receptors and to C1q protein as compared to a corresponding; parent IgG Fc construct.

In certain embodiments is a heteromultimer described herein, wherein the at least one amino acid modification in the modified lower hinge region of the first Fc polypeptide increases the net positive charge in the modified lower hinge region, and the at least one amino acid modification in the second Fc polypeptide increases the total number of negative charges or is charge neutral relative to the wild-type hinge region; or the at least one amino acid modification in the modified lower hinge region of the first Fc polypeptide increases the net negative charge in the modified lower hinge region, and the at least one amino acid modification in the second Fc polypeptide increases the total number of positive charges.

In some embodiments is a heteromultimer described herein, wherein the modified lower hinge region of at least one of said first and second Fc polypeptides comprises two or more amino acid modifications.

Provided herein is a heteromultimer comprising an IgG Fc construct having a first and a second Fc polypeptide, each Fc polypeptide comprising a modified hinge region wherein: the modified hinge region of said first Fc polypeptide comprises at least one amino acid modification that increases the net charge in the modified hinge region of the first Fc polypeptide at about physiological pH conditions, the modified hinge region of said second Fc polypeptide comprises at least one amino acid modification which is different from at least one amino acid modification of said first Fc polypeptide, and the IgG Fc construct displays reduced binding to all Fcγ receptors and to C1q protein as compared to a corresponding parent IgG Fc construct.

In some embodiments is a heteromultimer described herein wherein the increase in net charge is an increase in net positive charge on the first Fc polypeptide. In some embodiments, said increase in net positive charge is an increase in the total number of positively charged amino acids on the first Fc polypeptide, or a decrease in the total number of negatively charged amino acids on the first Fc polypeptide. In certain embodiments is a heteromultimer described herein, wherein the at least one amino acid modification on the modified hinge region of said first Fc polypeptide increases the total number of positively charged amino acids on said first Fc polypeptide, and the at least one amino acid modification on the modified hinge region of said second Fc polypeptide increases the total number of negative charges on said second Fc polypeptide or is charge neutral.

In an embodiment, the increase in net charge is an increase in the net negative charge on the first Fc polypeptide. In certain embodiments, the increase in net negative charge is an increase in the total number of negatively charged amino acids or a decrease in the total number of positively charged amino acids on the first Fc polypeptide. In certain embodiments when the net negative charge is an increase in the total number of negatively charged amino acids, the at least one amino acid modification on the second. Fc polypeptide increases the total number of positive charges.

In some embodiments is provided a heteromultimer described herein, wherein the at least one amino acid modification in the modified hinge region of the first Fc polypeptide combined with the at least one amino acid modification in the second Fc polypeptide increases the overall positive charge of the IgG Fc construct compared to a corresponding parent IgG Fc construct not comprising the hinge region modifications.

In certain embodiments is provided a heteromultimer described herein, wherein the modified hinge region of at least one of said first and second Fc polypeptides comprises two or more amino acid modifications.

In certain embodiments is provided a heteromultimer described herein, wherein the modified hinge region of said first and second Fc polypeptides comprises two or more amino acid modifications.

In certain embodiments is provided a heteromultimer described herein, wherein the at least one amino acid modification in the modified hinge region of the first and second Fc polypeptides is in the lower hinge region.

Provided is a heteromultimer described herein, wherein the IgG Fc construct has a $K_D$ of greater than 10 μM for FcγRIIaH, a $K_D$ of greater than 10 μM for FcγRIIaR, a $K_D$ of greater than 10 μM for FcγRIIb, a $K_D$ of greater than 6 μM for FcγRIIaF, a $K_D$ of greater than 6 μM for FcγRIIIaV, and a $K_D$ of greater than 6.5 nM for FcγRa.

In certain embodiments is provided a heteromultimer described herein, wherein the IgG Fc construct mediates reduced effector function compared to a corresponding IgG Fc construct not comprising the amino acid modifications. In some embodiments, the IgG Fc construct mediates less than 70%, less than 50%, less than 30%, or less than 10% of effector function as measured by $EC_{50}$. In some embodiments, the IgG Fc construct mediates less than 10%, less than 5%, less than 2%, or less than 1% of the effector function as measured by maximum lysis of cells. In an embodiment, the effector function is selected from ADCC, ADCP, CDC or any combination thereof.

In certain embodiments is provided a heteromultimer described herein, wherein the modified hinge region of at least one of said first and second Fc polypeptides comprises amino acid modifications at L234 and/or L235. In some embodiments, the modified hinge region of it least one of said first and second Fc polypeptides comprises amino acid modifications selected from L234K, L234R, L234A, L235K, L235R, and L235A. In a further embodiment one of said first and second Fc polypeptides further comprises an amino acid modification at E233. In some embodiments, said modification at E233 is selected from E233A, E233K. and E233R.

In certain embodiments is provided a heteromultimer described herein, wherein the modified hinge region of both said first and second Fc polypeptides comprises amino acid modifications at L234 and/or L235. In some embodiments, the modification at L234 and/or L235 is selected from L234A, L234K, L234R, L234D, L234E, L235K, L235R, L235E, L235A, and L235D. In a further embodiment, the modified hinge region of the first and/or the second Fc polypeptide further comprises an amino acid modification at E233. In some embodiments, either or both amino acid modifications are independently E233A or E233D.

In certain embodiments is provided a heteromultimer described herein, wherein the modified hinge region of at least one of said first and second Fc polypeptides comprises the amino acid modifications L234K/L235K, E233A/L234R/L235R, E233K/L234R/L235R, or E233KL234A/L235K.

In certain embodiments is provided a heteromultimer described herein, wherein the modified hinge region of the first or second Fc polypeptide comprises the amino acid modifications L234A/L235A, L234D/L235E, E233A/L234D/L235E, or E233A/L234K/L235A.

In certain embodiments is provided a heteromultimer described herein, wherein: the modified hinge region of the first Fc polypeptide comprises the amino acid modifications L234KL235K and the modified hinge region of the second Fc polypeptide comprises the amino acid modifications L234A/L235A; the modified hinge region of the first Fc polypeptide comprises the amino acid modifications L234K/L235K and the modified hinge region of the second Fc polypeptide comprises the amino acid modifications L234D/L235E; the modified hinge region of the first Fc polypeptide comprises the amino acid modifications E233A/L234R/L235R and the modified hinge region of the second Fc polypeptide comprises the amino acid modifications E233A/L234D/L235E; the modified hinge region of the first Fc polypeptide comprises the amino acid modification$ E233K/L234R/L235R and the modified hinge region of the second Fc polypeptide comprises the amino acid modifications L234D/L235E; or the modified hinge region of the first Fc polypeptide comprises the amino acid modifications E233K/L234R/L235K and the modified hinge region of the second Fc polypeptide comprises the amino acid modifications E233A/L234K/L235A.

In certain embodiments is provided a heteromultimer described herein, wherein: the first Fc polypeptide comprises the amino acid modifications L234D/L235E and the second Fc polypeptide comprises the amino acid modifications L234R/L235R/E233K; the first Fc polypeptide comprises the amino acid modifications L234D/L235E/D265S and the second Fc polypeptide comprises the amino acid modifications E233K/L234R/L235R/D265S; the first Fc polypeptide comprises the amino acid modifications L234D/L235E/E269K and the second Fc polypeptide comprises the amino acid modifications E233K/L234R/L235R/E269K; the first Fc polypeptide comprises the amino acid, modifications L234D/L235E/K322A and the second Fc polypeptide comprises the amino acid modifications E233K/L234R/L235R/K322A; the first Fc polypeptide comprises the amino acid modifications L234D/L235E/P329W and the second Fc polypeptide comprises the amino acid modifications E233K/L234R/L235R/P329W the first Fc polypeptide comprises the amino acid modifications L234D/L235E/E269K/D265S/K322A and the second Fc polypeptide comprises the amino acid modifications E233K/L234R/L235R/E269K/D265S/K322A; or the first Fc polypeptide comprises the amino acid modifications L234D/L235E/E269K/D265S/K322E/E333K and the second Fc polypeptide comprises the amino acid modifications E233K/L234R/L235R/E269K/D265S/K322E/E333K.

Provided herein is a heteromultimer comprising an IgG Fc construct having a first and a second Fc polypeptide, wherein: said first Fc polypeptide comprises the amino acid modifications E269Q/D270N and the second Fc polypeptide comprises the amino acid modifications E269K/D270R; or said first Fc polypeptide comprises the amino acid modifications L235K/A327K and the second Fc polypeptide does not comprise a modification at the hinge or lower hinge region; and wherein the IgG Fc construct displays reduced binding to all Fcγ receptors and to C1q protein as compared to a corresponding parent IgG Fc construct.

In some embodiments is a heteromultimer described herein, wherein the IgG Fc construct is aglycosylated. In some embodiments is a heteromultimer described herein, wherein the IgG Fc construct is deglycosylated.

In some embodiments is a heteromultimer described herein, wherein the onset of melting of the IgG Fc construct in a thermogram is greater than or equal to 68° C.

In some embodiments is a heteromultimer described herein, wherein the IgG Fc construct has a CH2 region with a melting temperature that is greater than or equal to the melting temperature of a corresponding parent CH2 region not comprising the hinge region modifications.

In an embodiment is the heteromultimer described herein, wherein the IgG Fc construct has a CH2 region with a melting temperature that is about 1 to 2° C. greater than the melting temperature of the parent CH2 region.

In an embodiment is the heteromultimer described herein, wherein the IgG Fc construct has a CH2 region with a melting temperature that is about 2 to 3° C. greater than the melting temperature of the parent CH2 region.

In an embodiment is the heteromultimer described herein, wherein the IgG Fc construct comprises a variant CH3 region comprising amino acid modifications that promote the formation of a heterodimeric Fc region in comparison to a homodimeric Fc region, when said heteromultimer is expressed. In some embodiments, one of said first and second Fc polypeptides comprises the CH3 amino acid modifications T366L/N390R/K392M/T394W and the other Fc polypeptide comprises the CH3 amino acid modifications L351Y/S400E/F405A/Y407V. In some embodiments, the first and/or second Fc polypeptides comprise the amino acid modification T350V. In a further embodiment, heteromultimers comprising a heterodimeric Fc region are resolved from expression products comprising a homodimeric Fc region using charge-based purification methods.

In an embodiment is the heteromultimer described herein, wherein the heteromultimer further comprises at least one antigen-binding construct fused to the IgG Fc construct.

In an embodiment is the heteromultimer described herein, wherein the at least one antigen-binding construct is selected from a Fab fragment, an scFv, an sdAb, an antigen binding peptide, an Fc fusion protein, or a protein or fragment thereof capable of binding the antigen. In some embodiments is a heteromultimer described herein, comprising one antigen-binding construct. In an embodiment is a heteromultimer described herein, comprising two antigen-binding constructs.

In an embodiment is a heteromultimer described herein, wherein the IgG Fc construct is linked to one or more toxic drug molecules.

In an embodiment is a heteromultimer described herein, wherein the IgG Fc construct is linked to one or more heterologous polypeptides. In some embodiments, the one or more heterologous polypeptides are selected from enzymes and toxins.

In an embodiment is a heteromultimer described herein, wherein the IgG is IgG1.

Provided herein is a nucleic acid encoding the first or second Fc polypeptide of the heteromultimer described herein. Provided is a host cell comprising the nucleic acid described herein. Provided is a method of preparing the heteromultimer described herein, the method comprising the steps of (a) culturing the host cell described herein; and (b) recovering the heteromultimer from the host cl culture. In certain embodiments is the method of preparing the heteromultimer, further comprising the step of isolating the heteromultimer using charge-based purification methods. In some embodiments is method of preparing the heteromultimer described herein, wherein the charge-based purification method is ion-exchange chromatography.

Provided is a pharmaceutical composition comprising the heteromultimer described herein and a pharmaceutically acceptable carrier. Provided is a method of treating a disease comprising providing to a patient in need thereof an effective amount of the pharmaceutical composition described herein. In some embodiments is use of the heteromultimer described herein in the preparation of a medicament for the treatment of a disease.

In some embodiments is use of a heteromultimer described herein for the treatment of a disease in a patient in need thereof.

Provided herein is a method of reducing the effector function of an antibody construct comprising: modifying the lower hinge region of a first and a second Fc polypeptide, wherein; the modified lower hinge region of said first Fc polypeptide comprises at least one amino acid modification, the modified lower hinge region of said second Fc polypeptide comprises at least one amino acid modification which is different from at least one amino acid modification of said first Fc polypeptide, and the IgG Fc construct displays reduced binding to all Fcγ receptors or to C1q protein as compared to a corresponding parent IgG Fc construct. In some embodiments, the modifications result in negligible binding to Fc receptors.

BRIEF DESCRIPTION OF THE FIGURES

These and other features of the invention will become more apparent in the following detailed description in which reference is made to the appended drawings.

denoting the loops and lower hinge of the CH2 domain of the Fc (shown in gray) that are involved in FcγR binding (shown in black). (B) Topology of the CH2 domain. Strands are denoted as S1, S2, S3, S4, S5, S6, and S7; Loops are denoted L1, L2, and L3.

Figure 1:
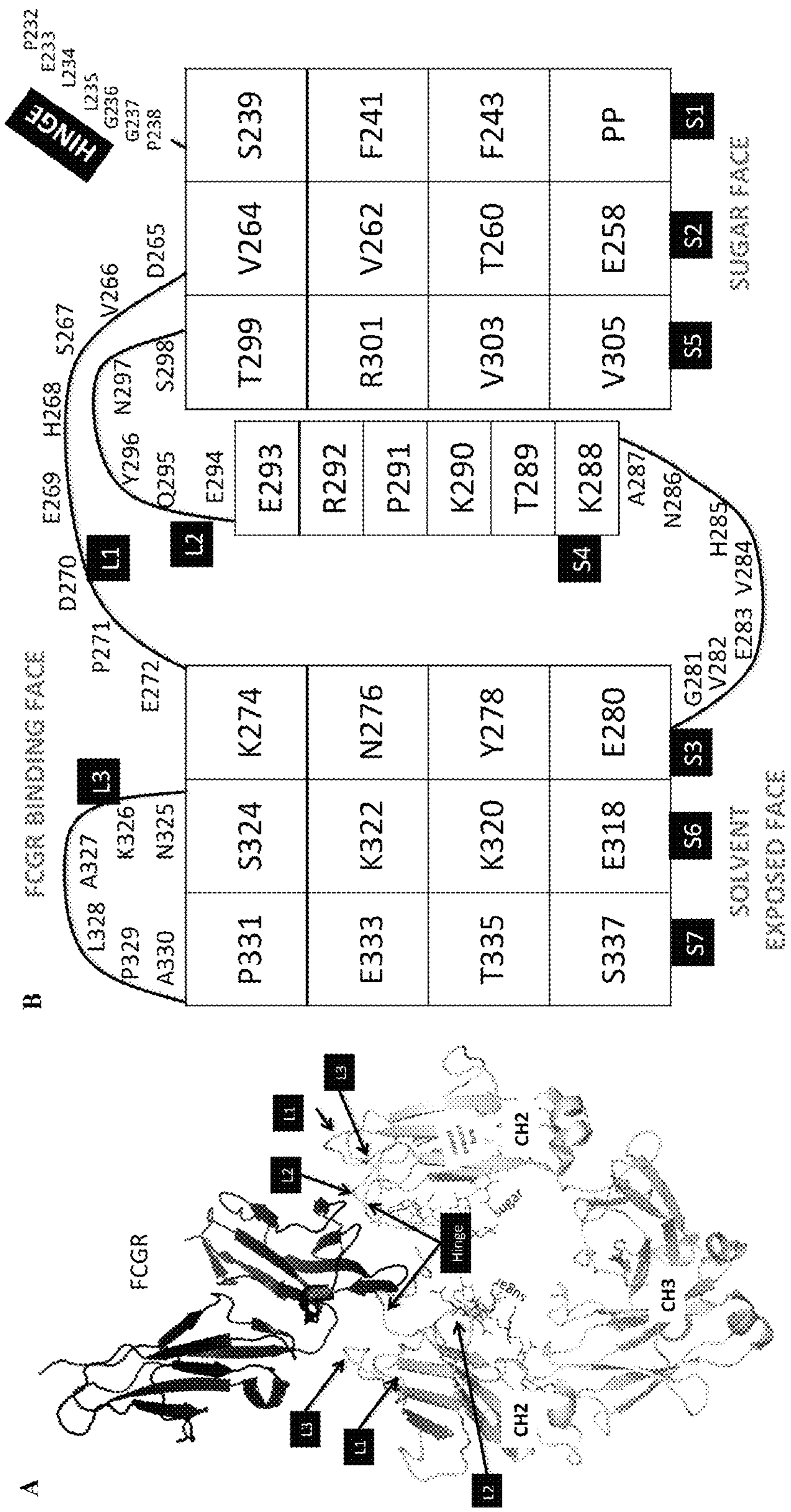
FIG. 1 depicts regions of the Fc region that are involved in FcγR binding. (A) 3b/Fc crystal structure (PDB:1E4K)
Figure 2:
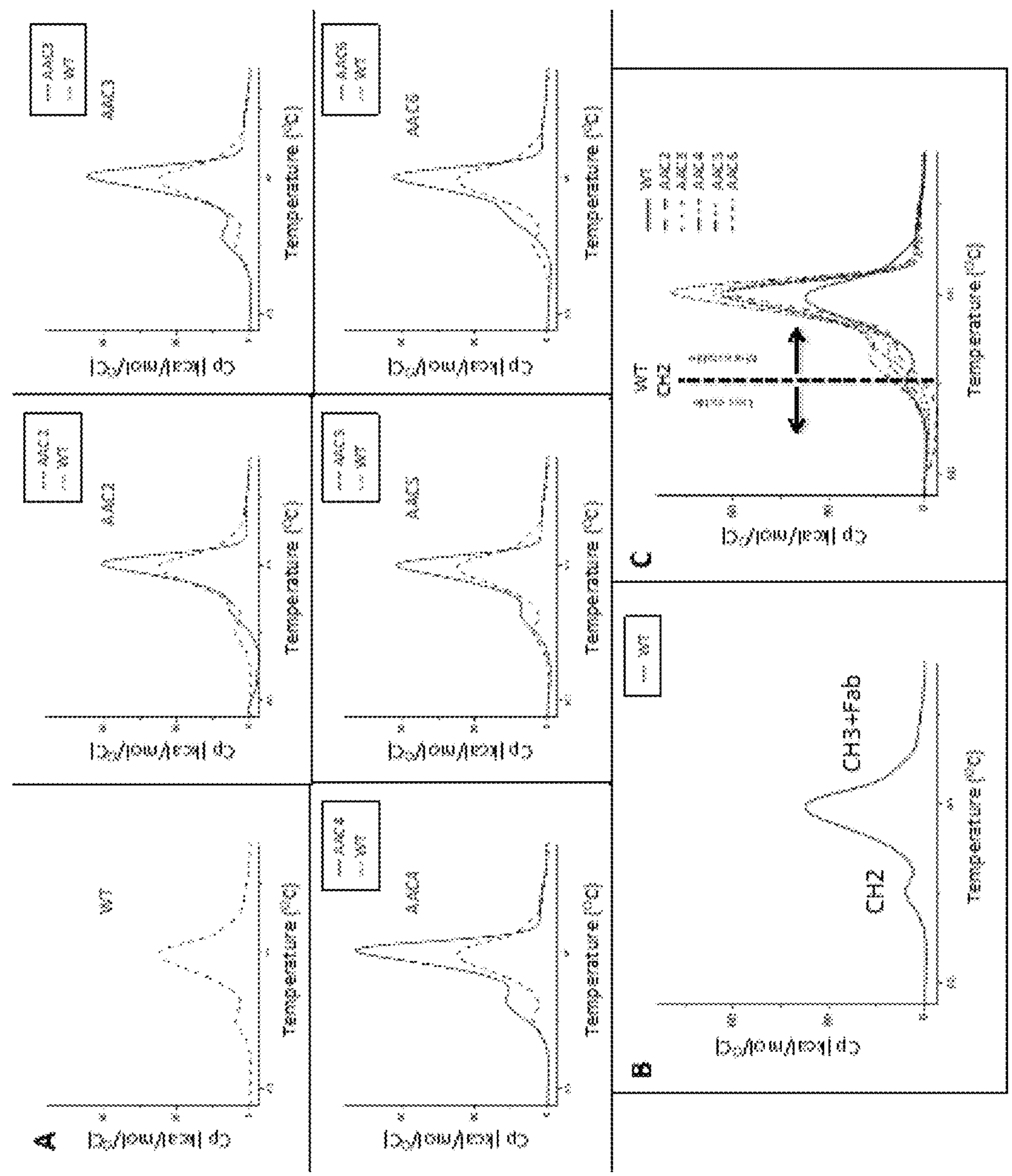

FIG. 2 depicts thermograms of exemplary asymmetric antibody constructs compared to wild-type antibody (WT). FIG. 2A depicts the thermograms for WT, and AAC2-AAC6. FIG. 2B depicts the identity of the two transitions in the WT. The first transition corresponds to the unfolding of the CH2 domain, the second transition corresponds to the unfolding of the CH3+Fab. FIG. 2C depicts the overlay of a number of samples showing how the CH2 transition of the variants has shifted to a higher Tm value, Indicating higher stability.

Figure 3A:
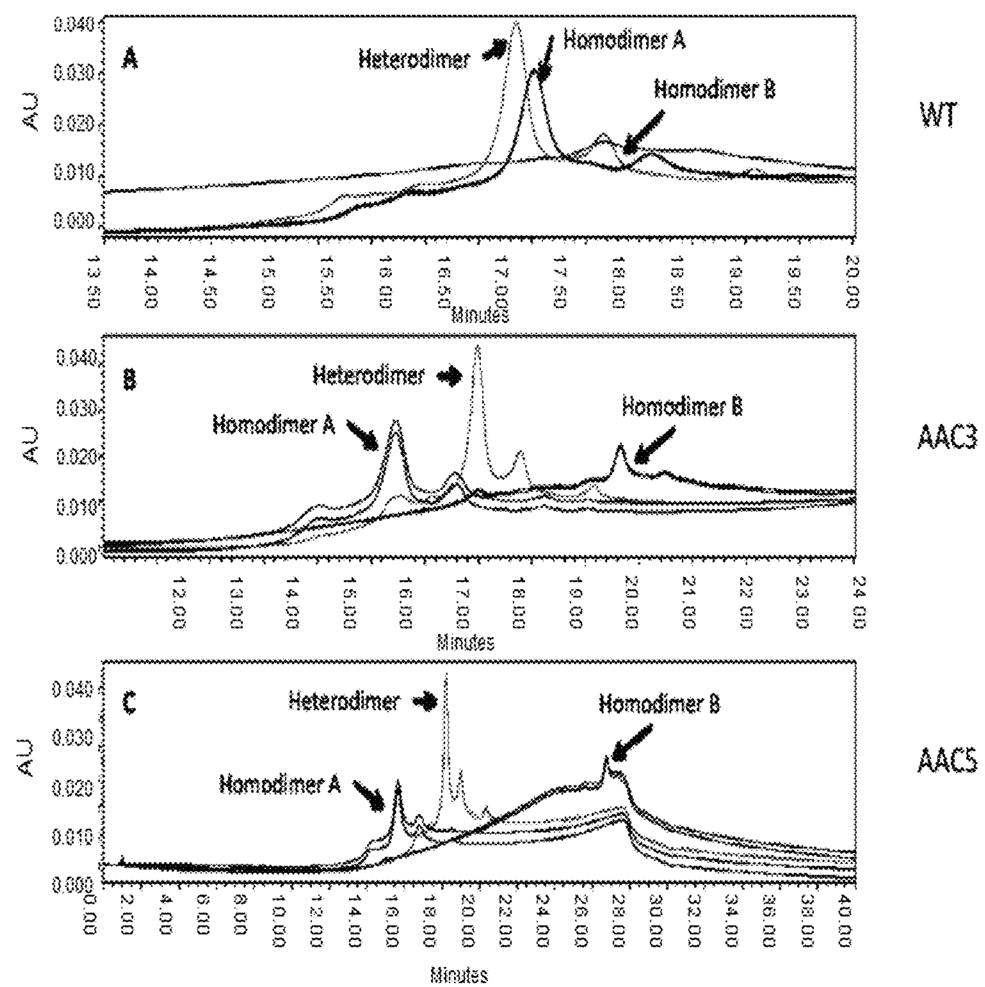
Figure 3B:
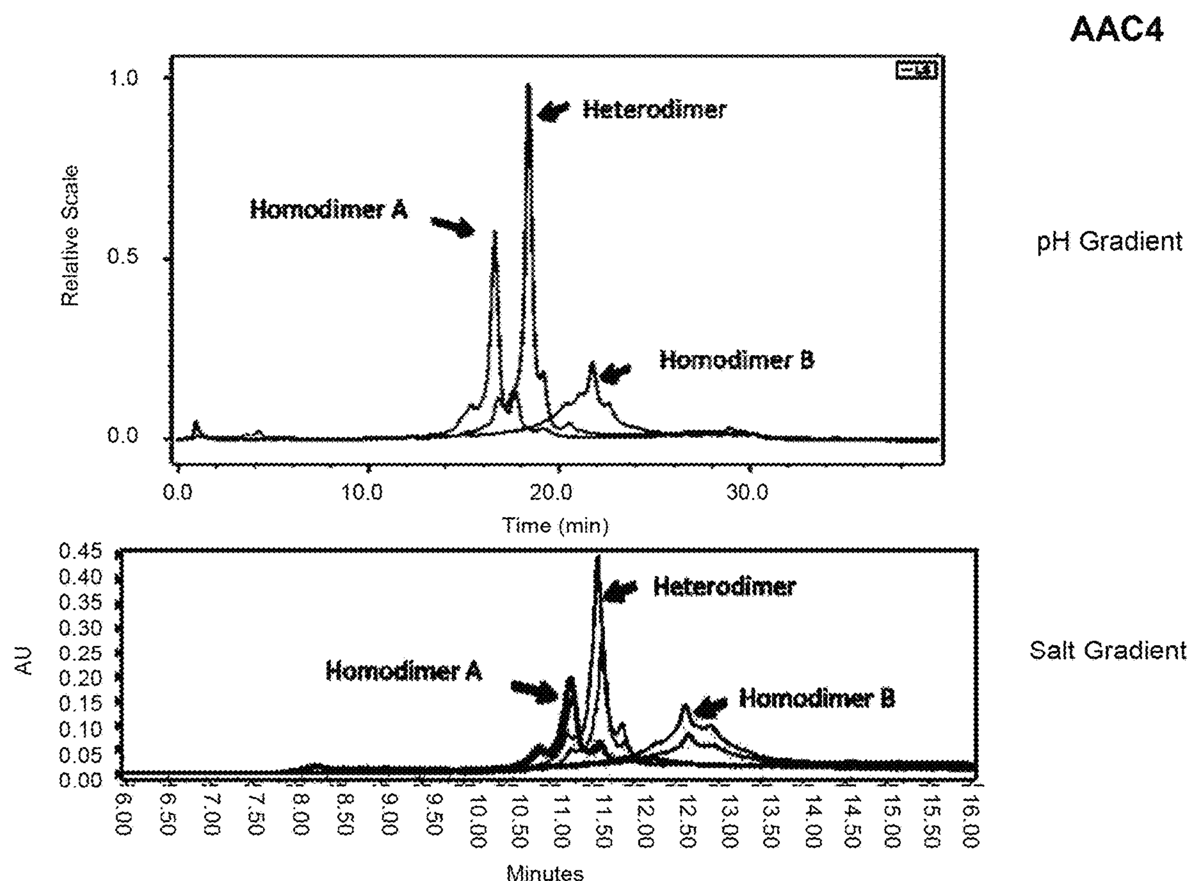

FIG. 3A depicts exemplary results showing the resolution by ion exchange chromatography of components produced when exemplary asymmetric antibody constructs are purified. FIG. 3B depicts separation of components using a pH gradient (upper panel), or a salt gradient (lower panel) using exemplary asymmetric variant AAC4.

Figure 4:
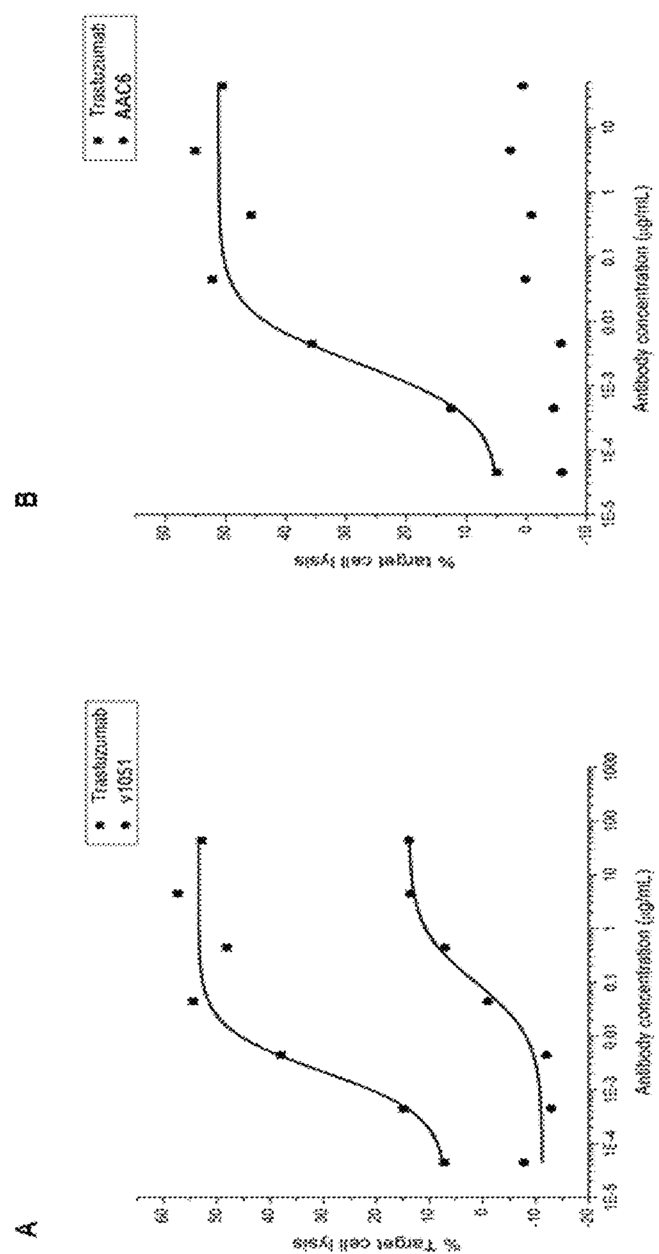

FIG. 4 depicts the ability of a control variant (v1051) and an exemplary heteromultimer of the invention (AAC6) to mediate ADCC.

FIG. 5 depicts the amino acid sequence of the human IgG1 Fc region (SEQ ID NO:1); the amino acid sequence of the heavy chain of trastuzumab (SEQ ID NO:2), the amino acid sequence of the light chain of trastuzumab (SEQ ID NO:3), the amino acid sequence of the heavy chain of rituximab (SEQ ID NO:4), the amino acid sequence of the light chain of rituximab (SEQ ID NO:5).

Figure 6:
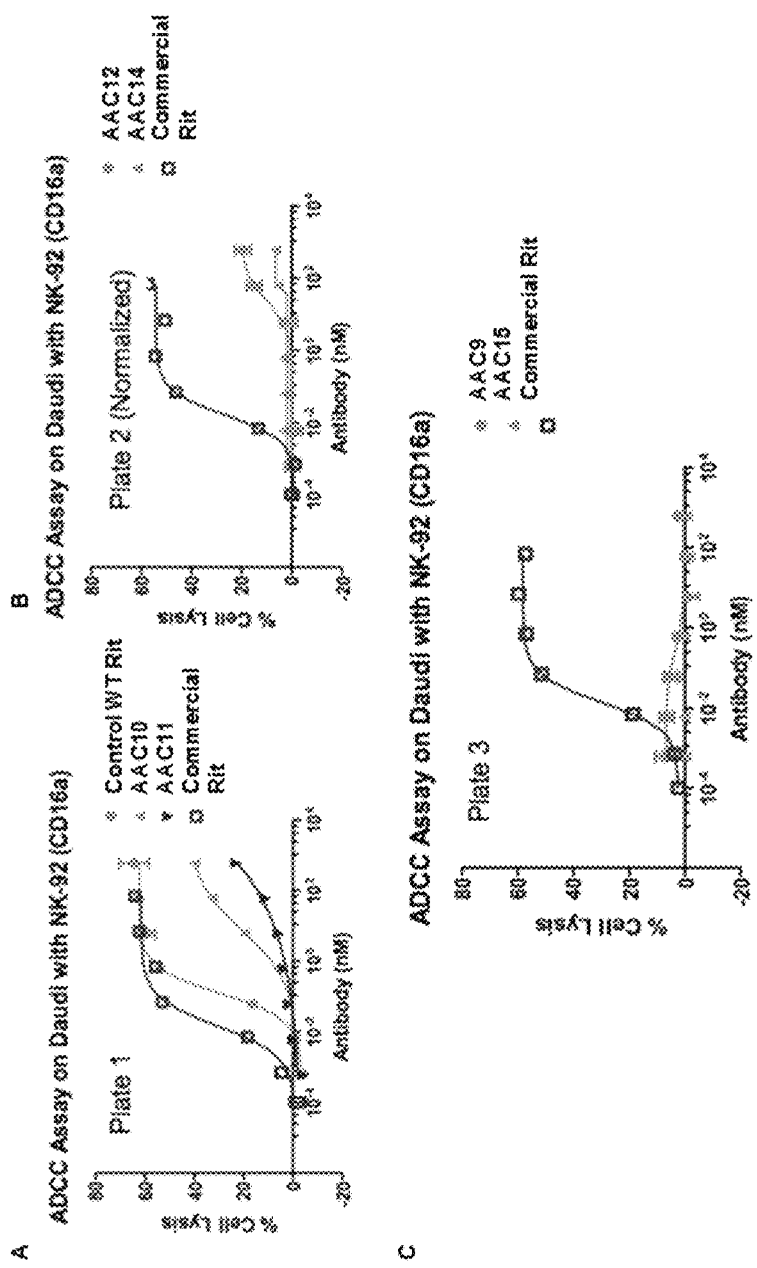

FIG. 6 depicts the ability of variants AAC9-AAC12, AAC14, and AAC15 to mediate ADCC in Daudi cells. FIG. 6A depicts the results for AAC10 and AAC11 compared to controls including commercially available rituximab; FIG. 6B depicts the results for AAC12 and AAC14 compared to controls including commercially available rituximb; FIG. 6C depicts' the results for AAC9 and AAC15 compared to controls including commercially available rituximab.

Figure 7:
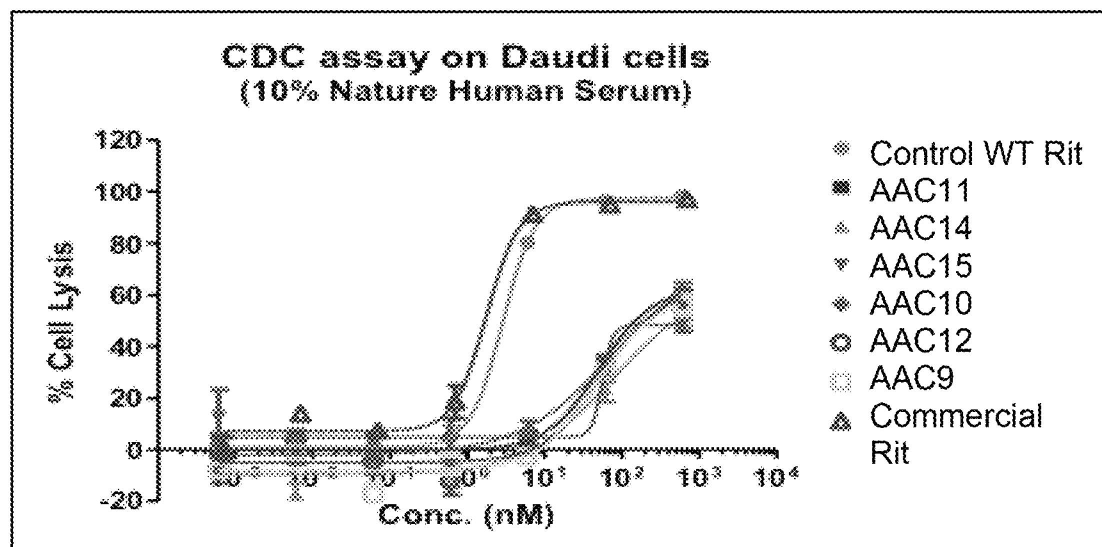

FIG. 7 depicts the ability of variants AAC9-AAC12, AAC14, and AAC15 to mediate CDC in Daudi cells.

FIG. 8A-8AA depicts sequences for SEQ ID NOs: 6-69 filed herewith.

DETAILED DESCRIPTION

The present invention provides a heteromultimer comprising an IgG Fc construct. The IgG Fc construct comprises two Fc polypeptides, each having a modified hinge region, wherein the modified hinge region comprises asymmetric amino acid modifications that reduce or eliminate binding of the IgG Fc construct to FcγRIIaH, FcγRIIaR, FcγRIIb FcγRIIIaF, FcγRIIIaV, and FcγRIa receptors and to complement factor C1q protein. Such reduction or elimination of this binding results in reduction or silencing of effector functions typically mediated by the wild-type IgG Fc region. As noted, the modified hinge region comprises asymmetric amino acid modifications and as such, the amino acid modifications in the hinge region of one polypeptide of the IgG Fc construct are different from those on the hinge region of the other polypeptide. In some embodiments, the isolated antibody constructs are stable and capable of binding to FcRn.

In certain embodiments, the modified hinge region of each polypeptide of the IgG Fc construct comprises one or more amino acid modifications, selected in order to increase the positive charge on one polypeptide of the IgG Fc construct compared to the other polypeptide of the IgG Fc construct. In certain embodiments, the modified hinge region of each polypeptide of the IgG Fc construct comprises one or more amino acid modifications, selected in order to increase the negative charge on one polypeptide of the IgG Fc construct compared to the other polypeptide of the IgG Fc construct.

The heteromultimer according to the invention can be useful in the development of therapeutic antibodies where effector functions are undesirable due to resulting side-effects such as cytotoxicity. In some embodiments, the heteromultimers also exhibit properties that facilitate their purification using charge-based methods.

Provided herein are heteromultimer constructs with reduced or silenced effector function. In an embodiment is provided a heteromultimer construct comprising an IgG Fc construct having a first and a second Fc polypeptide, each Fc polypeptide comprising a modified lower hinge region wherein: the modified lower hinge region of said first Fc polypeptide comprises at least one amino acid modification, the modified lower hinge region of said second Fc polypeptide comprises at least one amino acid modification which is different from at least one amino acid modification of said first Fc polypeptide, and the IgG Fc construct displays reduced binding to all Fcγ receptors and to C1q protein as compared to a corresponding parent IgG Fc construct. In certain embodiments, the heteromultimer construct displays negligible binding to Fcγ receptors as compared to a corresponding parent IgG Fc construct construct that does not have the modifications described herein. In some embodiments, the heteromultimer construct displays reduced binding to all Fcγ receptors and negligible binding to at least one Fcγ receptor. In certain embodiments, the heteromultimer construct described herein displays reduced binding to Fcγ receptors and negligible binding to C1q protein. In certain embodiments, at least one of said first and second Fc polypeptides comprises a further modification of at least one amino acid which is not in the lower hinge region. In certain embodiments, at least one of said first and second Fc polypeptides further comprises modification of at least one amino acid which is in the hinge region. In some embodiments, at least one of said first and second Fc polypeptides further comprises modification of at least one amino acid which is in the CH2 or CH3 region.

Provided herein is a heteromultimer comprising an IgG Fc construct having a first and a second Fc polypeptide, each Fc polypeptide comprising a modified hinge region wherein: the modified hinge region of said first Fc polypeptide comprises at least one amino acid modification that increases the net charge in the modified hinge region of the first Fc polypeptide at about physiological pH conditions, the modified hinge region of said second Fc polypeptide comprises at least one amino acid modification which is different from at least one amino acid modification of said first Fc polypeptide, and the IgG Fc construct displays reduced binding to all Foy receptors and to C1q protein as compared to a corresponding parent IgG Fc construct. In some embodiments, the increase in net charge is an increase in the net positive charge on the first Fc polypeptide. In an embodiment, the increase in the net positive charge is an increase in the total number of positively charged amino acids on the first Fc polypeptide. In certain embodiments, said increase in net charge is an increase in the net negative charges on the first Fc polypeptide. In a particular embodiment the increase in the net negative charge is an increase in the total number of negatively charged amino acids on the first Fc polypeptide. In some embodiments, the heteromultimer construct displays negligible binding to Fcγ receptors as compared to a corresponding parent IgG Fc construct construct that does not have the modifications described herein. In particular embodiments, the heteromultimer construct displays reduced binding to all Fcγ receptors and negligible binding to at least one Fcγ receptor. In an embodiment, the heteromultimer construct described herein displays reduced binding to Fcγ receptors and negligible binding to C1q protein. In certain embodiments, at least one of said first and second Fc polypeptides further comprises modification of at least one amino acid which is in the lower hinge region. In some embodiments, at least one of said first and second Fc polypeptides further comprises modification of at least one amino acid which is in the CH2 or CH3 region.

In some embodiments is the heteromultimer provided herein, wherein the one or more amino acid modifications in the modified hinge region of the second Fc polypeptide modifies the number of negative or positive charges in the hinge region, or is charge neutral relative to the wild-type hinge region. In certain embodiments is the heteromultimer described herein, wherein the modified hinge region of at least one of said first and second Fc polypeptides comprises two or more amino acid modifications. In an embodiment is provided the heteromultimer described herein, wherein the modified hinge region of said second Fc polypeptide comprises two or more amino acid modifications. In certain embodiments is a heteromultimer construct described herein, wherein the one or more amino acid modifications in the modified hinge region of the first and second Fc polypeptides are in the lower hinge region (amino acids 16-23 of SEQ ID NO:1, see FIG. 5).

In an embodiment is a heteromultimer described herein, wherein the IgG Fc construct has a $K_D$ of at least about 10 μM for FcγRIIaH, a $K_D$ of at least about 10 μM for FcγRIIaR, a $K_D$ of at least about 10 μM for FcγRIIb, a $K_D$ of at least about 6 μM for FcγRIIIaF, a $K_D$ of at least about 6 μM for FcγRIIIaV, and a $K_D$ of at least about 6.5 nM for FcγRIa. In some embodiments is a heteromultimer described herein, wherein the IgG Fc construct has a $K_D$ of greater than 10 μM for FcγRIIaH, a $K_D$ of greater than 10 μM for FcγRIIaR, a $K_D$ of greater than 10 μM for FcγRIIb, a $K_D$ of greater than 6 μM for FcγRIIIaF, a $K_D$ of greater than 6 μM for FcγRIIIaV, and a $K_D$ of greater than 6.5 nM for FcγRIa.

In some embodiments is a heteromultimer described herein, wherein the modified hinge region of at least one of said first and second Fc polypeptides comprises amino acid modifications of at least one of L234 and L235. In an embodiment is the heteromultimer described herein, wherein the modified hinge region of at least one of said first and second Fc polypeptides comprises amino acid modifications selected from L234K, L234R, L234A, L235K, L235R, and L235A. In an embodiment is the heteromultimer described herein, said one of first and second Fc polypeptides comprises an amino acid modification at E233. In an embodiment is the heteromultimer provided herein, wherein said modification at E233 is selected from E233A, E233K, and E233R. In some embodiments is the heteromultimer described herein, wherein the modified hinge region of at least one of said first and second Fc polypeptides comprises amino acid modifications at at least one of L234 and L235. In an embodiment is the heteromultimer described herein, wherein said modification at at least one of L234 and L235 is selected from L234A, L234K, L234R, L234D, L234E, L235K, L235R, L235E, 1235A, and L235D. In one embodiment is the heteromultimer described herein, wherein the modified hinge region of the second Fc polypeptide further comprises amino acid modifications at E233. In an embodiment, the first or second Fc polypeptide comprises amino acid modifications selected from E233A or E233D. In certain embodiments, at least one of said first or second Fc polypeptides further comprises at least one amino acid modification selected from D265S, E269K, K322A, P329W, and E333K. In some embodiments, said first and second Fc polypeptides further comprise at least one amino acid modification selected from D265S, E269K, K322A, P329W, and E333K.

Provided herein is a heteromultimer described herein, wherein the modified hinge region of at least one of said first and second Fc polypeptides comprises the amino acid modifications L234A/L235K E233A/L234R/L235R, E233K/L234R/L235R, or E233K/L234A/L235K. In some embodiments is a heteromultimer described herein, wherein the modified hinge region of the first or second Fc polypeptide comprises the amino acid modifications L234A/L235A, L234D/L235E, E233A/L234D/L235E, or E233A/L234K/L235A.

Provided herein is a heteromultimer as described herein, wherein the modified hinge region of the first Fc polypeptide comprises the amino acid modifications L234K/L235K and the modified hinge region of the second Fc polypeptide comprises the amino acid modifications L234A/L235K; the modified hinge region of the first Fc polypeptide comprises the amino acid modifications L234K/L235K and the modified hinge region of the second Fc polypeptide comprises the amino acid modifications L234D/L235E; the modified hinge region of the first Fc polypeptide comprises the amino acid modifications E233A/L234R/L235R and the modified hinge region of the second Fc polypeptide comprises the amino acid modifications E233A/L234D/L235E; the modified hinge region of the first Fc polypeptide comprises the amino acid modifications E233K/L234R/L235R and the modified hinge region of the second Fc polypeptide comprises the amino acid modifications L234D/L235E; or the modified hinge region of the first Fc polypeptide 'comprises the'amino acid modifications E233K/L234A/L235K and the modified hinge region of the second Fc polypeptide comprises the amino acid modifications E233A/L234K/L235A.

In some embodiments is the heteromultimer provided herein, wherein at least one of said first or second fc polypeptides further comprises at least one amino acid modification selected from D265S, E269K, K322A, P329W, and E333K. For instance, in an embodiment is a heteromultimer as described herein, wherein the first Fc polypeptide comprises the amino acid modifications L234D/L235E and the second Fc polypeptide comprises the amino acid modifications L234R/L235R/E233K. In another embodiment is a heteromultimer as described herein, wherein the first Fc polypeptide comprises the amino acid modifications L234D/L235E/D265S and the second Fc polypeptide comprises the amino acid modifications L234R/L235R/D265S. In a further embodiment is a heteromultimer as described herein, wherein the first Fc polypeptide comprises the amino acid modifications L234D/L235E/E269K and the second Fc polypeptide comprises the amino acid modifications E233K/L234R/L235R/E269K. In another embodiment is a heteromultimer as described herein, wherein the first Fc polypeptide comprises the amino acid modifications L234D/L235E/K322A and the second Fc polypeptide comprises the amino acid modifications E233K/L234R/L235R/K322A. In yet another embodiment is a heteromultimer as described herein, wherein the first Fc polypeptide comprises the amino acid modifications L234D/L235E/P329W and the second Fc polypeptide comprises the amino acid modifications E233K/

L234R/L235R/P329W. In an additional embodiment is a heteromultimer as described herein, wherein the first Fc polypeptide comprises the amino acid modifications L234D/L235E/E269K/D265S/K322A and the second-Fc polypeptide comprises; the amino acid modifications E233K/L234R/L235R/E269K/Q265S/K322A. In further embodiments is a heteromultimer as described, herein, wherein the first Fc polypeptide comprises the amino acid modifications L234D/L235E/E269K/D265S/K322E/E333K and the second Fc polypeptide comprises the amino acid modifications E233K/L234R/L235R/E269K/D265S/K322E/E333K.

Provided is a heteromultimer as described herein, wherein: the first Fc polypeptide comprises the amino acid modifications L234D/L235E and the second Fc polypeptide comprises the amino acid modifications L234R/L235R/E233K; the first Fc polypeptide comprises the amino acid modifications L234D/L235E/D265S and the second Fc polypeptide comprises the amino acid modifications L234R/L235R/D265S; the first Fc polypeptide comprises the amino acid modifications L234D/L235E/E269K and the second Fc polypeptide comprises the amino acid modifications E233K/L234R/L235R/E269K: the first Fc polypeptide comprises the amino acid modifications L234D/L235E/K322A and the second Fc polypeptide comprises the amino acid modifications. E233K/L234R/L235R/K322A; the first Fc polypeptide comprises the amino acid modifications L234D/L235E/P329W and the second Fc polypeptide comprises the amino acid modifications E233K/L234R/L235R/P329W the first Fc polypeptide comprises the amino acid modifications L234D/L235E/E269K/D265S/K322A and the second Fc polypeptide comprises the amino acid modifications E233K/L234R/L235R/E269K/D265S/K322A; or the first Fc polypeptide comprises the amino acid modifications L234D/L235E/E269K/D265S/K322E/E333K and the second Fc polypeptide comprises the amino acid modifications E233K/L234R/L235R/E269K/D265S/K322E/E333K.

Provided is a heteromultimer comprising an IgG Fc construct having a first and a second Fc poypeotide wherein: said first Fc polypeptide comprises the amino acid modifications E269Q/D270N and the second Fc polypeptide comprises the amino acid modifications E269K/D270R; or said first Fc polypeptide comprises the amino acid modifications L235K/A327K and the second Fc polypeptide does not comprise a modification at the hinge or lower hinge region; and wherein the IgG Fc construct displays reduced binding to all Fcγ receptors and to C1q protein as compared to a corresponding parent IgG Fc-construct.

In some embodiments is the heteromultimer provided herein, wherein the IgG Fc construct is aglycosylated. In an embodiment is the heteromultimer described herein, wherein the IgG Fc construct is deglycosylated.

In some embodiments is the heteromultimer described herein, wherein the onset of melting of the IgG Fc construct in a thermogram is greater than or equal to 68° C. In some embodiments is the heteromultimer described herein, wherein the IgG Fc construct has a CH2 region with a melting temperature that is comparable to the melting temperature of the parent CH2 region. In some embodiments is the heteromultimer described herein, wherein the IgG Fc construct has a CH2 region with a melting temperature that is greater than or about the same as the melting temperature of the parent CH2 region. In some embodiments is the heteromultimer described herein, wherein the IgG Fc construct has a CH2 region with a melting temperature that is about 1 to 2° C. greater than the melting temperature of the parent CH2 region. In an embodiment is the heteromultimer described herein, wherein the IgG Fc construct has a CH2 region with a melting temperature that is about 2 to 3° C. greater than the melting temperature of the parent CH2 region. In an embodiment is the heteromultimer described herein, wherein the IgG Fc construct has a CH2 region with a melting temperature that is about 5° C. greater than the melting temperature of the parent CH2 region.

Provided herein is a heteromultimer construct, wherein the IgG Fc construct comprises a variant CH3 region comprising amino acid modifications that promote the formation of a heterodimer Fc region.

In some embodiments is a heteromultimer construct described herein, wherein one of said first and second Fc polypeptides comprises the CH3 amino acid modifications T366L/N390R/K392M/T394W and the other Fc polypeptide comprises the CH3 amino acid modifications L351Y/S400E/F405A/Y407V.

In an embodiment is a heteromultimer construct described herein, wherein the IgG Fc construct comprises amino acid modifications that increase the stability of the CH3 region. In one embodiment the first and second Fc polypeptides comprise the amino acid modification T350V. In certain embodiments, any antibody constructs with homodimeric Fc constructs are clearly resolved from said heteromultimer using charge-based purification methods.

Provided are heteromultimers as described herein, wherein the heteromultimer further comprises at least one antigen-binding construct fused to the IgG Fc construct. In certain embodiments, the at least one antigen-binding construct is selected from a Fab fragment, an scFv, an sdAb, an antigen binding peptide, an Fc fusion protein, or a protein or fragment thereof capable of binding the antigen. In some embodiments is a heteromultimer comprising one antigen-binding construct. In some embodiments is a heteromultimer comprising two antigen-binding constructs. In an embodiment is a heteromultimer wherein the IgG Fc construct is linked to one or more toxic drug molecules. In certain embodiments, the IgG Fc construct is linked to one or more heterologous polypeptides. In some embodiments the one or more heterologous polypeptides is selected from enzymes and toxins.

Provided is a heteromultimer described herein, wherein the IgG is IgG1.

Provided herein is a nucleic acid encoding the first or second Fc polypeptide of the heteromultimer described herein. In some embodiments is a host cell comprising the nucleic acid described herein. In certain embodiments is a method of preparing the heteromultimer described herein, the method comprising the steps of (a) culturing the host cell described herein; and (b) recovering the heteromultimer from the host cell culture.

Provided herein are pharmaceutical compositions comprising the heteromultimer described herein and a pharmaceutically acceptable carrier. In certain embodiments is a method of treating a disease comprising providing to a patient in need thereof an effective amount of the pharmaceutical composition described herein. In some embodiments is the use of the heteromultimer described herein in the preparation of a medicament for the treatment of a disease. In some embodiments is the use of a therapeutic amount of the heteromultimer described herein for the treatment of a disease in a patient in need thereof.

Provided herein is a method of reducing the ADCC of an antibody construct comprising: modifying the lower hinge region of a first and a second Fc polypeptide, wherein the modified lower hinge region of said first Fc polypeptide comprises at least one amino acid modification, the modified lower hinge region of said second Fc polypeptide comprises at least one amino acid modification which is different from at least one amino acid modification of said first Fc polypeptide, and the IgG Fc construct displays reduced binding to all Fcγ receptors or to C1q protein as compared to a corresponding parent IgG Fc construct. In certain embodiments is the method of reducing ADCC, wherein said modifications result in negligible binding to Fc receptors.

Definitions

Unless defined otherwise, all technical and scientific terms used herein have the same meaning as is commonly understood by one of skill in the art to which the claimed subject matter belongs. In the event that there are a plurality of definitions for terms herein, those in this section prevail. Where reference is made to a URL or other such identifier or address, it is understood that such identifiers can change and particular information on the internet can come and go, but equivalent information can be found by searching the Internet Reference thereto evidences the availability and public dissemination of such information.

It is to be understood that the foregoing general description and the following detailed description are exemplary and explanatory only and are not restrictive of any subject matter claimed. In this application, the use of the singular includes the plural unless specifically stated otherwise.

"Parent CH2 domain" refers to a CH2 domain polypeptide of an Fc region comprising an amino acid sequence which lacks the one or more amino acid modifications in the hinge region of the first and second Fc polypeptides disclosed herein, but which may include one or more of disulfide hinge modifications, added CH2 disulfides, glycosylation modifications or different CH3 domain stabilities, and which differs in effector function compared to the CH2 domain of the heteromultimers of the invention. The parent CH2 domain may comprise a native sequence Fc region or an Fc region with pre-existing amino acid sequence modifications (such as additions, deletions and/or substitutions).

"Aglycosylated antibodes" refers to antibodies or heteromultimers that are not glycosylated during expression. Aglycosylated antibodies can be prepared by expression in systems lacking a mammalian glycosylation pathway, such as *E. coli*, or mutating one or more glycosylation sites such as N297.

"Deglycosylated antibodies" refers to antibodies or heteromultimers that are initially glycosylated during expression, but that subsequently undergo a biochemical reaction such as, for example, PNGase F treatment, that removed the glycan.

"Amino acid with neutral side chain" refers to an amino acid that contains a side chain that lacks a charge at neutral pH. A amino acids except lysine, arginine, aspartate, glutamate, and histidine are considered neutral. In some embodiments, depending on the structural environment it is found in, lysine, arginine, aspartate, glutamate and histidine are also considered neutral. In one embodiment, an "amino acid with neutral side chain" refers to an amino acid that contains a side chain that lacks overall charge at physiological pH.

"Amino acid with positively charged side chain" refers to a polar amino acid that contains a side chain that is protonated and hence positively charged at neutral pH. These amino acids are often referred as basic. Examples of amino acids with positively charged side chains include lysine, arginine. In some embodiments, depending on the structural environment it is found in, histidine can also be protonated and have a positively charged side chain. In one embodiment, an "amino acid with a positively charged side chain" refers to an amino acid that contains a side chain that is positively charged at physiological pH.

"Amino acid with a negatively charged side chain" is a polar amino acid whose side chain is deprotonated and hence negatively charged at neutral pH. These amino acids are often referred as acidic. Examples of amino acids with negatively charged side chains include aspartic acid and glutamic acid. In one embodiment, an "amino acid with a negatively charged side chain" refers to an amino acid that contains a side chain that is negatively charged at physiological pH.

"Binding affinity" generally refers to the strength of the sum total of noncovalent interactions between a single binding site of a molecule (e.g., an antibody) and its binding partner (e.g., an antigen or FcγR). The affinity of a molecule X for its partner Y can generally be represented by the dissociation constant (Kd or $K_D$). Affinity can be measured by common methods known in the art, including those described herein. Low-affinity antibodies bind antigen (or FcγR) weakly and tend to dissociate readily, whereas high-affinity antibodies bind antigen (or FcγR) more tightly and remain bound longer.

The term "Fc region" (or fragment crystallizable region) Is used to define the C-terminal region of an antibody. The Fc region is composed of two identical protein fragments, derived from the second and third constant domains of the antibody's two heavy chains: Chain A and Chain B. The second and third constant domains are known as the CH2 domain and the CH3 domain, respectively. The CH2 domain comprises a CH2 domain sequence of Chain A and a CH2 domain sequence of Chain B. The CH3 domain comprises a CH3 domain sequence of Chain A and a CH3 domain sequence of Chain B. As used herein, the Fc region includes the hinge region as defined below.

The term "Fc region sequence" I used to define a C-terminal region of an immunoglobulin heavy chain. The "Fc region sequence" may be a native Fc region sequence or a variant Fc region sequence. Although the boundaries of the Fc region sequence of an immunoglobulin heavy chain might vary, the human IgG heavy chain Fc region sequence is usually defined to stretch from an amino acid residue at position Cys226, or from Pro230, to the carboxyl-terminus thereof.

The "CH2 domain sequence" of a human IgG Fc region sequence (also referred to as "Cγ2" domain sequence) usually extends from about amino acid 231 to about amino acid 340. The CH2 domain sequence is unique in that it is not closely paired with another domain sequence. Rather, two N-linked branched carbohydrate chains are interposed between the two CH2 domain sequences of an intact native IgG molecule. It has been speculated that the carbohydrate may provide a substitute for the domain-domain pairing and help stabilize the CH2 domain. Burton, Molec. Immunol. 22: 161-206 (1985).

The "CH3 domain sequence" comprises the stretch of residues C-terminal to a CH2 domain sequence in an Fc region sequence (i.e. from about amino acid residue 341 to about amino acid residue 447 of an IgG).

A "functional Fc region" possesses the "effector functions" of a native Fc region. Exemplary "effector functions" include C1q binding; complement dependent cytotoxicity; Fc receptor binding; antibody-dependent cell-mediated cytotoxicity (ADCC) phagocytosis; down regulation of cell surface receptors (e.g. B cell receptor; BCR), etc. Such effector functions generally require the Fc region to be combined with a binding domain (e.g. an antibody variable domain) and can be assessed using various assays as herein disclosed, for example.

A "native Fc region sequence" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region sequence" comprises an amino acid sequence which differs from that of a native Fc region sequence by virtue of "one or more amino acid modifications" as herein defined. The variant Fc region sequence has at least one amino acid substitution compared to a native Fc region sequence or to the Fc region sequence of a parent polypeptide, e.g. from about one to about ten amino acid substitutions, and preferably from about one to about five amino acid substitutions in a native Fc region sequence or in the Fc region sequence of the parent polypeptide. In certain embodiments, the variant Fc region sequence herein possesses at least about 80% identity with a native Fc region sequence and/or with an Fc region sequence of a parent polypeptide, and most preferably at least about 90% identity therewith, more preferably at least about 95% identity therewith.

The terms "Fc receptor" or "FcR" are used to describe a receptor that binds to the Fc region of an antibody. The preferred FcR is a native human FcR. Moreover, in certain embodiments, the FcR is one which binds an IgG antibody (a gamma receptor, FcγR) and includes receptors of the FcγRI (CD64), FcγRII (CD32), and FcγRIII (CD16) subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRiB contains an immunoreceptor tyrosine-based inhibition motif (ITIM) in its cytoplasmic domain, (see review M. in Daeron, Annu. Rev. Immunol. 15:203-234 (1997)). FcRs are reviewed in Ravetch and Kinet, Annu. Rev. Immunol 9:457-92 (1991); Capel et al., Immunomethods 4:25-34 (1994); and de Haas et al., J. Lab. Clin. Med. 126:330-41 (1995). Other FcRs, Including those to be identified in the future are encompassed by the term "FcR" herein. The term "FcR" also includes the neonatal receptor, FcRn, which is responsible for the transfer of maternal IgGs to the fetus (Guyer et al., J. Immunol. 1 17:587 (1976) and Kim et al., J. Immunol. 24:249 (1994)). The term "FcγR" does not incude the FcRn.

"Antibody-dependent cell-mediated cytotoxicity" and "ADCC" refer to a cell-mediated reaction in which nonspecific cytotoxic cells that express FcRs (e.g. Natural Killer (NK) cells, neutrophils, and macrophages) recognize bound antibody on a target cell and subsequently cause lysis of the target cell. The primary cells for mediating ADCC, NK cells, express FcγRIII and low levels of FcγRIIc, whereas monocytes express FcγR, FcγRIII and FcγRII. FcR expression on hematopoietic cells is summarized in Table 3 on page 464 of Ravetch and Kinet, Annu. Rev. Immunol 9:457-92 (1991).

"Human effector cells" are leukocytes which express one or more FcRs and perform effector functions. Preferably, the cells express at least FcγRIII and perform ADCC effector function. Examples of human leukocytes which mediate ADCC include peripheral blood mononuclear cells (PBMC), natural killer (NK) cells, monocytes, cytotoxic T cells and neutrophils; with PBMCs and NK cells being preferred. The effector cells may be isolated from a native source thereof, e.g. from blood or PBMCs as described herein.

A heteromultimer with "greatly reduced," "silenced," "negligible" or "ablated" FcγR binding affinity and C1q binding affinity is one which has diminished FcγR binding activity and C1q binding activity compared to a parent polypeptide or to a polypeptide comprising a native Fc region sequence. In some embodiments, an heteromultimer with "greatly reduced," "silenced," negligible" or "ablated" FcγR binding affinity and C1q binding affinity is also a heteromultimer with "greatly reduced," "silenced," negligible" or "ablated" ADCC, ADCP and CDC activity compared to a parent polypeptide or to a polypeptide comprising a native Fc region sequence. A heteromultimer which "displays decreased or undetectable binding" to FcγR binds all FcγRs with lower affinity than the parent polypeptide. Such variants which display decreased binding to an FcγR may possess little or no appreciable binding to an FcγR. In one embodiment, the variant displays 0-20% binding to the FcγR compared to a native IgG Fc region, e.g. as determined in the Examples herein or as measured by change in equilibrium constant. In one embodiment, the variant displays 0-10% binding to the FcγR compared to a native IgG Fc region. In one embodiment, the variant displays 0-5% binding to the FcγR compared to a native IgG Fc region. In one embodiment, the variant displays 0-1% binding to the FcγR compared to a native IgG Fc region.

In another embodiment, a heteromultimer with "greatly reduced," "silenced," negligible" or "ablated" binding to FcγRIIaH has a Kd for FcγRIIaH that is greater than 5 μM as measured by SPR (surface plasmon resonance). In another embodiment, a heteromultimer with "greatly reduced," "silenced," negligible" or "ablated" binding to FcγRIIaR has a Kd for FcγRIIaR that is greater than 10 μM as measured by SPR (surface plasmon resonance). In another embodiment, a heteromultimer with "greatly reduced," "silenced," negligible" or "ablated" binding to FcγRIIb has a $K_D$ for FcγRIIb that is greater than 30 μM as measured by SPR (surface plasmon resonance). In another embodiment, a heteromultimer with "greatly reduced," "silenced," negligible" or "ablated" binding to FcγRIIIaF has a $K_D$ for FcγRIIIaF that is greater than 20 μM as measured by SPR (surface plasmon resonance). In another embodiment, a heteromultimer with "greatly reduced," "silenced," negligible" or "ablated" binding to FcγRIIIaV has a $K_D$ for FcγRIIIaV that is greater than 6 μM as measured by SPR (surface plasmon resonance). In another embodiment, a heteromultimer with "greatly reduced," "silenced," negligible" or "ablated" binding to FcγRIa has a $K_D$ for FcγRIa that is greater than 6.5 nM as measured by SPR (surface plasmon resonance).

The heteromultimer which "mediates antibody-dependent cell-mediated cytotoxicity (ADCC) in the presence of human effector cells more effectively" than a parent antibody is one which in vitro or in vivo is substantially more effective at mediating ADCC, when the amounts of heteromultimer and parent antibody used in the assay are essentially the same. Generally, such polypeptides will be identified using the in vitro ADCC assay as herein disclosed, but other assays or methods: for determining ADCC activity, e.g. in an animal model etc, are contemplated. The preferred polypeptide is from about 1.5 fold to about 100 fold, e.g.

from about two fold to about fifty fold, more effective at mediating ADCC than the parent, e.g. In the in vitro assay disclosed herein.

A "parent antibody," "parent polypeptide," or "polypeptide comprising a native Fc region" refers to a construct that does not comprise amino acid modifications to the hinge region. In one embodiment, the parent antibody is one that does not comprise amino acid modifications to the hinge region and comprises modifications to the CH3 domain that promote the formation of a heterodimeric Fc region.

An "amino acid modification" refers to a change in the amino acid sequence of a predetermined amino acid sequence. Exemplary modifications include an amino acid substitution, insertion and/or deletion. In certain embodiments the amino acid modification herein is a substitution. An "amino acid modification at" a specified position, e.g. of the Fc region, refers to the substitution or deletion of the specified residue, or the insertion of at least one amino acid residue adjacent the specified residue. By insertion "adjacent" a specified residue is meant insertion within one to two residues thereof. In certain embodiments the insertion is N-terminal or C-terminal to the specified residue.

An "amino acid substitution" refers to the replacement of at least one existing amino acid residue in a predetermined amino acid sequence with another different "replacement" amino acid residue. The replacement residue or residues may be "naturally occurring amino acid residues" (i.e. encoded by the genetic code) and selected from the group consisting of: alanine (Ala); arginine (Arg); asparagine (Asn); aspartic acid (Asp); cysteine (Cys); glutamine (Gin); glutamic acid (Glu); glycine (Gly); histidine (His); Isoleucine (lie); leucine (Leu); lysine (Lys); methionine (Met); phenylalanine (Phe); proline (Pro): serine (Ser); threonine (Thr); tryptophan (Trp); tyrosine (Tyr); and valine (Val). Preferably, the replacement residue is not cysteine. Substitution with one or more non-naturally occurring amino acid residues is also encompassed by the definition of an amino acid substitution herein. A "non-naturally occurring amino acid residue" refers to a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine and other amino acid residue analogues such as those described in Ellman et al. Meth. Enzym. 202:301-336 (1991). To generate such non-naturally occurring amino acid residues, the procedures of Noren et al. Science 244: 182 (1989) and Ellman et al., supra, can be used. Briefly, these procedures involve chemically activating a suppressor tRNA with a non-naturally occurring amino acid residue followed by in vitro transcription and translation of the RNA.

An "amino acid insertion" refers to the incorporation of at least one amino acid into a predetermined amino acid sequence. In certain embodiments, the insertion, consists of the insertion of one or two amino acid residues. In certain other embodiments are larger "peptide insertions", e.g. insertion of about three to about five or even up to about ten amino acid residues. In these embodiments the inserted residue(s) are naturally occurring or non-naturally occurring as disclosed above.

An "amino acid deletion" refers to the removal of at least one amino acid residue from a predetermined amino acid sequence.

"Hinge region" is generally defined from Glu216 to Pro238 of human IgG1, of which Cys226 to Pro230 form the 'core' hinge region (Burton, Molec. Immunol.22: 161-206 (1985)), while Ala231 to Pro238 form the 'lower' hinge region. Glu216 to Thr225 form the "upper" hinge region. Hinge regions of other IgG isotypes may be aligned with the IgG 1 sequence by placing the first and last cysteine residues forming inter-heavy chain S—S bonds in the same positions.

"C1q" is a mulitmer of polypeptides that includes a binding site for the Fc region of an immunoglobulin. C1q together with two serine proteases, C1r and C1s, forms the complex C1, the first component of the complement dependent cytotoxicity (CDC) pathway. Human C1q can be purchased commercially from, e.g. Quidel, San Diego, Calif.

The term "binding domain" refers to the region of a polypeptide that binds to another molecule. In the case of an FcR, the binding domain can comprise a portion of a polypeptide chain thereof (e.g. the α chain thereof) which is responsible for binding an Fc region. One useful binding domain is the extracellular domain of an FcRα chain.

The term "antibody" is used in the broadest sense and specifically covers monoclonal antibodies (including full length monoclonal antibodies), polyclonal antibodies, multispecific antibodies (e.g., bi-specific antibodies), and antibody fragments so long as they exhibit the desired biological activity.

"Antibody fragments", as defined herein, comprise a portion of an intact antibody, generally including at least one antigen binding or variable region of the intact antibody or the Fc region of an antibody. Examples of antibody fragments include linear antibodies; single-chain antibody molecules; and multi-specific antibodies formed from antibody fragments. In certain embodiments, the antibody fragments retain at least part of the hinge and optionally the CH1 region of an IgG heavy chain. In some embodiments the antibody fragments retain the entire constant region of an IgG heavy chain, and include an IgG light chain.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal," indicates the character of the antibody as being obtained from a substantially homogeneous population of antibodies, and is not to be construed as requiring production of the antibody by any particular method. In certain embodiments the monoclonal antibodies to be used in accordance with the present disclosure are made by the hybridoma method first described by Kohler et al., Nature 256:495 (1975), or may be made by recombinant DNA methods (see, e.g., U.S. Pat. No. 4,816,567). In some embodiments "monoclonal antibodies" are isolated from phage antibody libraries using the techniques described in Clackson et al., Nature 352:624-628 (1991) and Marks et al., J. Mol. Biol. 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

A "disorder" is any condition that would benefit from treatment with the polypeptide variant. This includes chronic and acute disorders or diseases including those pathological conditions which predispose the mammal to the disorder in question. In one embodiment, the disorder is cancer.

The word "label" when used herein refers to a detectable compound or composition which is conjugated directly or indirectly to the polypeptide. In certain embodiments the label is itself detectable (e.g., radioisotope labels or fluorescent labels). In some other embodiments, the label catalyzes chemical alteration of a substrate compound or composition which is detectable. An exemplary embodiment comprises an enzymatic label that catalyzes a chemical alteration of a substrate compound or composition which is detectable.

An "isolated" nucleic acid molecule is a nucleic acid molecule that is identified and separated from at least one contaminant nucleic acid molecule with which it is ordinarily associated in the natural source of the polypeptide nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the polypeptide where, for example, the nucleic acid molecule is in a chromosomal location different from that of natural cells.

The expression "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to utilize promoters, polyadenylation signals, and enhancers.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished, by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

The phrase "low affinity receptor" denotes a receptor that has a weak binding affinity for a ligand of interest, e.g. having a dissociation constant of about 50 nM or worse affinity. Exemplary low affinity receptors include FcγRII and FcγRIII.

By "Fc-fusion" as used herein is meant a protein wherein one or more polypeptides is operably linked to an Fc region or a derivative thereof. Fc fusion is herein meant to be synonymous with the terms "immunoadhesin", "Ig fusion", "Ig chimera", and "receptor globulin" (sometimes with dashes) as used in the art (Chamow et al., 1996, Trends Biotechnol 14:52-60; Ashkenazi et al., 1997, Curr Opin Immunol 9:195-200). An Fc fusion combines the Fc region of an immunoglobulin with a fusion partner, which in general can be any protein or small molecule. The role of the non-Fc part of an Fc fusion, i.e. the fusion partner, is to mediate target binding, and thus it is functionally analogous to the variable regions of an antibody. Virtually any protein or small molecule may be linked to Fc to generate an Fc fusion. Protein fusion partners may include, but are not limited to, the target-binding region of a receptor, an adhesion molecule, a ligand, an enzyme, a cytokine, a chemokine, or some other protein or protein domain. Small molecule fusion partners may include any therapeutic agent that directs the Fc fusion to a therapeutic target. Such targets may be any molecule, preferably an extracellular receptor, that is implicated in disease. Two families of surface receptors that are targets of a number of approved small molecule drugs are G-Protein Coupled Receptors (GPCRs), and ion channels, including .+, Na+, Ca+ channels. Nearly 70% of all drugs currently marketed worldwide target GPCRs. Thus the Fc proteins described herein may be fused to a small molecule that targets, for example, one or more GABA receptors, purinergic receptors, adrenergic receptors, histaminergic receptors, opioid receptors, chemokine receptors, glutamate receptors, nicotinic receptors, the 5HT (serotonin) receptor, and estrogen receptors. A fusion partner may be a small-molecule mimetic of a protein that targets a therapeutically useful target. Specific examples of particular drugs that may serve as Fc fusion partners can be found in L. S. Goodman et al., Eds., Goodman and Gilman's The Pharmacological Basis of Therapeutics (McGraw-Hill, New York, ed. 9, 1996). Fusion partners include not only small molecules and proteins that bind known targets for existing drugs, but orphan receptors that do not yet exist as drug targets. The completion of the genome and proteome projects are proving to be a driving force in drug discovery, and these projects have yielded a trove of orphan receptors. There is enormous potential to validate these new molecules as drug targets, and develop protein and small molecule therapeutics that target them. Such protein and small molecule therapeutics are contemplated as Fc fusion partners that employ the IgG Fc constructs described herein. A variety of linkers, defined and described below, may be used to covalently link Fc to a fusion partner to generate an Fc fusion.

By "target antigen" as used herein is meant the molecule that is bound specifically by the variable region of a given antibody. A target antigen may be a protein, carbohydrate, lipid, or other chemical compound.

By "target cell" as used herein is meant a cell that expresses a target antigen.

Throughout the present specification and claims, the numbering of the residues in an immunoglobulin heavy chain is that of the EU index as in Kabat et al., Sequences of Proteins of Immunological Interest, 5th Ed. Public Health Service, National Institutes of Health, Bethesda, Md. (19 1), expressly incorporated herein by reference. The "EU index as in Kabat" refers to the residue numbering of the human IgG1 EU antibody.

1. Heteromultimers Comprising an IgG Fc Construct

Provided herein are heteromultimer constructs with reduced or silenced effector function. In an embodiment is provided a heteromultimer construct comprising an IgG Fc construct having a first and a second Fc polypeptide, each Fc polypeptide comprising a modified hinge region wherein: the modified hinge region of said first Fc polypeptide comprises at least one amino acid modification, the modified hinge region of said second Fc polypeptide comprises at least one amino acid modification which is different from at least one amino acid modification of said first Fc polypeptide, and the IgG Fc construct displays reduced binding to all Fcγ receptors and to C1q protein as compared to a corresponding parent IgG Fc construct.

Provided herein are heteromultimer constructs with reduced or silenced effector function. In an embodiment is provided a heteromultimer construct comprising an IgG Fc construct having a first and a second Fc polypeptide, each Fc polypeptide comprising a modified lower hinge region wherein: the modified lower hinge region of said first Fc polypeptide comprises at least one amino acid modification, the modified lower hinge region of said second Fc polypeptide comprises at least one amino acid modification which is different from at least one amino acid modification of said first Fc polypeptide, and the IgG Fc construct displays reduced binding to all Fcγ receptors and to C1q protein as compared to a corresponding parent IgG Fc construct. In certain embodiments, the heteromultimer construct displays negligible binding to Fcγ receptors as compared to a corresponding parent IgG Fc construct that does not have the modifications described herein. In some embodiments, the heteromultimer construct displays reduced binding to all Fcγ receptors and negligible binding to at least one Fcγ receptor. In certain embodiments, the heteromultimer construct described herein displays reduced binding to Fcγ receptors and negligible binding to C1q protein.

Provided herein is a heteromultimer comprising an IgG Fc construct having a first and a second Fc polypeptide, each Fc polypeptide comprising a modified hinge region wherein: the modified hinge region of said first Fc polypeptide comprises at least one amino acid modification that increases the net charge in the modified hinge region of the first Fc polypeptide at about physiological pH conditions, the modified hinge region of said second Fc polypeptide comprises at least one amino acid modification which is different from at least one amino acid modification of said first Fc polypeptide, and the IgG Fc construct displays reduced binding to all Fcγ receptors and to C1q protein as compared to a corresponding parent IgG Fc construct. In some embodiments, the increase in net charge is an increase in the net positive charge on the first Fc polypeptide. In an embodiment, the increase in the net positive charge is an increase in the total number of positively charged amino acids on the first Fc polypeptide. In certain embodiments, said increase in net charge is an increase in the net negative charge on the first Fc polypeptide. In a particular embodiment, the increase in the net negative charge is an increase in the total number of negatively charged amino acids on the first Fc polypeptide. In some embodiments, the heteromultimer construct displays negligible binding to Fcγ receptors as compared to a corresponding parent IgG Fc construct construct that does not have the modifications described herein. In particular embodiments, the heteromultimer construct displays reduced binding to all Fcγ receptors and negligible binding to at least one Fcγ receptor. In an embodiment, the heteromultimer construct described herein displays reduced binding to Fcγ receptors and negligible binding to C1q protein.

Provided are heteromultimers comprising an IgG Fc construct, said IgG Fc construct having a first and a second Fc polypeptide, each Fc polypeptide comprising a modified hinge region wherein the modified hinge region of said first Fc polypeptide comprises one or more amino acid modifications that increase the number of positive charges in the modified hinge region of the first Fc polypeptide, wherein the modified hinge region of said second Fc polypeptide comprises one or more amino acid modifications different from the one or more amino acid modifications of said first Fc polypeptide, and wherein the IgG Fc construct does not bind to Fcγ receptors or to C1q protein.

1.1 Fc Region and Hinge Region

The heteromultimers comprise an IgG Fc construct (Fc region) which includes the hinge region. The Fc region of an antibody typically comprises two polypeptide chains, each of which comprises a C-terminal fragment of an IgG heavy chain polypeptide. Accordingly, the IgG Fc construct has two Fc polypeptides, each derived from an IgG heavy chain polypeptide and including the regions that mediate binding to FcγRs, complement, and FcRn, as well as the hinge region.

In one embodiment the heteromultimer comprises an IgG Fc construct that is derived from a human IgG heavy chain polypeptide. Several human IgG heavy chain polypeptides sub-types are known in the art and include IgG1, IgG2, IgG3, and IgG4. Of these human IgG sub-types, IgG1, IgG2, and IgG3 are known to activate complement, and IgG1 and IgG3 mediate the effector function ADCC (antibody-dependent cell-mediated cytotoxicity) more effectively than IgG2 and IgG4. In one embodiment, the heteromultimer comprises an IgG Fc construct that is derived from a human IgG1 heavy chain polypeptide. The amino acid sequence of the human IgG1 heavy chain is known in the art (see for example IMGT Accession No. J00228). In one embodiment, the heteromultimer comprises an IgG Fc construct that is derived from a human IgG3 heavy chain polypeptide. The sequence of the human IgG3 heavy chain is known in the art (see for example IMGT Accession No. X03604). In one embodiment, the heteromultimer comprises an IgG Fc construct that is derived from a human IgG4 heavy chain polypeptide. The sequence of the human IgG4 heavy chain is known in the art (see for example IMGT Accession No. K01316). The amino acid sequence of a human IgG1 Fc region, including the hinge region is shown in FIG. 5 (SEQ ID NO:1).

In a further embodiment, the heteromultimer can comprise an IgG Fc region that is derived from an allotype of IgG. IgG allotypes are known in the art (see, for example, Jefferies et al. (2009) Mabs 1(4):332-338).

In one embodiment, the IgG Fc region is derived from a humanized monoclonal antibody with therapeutic potential, selected from: alemtuzumab, apolizumab, aselizumab, atlizumab, bapineuzumab, bevacizumab, bivatuzumab, cantuzumab, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

In another embodiment, the IgG Fc region is derived from a therapeutic antibody such as, for example, rituximab.

Each Fc polypeptide of the IgG Fc construct comprises at least a portion of the Fc region of the IgG heavy chain polypeptide including the hinge region. The Fc region of IgG polypeptides includes binding sites for multiple receptors that mediate the effector functions of the Fc region. Examples of such receptors include FcγRIa, FcγRIIa, FcγRIIb, FcγRIIIa. The Fc region further comprises a region that binds to complement factor C1q protein.

The Fc region of the human IgG1 heavy chain polypeptide comprises amino acids 216-447 of the IgG1 heavy chain (see SEQ ID NO:2, FIG. 5). The length and sequence of the human IgG hinge region varies with the IgG isotype as shown in Table 1 below:

TABLE 1

Comparison of human IgG hinge region amino acid sequences

| IgG | length | CH1 | 'upper' hinge | 'core' hinge | 'lower' hinge (CH2) |
|---|---|---|---|---|---|
| IgG1 | 15 | VDKRV [SEQ ID NO: 71] | EPKSCDKTHT [SEQ ID NO: 72] | CPPCP [SEQ ID NO: 73] | APELLGGP [SEQ ID NO: 74] |
| IgG2 | 12 | VDKTV [SEQ ID NO: 75] | ELK CCVE [SEQ ID NO: 76] | CPPCP [SEQ ID NO: 73] | APPVAGP [SEQ ID NO: 77] |
| IgG3 | 62 | VDKRV [SEQ ID NO: 71] | ELKTPLGDTT HT [SEQ ID NO: 78] | CPRCP (EPKSCDTPPPC PRCP)x3 [SEQ ID NO: 79] | APELLGGP [SEQ ID NO: 74] |
| IgG4 | 12 | VDKRV [SEQ ID NO: 71] | ESKYGPP [SEQ ID NO: 80] | CPPCP [SEQ ID NO: 81] | APELLGGP [SEQ ID NO: 74] |

The hinge region of the IgG1 polypeptide comprises amino acid residues from 216 to 238, while the lower hinge region of the human IgG1 polypeptide comprises amino acid residues from 231 to 238.

Thus, in one embodiment, each Fc polypeptide of the IgG Fc construct comprises amino acids 216 to 447 of the human IgG1 heavy chain, wherein said first Fc polypeptide includes at least one modification in the hinge region comprising amino acid residues 216 to 238, and said second Fc polypeptide comprises at least one amino acid modification in the hinge region which is different from the at least one amino acid modification in the first Fc polypeptide. In another embodiment, each Fc polypeptide of the IgG Fc construct comprises amino acids 231 to 447 of the human IgG1 heavy chain, wherein said first Fc polypeptide includes at least one modification in the lower hinge region comprising amino acid residues 231 to 238, and said second Fc polypeptide comprises at least, one amino acid modification in the lower hinge region that is different from the at least one amino acid modification in the first Fc polypeptide.

1.1.2 Amino Acid Modifications in the Modified Hinge Region

The first and second Fc polypeptides of the IgG Fc constructs comprise a modified hinge region that is asymmetrically modified to generate heteromultimers with greatly decreased or ablated effector function. The terms "first" and "second" with reference to Fc polypeptide can be used interchangeably provided that each IgG Fc construct comprises one first Fc polypeptide and one second Fc polypeptide. The amino acid modifications are introduced into the hinge region of the first and second Fc polypeptides in an asymmetric fashion as described in more detail below.

The heteromultimers comprise first and second Fc polypeptide comprising core amino acid modifications described in the following paragraphs.

In some embodiments is a heteromultimer described herein, wherein the modified hinge region of at least one of said first and second Fc polypeptides comprises amino acid modifications at least one of L234 and L235. In an embodiment is the heteromultimer described herein, wherein the modified hinge region of at least one of said first and second Fc polypeptides comprises amino acid modifications selected from L234K, L234R, L234A, L235K, L235R, and L235A. In an embodiment is the heteromultimer described herein, said one of first and second Fc polypeptides further comprises an amino acid modification at E233. In an embodiment is the heteromultimer provided herein, wherein said modification at E233 is selected from E233A, E233K, and E233R. In some embodiments is the heteromultimer described herein, wherein the modified hinge region of at least one of said first and second Fc polypeptides comprises amino acid modifications at at least one of L234 and L235. In an embodiment is the heteromultimer described herein, wherein said modification at least one of L234 and L235 is selected from L234A, L234K, L234R, L234D, L234E, L235K, L235R, L235E, L235A, and L235D. In one embodiment is the heteromultimer described herein, wherein the modified hinge region of the second Fc polypeptide further comprises amino acid modifications at E233. In an embodiment, the first or second Fc polypeptide comprises amino acid modifications selected from E233A or E233D.

Provided herein is a heteromultimer described herein, wherein the modified hinge region of at least one of said first and second Fc polypeptides comprises the amino acid modifications L234A/L235K, L234K/L235K, E233A/L234R/L235R, E233K/L234R/L235R, or E233K/L234A/L235K. In some embodiments is a heteromultimer described herein, wherein the modified hinge region of the first or second Fc polypeptide comprises the amino acid modifications L234A/L235A, L234D/L235E, E233A/L234D/L235E, or E233A/L234K/L235A.

Provided herein is a heteromultimer as described herein, wherein the modified hinge region of the first Fc polypeptide comprises the amino acid modifications L234K/L235K and the modified hinge region of the second Fc polypeptide comprises the amino acid modifications L234A/L235K; the modified hinge region of the first Fc polypeptide comprises the amino acid modifications L234K/L235K and the modified hinge region of the second Fc polypeptide comprises the amino acid modifications L234A/L235A; the modified hinge region of the first Fc polypeptide comprises the amino acid modifications L234K/L235K and the modified hinge region of the second Fc polypeptide comprises the amino acid modifications L234D/L235E; the modified hinge region of the first Fc polypeptide comprises the amino acid modifications E233A/L234R/L235R and the modified hinge region of the second Fc polypeptide comprises the amino acid modifications E233A/L234D/L235E; the modified hinge region of the first Fc polypeptide comprises the amino acid modifications E233K/L234R/L235R and the modified hinge region of the second Fc polypeptide comprises the amino acid modifications L234D/L235E; or the modified hinge region of the first Fc polypeptide comprises the amino acid modifications E233K/L234A/L235K and the modified hinge region of the second Fc polypeptide comprises the amino acid modifications E233A/L234K/L235A.

In some embodiments, the heteromultimer comprise first and second polypeptides comprising the core amino acid modifications, and comprise the following additional amino acid modification. Thus in some embodiments is the heteromultimer provided herein, wherein at least one of said first or second Fc polypeptides further comprises at least one amino acid modification selected from D265S, E269K, K322A, P329W, and E333K. For instance, in an embodiment is a heteromultimer as described herein, wherein the first Fc polypeptide comprises the amino acid modifications L234D/L235E and the second Fc polypeptide comprises the amino acid modifications L234R/L235R/E233K. In another embodiment is a heteromultimer as described herein, wherein the first Fc polypeptide comprises the amino acid modifications L234D/L235E/D265S and the second Fc polypeptide comprises the amino acid modifications L234R/L235R/D265S. In a further embodiment is a heteromultimer as described herein, wherein the first Fc polypeptide comprises the amino acid modifications L234D/L235E/E269K and the second Fc polypeptide comprises the amino acid modifications E233K/L234R/L235R/E269K. In another embodiment is a heteromultimer as described herein, wherein the first Fc polypeptide comprises the amino acid modifications L234D/L235E/K322A and the second Fc polypeptide comprises the amino acid modifications E233K/L234R/L235R/K322A. In yet another embodiment is a heteromultimer as described herein, wherein the first Fc polypeptide comprises the amino acid modifications L234D/L235E/P329W and the second Fc polypeptide comprises the amino acid modifications E233K/L234R/L235R/P329W. In an additional embodiment is a heteromultimer as described herein, wherein the first Fc polypeptide comprises the amino acid modifications L234D/L235E/E269K/D265S/K322A and the second Fc polypeptide comprises the amino acid modifications E233K/L234R/L235R/E269K/D265S/K322A. In further embodiments is a heteromultimer as described herein, wherein the first Fc polypeptide comprises the amino acid modifications L234D/L235E/E269K/D265S/K322E/E333K and the second Fc polypeptide comprises the amino acid modifications E233K/L234R/L235R/E269K/D265S/K322E/E333K.

Provided is a heteromultimer as described herein, wherein: the first Fc polypeptide comprises the amino acid modifications L234D/L235E and the second Fc polypeptide comprises the amino acid modifications L234R/L235R/E233K; the first Fc polypeptide comprises the amino acid modifications L234D/L235E/D265S and the second Fc polypeptide comprises the amino acid modifications L234R/L235R/D265S; the first Fc polypeptide comprises the amino acid modifications L234D/L235E/E269K and the second Fc polypeptide comprises the amino acid modifications E233K/L234R/L235R/E269K; the first Fc polypeptide comprises the amino acid modifications L234D/L235E/K322A and the second Fc polypeptide comprises the amino acid modifications E233K/L234R/L235R/K322A; the first Fc polypeptide comprises the amino acid modifications L234D/L235E/P329W and the second Fc polypeptide comprises the amino acid modifications E233K/L234R/L235R/P329W; the first Fc polypeptide comprises the amino acid modifications L234D/L235E/E269K/D265S/K322A and the second Fc polypeptide comprises the amino acid modifications E233K/L234R/L235R/E269K/D265S/K322A; or the first Fc polypeptide comprises the amino acid modifications L234D/L235E/E269K/D265S/K322E/E333K and the second Fc polypeptide comprises the amino acid modifications E233K/L234R/L235R/E269K/D265S/K322E/E333K.

First Fc Polypeptide

Each of the two Fc polypeptides of the IgG Fc construct comprises a modified hinge, region. The modified hinge region of the first Fc polypeptide comprises one or more amino acid modifications that increase the positive charge of the modified hinge region of that Fc polypeptide. By "increase the positive charge of the modified hinge region" is meant that the modified hinge region with one or more amino acid modifications has an overall positive charge that is greater than that of the wild-type, unmodified hinge region. The modified hinge region of the second Fc polypeptide comprises one or more amino acid modifications that are different from the one or more amino acid modifications of the other Fc polypeptide. As used herein, asymmetric amino acid modifications are any modification wherein an amino acid at a specific position on one polypeptide (e.g., "first polypeptide") is different from the amino acid on the second polypeptide (e.g., "second polypeptide") at the same position. This can be a result of modification of only one of the two amino acids or modification of both amino acids to two different amino acids from the first or second polypeptide of the IgG Fc construct.

For example, if the first Fc polypeptide comprises the amino acid modification L235K, amino acid modifications that are different would include modification of other amino acids in the hinge region, such as L234 or E233, or modification of L235 other than L235K, such as L235A or L235D. Thus, in one embodiment, the modified hinge region of a first Fc polypeptide comprises one or more amino acid modifications that increase the positive charge of the modified hinge region of the first Fc polypeptide, and the modified hinge region of a second Fc polypeptide comprises one or more amino acid modifications different from the two or more amino acid modifications of said first Fc polypeptide. In another embodiment, the modified hinge region of said first Fc polypeptide comprises two or more amino acid modifications that increase the positive charge of the modified hinge region of the first Fc polypeptide, and the modified hinge region of said second Fc polypeptide comprises one or more amino acid modifications different from the one or more amino acid modifications of said first Fc polypeptide. In an alternate embodiment, the modified hinge region of said first Fc polypeptide comprises two or more amino acid modifications that increase the positive charge of the modified hinge region of the first Fc polypeptide, and the modified hinge region of said second Fc polypeptide comprises two or more amino acid modifications different from the two or more amino acid modifications of said first Fc polypeptide.

In one embodiment, when the modified hinge region of the first Fc polypeptide of the IgG Fc construct comprises one amino acid modification, the amino acid modification is made to substitute an amino acid having a neutral or negatively charged side chain with an amino acid having a positively charged side chain. For example, L234 or L235 of the hinge region can be substituted with Lys (K), Orn (O) or Arg (R). Thus, in embodiments where the modified hinge region of the first Fc polypeptide of the IgG Fc construct comprises one amino acid modification, the following amino acid residues of the lower hinge region of human IgG1 can be substituted with Lys, Orn, or Arg: A231, P232, E233, L234, L235, G236, G237, or P238.

In embodiments where the modified hinge region of the first Fc polypeptide comprises two or more amino acid modifications, the overall result of the combination of modifications is an increase in positive charge of the modified hinge region. This overall increase in positive charge can result from combinations of amino acid modifications substituting amino acids having negatively charged or neutral side chains with amino acids having positively charged side chains or neutral side chains. For example, in one embodiment, the two or more amino acid modifications that increase the positive charge of the lower hinge region of the first Fc polypeptide of an IgG1 IgG Fc construct can be selected from E233K, E233R, E233A, L234K, L234R, L234A, L235K, L235R, and L235A provided that the combination of the two or more amino acid modifications increases the positive charge of the modified hinge region. Similarly, other amino acid modifications within the hinge region may be made as long as they increase the positive charge of the hinge region.

In one embodiment, the modified hinge region of the first Fc polypeptide of the IgG Fc construct comprises amino acid modifications at L234 or L235 that increase the positive charge of the modified hinge region. In another embodiment, the modified hinge region of the first Fc polypeptide of the IgG Fc construct comprises amino acid modifications at L234 and L235 that increase the positive charge of the modified hinge region. In another embodiment, the modified hinge region of the first Fc polypeptide of the IgG Fc construct comprises amino acid modifications at L234, L235 or E233 that increase the positive charge of the modified hinge region. In another embodiment, the modified hinge region of the first Fc polypeptide of the IgG Fc construct comprises amino acid modifications at L234 and E233 that increase the positive charge of the modified hinge region. In another embodiment, the modified hinge region of the first Fc polypeptide of the IgG Fc construct comprises amino acid modifications at L235 and E233 that increase the positive charge of the modified hinge region. In another embodiment, the modified hinge region of the first Fc polypeptide of the IgG Fc construct comprises amino acid modifications at L234, L235 and E233 that increase the positive charge of the modified hinge region.

In one embodiment, the first Fc polypeptide of the IgG Fc construct comprises a modified hinge region comprising the amino acid modifications L234A/L235K, E233A/L234R/L235R, E233K/L234R/L235R, or E233K/L234A/L235K.

Second Fc Polypeptide

In one embodiment, the modified hinge region of the second Fc polypeptide of the IgG Fc construct comprises one or more amino acid modifications that are different from the amino acid modifications of the first Fc polypeptide, and that increase the negative charge of the modified hinge region or that are charge neutral relative to the wild-type hinge region. By "increase the negative charge of the modified hinge region" is meant that the modified hinge region of the second Fc polypeptide of the IgG Fc construct with one or more amino acid modifications has an overall negative charge that is greater that that of the wild-type, unmodified hinge region. By "charge neutral" is meant that the one or more amino acid modifications do not result in a change in the overall charge of the modified hinge region of the second Fc polypeptide of the IgG Fc construct compared to that of the wild-type hinge region. Thus, amino acid modifications of the second polypeptide of the IgG Fc construct include combinations of amino acid modifications that replace amino acids having a neutral side chain with amino acids having a negatively charged side chain, a positively charged sided chain or a different neutral side chain, and/or amino acid modifications that replace amino acids having a negatively charged side chain with amino acids having a neutral side chain. Combinations of these amino acid modifications are suitable as long as they result in an increase in the negative charge of the modified hinge region or are charge neutral with respect to the wild-type hinge region.

In one embodiment, the second Fc polypeptide of the IgG Fc construct comprises an amino acid modification at L234 or L235. In another embodiment, the second Fc polypeptide of the IgG Fc construct comprises amino acid modifications at L234 and L235. In one embodiment, the second Fc polypeptide of the IgG Fc construct comprises amino acid modifications selected from L234A, L234K, L234R, L234D, L234E, L235K, L235R, L235E, L235A, and L235D.

In one embodiment, the second Fc polypeptide of the IgG Fc construct comprises amino acid modifications at L234 and/or L235, and E233. In one embodiment, the second Fc polypeptide of the IgG Fc construct comprises amino acid modifications selected from L234A, L234K, L234R, L234D, L234E, L235K, L235R, L235E, L235A, L235D, E233A and E233D.

In one embodiment, the modified hinge region of the second Fc polypeptide of the IgG Fc construct comprises the amino acid modifications L234A/L235A, L234D/L235E, E233A/L234D/L235E, or E233A/L234K/L235A.

2. Other Modifications to the IgG Fc Construct

In some embodiments, the heteromultimers according to the invention comprise additional modifications as described below.

In one embodiment of the invention, the heteromultimer comprises an IgG Fc construct comprising modified Fc polypeptides that have been further modified promote the formation of a heterodimeric Fc region. Such further modified Fc polypeptides are useful in the production of heteromultimers in the context of bi-specific antibodies. In one embodiment, the Fc polypeptides comprise variant CH3 domains having amino acid modifications that promote the formation of heterodimeric Fc regions. Suitable variant CH3 domains are known in the art and include, for example, those described in International Patent Publication No. WO 2012/058768, and U.S. Pat. Nos. 5,821,333, 7,695,936. In one embodiment, the heteromultimer according to the invention comprises an IgG Fc construct wherein one of said first and second Fc polypeptides comprises the CH3 amino acid modifications T366L/N390R/K392M/T394W and the other Fc polypeptide comprises the CH3 amino acid modifications L351Y/S400E/F405A/Y407V.

Additional methods for modifying Fc polypeptides to promote heterodimeric Fc formation are described in International Patent Publication No. WO 96/027011 (knobs into holes), in Gunasekaran ef al. (Gunasekaran K. et al. (2010) J Biol Chem. 285, 19637-46, electrostatic design to achieve selective heterodimerization), in Davis et al. (Davis, J H. et al. (2010) Prot Eng Des Sel; 23(4): 195-202, strand exchange engineered domain (SEED) technology), and in Moore et al (2011) Mabs 3:6, 546-557.

In one embodiment, the heteromultimer comprises an IgG Fc construct further comprising amino acid modifications that promote the formation of a heterodimeric Fc region. In one embodiment, the heteromultimer comprises an IgG Fc construct further comprising amino acid modifications in the CH3 region of each Fc polypeptide that promote the formation of a heterodimeric Fc region.

In some embodiments, the heteromultimer comprises an IgG Fc construct further comprising amino acid modifications that increase the stability of the IgG Fc construct, as determined by the melting temperature of the CH2 domain. Suitable amino acid modifications are known in the art and include, for example, those described in International Patent Application No. PCT/CA2012/050780. Specifically, in one embodiment, the heteromultimer comprises an IgG Fc construct comprising the amino acid modification T350V in both the first Fc polypeptide and the second Fc polypeptide.

Provided is a heteromultimer comprising an IgG Fc construct having a first and a second Fc polypeptide wherein: said first Fc polypeptide comprises the amino acid modifications E269Q/D270N and the second Fc polypeptide comprises the amino acid modifications E269K/D270R; or said first Fc polypeptide comprises the amino acid modifications L235K/A327K and the second Fc polypeptide does not comprise a modification at the hinge or lower hinge region; and wherein the IgG Fc construct displays reduced binding to all Fcγ receptors and to C1q protein as compared to a corresponding parent IgG Fc construct.

In one embodiment, the Fc is an IgG1 Fc construct, and IgG2 Fc construct, an IgG3 Fc construct, or an IgG4 Fc construct.

In some embodiments, an IgG Fc construct comprises at least one CH3 domain that has at least one amino acid modification that promotes the formation of a heterodimeric Fc with stability comparable to a wild-type homodimeric Fc. Exemplary modifications are described below. In some embodiments, the dimerized CH3 domains of the heterodimeric Fc have a melting temperature (Tm) as measured by differential scanning calorimetry (DSC) of about 68, 69, 70, 71, 72, 73, 74, 75, 76, 77, 77.5, 78, 79, 80, 81, 82, 83, 84, or 85° C.: or higher. In some embodiments, the dimeric Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when produced; or wherein the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed or when expressed via a single cell.

In some aspects, the Fc comprises one or more modifications in at least one of the $C_{H3}$ sequences. In some aspects, the Fc comprises one or more modifications in at least one of the $C_{H3}$ sequences.

In some aspects, Fc is a Fc described in patent applications PCT/CA2011/001238, filed Nov. 4, 2011 or PCT/CA2012/050780, filed Nov. 2, 2012, the entire disclosure of each of which is hereby incorporated by reference in its entirety for all purposes.

In some aspects, a Fc construct described herein comprises a heterodimeric Fc comprising a modified CH3 domain that has been asymmetrically modified. The heterodimeric Fc can comprise two heavy chain constant domain polypeptides: a first heavy chain polypeptide and a second heavy chain polypeptide, which can be used interchangeably provided that Fc comprises one first heavy chain polypeptide and one second heavy chain polypeptide. Generally, the first heavy chain polypeptide comprises a first CH3 sequence and the second heavy chain polypeptide comprises a second CH3 sequence.

Two CH3 sequences that comprise one or more amino acid modifications introduced in an asymmetric fashion generally results in a heterodimeric Fc, rather than a homodimer, when the two CH3 sequences dimerize. As used herein, "asymmetric amino acid modifications" refers to any modification where an amino acid at a specific position on a first CH3 sequence is different from the amino acid on a second CH3 sequence at the same position, and the first and second CH3 sequence preferentially pair to form a heterodimer, rather than a homodimer. This heterodimerization can be a result of modification of only one of the two amino acids at the same respective amino acid position on each sequence; or modification of both amino acids on each sequence at the same respective position on each of the first and second CH3 sequences. The first and second CH3 sequence of a heterodimeric Fc can comprise one or more than one asymmetric amino acid modification.

Table X provides the amino acid sequence of a human IgG1 Fc sequence, corresponding to amino acids 231 to 447 of a full-length human IgG1 heavy chain. The CH3 sequence comprises amino acid 341-447 of the full-length human IgG1 heavy chain. Typically an Fc can include two contiguous heavy chain sequences (A and B) that are capable of dimerizing. In some aspects, one or both sequences of an Fc include one or more mutations or modifications at the following locations: L351, F405, Y407, T366, K392, T394, T350, S400, and/or N390, using EU numbering. In some aspects, a Fc includes a mutant sequence shown in Table X. In some aspects, a Fc includes the mutations of Variant 1 A-B. In some aspects, a Fc includes the mutations of Variant 2 A-B. In some aspects, a Fc includes the mutations of Variant 3 A-B. In some aspects, a Fc includes the mutations of Variant 4 A-B. In some aspects, a Fc includes the mutations of Variant 5 A-B.

TABLE X

Exemplary Fc sequence and CH3 modifications

| Human IgG1 Fc sequence 231-447 (EU-numbering) | APELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSRDELTKNQVSLTCLVKGFYPSDIAVEWESNGQPENNYKTTPPVLDSDGSFFLYSKLTVDKSRWQQGNVFSCSVMHEALHNHYTQKSLSLSPGK (SEQ ID NO: 70) | |
|---|---|---|
| **Variant IgG1 Fc sequence (231-447)** | **Chain** | **Mutations** |
| 1 | A | L351Y_F405A_Y407V |
| 1 | B | T366L_K392M_T394W |
| 2 | A | L351Y_F405A_Y407V |
| 2 | B | T366L_K392L_T394W |
| 3 | A | T350V_L351Y_F405A_Y407V |
| 3 | B | T350V_T366L_K392L_T394W |
| 4 | A | T350V_L351Y_F405A_Y407V |
| 4 | B | T350V_T366L_K392M_T394W |
| 5 | A | T350V_L351Y_S400E_F405A_Y407V |
| 5 | B | T350V_T366L N390R_K392M_T394W |

The first and second CH3 sequences can comprise amino acid mutations as described herein, with reference to amino acids 231 to 447 of the full-length human IgG1 heavy chain. In one embodiment, the heterodimeric Fc comprises a modified CH3 domain with a first CH3 sequence having amino acid modifications at positions F405 and Y407, and a second CH3 sequence having amino acid modifications at position T394. In one embodiment, the heterodimeric Fc comprises a modified CH3 domain with a first CH3 sequence having one or more amino acid modifications selected from L351Y, F405A, and Y407V, and the second CH3 sequence having one or more amino acid modifications selected from T366L, T366I, K392L, K392M, and T394W.

In one embodiment, an Fc construct comprises a heterodimeric Fc which comprises a modified CH3 domain with a first CH3 sequence having amino acid modifications at positions L351, F405 and Y407, and a second CH3 sequence having amino acid modifications at positions T366, K392, and T394, and one of the first or second CH3 sequences further comprising amino acid modifications at position Q347, and the other CH3 sequence further comprising amino acid modification at position K360. In another embodiment, a heterodimeric Fc comprises a modified CH3 domain with a first CH3 sequence having amino acid modifications at positions L351, F405 and Y407, and a second CH3 sequence having amino acid modifications at position T366, K392, and T394, one of the first or second CH3 sequences further comprising amino acid modifications at position Q347, and the other CH3 sequence further comprising amino acid modification at position K360, and one or both of said CH3 sequences further comprise the amino acid modification T350V.

In one embodiment, an Fc construct provided herein comprises a heterodimeric Fc comprises a modified CH3 domain with a first CH3 sequence having amino acid modifications at positions L351, F405 and Y407, and a second CH3 sequence having amino acid modifications at positions T366, K392, and T394 and one of said first and second CH3 sequences further comprising amino acid modification of D399R or D399K and the other CH3 sequence comprising one or more of T4-11E, T411D, K409E, K409D, K392E and K392D. In another embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, one of said first and second CH3 sequences further comprises amino acid modification of D399R or D399K and the other CH3 sequence comprising one or more of T411E, T411D, K409E, K409D, K392E and K392D, and one or both of said CH3 sequences further comprise the amino acid modification T350V.

In one embodiment, a heterodimeric Fc comprises a modified CH3 domain with a first CH3 sequence having amino acid modifications at positions L351, F405 and Y407, and a second CH3 sequence having amino acid modifications at positions T366, K392, and T394, wherein one or both of said CH3 sequences further comprise the amino acid modification of T350V.

In one embodiment, a heterodimeric Fc comprises a modified CH3 domain comprising the following amino acid modifications, where "A" represents the amino acid modifications to the first CH3 sequence, and "B" represents the amino acid modifications to the second CH3 sequence: A:L351Y_F405A_Y407V, B:T366L_K392M_T394W, A:L351Y_F405A_Y407V, B:T366L_K392L_T394W, A:T350V_L351Y_F405A_Y407V, B:T350V_T366L_K392L_T394W, A:T350V_L351Y_F405A_Y407V, B:T350V_T366L_K392M_T394W, A:T350V_L351Y_S400E_F405A_Y407V, and/or B:T350V_T366L_N390R_K392M_T394W.

The one or more asymmetric amino acid modifications can promote the formation of a heterodimeric Fc in which the heterodimeric CH3 domain has a stability that is comparable to a wild-type homodimeric CH3 domain. In an embodiment, the one or more asymmetric amino acid modifications promote the formation of a heterodimeric Fc domain in which the heterodimeric Fc domain has a stability that is comparable to a wild-type homodimeric Fc domain. In an embodiment, the one or more asymmetric amino acid modifications promote the formation of a heterodimeric Fc domain in which the heterodimeric Fc domain has a stability observed via the melting temperature (Tm) in a differential scanning calorimetry study, and where the melting temperature is within 4° C. of that observed for the corresponding symmetric wild-type homodimeric Fc domain. In some aspects, the Fc comprises one or more modifications in at least one of the CH3 sequences that promote the formation of a heterodimeric Fc with stability comparable to a wild-type homodimeric Fc.

In one embodiment, the stability of the CH3 domain can be assessed by measuring the melting temperature of the CH3 domain, for example by differential scanning calorimetry (DSC). Thus, in a further embodiment, the CH3 domain has a melting temperature of about 68° C. or higher. In another embodiment, the CH3 domain has a melting temperature of about 70° C. or higher. In another embodiment, the CH3 domain has a melting temperature of about 72° C. or higher. In another embodiment, the CH3 domain has a melting temperature of about 73° C. or higher. In another embodiment, the CH3 domain has a melting temperature of about 75° C. or higher. In another embodiment, the CH3 domain has a melting temperature of about 78° C. or higher. In some aspects, the dimerized CH3 sequences have a melting temperature (Tm) of about 68, 69, 70, 71, 72, 73, 74, 75, 76, 77, 77.5, 78, 79, 80, 81, 82, 83, 84, or 85° C. or higher.

In some embodiments is a Fc construct comprising a heterodimeric Fc further comprising modified CH3 sequences can be formed with a purity of at least about 75% as compared to homodimeric Fc in the expressed product. In another embodiment, the heterodimeric Fc is formed with a purity greater than about 80%. In another embodiment, the heterodimeric Fc is formed with a purity greater than about 85%. In another embodiment, the heterodimeric Fc is formed with a purity greater than about 90%. In another embodiment, the heterodimeric Fc is formed with a purity greater than about 95%. In another embodiment, the heterodimeric Fc is formed with a purity greater than about 97%: In some aspects, the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed. In some aspects, the Fc is a heterodimer formed with a purity greater than about 75, 76, 77, 78, 79, 80, 81, 82, 83, 84, 85, 86, 87, 88, 89, 90, 91, 92, 93, 94, 95, 96, 97, 98, or 99% when expressed via a single cell.

Additional methods for modifying monomeric Fc polypeptides to promote heterodimeric Fc formation are described in International Patent Publication No. WO 96/027011 (knobs into holes), in Gunasekaran et al. (Gunasekaran K. et al. (2010) J Biol Chem. 285, 19637-46, electrostatic design to achieve selective heterodimerization), in Davis et al. (Davis, J H. et al. (2010) Prot Eng Des Sel; 23(4): 195-202, strand exchange engineered domain (SEED) technology), and in Labrijn et al [Efficient generation of stable bi-specific IgG1 by controlled Fab-arm exchange. Labrijn A F, Meesters J I, de Goeij B E, van den Bremer E T, Neijssen J, van Kampen M D, Strumane K, Verploegen S, Kundu A, Gramer M J, van Berkel P H, van de Winkel J G, Schuurman J, Parren P W. Proc Natl Acad Sci USA. 2013 Mar. 26; 110(13):5145-50.

3. Functional Characteristics of Heteromultimers

The heteromultimers according to the invention exhibit greatly reduced/ablated binding to FcγRs and to C1q. In addition, in certain embodiments, the heteromultimers also exhibit additional desirable properties such as stability, the ability to bind FcRn, and properties that facilitate purification of desired expression products from undesired products or impurities.

In one embodiment, the present invention contemplates an heteromultimer comprising an IgG Fc construct that does not measurably bind to FcγR receptors, but does bind to FcRn, which makes it a desired candidate for applications in which the half life of the antibody in vivo is important yet effector functions (such as CDC, ADCP and ADCC) are unnecessary or deleterious.

Methods for determining the ability of the heteromultimers comprising IgG Fc constructs to either bind to FcγRs or C1q are known in the art and described elsewhere, herein.

3a. Reduced/Ablated Binding to FcγR and Complement

The heteromultimers according to the invention exhibit reduced/ablated binding to FcγR and C1q as compared to the parent polypeptide. In one embodiment, the heteromultimer according to the invention exhibits $K_D$s for FcγRs and C1q that are at least 5 times higher than the $K_D$ of the parent polypeptide. In another embodiment, the heteromultimer according to the invention exhibits $K_D$s for FcγRs and C1q that are at least 10 times greater than that of the parent polypeptide, as measured by binding assays known in the art. Binding assays known in the art, include but are not limited to FRET (Fluorescence Resonance Energy Transfer) and BRET (Bioluminescence Resonance Energy Transfer)-based assays, AlphaScreen™ (Amplified Luminescent Proximity Homogeneous Assay), Scintillation Proximity Assay, ELISA (Enzyme-Linked Immunosorbent Assay), SPR (Surface Plasmon Resonance, also known as Biacore™), isothermal titration calorimetry, differential scanning calorimetry, gel electrophoresis, and chromatography including gel filtration. These and other methods may take advantage of some fusion partner or label of the antibody. Assays may employ a variety of detection methods including but not limited to chromogenic, fluorescent, luminescent, or isotopic labels.

In one embodiment, the heteromultimer comprising an IgG Fc construct has a $K_D$ of greater than 5 μM for FcγRIIaH, a $K_D$ of greater than 10 μM for FcγRIIaR, a $K_D$ of greater than 30 μM for FcγRIIb, a $K_D$ of greater than 20 μM for FcγRIIIaF, a $K_D$ of greater than 6 μM for FcγRIIIaV, and a $K_D$ of greater than 6.5 nM for FcγRIa, as measured by surface plasmon resonance (SPR). In another embodiment, the heteromultimer comprising an IgG Fc construct has a $K_D$ of greater than 10 μM for FcγRIIaH, a $K_D$ of greater than 10 μM for FcγRIIaR, a $K_D$ of greater than 10 μM for FcγRIIb, a $K_D$ of greater than 6 μM for FcγRIIIaF, a $K_D$ of greater than 6 μM for FcγRIIIaV, a $K_D$ of greater than 30 nM for FcγRIa, and does not bind to C1q, as measured by surface plasmon resonance (SPR).

In one embodiment, the heteromultimers comprising an IgG Fc construct do not exhibit detectable levels of ADCC, ADCP, and CDC as measured by standard assays. Non-limiting examples of standard assays to test effector function include those describe in the Examples provided here.

3b. Stability

The biophysical properties of the heteromultimers including for example stability, is assessed using a variety of methods known in the art. Protein stability may be determined by measuring the thermodynamic equilibrium between folded and unfolded states. For example, heteromultimers of the present invention may be unfolded using chemical denaturant, heat, or pH, and this transition may be monitored using methods including but not limited to circular dichroism spectroscopy, fluorescence spectroscopy, absorbance spectroscopy, NMR spectroscopy, calorimetry, and proteolysis. As will be appreciated by those skilled in the art, the kinetic parameters of the folding and unfolding transitions may also be monitored using these and other techniques. The solubility and overall structural integrity of heteromultimer may be quantitatively or qualitatively determined using a wide range of methods that are known in the art.

Methods which can be used to characterize the biophysical properties of heteromultimers include gel electrophoresis, isoelectric focusing, capillary electrophoresis, chromatography such as size exclusion chromatography, ion-exchange chromatography, and reversed-phase high performance liquid chromatography, peptide mapping, oligosaccharide mapping, mass spectrometry, ultraviolet absorbance spectroscopy, fluorescence spectroscopy, circular dichroism spectroscopy, isothermal titration calorimetry, differential scanning calorimetry, analytical ultra-centrifugation, dynamic light scattering, proteolysis, and cross-linking, turbidity measurement, filter retardation assays, immunological assays, fluorescent dye binding assays, protein-staining assays, microscopy, and detection of aggregates via ELISA or other binding assay. Structural analysis employing X-ray crystallographic techniques and NMR spectroscopy may also find use. In one embodiment, stability and/or solubility may be measured by determining the amount of protein solution after some defined period of time. In this assay, the protein may or may not be exposed to some extreme condition, for example elevated temperature, low pH, or the presence of denaturant. Because function typically requires a stable, soluble, and/or well-folded/structured protein, the aforementioned functional and binding assays also provide ways to perform such a measurement. For example, a solution comprising an heteromultimer could be assayed for its ability to bind target antigen, then exposed to elevated temperature for one or more defined periods of time, then assayed for antigen binding again. Because unfolded and aggregated protein is not expected to be capable of binding antigen, the amount of activity remaining provides a measure of the antibody's stability and solubility.

In one embodiment, the heteromultimers comprising an IgG Fc construct are stable as measured by the melting temperature of one or more domains of the heteromultimer comprising an IgG Fc construct. The melting temperature of the heteromultimers can be determined according to methods known in the art and described in more detail elsewhere herein. For example, the melting temperature of the heteromultimers can be determined by differential scanning calorimetery (DSC), and a thermogram of the heteromultimer generated. In one embodiment, the heteromultimer comprises an IgG Fc construct wherein the onset of melting of the IgG Fc construct in a thermogram is greater than or equal to 65° C. In one embodiment, the heteromultimer comprises an IgG Fc construct wherein the onset of melting of the IgG Fc construct in a thermogram is greater than or equal to 66° C. In one embodiment, the heteromultimer comprises an IgG Fc construct wherein the onset of melting of the IgG Fc construct in a thermogram is greater than or equal to 68° C. In one embodiment, the heteromultimer comprises an IgG Fc construct wherein the onset of melting of the IgG Fc construct in a thermogram, is greater than or equal to 70° C.

In another embodiment, the heteromultimer comprises an IgG Fc construct wherein the IgG Fc construct has a CH2 domain with a melting temperature that is greater than or equal to the melting temperature of the CH2 domain of the parent polypeptide or antibody. In one embodiment the heteromultimer comprises an IgG Fc construct, wherein the IgG Fc construct has a CH2 domain with a melting temperature that is about 1 to 2° C. greater than the melting temperature of the parent CH2 domain. In one embodiment the heteromultimer comprises an IgG Fc construct, wherein the IgG Fc construct has a CH2 domain with a melting temperature that is about 2 to 3° C. greater than the melting temperature of the parent CH2 domain. In one embodiment, the heteromultimer comprises an IgG Fc construct, wherein the IgG Fc construct has a CH2 domain with a melting temperature that is about 1 to 2° C. greater than the melting temperature of the parent CH2 domain, wherein the heteromultimer comprises the amino acid modifications exemplified by AAC4 and AAC5. In one embodiment, the heteromultimer comprises an IgG Fc construct, wherein the IgG Fc construct has a CH2 domain with a melting temperature that is about 2 to 3° C. greater than the melting temperature of the parent CH2 domain, wherein the heteromultimer comprises the amino acid modifications exemplified by AAC2, AAC9, AAC10, AAC11, AAC12, AAC13, AAC14, and AAC15. In another embodiment, the heteromultimer comprises an IgG Fc construct, wherein the IgG Fc construct has a CH2 domain with a melting temperature that is about 4° C. greater than the melting temperature of the parent CH2 domain, wherein the heteromultimer comprises the amino acid modifications exemplified by AAC6.

3c. FcRn Binding

As is known in the art, binding to FcRn recycles endocytosed antibody from the endosome back to the bloodstream (Raghavan et al., 1996, Annu Rev Cell Dev Biol 12:181-220; Ghetie et al., 2000, Annu Rev Immunol 18:739-766). This process, coupled with preclusion of kidney filtration due to the large size of the full-length molecule, results in favorable antibody serum half-lives ranging from one to three weeks. Binding of Fc to FcRn also plays a key role in antibody transport. Thus, in one embodiment, the heteromultimers of the invention are able to bind FcRn.

4. Format of Heteromultimer

4a. Antigen-Binding Domains

In one embodiment, the heteromultimer according to the invention consists only of an IgG Fc construct. In other embodiments, the heteromultimer according to the invention comprises an IgG Fc construct and one or more antigen binding domains. In one embodiment, the heteromultimer according to the invention comprises an IgG Fc construct and one antigen-binding domain. In another embodiment, the heteromultimer according to the invention comprises an IgG Fc construct and two antigen binding domains. In another embodiment, the heteromultimer according to the invention comprises an IgG Fc construct and three antigen binding domains. In another embodiment, the heteromultimer according to the invention comprises an IgG Fc construct and four antigen binding domains. In another embodiment, the heteromultimer according to the invention comprises an IgG Fc construct and up to six antigen binding domains.

The antigen-binding domains can be fused to the IgG Fc construct according to methods known in the art.

In one embodiment, the heteromultimer according to the invention comprises an IgG Fc construct comprising at least one antigen-binding domain, wherein the at least one antigen-binding domain is selected from a Fab fragment, an scFv, an sdAb, an antigen binding peptide, an Fc fusion protein, or a protein domain capable of binding an antigen.

In one embodiment, the heteromultimer comprises an IgG Fc construct comprising at least one antigen-binding domain, wherein the at least one antigen-binding domain binds a target antigen selected from α-chain (CD25) of IL-2R, Amyloid beta, EpCAM, CD3, BLyS (or BAFF), CD11a, CD20, CD22, CD23, CD3, CD4; CD52, CD80, CTLA-4, EGFR, F protein of RSV, G250, glycoprotein IIb/IIIa R, HER2, HER2/neu receptor, Hsp90, IgE antibody, IL-12/IL-23, IL-Iβ, IL-5, IL-6 receptor, Integrin alpha-4/beta-1, Mucin 16/CA-125, RAN L, TNF alpha, VEGF-A, and other therapeutically advantageous targets.

In one embodiment, the heteromultimer comprises an IgG Fc construct having a first and a second Fc polypeptide, each Fc polypeptide comprising a modified hinge region, wherein the heteromultimer is derived from a humanized monoclonal antibody with therapeutic potential, selected from: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

In another embodiment, the heteromultimer comprises an IgG Fc construct derived from a therapeutic antibody such as, for example, rituximab or trastuzumab.

4b. Antibody-Drug Conjugates.

It is further contemplated that the heteromultimer according to the invention can comprise one or more toxic drug molecules linked to the IgG Fc construct and/or to other domains of the heteromultimer. Toxic drug molecules include substances that inhibit or prevent the function of cells and/or cause destruction of cells. In one embodiment, the one or more toxic drug molecules can be linked to an heteromultimer comprising an IgG Fc construct. In another embodiment, the one or more toxic drug molecules can be linked to a heteromultimer comprising an IgG Fc construct and at least one antigen-binding domain. Suitable toxic drug molecules that can be linked to the IgG Fc construct are selected from radioactive isotopes (e.g. $At^{211}$, $I^{131}$, $I^{125}$, $Y^{90}$, $Re^{185}$, $Re^{188}$, $Sm^{183}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

Suitable chemotherapeutic agents that can be linked to the IgG Fc construct are selected from alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiyienethiophosphoramide and trimethylolomelamine;

acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammall and calicheamicin omegaM (see, e.g., Agnew, Chem Inti. Ed. Engl., 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JjHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluoromethylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

4c. Heterologous Peptides or Polypeptides

It is further contemplated that the heteromultimers according to the invention comprises an IgG Fc construct that is linked to one or more heterologous peptides or polypeptides. The one or more heterologous peptide or polypeptides is selected from, for example, a detectable marker, a member of a ligand-receptor pair, a member of an enzyme-substrate pair and a member of a fluorescence resonance energy transfer pair.

5. Methods of Making and Purifying Heteromultimers

As described above, the heteromultimer according to the invention comprises an IgG Fc construct comprising a first and a second Fc polypeptide. Both Fc polypeptides can readily be prepared using recombinant DNA technology known in the art, whether in embodiments where the heteromultimer comprises an IgG Fc region alone, or in embodiments where the heteromultimers further comprise one or more antigen-binding domains or heterologous proteins. The design of nucleic acid that encode such molecules is well within the common knowledge of a worker skilled in the art. Standard techniques such as, for example, those described in Sambrook and Russell, Molecular Cloning: A Laboratory Manual (Cold Spring Harbor Laboratory Press, Cold Spring Harbor, N.Y., 3rd ed., 2001); Sambrook et al., Molecular Cloning: A Laboratory Manual (Cold Spring Harbor Laboratory Press, Cold Spring Harbor, N.Y., 2nd ed., 1989); Short Protocols in Molecular Biology (Ausubel et al., John Wiley and Sons, New York, 4th ed., 1999); and Glick and Pasternak, Molecular Biotechnology: Principles and Applications of Recombinant DNA (ASM Press, Washington, D.C., 2nd ed., 1998) can be used for recombinant nucleic acid methods, nucleic acid synthesis, cell culture, transgene incorporation, and recombinant protein expression.

As indicated elsewhere herein, the nucleic acid and amino acid sequences of the Fc polypeptides derived from the IgG heavy chain are known in the art or can be readily determined using nucleic acid and/or protein sequencing methods. Methods of genetically fusing the heterologous proteins or toxic drug molecules described herein to the Fc polypeptides are known in the art, and some are described below and in the Examples.

Expression vectors and host cells suitable for expression of the Fc polypeptides and, where required polypeptides encoding antigen-binding domains are also well known in the art as described below.

5.1 Vectors and Host Cells

Recombinant expression of the polypeptides of the heteromultimer requires construction of an expression vector containing a polynucleotide that encodes the necessary polypeptides. Once a polynucleotide encoding the polypeptide has been obtained, the vector for the production of the polypeptide may be produced by recombinant DNA technology using techniques well known in the art. Thus, methods for preparing a protein by expressing a polynucleotide containing the polypeptide-encoding nucleotide sequence are described herein. Methods that are well known to those skilled in the art can be used to construct expression vectors containing polypeptide coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding polypeptides of the heteromultimer, operably linked to a promoter.

The expression vector is transferred to a host cell by conventional techniques and the transfected cells are then cultured by conventional techniques to produce the polypeptide for use in the method of the invention. In specific embodiments the polypeptide for use in the method are co-expressed in the host cell for expression of an entire immunoglobulin molecule, as detailed below.

A variety of host-expression vector systems may be utilized to express the polypeptides. Such host-expression systems represent vehicles by which the coding sequences of interest may be produced and subsequently purified, but also represent cells which may, when transformed or transfected with the appropriate nucleotide coding sequences, express the polypeptides in situ. These include but are not limited to microorganisms such as bacteria (e.g., *E. coli* and *B. subtilis*) transformed with recombinant bacteriophage DNA, plasmid DNA or cosmid DNA expression vectors containing the polypeptide coding sequences; yeast (e.g., *Saccharomyces Pichia*) transformed with recombinant yeast expression vectors containing modified heavy and light chain coding sequences; insect cell systems infected with recombinant virus expression vectors (e.g., baculovirus) containing polypeptide coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing polypeptide coding sequences; or mammalian cell systems (e.g., COS, CHO, BHK, HEK-293, NSO, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In certain embodiments, bacterial cells such as *Escherichia coli*, or eukaryotic cells, are used for the expression of polypeptide, which is a recombinant antibody or fusion protein molecules. For example, mammalian cells such as Chinese hamster ovary cells (CHO), in conjunction with a vector such as the major intermediate early gene promoter element from human cytomegalovirus is an effective expression system for antibodies (Foecking et al., 1986, Gene 45:101; and Cockett et al., 1990, Bio/Technology 8:2). In a specific embodiment, the expression of nucleotide sequences encoding the immunoglobulin heavy and light chains of each heterodimer is regulated by a constitutive promoter, inducible promoter or tissue specific promoter.

In mammalian host cells, a number of viral-based expression systems may be utilized. In cases where an adenovirus is used as an expression vector, the modified heavy and light chain coding sequences of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and, capable of expressing the polypeptide in infected hosts (e.g., see Logan & Shenk, 1984, Proc. Natl. Acad. Sci. USA 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see, e.g., Bittner et al., 1987, Methods in Enzymol. 153:516-544).

The expression of the polypeptides of the heteromultimers may be controlled by any promoter or enhancer element known in the art. Promoters which may be used to control the expression of the gene encoding polypeptide include, but are not limited to, the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. U.S.A. 78.1441-1445), the regulatory sequences of the metallothionein gene (Brinster et al., 1982, Nature 296:39-42), the tetracycline (Tet) promoter (Gossen et al., 1995, Proc. Nat. Acad. Sci. USA 89:5547-5551); prokaryotic expression vectors such as the β-lactamase promoter (Villa-Kamaroff et al, 1978, Proc. Natl. Acad. Sci. U.S.A. 75:3727-3731), or the tac promoter (DeBoer et al., 1983, Proc. Natl. Acad. Sci. U.S.A. 80:21-25; see also "Useful proteins from recombinant bacteria" in Scientific American, 1980, 242:74-94); plant expression vectors comprising the nopaline synthetase promoter region (Herrera-Estrella et al., Nature 303:209-213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286); neuronal-specific enolase (NSE) which is active in neuronal cells (Morelli et al., 1999, Gen. Virol. 80:571-83); brain-derived neurotrophic factor (BDNF) gene control region which is active in neuronal cells (Tabuchi et al., 1998, Biochem. Biophysic. Res. Com. 253:818-823); glial fibrillary acidic protein (GFAP) promoter which is active in astrocytes (Gomes et al., 1999, Braz J Med Biol Res 32(5): 619-631; Morelli et al., 1999, Gen. Virol. 80:571-83) and gonadotropic releasing hormone gene control region which is active in the hypothalamus (Mason et al., 1986, Science 234:1372-1378).

In addition, a host cell strain may be chosen which modulates the expression of the inserted sequences, or modifies and processes the gene product in the specific fashion desired. Expression from certain promoters can be elevated in the presence of certain inducers; thus, expression of the genetically engineered fusion protein may be controlled. Furthermore, different host cells have characteristic and specific mechanisms for the translational and post-translational processing and modification (e.g., glycosylation, phosphorylation of proteins). Appropriate cell lines or host systems can be chosen to ensure the desired modification and processing of the foreign protein expressed. For example, expression in a bacterial system will produce an unglycosylated product and expression in yeast will produce a glycosylated product. Eukaryotic host cells that possess the cellular machinery for proper processing of the primary transcript (e.g., glycosylation, and phosphorylation) of the gene product may be used. Such mammalian host cells include, but are not limited to, CHO, VERY, BHK, Hela, COS, MDCK, HEK-293, 3T3, WI38, NSO, and in particular, neuronal cell lines such as, for example, SK-N-AS, SK-N-FI, SK-N-DZ human neuroblastomas (Sugimoto et al., 1984, J. Natl. Cancer Inst. 73: 51-57), SKN-SH human neuroblastoma (Biochim. Biophys. Acta, 1982, 704: 450-460), Daoy human cerebellar medulloblastoma (He et al., 1992, Cancer Res. 52: 1144-1148) DBTRG-05MG glioblastoma cells (Kruse et al., 1992, In Vitro Cell. Dev. Biol. 28A: 609-614), IMR-32 human neuroblastoma (Cancer Res., 1970, 30: 2110-2118), 1321 N1 human astrocytoma (Proc. Natl. Acad. Sci. USA, 1977, 74: 4816), MOG-G-CCM human astrocytoma (Br. J. Cancer, 1984, 49: 269), U87MG human glioblastoma-astrocytoma (Acta Pathol. Microbiol. Scand., 1968, 74: 465-486), A172 human glioblastoma (Olopade et al., 1992, Cancer Res. 52: 2523-2529), C6 rat glioma cells (Benda et al., 1968, Science 161: 370-371), Neuro-2a mouse neuroblastoma (Proc. Natl; Acad. Sci. USA, 1970, 65: 129-136), NB41A3 mouse neuroblastoma (Proc. Natl. Acad. Sci. USA, 1962, 48: 1184-1190), SCP sheep choroid plexus (Bolin et al., 1994, J. Virol. Methods 48: 211-221), G355-5, PG-4 Cat normal astrocyte (Haapala et al., 1985, J. Virol. 53: 827-833), Mpf ferret brain (Trowbridge et al., 1982, In Vitro 18: 952-960), and normal cell lines such as, for example, CTX TNA2 rat normal cortex brain (Radany et al., 1992, Proc. Natl. Acad. Sci. USA 89: 6467-6471) such as, for example, CRL7030 and Hs578Bst. Furthermore, different vector/host expression systems may effect processing reactions to different extents.

For long-term, high-yield production of recombinant proteins, stable expression is often preferred. For example, cell lines that stably express the polypeptide of the invention (e.g., antibody or fusion protein) may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci that in turn can be cloned and expanded into cell lines.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk-, hgprt- or aprt-cells, respectively. Also, anti-metabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes.

Methods of preparing antibody-drug conjugates are known in the art and a description of same is found in US Patent Publication No. 2011/0200596.

5.2 Purification of Heteromultimers

When using recombinant techniques, the heteromultimers can be produced intracellularly, or directly secreted into the medium. If the heteromultimer is produced intracellularly, as a first step, the particulate debris, either host cells or lysed fragments, are removed, for example, by centrifugation or ultrafiltration. Where the heteromultimer is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The heteromultimers composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc region that is present in the heteromultimer. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the heteromultimers comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the heteromultimer to be recovered.

Following any preliminary purification step(s), the mixture comprising the heteromultimer of interest and contaminants may be subjected to low pH hydrophobic interaction chromatography using an elution buffer at a pH between about 2.5-4.5, preferably performed at low salt concentrations (e.g., from about 0-0.25M salt).

The heteromultimers of the invention comprise asymmetric amino acid modifications in the first and second Fc polypeptides of the IgG Fc construct. Accordingly, due to the inherent properties of the Fc polypeptides, when the Fc polypeptides are expressed together, the products that result will include homodimers of the first Fc polypeptide, homodimers of the second Fc polypeptide, and heterodimers of the first and second polypeptide.

In one embodiment, heteromultimers are purified or isolated after expression. Methods of expression are described elsewhere herein. Proteins may be isolated or purified in a variety of ways known to those skilled in the art. Standard purification methods include chromatographic techniques, including ion exchange, hydrophobic interaction, affinity, sizing or gel filtration, and reversed-phase, carried out at atmospheric pressure or at high pressure using systems such as FPLC and HPLC. Purification methods also include electrophoretic, immunological, precipitation, dialysis, and chromatofocusing techniques. Ultrafiltration and diafiltration techniques, in conjunction with protein concentration, are also useful. As is well known in the art, a variety of natural proteins bind Fc and antibodies, and these proteins can find use in the present invention for purification of heteromultimers. For example, the bacterial proteins A and G bind to the Fc region. Likewise, the bacterial protein L binds to the Fab region of some antibodies, as of course does the antibody's target antigen. Purification can often be enabled by a particular fusion partner. For example, antibodies may be purified using glutathione resin if a GST fusion is employed, Ni+2affinity chromatography if a His-tag is employed, or immobilized anti-flag antibody if a flag-tag is used. For general guidance in suitable purification techniques, see, e.g. Protein Purification: Principles and Practice, 3rd Ed., Scopes, Springer-Verlag, NY, 1994, incorporated herein it its entirety by reference. The degree of purification necessary will vary depending on the screen or use of the antibodies. In some instances no purification is necessary. For example in one embodiment, if the antibodies are secreted, screening may take place directly from the media. As is well known in the art, some methods of selection do not involve purification of proteins. Thus, for example, if a library of antibodies is made into a phage display library, protein purification may not be performed.

Thus, in one embodiment, the heteromultimers comprising an IgG Fc construct, when expression of said IgG Fc construct results in a mixture of IgG Fc constructs with homodimeric Fc regions and IgG Fc constructs with heterodimeric Fc regions, the IgG Fc constructs with homodimeric Fc regions are clearly resolved from the IgG Fc constructs with heterodimeric Fc regions using charge-based purification methods, such as, for example ion exchange chromatography.

In an additional embodiment, heteromultimers comprising an IgG Fc construct described herein can also comprise a variant CH3 region comprising amino acid modifications that promote the formation of a heterodimeric Fc region rather than formation of a homodimeric Fc region. Expression of these heteromultimers may result in a mixture of heteromultimers having homodimeric Fc regions and heterodimeric Fc regions. Such mixtures can also be resolved using charge-based purification methods as indicated above. Exemplary variants that can be purified in this manner include AAC3, AAC4, and AAC5.

6. Testing of Heterorvultimers 6.1 FcγR, FcRn and C1q Binding

In certain embodiments, the Fc activities of the produced immunoglobulin are measured to ensure that only the desired properties are maintained. In vitro and/or in vivo cytotoxicity assays can be conducted to confirm the reduction/depletion of CDC and/or ADCC activities. Methods of assessing effector function are described in Jiang et al. (2011) Nature Reviews Drug Discovery 10:101-111. For example, Fc receptor (FcR) binding assays can be conducted to ensure that the heteromultimer lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. PNAS (USA) 95:652-656 (1998). C1q binding assays may also be carried out to confirm that the heteromultimer is unable to bind C1q and hence lacks CDC activity. To assess complement activation, a CDC assay, e.g. as described in Gazzano-Santoro et al., J. Immunol. Methods 202:163 (1996), may be performed. FcRn binding and in vivo clearance/half life determinations can also be performed using methods known in the art.

FcγR and C1q binding can also be measured by Surface Plasmon Resonance (SPR), or ELISA-based methods. FcγR binding can also be measured by FACS (fluorescence activated cell sorting). Commercially available may also be used to measure the ability of the heteromultimers to bind to FcγR or C1q.

6.2 Stability

The thermal stability of the heteromultimers can be determined according to methods known in the art. The melting temperature of the IgG Fc construct is indicative of its thermal stability. The melting point of the IgG Fc construct may be measured using techniques such as differential scanning calorimetry (Chen et al (2003) Pharm Res 20:1952-60; Ghirlando et al (1999) Immunol Lett 68:47-52). Alternatively, the thermal stability of the IgG Fc construct may be measured using circular dichroism (Murray et al. (2002) J. Chromatogr Sci 40:343-9).

The methodology for determining the Tm of the parent CH2 domain is well described in the art (see for example Ionescu et al (2008) J Pharm Sci 97(4): 1414-26). In short, melting of the Fc region of IGG1 produces two transitions: one for the melting of the CH2 domain and one for that of the CH3 domain. These transitions are independent of the Fab present, but can be masked by the Fab transition. Typically, melting of IGG1 Fc gives a transition with a Tm of 71° C. for the CH2 domain and one with a Tm of 82° C. for the CH3 domain. The Tm of the CH2 domain is affected by its glycosylation state, the nature of the hinge region, and the intrinsic stability of the CH3 domain. Aglycosylation and deglycosylation are known to decrease the Tm of the CH2 domain by 10° C. Removal of hinge disulfides are known to decrease the Tm of the CH2 domain by more than 10° C. Changes to the CH3 domain that decrease its stability below that of the CH2 domain are likely to produce changes in the Tm of the CH2 domain, but the effect is harder to predict.

7. Pharmaceutical Compositions

The present invention also provides pharmaceutical compositions comprising the heteromultimers according to the invention. Such compositions comprise a therapeutically effective amount of the heteromultimer and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical, carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In certain embodiments, the composition comprising the heteromultimer is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anaesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachet indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

In certain embodiments, the compositions described herein are formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxide isopropylamine, triethylamine, 2-ethylamino ethanol, histidine, procaine, etc.

The amount of the composition described herein which will be effective in the treatment, inhibition and prevention of a disease or disorder associated with aberrant expression and/or activity of a therapeutic protein can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses are extrapolated from dose-response curves derived from in vitro or animal model test systems.

8. Methods of Treatment/Uses

The heteromultimers generated by any of the above described methods may be used to diagnose, treat, detect, or modulate human disease or specific pathologies in cells, tissues, organs, fluid, or, generally, a host. As taught herein, modification of the Fc region of an antibody, Fc-fusion protein, or Fc fragment to reduce or ablate Fc gamma receptor binding and specified effector functions, but where the heteromultimer retains the original targeting properties, provides antibodies and IgG Fc constructs with a superior spectrum of activities, biophysical properties, stability and ability to persist in the body of a host.

The diseases or pathologies that may be amenable to treatment using a composition provided by the invention include, but are not limited to: neurological disorders, such as but not limited to Alzheimer's disease and including neuropathic pain; dermatological disease; metabolic diseases; osteoarthritis; and conditions resulting from burns or injury; cardiovascular disorders including but not limited to myocardial infarction, congestive heart failure, stroke, ischemic stroke, and hemorrhage; as well as general immune mediated disorders, including the rheumatic diseases, psoriasis, and scleroderma.

In one embodiment, the heteromultimers according to the present invention are used in the treatment of diseases where antibodies are used to target cell surface molecules where depletion of these molecules resulting from FcγR mediated effector function has adverse effects.

In one embodiment, the heteromultimers according to the present invention are used to improve the safety index for antibodies that form immune complexes with their targets.

Strohl, W R and Strohl L M, "Antibody Fc engineering for optimal antibody performance" In Therapeutic Antibody Engineering, Cambridge: Woodhead Publishing (2012), pp 225-249, provides a description of the advantages of using antibodies that lack FcγR- and complement-mediated effector functions for the treatment of disease. It is contemplated that heteromultimers comprising the IgG Fc constructs according the present invention are useful in preparing antibodies that lack FcγR- and complement-mediated effector functions for the treatment of disease.

9. Kits

The present invention additionally provides for kits comprising one or more heteromultimers. Individual components of the kit would be packaged in separate containers and, associated with such containers, can be a notice in the form prescribed by a governmental agency regulating the manufacture, use or sale of pharmaceuticals or biological products, which notice reflects approval by the agency of manufacture, use or sale. The kit may optionally contain instructions or directions outlining the method of use or administration regimen for the heterodimer pairs.

When one or more components of the kit are provided as solutions, for example an aqueous solution, or a sterile aqueous solution, the container means may itself be an inhalant, syringe, pipette, eye dropper, or other such like apparatus, from which the solution may be administered to a subject or applied to and mixed with the other components of the kit.

The components of the kit may also be provided in dried or lyophilised form and the kit can additionally contain a suitable solvent for reconstitution of the lyophilised components. Irrespective of the number or type of containers, the kits of the invention also may comprise an instrument for assisting with the administration of the composition to a patient. Such an instrument may be an inhalant, nasal spray device, syringe, pipette, forceps, measured spoon, eye dropper or similar medically approved delivery vehicle.

It is understood that the examples and embodiments described herein are for illustrative purposes only and that various modifications or changes in light thereof will be suggested to persons skilled in the art and are to be included within the spirit and purview of this application and scope of the appended claims.

EXAMPLES

The examples below are given so as to illustrate the practice of this invention. They are not intended to limit or define the entire scope of this invention.

Example 1: Preparation and Expression of Antibody Constructs (Heteromultimers)

The following antibody constructs were prepared. All antibody constructs were based on the sequence of the wild-type anti-Her2 antibody trastuzumab (see FIG. 5, SEQ ID NO:2 for wild-type trastuzumab Heavy chain amino acid sequence, SEQ ID NO:3 for wild-type trastuzumab light chain sequence) with the following added modifications in the heavy chain CH3 domain introduced in order to promote the formation of a heterodimer Fc domain with increased stability as compared to a CH3 domain that does not comprise amino acid mutations.

Chain A: T350V/L351Y/S400E/F405A/Y407V, and
Chain B: T350V/T366L/N390R/K392M/T394W This construct, with the above modifications is referred to as v791. All sequences described herein are numbered using the EU numbering system.

Additional variants were constructed based on v791, with amino acid modifications in the hinge region and or CH2 domain of the heavy chain as shown in Table A1. All variants included the trastuzumab light chain sequence as set forth in SEQ ID NO: 67 (amino acid) and/or SEQ ID NO:34 (DNA).

TABLE A1

Asymmetric antibody constructs based on trastuzumab

| Variant | Heavy Chain A | SEQ ID No.: (amino acid/DNA) | Heavy Chain B | SEQ ID No.: (amino acid/DNA) |
|---|---|---|---|---|
| 1051/ control | L234A/L235A | 6/7 | L234A/L235A | 8/9 |
| AAC1 | L234A/L235A | 6/7 | — | 20/21 |
| AAC2 | L234A/L235A | 6/7 | L234K/L235K | 22/23 |
| AAC3 | L234D/L235E | 10/11 | L234K/L235K | 22/23 |
| AAC4 | E233A/L234D/ L235E | 12/13 | E233A/L234R/ L235R | 24/25 |
| AAC5 | L234D/L235E | 10/11 | E233K/L234R/ L235R | 26/27 |
| AAC6 | E233A/L234K/ L235A | 14/15 | E233K/L234A/ L235K | 28/29 |
| AAC7 | E269Q/D270N | 16/17 | E269K/D270R | 30/31 |
| AAC8 | — | 18/19 | L235K/A327K | 32/33 |

1051 is a control variant described in Strohl (2009) Current Opinion in Biotechnology 20:685-691.

AAC1 is another control variant which is an asymmetric version of 1051, in which only one of the heavy chains has the L234/L235 double mutation.

AAC2-AAC8 are asymmetric designs.

The antibodies and controls were cloned and expressed as follows. v791 was prepared by site-directed mutagenesis using standard methods. The final DNA was sub-cloned into the vector pTT5 (see International Patent Publication No. WO 2009/137911). Expression was carried out in either 2 mL or 50 mL or 500 mL CHO 3E7 cells. CHO cells were transfected in exponential growth phase (1.5 to 2 million cells/mL) with aqueous 1 mg/mL 25 kDa polyethylenimine (PEI, Polysciences) at a PEI:DNA ratio of 2.5:1. (Raymond C. et al. A simplified polyethylenimine-mediated transfection process for large-scale and high-throughput applications. Methods. 55(1):44-51 (2011)). In order to determine the optimal concentration range for forming heterodimers, the DNA was transfected in optimal DNA ratios of the heavy chain A (HC-A), light chain (LC), and heavy chain B that allow for heterodimer formation (e.g. HC-A/HC-B/LC ratios=25:25:50%). Transfected cells were harvested after 5-6 days with the culture medium collected after centrifugation at 4000 rpm and clarified using a 0.45 μm filter.

Purification protocols: The clarified culture medium was loaded onto a MabSelect SuRe (GE Healthcare) Protein-A column and washed with 10 column volumes of PBS buffer at pH 7.2. The antibody was eluted with 10 column volumes of citrate buffer at pH 3.6 with the pooled fractions containing the antibody neutralized with TRIS at pH 11. The Protein-A purified antibody was further purified by gel filtration (SEC). For gel filtration, 3.5 mg of the antibody mixture was concentrated to 1.5 mL and loaded onto a Sephadex 200 HiLoad 16/600 200 pg column (GE Healthcare) via an Ä KTA Express FPLC at a flow-rate of 1 mL/min. PBS buffer at pH 7.4 was used at a flow-rate of 1 mL/min. Fractions corresponding to the purified antibody were collected, concentrated to 1 mg/mL and stored at −80° C.

TABLE A2 summarizes the expression yields for the various samples.

| Variant | 50 mL Expression Protein-A yield [mg/L] | 50 mL Expression SEC yield [mg/L] | 500 mL Expression Protein-A yield [mg/L] | 500 mL Expression SEC yield [mg/L] |
|---|---|---|---|---|
| WT | 30 | n/d* | n/d | n/d |
| 1051/control | 48 | 20 | 48 | 23 |
| AAC1 | n/d | n/d | n/d | n/d |
| AAC2 | 63 | 24 | n/d | n/d |
| AAC3 | 39 | 20 | n/d | n/d |
| AAC4 | 42 | 26 | n/d | n/d |
| AAC5 | 44 | 16 | n/d | n/d |
| AAC6 | 31 | 13 | 15 | 10 |
| AAC7 | n/d | n/d | n/d | n/d |
| AAC8 | n/d | n/d | n/d | n/d |

*n/d = not determined

The majority of the samples showed levels of expression similar to the WT or control.

Example 2: Asymmetric Antibody Constructs Based on Trastuzumab do not Bind to FcγR The ability of the asymmetric antibody constructs to bind to FcγRIIaH, FcγRIIaR, FcγRIIb FcγRIIIaF, FcγRIIIaV, and FcγRIa was assessed by surface plasmon resonance (SPR).

Affinity of FcγRs to antibody Fc was measured by SPR using a ProteOn XPR36 at 25° C. with 10 mM HEPES, 150 mM NaCl, 3.4 mM EDTA, and 0.05% Tween 20 at pH 7.4. Recombinant HER-2 was captured on the activated GLM sensorchip by injecting 4.0 μg/mL in 10 mM NaOAc (pH 4.5) at 25 μL/min until approx. 3000 resonance units (RUs) were immobilized with the remaining active groups quenched. 40 μg/mL of purified HER-2/neu-based antibodies were indirectly captured when injected at 25 μL/min for 240s (resulting in approx. 500RUs) following a buffer injection to establish a stable baseline. FcγRs were injected at 60 μL/min for 120s with a 180s dissociation phase to obtain a set of binding sensograms. Resultant kD values were determined from binding isotherms using the Equilibrium Fit model with reported values as the mean of two or three independent runs.

The in vitro binding Ka ratio with respect to the WT for each variant, as determined by SPR, is shown in Table B.

TABLE B

SPR Ka ratio for binding to Fcγ receptors with respect to wild-type trastuzumab

| Variant | 2aH[1] | 2aR[2] | 2b[3] | 3aF[4] | 3aV[5] | 1a[6] |
|---|---|---|---|---|---|---|
| WT | 1.00 | 1.00 | 1.00 | 1.00 | 1.00 | 1.00 |
| control/1051 | 0.06 | 0.18 | 0.52 | 0.29 | 0.10 | 0.01 |
| AAC1 | n/d* | n/d | n/d | 0.87 | 0.71 | 0.48 |
| AAC2 | NB | NB | NB | LOW | LOW | LOW |
| AAC3 | NB | NB | NB | LOW | LOW | LOW |
| AAC4 | NB | NB | NB | LOW | LOW | LOW |
| AAC5 | NB | NB | NB | LOW | LOW | LOW |
| AAC6 | NB | NB | NB | NB | LOW | LOW |
| AAC7 | n/d | n/d | n/d | LOW | LOW | 0.15 |
| AAC8 | n/d | n/d | n/d | 0.19 | 0.10 | 0.13 |

*n/d = not determined

[1]The Kd of 2ah was 0.48 μM. Receptor was run at 10 μM. LOW means that Kd >> 10 μM, NB means Kd >> 100 μM where >> indicates "much greater than".

[2]The Kd of 2ar was 0.87 μM. Receptor was run at 10 M. LOW means that Kd >> 10 μM, NB means Kd >> 100 μM.

[3]The Kd of 2b was 3.4 μM. Receptor was run at 10 μM. LOW means that Kd >> 10 μM, NB means Kd >> 100 μM.

[4]The Kd of 3af was 1.9 μM. Receptor was run at 6 μM. LOW means that Kd >> 6 μM, NB means Kd >> 60 μM.

[5]The Kd of 3av was 0.60 μM. Receptor was run at 6 μM. LOW means that Kd >>6 μM, NB means Kd >> 60 μM.

[6]The Kd of 1a was 0.65 nM. Receptor was run at 30 nM. LOW means that Kd >> 30 nM, NB means Kd >> 300 nM.

All of the variants showed significantly decreased binding to all of the receptors. In most cases the binding was undetectable or unquantifiable due to the low affinity.

Example 3: Asymmetric Antibody Constructs Based on Trastuzumab do not Bind to C1q The ability of the asymmetric antibody constructs to bind to C1q was tested as follows. Human C1q was purchased from GenWay Biotech (San Diego, Calif.). SPR chip immobilization of antibodies was as described in Example 2. 30 nM C1q injected over mAb variants captured onto a HER2 SPR surface using standard protocols as also described in Example 2. The results are shown in Table C below.

TABLE C

Results of C1q binding assay

| Variant | C1q[1] |
|---|---|
| WT | yes |
| Control/1051 | NB |
| AAC1 | partial |
| AAC2 | NB |
| AAC3 | NB |
| AAC4 | NB |
| AAC5 | NB |
| AAC6 | NB |
| AAC7 | NB |
| AAC8 | NB |

[1]C1q is a hexamer of heterotrimers witha potential stoichiomentry mAb:C1q of 6:1. The binding kinetics were very complex, and a proper Kd could not be determined. Receptor was tested at 30 nM. 'partial' means diminished binding, 'NB' means no detectable binding All of the variants showed undetectable binding to C1q, except for AAC1 which showed decreased, but detectable binding to C1q.

Example 4: Asymmetric Antibody Constructs Based on Trastuzumab Bind to FcRn

The ability of the asymmetric antibodies to bind to FcRn was tested by SPR as follows.

SPR chip capture surface was prepared with goat anti-hIgG polyclonal. Variants were captured from supernatants on the vertical line. A flow of FcRn at 1 μM maximum with a 3× dilution series was run on the horizontal line. Duplicate runs at pH 6 produced similar results. One run at pH 7.4 was performed to check for lack of binding. The results are shown in Table D below.

TABLE D

| FcRn binding | |
|---|---|
| Variant | FcRn[1] |
| WT | Yes |
| Control/1051 | Yes |
| AAC1 | n/d* |
| AAC2 | Yes |
| AAC3 | Yes |
| AAC4 | Yes |
| AAC5 | Yes |
| AAC6 | Yes |
| AAC7 | n/d |
| AAC8 | n/d |

*n/d = not determined

[1]FcRn binding was measured at pH 6.5 and 7.4. Variants with WT binding at pH 6.5 and no detectable binding at pH 7.4 are denoted as 'Yes'

Example 5: Asymmetric Antibody Constructs are Thermally Stable

The thermal stability of the CH2 domains of the asymmetric antibody constructs was determined using differential scanning calorimetry as follows. Each antibody construct was purified as described in Example 1 and diluted to 0.2 mg/mL in PBS, and a total of 400 μL was used for DSC analysis with a VP-Capillary DSC (GE Healthcare). At the start of each DSC run, five buffer blank injections were performed to stabilize the baseline, and a buffer injection was placed before each antibody construct injection for referencing. Each sample was scanned from 20 to 100° C. at a 60° C./hr rate, with low feedback, 8 sec filter, 5 min preTstat, and 70 psi nitrogen pressure. The resulting thermograms were referenced and analyzed using Origin 7 software.

Thermal unfolding curves for the heterodimers tested are shown in FIG. 2. The melting temperatures of the heteromultimers tested are shown in Table E below.

TABLE E

| Thermal stability of heteromultimers | | |
|---|---|---|
| Variant | Tm onset (WT ~66.5C)[1] | Tm (WT ~71.0C)[2] |
| Control/1051 | 66.5 | 71.8 |
| AAC1 | n/d | n/d* |
| AAC2 | 70.5 | 74 |
| AAC3 | 65.8 | 71.5 |
| AAC4 | 66.7 | 72.8 |
| AAC5 | 67.0 | 72.9 |
| AAC6 | 68.7 | 75.0 |
| AAC7 | n/d | n/d |
| AAC8 | n/d | n/d |

*n/d = not determined

[1]Tm onset was visually taken as the first point where the thermogram in FIG. 2 significantly goes above baseline.

[2]The Tm was measured by deconvolution using a non-2 state model of the first transition in the thermograms shown in FIG. 2.

These results indicate that a number of designs have higher Tm onset and Tm of the CH2 domain when compared to the control WT.

Example 6: Purification of Asymmetric Antibody Constructs Based on Trastuzumab Selected asymmetric antibody constructs were expressed and purified by UPLC IEX (Ultra Performance Liquid Chromatography—Ion exchange chromatography) as follows.

Chain A and Chain B of variants 791 (WT heterodimer), AAC3 (L234D/L235E[Chain A]L234K/L235K[Chain B]) and AAC5 (L234D/L235E[Chain A]E233K/L234K/L235K [Chain B]) were expressed in ratios 1:0 (A), 1:1 (C) and 0:1 (E) in 50 mL CHO cultures. Ratios A and E produced homodimers of Chain A and Chain B, respectively. All of the samples were purified by Protein A, and then by Size Exclusion Chromatography (SEC) using a Superdex 200 16/600 column in PBS buffer prior to loading them into the UPLC IEX. UPLC IEX was carried out under the following conditions (pH gradient): Solvents: A, 0.1 M $NaH_2PO_4$, pH 4.44; B, 0.1 M $Na_2HPO_4$, pH 9.20; C, MilliQ water; D, 0.5 M Na Acetate, pH 9.13 (lot #3 Dec. 2012). Initial Buffer: 18% A, 2% B, 68% $C_{1-12}$% D=20 mM $NaPO_4$, 60 mM NaAcetate, pH~5.9; Gradient: to 2% A, 18% B, 68% $C_{1-12}$% D=20 mM $NaPO_4$, 60 mM NaAcetate, pH ~7.9 in 7.2 column volumes. Flow rate: 0.3 ml/min. Temperature: 30° C. Pressure: 4200 psi. Column: Agilent BioMAb, 4.6×50 mm, 1.7 μm particles, SN USDJA01061.

The results are shown in FIG. 3A. Traces for ratios A, C, and E corresponding to the homodimers or heterodimers are labelled. Repeat runs, when carried out, are also shown.

FIG. 3A shows that, the introduction of asymmetric charges on the lower hinge region result in a design that not only has lower receptor binding (Example 3) and higher thermal stability (Example 5), but it also can be purified from homodimer impurities by Ion Exchange Chromatography.

The separation of one variant, AAC4, was tested under two conditions. It was eluted under a pH gradient as described above, or under a salt gradient as follows: Solvents: A 0.1 M NaH2PO4, pH 4.44; B 0.1 M Na2HPO4, pH 9.20; C MilliQ water; D 0.5 M NaCl. Initial Buffer: 18% A, 2% B, 68% $C_{1-12}$% D=20 mM NaP04, 60 mM NaCl, pH ~5.9. Salt gradient to 18% A, 2% B, 0% $C_{1-80}$% D (=20 mM $NaPO_4$, 400 mM NaCl, pH ~5.9) in 7.2 column volumes.

The results are shown in FIG. 3B. The figure shows that the separation of the homodimers and heterodimers with a salt gradient was similar to that with a pH gradient.

Example 7: Asymmetric Antibody Constructs Based on Trastuzumab do not Stimulate ADCC (Antibody-Dependent Cell-Mediated Cytotoxicity) in SK-BR-3 Cells An exemplary variant was tested for its ability to stimulate ADCC in SK-BR-3 cells in order to assess whether the lack of measured binding to FcγR translated into an inability to mediate effector function as measured by ADCC. SK-BR-3 cells express HER2 on their surface and thus bind to trastuzumab, allowing for NK cell mediated ADCC in the presence of trastuzumab. The activity of AA6 in this assay was compared to that of the control variant described in Table A, and to the positive control trastuzumab.

Cell lines used: SK-BR-3 cell line (ATCC #HTB-30), NK92/CD16a(158V/V) Detection device: FlexStation3, Molecular Devices.

Positive control antibody: Herceptin™ (Trastuzumab).

Cell Culture. Frozen cells were thawed by gently swirling the vial in the 37° C. water bath. After 1-2 min, the medium in the vial was completely thawed. The outside of the vial was wiped with 70% ethanol. The cell suspension was then transferred to a 15 ml centrifuge tube, followed by addition of 5 ml of pre-warmed complete medium. After centrifugation for 3-5 min at 500 g, the supernatant was aspirated. 10 ml of complete medium was added and the cells were resuspended by pipetting up and down for a few times. Cell viability was determined by Trypan blue staining method. The cell suspension was then seeded in flasks. The cells were incubated at 37° C., 5% CO2 overnight.

Cells were maintained at 37° C./5% CO2 and regularly sub-cultured with suitable medium supplemented with 10% FBS according to protocol from ATCC.

The antibody sample and the Standard were delivered in dry shipper and stored at −20° C. before testing. The sample and the Standard were stored at 4° C. after they were thawed on ice. The sample and the Standard were diluted with Phenol red free MEM medium (supplemented with 1% FBS and 1% Pen/Strep) and applied to the tests.

ADCC assay buffer was composed of 98% Phenol red free MEM medium, 1% Pen/Strep and 1% FBS.

NK92/FcRγ3a(158V/V) cells were conventionally maintained.

Target cells were harvested by centrifugation at 800 rpm for 3 min, washed with assay medium once and centrifuged; the medium above the pellet was removed completely. Cells were gently suspended with assay medium to make single cell solution. The target cell number was adjusted to 4× cell stock (10,000 cells in 50 μl assay medium). Test articles were prepared at interested concentrations. 50 μl 4× target cell stock were seeded to 96-well assay plates and 50 μl 4× sample diluents added. The plates were incubated at room temperature for 30 min in cell culture incubator. 100 μl effector cells (E/T=5:1, i.e, 50,000 effector cells per well) were added to initiate the reaction and mixed gently by cross shaking. Triton X-100 was added to cell controls without effector cells and antibody in a final concentration of 1% to lyze the target cells and it served as the maximum lysis control; assay buffers were added in to cell controls without effector cells and antibody and it served as the minimum LDH release control. Target cells incubated with effector cells without the presence of antibodies were set as background control of non-specific LDH release when both cells were incubated together. Plate was incubated at 37° C./5% CO2 incubator for 4-6 hours. The cell viability was assayed with an LDH kit. The absorbance data at OD492 nm and OD650 nm were measured on Flexstation 3.

The background (OD650 nm) subtracted OD492 nm data was analyzed to study the LDH release. The percentages of cell lysis were calculated according to the formula:

Cell lysis %=100*(1−(*OD*Sample data−*OD*tumor cells plus effector cells)/(*OD*Maximum release−*OD*Minimum release))

The results are shown in FIG. 4 and indicate that exemplary heteromultimer AA6 is able to silence ADCC activity in this assay.

Example 8: Preparation and Expression of Antibody Constructs Based on the Anti-CD20 Antibody, Rituximab (Heteromultimers)

The following antibody constructs were prepared. All antibody constructs were based on the sequence of the wild-type anti-CD20 antibody rituximab (see FIG. 5, SEQ ID NO:4 for wild-type rituximab Heavy chain amino acid sequence, SEQ ID NO:5 for wild-type rituximab light chain sequence) with the following added modifications in the heavy chain CH3 domain introduced in order to promote the formation of a heterodimer Fc domain with increased stability as compared to a CH3 domain that does not comprise amino acid mutations:

Chain A: T350V/L351Y/F405A/Y407V, and
Chain B: T350V/T366L/K392L/T394W

This construct with the above mutations is referred to as v1261.

Additional variants were constructed based on v1261, with amino acid modifications in the hinge region and or CH2 domain of the heavy chain as shown in Table F. All variants additionally comprise the light chain sequence as set forth in SEQ ID NO: 68 (amino acid) and or SEQ ID NO:69 (DNA).

TABLE F

Asymmetric antibody constructs based on rituximab

| Variant | Chain A | SEQ ID No.: (amino acid/DNA) | Chain B | SEQ ID No.: (amino acid/DNA) |
|---|---|---|---|---|
| Control WT Rituximab 1261 | — | 35/36 | — | 37/38 |
| AAC9 | L234D/L235E | 39/40 | E233K/L234R/L235R | 41/42 |
| AAC10 | L234D/L235E + D265S | 43/44 | E233K/L234R/L235R + D265S | 45/46 |
| AAC11 | L234D/L235E + E269K | 47/48 | E233K/L234R/L235R + E269K | 49/50 |
| AAC12 | L234D/L235E + K322A | 51/52 | E233K/L234R/L235R + K322A | 53/54 |
| AAC13 | L234D/L235E + P329W | 55/56 | E233K/L234R/L235R + P329W | 57/58 |
| AAC14 | L234D/ L235E + E269K + D265S + K322A | 59/60 | E233K/L234R/L235R + E269K + D265S + K322A | 61/62 |
| AAC15 | L234D/L235E + E269K + D265S + K322E + E333K | 63/64 | E233K/L234R/L235R + E269K + D265S + K322E + E333K | 65/66 |

The antibodies and controls were cloned and expressed as follows. V1261 was prepared by site-directed mutagenesis using standard methods. The final DNA was sub-cloned into the vector pTT5 (see International Patent Publication No. WO 2009/137911). Expression was carried out in either 50 mL or 250 mL CHO 3E7 cells. CHO cells were transfected in exponential growth phase (1.5 to 2 million cells/mL) with aqueous 1 mg/mL 25 kDa polyethylenimine (PEI, Polysciences) at a PEI:DNA ratio of 2.5:1. (Raymond C. et al. A simplified polyethylenimine-mediated transfection process for large-scale and high-throughput applications. Methods. 55(1):44-51 (2011)). The DNA was transfected in a DNA ratios of the heavy chain A (HC-A), light chain (LC), and heavy chain B of HC-A/HC-B/LC ratios=30:30:40%). Transfected cells were harvested after 5-6 days with the culture medium collected after centrifugation at 4000 rpm and clarified using a 0.45 μm filter.

Purification protocols: The clarified culture medium was loaded, onto a MabSelect SuRe (GE Healthcare) Protein-A column and washed with 10 column volumes of PBS buffer at pH 7.2. The antibody was eluted with 10 column volumes of citrate buffer at pH 3.6 with the pooled fractions containing the antibody neutralized with TRIS at pH 11. The Protein-A purified antibody was further purified by gel filtration (SEC). For gel filtration, 3.5 mg of the antibody mixture was concentrated to 1.5 mL and loaded onto a Sephadex 200 HiLoad 16/600 200 pg column (GE Healthcare) via an AKTA Express FPLC at a flow-rate of 1 mL/min. PBS buffer at pH 7.4 was used at a flow-rate of 1 mL/min. Fractions corresponding to the purified antibody were collected, concentrated to ~1 mg/mL and stored at −80° C.

The expression yields are the following:

TABLE G

| Expression yields | | | | |
|---|---|---|---|---|
| Variant | 50 mL Expression Protein-A yield [mg/L] | 50 mL Expression SEC yield [mg/L] | 250 mL Expression Protein-A yield [mg/L] | 250 mL Expression SEC yield [mg/L] |
| Control WT Rituximab 1261 | | | 28 | 15 |
| AAC9 | 11 | 6 | 8 | 3 |
| AAC10 | 12 | 5 | 24 | 11 |
| AAC11 | 12 | 3 | 24 | 9 |
| AAC12 | 11 | 4 | 11 | 9 |
| AAC13 | 15 | 5 | 7 | 3 |
| AAC14 | 10 | 3 | 13 | 11 |
| AAC15 | 18 | 5 | 8 | 3 |

Considering the batch to batch variablity in yield, all samples expressed well to levels comparable to the control WT Rituximab.

Example 9: Asymmetric Antibody Constructs Based on Rituximab do not Bind to FcγR The ability of the asymmetric antibody constructs based on rituximab to bind to FcγRIIaH, FcγRIIaR, FcγRIIb FcγRIIIaF, and FcγRIIIaV was assessed by surface plasmon resonance (SPR).

Affinity of FcgR to antibody Fc was measured by SPR using a ProteOn XPR36 at 25° C. with PBS containing 3.4 mM EDTA, and 0.05% Tween 20 at pH 7.4 as the running buffer. Goat polyclonal anti-IgG antibodies were immobilized on a NHS/EDC activated GLC sensorchip by injecting 4.0 μg/mL in 10 mM NaOAc (pH 4.5) at 25 μL/min until approximately 3000 resonance units (RUs) was reached, which was followed by quenching the remaining active groups with ethanolamine. 40 μg/mL of purified rituximab-based antibodies were indirectly captured by injecting at 25 μL/min for 240s (resulting in approx. 500RUs capture) in the ligand direction, following a buffer injection to establish a stable baseline in the analyte direction. FcγRs were subsequently injected at 50 μL/min for 120s with a 180s dissociation phase to obtain a set of binding sensorgrams. Resultant Kd (affinity) values were determined from double-referenced sensorgrams using the Equilibrium Fit model in the Proteon Manager software. Reported values as the mean of two or three independent runs.

The in vitro binding Ka ratio with respect to the WT for each variant, as determined by SPR, is shown in Table H.

TABLE H

| SPR Ka ratio for binding to Fcγ receptors with respect to wild-type trastuzumab | | | | | |
|---|---|---|---|---|---|
| Variant | CD16aF | CD16aV | CD32b | CD32aH | CD32aR |
| Trastuzumab | 1.00 | 1.00 | 1.00 | 1.00 | 1.00 |
| Control WT Rituximab 1261 | 1.36 | 1.34 | 1.85 | 1.87 | 1.47 |
| AAC9 | NB | 0.08 | NB | NB | NB |
| AAC10 | NB | LOW | NB | NB | NB |
| AAC11 | NB | LOW | NB | NB | NB |
| AAC12 | NB | 0.08 | NB | NB | NB |
| AAC13 | NB | LOW | NB | NB | NB |
| AAC14 | NB | LOW | NB | NB | NB |
| AAC15 | NB | LOW | NB | NB | NB |

The heterodimer driving mutations on the control WT Rituximab 1261 marginally brought up affinity towards the receptors when compared to homodimeric WT trastuzumab. The mutants, which contained the heterodimer driving mutations, showed significantly reduced or undetectable binding to the Fcγ receptors.

Example 10: Asymmetric Antibody Constructs Based on Rituximab are Thermally Stable The thermal stability of the CH2 domains of the asymmetric antibody constructs based on rituximab was determined using differential scanning calorimetry as follows. Each antibody construct was purified as described in Example 8 and diluted to 0.2 mg/mL in PBS, and a total of 400 μL was used for DSC analysis with a VP-Capillary DSC (GE Healthcare). At the start of each DSC run, five buffer blank injections were performed to stabilize the baseline, and a buffer injection was placed before each antibody construct injection for referencing. Each sample was scanned from 20 to 100° C. at a 60° C./hr rate, with low feedback, 8 sec filter, 5 min preTstat, and 70 psi nitrogen pressure. The resulting thermograms were referenced and analyzed using Origin 7 software.

The melting temperatures of the heteromultimers tested are shown in Table I below.

TABLE I

| Thermal stability of heteromultimers | |
|---|---|
| Variant | Tm [° C.][1] |
| Control WT Rituximab 1261 | 73.0 |
| AAC9 | 75.3 |
| AAC10 | 75.3 |
| AAC11 | 75.4 |
| AAC12 | 75.4 |
| AAC13 | 75.4 |
| AAC14 | 75.2 (noisy) |
| AAC15 | 67.5 |

[1]The first transition included the unfoldingof both the Rituximab FAB and CH2 domain. The Tm was measured by deconvolution using a non-2 state model of the first transition.

These results indicate that a number of designs have higher Tm onset and Tm of the CH2 domain when compared to the control WT.

Example 11: Asymmetric Antibody Constructs Based on Rituximab do not Stimulate ADCC in Daudi Cells Selected variants were tested for their ability to stimulate ADCC in Daudi cells in order to assess whether the lack of measured binding to FcγR translated into an inability to mediate effector function as measured by ADCC. Daudi cells express CD20 on their surface and thus bind to rituximab, allowing for NK cell mediated ADCC in the presence of rituximab. The activity of the selected variants in this assay was compared to that of the control rituximab variant described in Table F, and to commerically obtained rituximab.

Cell lines used: Daudi cell line (ATCC, Cat # CCL-213), NK92/CD16a (158V/V) Detection device: FlexStation3, Molecular Devices.

Positive control antibody: Rituximab.

Cell Culture. Frozen cells were thawed by gently swirling the vial in the 37° C. water bath. After 1-2 min, the medium in the vial was completely thawed. The outside of the vial was wiped with 70% ethanol. The cell suspension was then transferred to a 15 ml centrifuge tube, followed by addition of 5 ml of pre-warmed complete medium. After centrifugation for 3-5 min at 500 g, the supernatant was aspirated. 10 ml of complete medium was added and the cells were resuspended by pipetting up and down for a few times. Cell viability was determined by Trypan blue staining method. The cell suspension was then seeded in flasks. The cells were incubated at 37° C., 5% CO2 overnight.

Cells were maintained at 37° C./5% CO2 and regularly sub-cultured with suitable medium supplemented with 10% FBS according to protocol from ATCC.

The antibody sample and the Standard (Rituximab) were delivered in dry shipper and stored at −20° C. before testing. The sample and the Standard were stored at 4° C. after they were thawed on ice. The sample and the Standard were diluted with Phenol red free MEM medium (supplemented with 1% FBS and 1% Pen/Strep) and applied to the tests.

ADCC assay buffer was composed of 98% Phenol red free MEM medium, 1% Pen/Strep and 1% FBS.

NK92/FcRγ3a(158V/V) cells were conventionally maintained.

Target cells were harvested by centrifugation at 800 rpm for 3 min, washed with assay medium once and centrifuged; the medium above the pellet was removed completely. Cells were gently suspended with assay medium to make single cell solution. The target cell number was adjusted to 4× cell stock (10,000 cells in 50 μl assay medium). Test articles were prepared at interested concentrations. 50 μl 4× target cell stock were seeded to 96-well assay plates and 50 μl 4× sample diluents added. The plates were incubated at room temperature for 30 min in cell culture incubator. 100 μl effector cells (E/T=5:1, i.e, 50,000 effector cells per well) were added to initiate the reaction and mixed gently by cross shaking. Triton X-100 was added to cell controls without effector cells and antibody in a final concentration of 1% to lyze the target cells and it sierved as the maximum lysis control; assay buffers were added in to cell controls without effector cells and antibody and it served as the minimum LDH release control. Target cells incubated with effector cells without the presence of antibodies were set as background control of non-specific LDH release when both cells were incubated together. Plate was incubated at 37° C./5% CO2 incubator for 4-6 hours. The cell viability was assayed with an LDH kit. The absorbance data at OD492 nm and OD650 nm were measured on Flexstation 3.

The background (OD650 nm) subtracted OD492 nm data was analyzed to study the LDH release. The percentages of cell lysis were calculated according to the formula:

Cell lysis %=100*(1−(*OD*Sample data−*OD*tumor cells plus effector cells)/(*OD*Maximum release−*OD*Minimum release))

The results are shown in FIG. 6 and indicate that all variants showed significantly decreased or undetectable ADCC activity.

The following table summarizes the results:

TABLE J

ADCC activity of the variants

| Variant | EC50 [nM] | Maximum Lysis |
|---|---|---|
| Control WT Rituximab 1261 | 0.1 | 66 |
| AAC9 | Non-lytic | Non-lytic |
| AAC10 | 7.4 | 45 |
| AAC11 | >100 | Low |
| AAC12 | 23.1 | 20 |
| AAC13 | n/d* | n/d* |
| AAC14 | Non-lytic | Non-lytic |
| AAC15 | Non-lytic | Non-lytic |

*n/d = not determined

The KO variants showed significantly decreased ADCC lytic activity, and for many variants, no activity was detected at all.

Example 12: Asymmetric Antibody Constructs Based on Rituximab Reduce CDC (Complement-Dependent Cytotoxicity) in Daudi Cells Although not tested for their ability to bind to C1q, selected variants were tested to determine whether they were able to mediate CDC in Daudi cells. The activity of the selected variants in this assay was compared to that of the control rituximab variant described in Table F, and to commerically obtained rituximab.

Cell lines used: Daudi cell line (ATCC, Cat # CCL-213), NK92/CD16a (158V/V). Detection device: F PHER-AstarPlus, BMG Labtech. Positive control antibody: Rituximab.

Cell Culture. Daudi cells were harvested by centrifugation and the pallets were washed with assay buffer once. Viable cells were counted by Trypan Blue dye. Cell population was only allowed of >99% viability for the assay. The cell concentration was adjusted and 5,000 cells were seeded in 20 μl CDC buffer. 10 μl diluted samples were added (8 concentrations with a dilution factor of 1:10 descending from 600 nM, in triplicates). Samples and Rituxan control were incubated at room temperature for 30 min. 10 μl NHS (10% final concentration in 40 μl reaction volume) were added to each well to initiate the CDC assay. Plate was incubated at 37° C./5% CO2 incubator for 2 hours. Cell viability test was performed with CellTiter-Glo® Luminescent Cell Viability Assay Kit. Luminescence was read on PHERAStar Plus and record the relative light unit data.

Data Analysis

The percentage of cell lysis was calculated with the formula:

% Cell lysis=100*(1−(*RLU*sample)/(*RLU*cell+NHS), in which NHS stands for normal human serum.

The results are shown in FIG. 7 and indicate that all samples showed significantly lower CDC activity.

TABLE K

CDC activity of the variants

| Variant | EC50 [nM] | Maximum Lysis |
|---|---|---|
| Control WT Rituximab 1261 | 2.9 | 96 |
| AAC9 | 47.9 | 68 |
| AAC10 | 82.8 | 79 |
| AAC11 | 51.6 | 63 |
| AAC12 | 54.6 | 67 |
| AAC13 | n/d* | n/d* |
| AAC14 | 69.7 | 72 |
| AAC15 | ~55.87 | 43 |

*n/d = not determined

The KO variants showed significantly decreased CDC lytic activity.

The reagents employed in the examples are commercially available or can be prepared using commercially available instrumentation, methods, or reagents known in the art. The foregoing examples illustrate various aspects of the invention and practice of the methods of the invention. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

All publications, patents and patent applications mentioned in this specification are herein incorporated by reference into the specification to the same extent as if each individual publication, patent or patent application was specifically and individually indicated to be incorporated herein by reference.

I claim:

1. A heteromultimer comprising an IgG Fc construct having a first and a second Fc polypeptide, each Fc polypeptide comprising a modified lower hinge region, wherein:

a. the modified lower hinge region of the first Fc polypeptide comprises the amino acid modifications L234K/L235K and the modified lower hinge region of the second Fc polypeptide comprises the amino acid modifications L234A/L235A; or b. the modified lower hinge region of the first Fc polypeptide comprises the amino acid modifications L234K/L235K and the modified lower hinge region of the second Fc polypeptide comprises the amino acid modifications L234D/L235E; or c. the modified lower hinge region of the first Fc polypeptide comprises the amino acid modifications E233A/L234R/L235R and the modified lower hinge region of the second Fc polypeptide comprises the amino acid modifications E233A/L234D/L235E, or d. the modified lower hinge region of the first Fc polypeptide comprises the amino acid modifications E233K/L234R/L235R and the modified lower hinge region of the second Fc polypeptide comprises the amino acid modifications L234D/L235E; or e. the modified lower hinge region of the first Fc polypeptide comprises the amino acid modifications E233K/L234A/L235K and the modified lower hinge region of the second Fc polypeptide comprises the amino acid modifications E233A/L234K/L235A; or f. the first Fc polypeptide comprises the amino acid modifications E233K/L234R/L235R/D265S and the second Fc polypeptide comprises the amino acid modifications L234D/L235E/D265S; or g. the first Fc polypeptide comprises the amino acid modifications E233K/L234R/L235R/E269K and the second Fc polypeptide comprises the amino acid modifications L234D/L235E/E269K; or h. the first Fc polypeptide comprises the amino acid modifications E233K/L234R/L235R/K322A and the second Fc polypeptide comprises the amino acid modifications L234D/L235E/K322A; or i. the first Fc polypeptide comprises the amino acid modifications E233K/L234R/L235R/P329W and the second Fc polypeptide comprises the amino acid modifications L234D/L235E/P329W; or j. the first Fc polypeptide comprises the amino acid modifications E233K/L234R/L235R/E269K/D265S/K322A and the second Fc polypeptide comprises the amino acid modifications L234D/L235E/E269K/D265S/K322A; or k. the first Fc polypeptide comprises the amino acid modifications E233K/L234R/L235R/E269K/D265S/

K322E/E333K and the second Fc polypeptide comprises the amino acid modifications L234D/L235E/E269K/D265 S/K322E/E333K, wherein the IgG Fc construct displays reduced binding to the FcγRIa, FcγRIIa, FcγRIIb and FcγRIIIa receptors as compared to a corresponding parent IgG Fc construct, wherein the IgG Fc construct is an IgG1, IgG3 or IgG4 Fc construct, and wherein the numbering of amino acids is according to the EU index as in Kabat.

2. The heteromultimer according to claim 1, wherein the IgG Fc construct is aglycosylated or deglycosylated.

3. The heteromultimer according to claim 1, wherein one of the first and second Fc polypeptides comprises the CH3 amino acid modifications T366L/N390R/K392M/T394W and the other Fc polypeptide comprises the CH3 amino acid modifications L351Y/S400E/F405A/Y407V.

4. The heteromultimer according to claim 1, wherein the heteromultimer further comprises at least one antigen-binding construct fused to the IgG Fc construct.

5. The heteromultimer according to claim 4, wherein the at least one antigen-binding construct is a Fab fragment, an scFv, an sdAb, an antigen binding peptide, an Fc fusion protein, or a protein or fragment thereof capable of binding the antigen.

6. The heteromultimer according to claim 4, comprising one or two antigen-binding constructs.

7. The heteromultimer according to claim 1, wherein the IgG Fc construct is linked to one or more toxic drug molecules or one or more heterologous polypeptides.

8. The heteromultimer according to claim 7, wherein the one or more heterologous polypeptides are selected from enzymes and toxins.

9. The heteromultimer according to claim 1, wherein the IgG Fc construct is an IgG1 Fc construct.

10. A pharmaceutical composition comprising the heteromultimer according to claim 1 and a pharmaceutically acceptable carrier.

11. The heteromultimer according to claim 1, wherein the IgG Fc construct further displays reduced binding to C1q protein as compared to the corresponding parent IgG Fc construct.

12. The heteromultimer according to claim 1, wherein one of the first and second Fc polypeptides comprises the CH3 amino acid modifications L351Y/F405A/Y407V and the other Fc polypeptide comprises the CH3 amino acid modifications T366L/K392M/T394W.

13. The heteromultimer according to claim 1, wherein one of the first and second Fc polypeptides comprises the CH3 amino acid modifications L351Y/F405A/Y407V and the other Fc polypeptide comprises the CH3 amino acid modifications T366L/K392L/T394W.

14. The heteromultimer according to claim 1, wherein one of the first and second Fc polypeptides comprises the CH3 amino acid modifications T350V/L351Y/F405A/Y407V and the other Fc polypeptide comprises the CH3 amino acid modifications T350V/T366L/K392L/T394W.

15. The heteromultimer according to claim 1, wherein one of the first and second Fc polypeptides comprises the CH3 amino acid modifications T350V/L351Y/F405A/Y407V and the other Fc polypeptide comprises the CH3 amino acid modifications T350V/T366L/K392M/T394W.

16. The heteromultimer according to claim 1, wherein one of the first and second Fc polypeptides comprises the CH3 amino acid modifications T350V/L351Y/S400F/F405A/Y407V and the other Fc polypeptide comprises the CH3 amino acid modifications T350V/T366L/N390R/K392M/T394W.

* * * * *